(12) United States Patent
Brinkmann et al.

(10) Patent No.: US 12,297,290 B2
(45) Date of Patent: May 13, 2025

(54) METHOD FOR GENERATING MULTISPECIFIC ANTIBODIES FROM MONOSPECIFIC ANTIBODIES

(71) Applicant: Hoffmann-La Roche Inc., Little Falls, NJ (US)

(72) Inventors: Ulrich Brinkmann, Penzberg (DE); Stefan Dengl, Penzberg (DE); Guy Georges, Penzberg (DE); Eike Hoffmann, Penzberg (DE); Klaus Mayer, Penzberg (DE); Felix Bormann, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 964 days.

(21) Appl. No.: 16/849,223

(22) Filed: Apr. 15, 2020

(65) Prior Publication Data
US 2020/0392253 A1    Dec. 17, 2020

Related U.S. Application Data

(63) Continuation of application No. PCT/EP2018/078675, filed on Oct. 19, 2018.

(30) Foreign Application Priority Data

Oct. 20, 2017    (EP) ..................... 17197616

(51) Int. Cl.
*A61K 39/395* (2006.01)
*C07K 1/22* (2006.01)
*C07K 16/42* (2006.01)

(52) U.S. Cl.
CPC ........... *C07K 16/42* (2013.01); *C07K 1/22* (2013.01); *C07K 2317/522* (2013.01); *C07K 2317/524* (2013.01); *C07K 2317/526* (2013.01); *C07K 2317/53* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,624,821 A | 4/1997 | Winter et al. | |
| 5,648,260 A | 7/1997 | Winter et al. | |
| 5,821,337 A | 10/1998 | Carter et al. | |
| 6,194,551 B1 | 2/2001 | Idusogie et al. | |
| 6,737,056 B1 | 5/2004 | Presta et al. | |
| 7,183,076 B2 | 2/2007 | Arathoon et al. | |
| 7,332,581 B2 | 2/2008 | Presta et al. | |
| 7,371,826 B2 | 5/2008 | Presta et al. | |
| 7,951,917 B1 | 5/2011 | Arathoon et al. | |
| 8,076,459 B2 | 12/2011 | Hofmeister et al. | |
| 8,592,562 B2 | 11/2013 | Kannan et al. | |
| 8,642,745 B2 | 2/2014 | Arathoon et al. | |
| 8,765,412 B2 | 7/2014 | Arathoon et al. | |
| 9,409,989 B2 | 8/2016 | Arathoon et al. | |
| 9,670,269 B2 | 6/2017 | Igawa et al. | |
| 9,688,762 B2 | 6/2017 | Igawa et al. | |
| 9,914,776 B2 | 3/2018 | Ast et al. | |
| 10,011,858 B2 | 7/2018 | Igawa et al. | |
| 10,611,840 B2 | 4/2020 | Ast et al. | |
| 10,611,841 B2 | 4/2020 | Ast et al. | |
| 10,633,457 B2 | 4/2020 | Brinkmann et al. | |
| 10,934,344 B2 | 3/2021 | Igawa et al. | |
| 11,117,965 B2 | 9/2021 | Ast et al. | |
| 11,124,576 B2 | 9/2021 | Igawa et al. | |
| 11,155,639 B2 * | 10/2021 | Kim ..................... | C07K 16/468 |
| 11,168,344 B2 | 11/2021 | Igawa et al. | |
| 11,332,533 B2 | 5/2022 | Igawa et al. | |
| 2005/0014934 A1 | 1/2005 | Hinton et al. | |
| 2010/0286374 A1 | 11/2010 | Kannan et al. | |
| 2014/0024111 A1 | 1/2014 | Kannan et al. | |
| 2019/0382484 A1 | 12/2019 | Igawa et al. | |
| 2022/0267822 A1 | 8/2022 | Igawa et al. | |
| 2022/0403027 A1 | 12/2022 | Ast et al. | |

FOREIGN PATENT DOCUMENTS

| | | |
|---|---|---|
| CN | 106459191 A | 2/2017 |
| CN | 107074966 A | 8/2017 |
| EP | 1536005 A1 | 6/2005 |
| EP | 1693386 A1 | 8/2006 |
| EP | 1870459 A1 | 12/2007 |
| JP | 2014510084 A | 4/2014 |
| JP | 2016-093175 A | 5/2016 |
| JP | 2017-525690 A | 9/2017 |

(Continued)

OTHER PUBLICATIONS

Angal, S., et al., "A single amino acid substitution abolishes the heterogeneity of chimeric mouse/human (IgG4) antibody" Molec Immunol 30(1):105-108 (Jan. 1, 1993).

Atwell, S., et al., "Stable Heterodimers from Remodeling the Domain Interface of a Homodimer using a Phage Display Library" J Mol Biol 270(1):26-35 (Jul. 4, 1997).

Bruggemann, M., et al., "Comparison of the Effector Functions of Human Immunogobulins Using a Matched set of Chimeric Antibodies" J Exp Med 166(5):1351-1361 (Oct. 1, 1987).

Carter, P. et al., "'Knobs-into-holes' provides a rational design strategy for engineering antibody CH3 domains for heavy chain heterodimerization" Immunotechnology 2(1):73 (Jan. 1, 1996).

(Continued)

*Primary Examiner* — Meera Natarajan
(74) *Attorney, Agent, or Firm* — GENENTECH, INC.

(57) ABSTRACT

Herein is reported a method for the generation of multispecific antibodies by a half-antibody exchange reaction between two 2/3-IgGs destabilized in one half by asymmetric perturbing mutations fostering the generation of correctly assemble full length bispecific antibodies. The method can be performed in the absence of reducing agents and does not require hinge region disulfide bonds in the starting 2/3-IgGs.

15 Claims, 34 Drawing Sheets

Specification includes a Sequence Listing.

(56) References Cited

FOREIGN PATENT DOCUMENTS

| | | |
|---|---|---|
| WO | 93/11162 A1 | 6/1993 |
| WO | 94/09131 A1 | 4/1994 |
| WO | 94/29351 A2 | 12/1994 |
| WO | 96/027011 A1 | 9/1996 |
| WO | 98/050431 A2 | 11/1998 |
| WO | 99/051642 A1 | 10/1999 |
| WO | 2004/056312 A2 | 7/2004 |
| WO | 2004/056312 A3 | 7/2004 |
| WO | 2005/062916 A2 | 12/2004 |
| WO | 2005/000898 A2 | 1/2005 |
| WO | 2005/100402 A1 | 10/2005 |
| WO | 2006/029879 A2 | 3/2006 |
| WO | 2006/029879 A3 | 3/2006 |
| WO | 2006/047340 A2 | 5/2006 |
| WO | 2007/062466 A1 | 6/2007 |
| WO | 2007/110205 A2 | 10/2007 |
| WO | 2007/147901 A1 | 12/2007 |
| WO | 2008/119353 A1 | 10/2008 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 2010/151792 A2 | 12/2010 |
| WO | 2010/129304 A2 | 2/2011 |
| WO | 2010/129304 A3 | 2/2011 |
| WO | 2011/090754 A1 | 7/2011 |
| WO | 2011/090762 A1 | 7/2011 |
| WO | 2011/131746 A2 | 10/2011 |
| WO | 2011/131746 A3 | 10/2011 |
| WO | 2011/133886 A2 | 10/2011 |
| WO | 2011/133886 A3 | 10/2011 |
| WO | 2011/143545 A1 | 11/2011 |
| WO | 2012/025530 A1 | 3/2012 |
| WO | 2012/058768 A1 | 6/2012 |
| WO | 2012/058768 A8 | 6/2012 |
| WO | 2012/123949 A1 | 9/2012 |
| WO | 2013/060867 A2 | 5/2013 |
| WO | 2013/060867 A3 | 5/2013 |
| WO | 2013/096291 A2 | 6/2013 |
| WO | 2013/096291 A3 | 6/2013 |
| WO | 2013/157954 A1 | 10/2013 |
| WO | 2014/081955 A1 | 5/2014 |
| WO | 2015/189249 A1 | 12/2015 |
| WO | 2016/020309 | 2/2016 |
| WO | 2016/071377 A1 | 5/2016 |
| WO | 2016/087416 A1 | 6/2016 |
| WO | 2016/087650 A1 | 6/2016 |
| WO | 2017/191101 A1 | 11/2017 |

OTHER PUBLICATIONS

Clynes, R., et al., "Fc receptors are required in passive and active immunity to melanoma" PNAS USA 95(2):652-656 (Jan. 1, 1998).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
DeNardis, C., et al., "A new approach for generating bispecific antibodies based on a common light chain format and the stable architecture of human immunoglobulin G1" J Biol Chem 292(35):14706-14717 (Jun. 27, 2017).
Duncan, A., et al., "The Binding Site for C1q on IgG" Nature 332(6166):738-740 (Apr. 21, 1988).
Elliott, J., et al., "Antiparallel Conformation of Knob and Hole Aglycosylated Half-Antibody Homodimers Is Mediated by a CH2—CH3 Hydrophobic Interaction" J Mol Biol 426(9):1947-1957 (May 1, 2014).
Gazzano-Santoro, H., et al., "A non-radioactive complement-dependent cytotoxicity assay for anti-CD20 monoclonal antibody" J Immunol Methods 202(2):163-171 (Mar. 28, 1997).

Gunasekaran, K et al., "Enhancing Antibody Fc Heterodimer Formation through Electrostatic Steering Effects: Applications to Bi-Specific Molecules and Monovalent IgG" J Biol Chem 285(25):19637-19646 (Jun. 18, 2010).
Guyer, R., et al., "Immunoglobulin binding by mouse intestinal epithelial cell receptors" J Immunol 117(2):587-593 (Aug. 1, 1976).
Hellstrom, I., et al., "Antitumor effects of L6, an IgG2a antibody that reacts with most human carcinomas" PNAS USA 83(18):7059-7063 (Sep. 1, 1986).
Hellstrom, I., et al., "Strong antitumor activities of IgG3 antibodies to a human melanoma-associated ganglioside" PNAS USA 82(5):1499-1502 (Mar. 1, 1985).
Idusogie, E.E., et al., "Mapping of the C1q Binding Site on Rituxan, A Chimeric Antibody with a Human IgG1 Fc" J Immunol 164(8):4178-4184 (Apr. 15, 2000).
"International Preliminary Report on Patentability—PCT/EP2018/078675,": pp. 1-21 (Sep. 17, 2019).
"International Search Report—PCT/EP2018/078675,": pp. 1-17 (Dec. 6, 2018).
Kim, J., et al., "Localization of the site of the murine IgG1 molecule that is involved in binding to the murine intestinal Fc receptor" Eur J Immunol 24(10):2429-2434 (Oct. 1, 1994).
Kostelny, S., et al., "Formation of a bispecific antibody by the use of leucine zippers" J Immunol 148(5):1547-1553 (Mar. 1, 1992).
Labrijn, A.F., et al., "Efficient generation of stable bispecific IgG1 by controlled Fab-arm exchange" PNAS USA 110(13):5145-5150 (Mar. 26, 2013).
Liu, Z., et al., "A Novel Antibody Engineering Strategy for Making Monovalent Bispecific Heterodimeric IgG Antibodies by Electrostatic Steering Mechanism" J Biol Chem 290(12):7535-7562 (Mar. 20, 2015).
Merchant, A., et al., "An efficient route to human bispecific IgG" Nat Biotechnol 16(7):677-681 (Jul. 1, 1998).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Pokala, N., et al., "Energy Functions for Protein Design: Adjustment with Protein-Protein Complex Affinities, Models for the Unfolded State, and Negative Design of Solubility and Specificity" J Mol Biol 347(1):203-227 (Mar. 18, 2005).
Ravetch, J., et al., "Fc receptors" Annu Rev Immunol 9:457-492 (Apr. 1, 1991).
Ridgway, J., et al., "'Knobs-into-holes' engineering of antibody CH3 domains for heavy chain heterodimerization" Protein Eng 9(7):617-621 (Jul. 1, 1996).
Rispens, T., et al., "Dynamics of Inter-heavy Chain Interactions in Human Immunoglobulin G (IgG) Subclasses Studied by Kinetic Fab Arm Exchange" J Biol Chem 289(9):6098-6109 (Feb. 28, 2014).
Schaefer, W., et al., "Immunoglobulin domain crossover as a generic approach for the production of bispecific IgG antibodies" PNAS USA 108(27):11187-11192 (Jul. 5, 2011).
Segal, D.M., et al., "Bispecific antibodies in cancer therapy" Curr Opin Immunol 11(5):558-562 (Oct. 1, 1999).
Shields, R., et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Anthony, J., et al., "Production of stable anti-digoxin Fv in *Escherichia coli*" Mol Immunol 29(10):1237-1247 (Oct. 1, 1992).
Banaszek, A., et al., "Dual Antigen-Restricted Complementation of a Trispecific Antibody Construct for Targeted Immunotherapy of Blood Cancer" Abstract (T-10) Eighth Fabisch-Symposium for Cancer Research and Molecular Cell Biology, Berlin, Germany, pp. 1-6 (Mar. 21-23, 2012).
Banaszek, A.,, "Dual Antigen-Restricted Complementation of a Two-Part Trispecific Antibody for Targeted Immunotherapy of Blood Cancer" Julius-Maximilians Universitat—Würzburg, Germany (Ph. D Dissertation),: 1-142 (Sep. 20, 2013) https://d-nb.info/1110027168/34.
Brinkmann, U., et al., "The making of bispecific antibodies" MABS 9(2):182-212 (Jan. 10, 2017).

(56) References Cited

OTHER PUBLICATIONS

European Medicines Agency [EMA], "Blincyto—Annex I—Summary of Product Characteristics-" (Amgen; EMEA/H/C/003731-II/0047/G),: 1-56 (Dec. 7, 2015).
Glockshuber, R., et al., "A comparison of strategies to stabilize immunoglobulin Fv-fragments" ACS Biochemistry 29(6):1362-1367 (Feb. 13, 1990).
Hamel, P.A., et al., "Relative noncovalent association constant between immunoglobulin H and L chains is unrelated to their expression or antigen-binding activity" J Immunol 139(9):3012-3020 (Nov. 1, 1987).
Hochman, J., et al., "An active antibody fragment (Fv) composed of the variable portions of heavy and light chains" ACS Biochemistry 12(6):1130-1135 (Mar. 13, 1973).
Hochman, J., et al., "Folding and interaction of subunits at the antibody combining site" ACS Biochemistry 15(12):2706-2710 (Jun. 15, 1976).
Horne, C., et al., "Noncovalent association of heavy and light chains of human immunoglobulins. III. Specific interactions between VH and VL" J Immunol 129(2):660-664 (Aug. 1, 1982).
Hu, S., et al., "Minibody: A novel engineered anti-carcinoembryonic antigen antibody fragment (single-chain Fv-CH3) which exhibits rapid, high-level targeting of xenografts" Cancer Res 56(13):3055-3061 (Jul. 1, 1996).
"International Preliminary Report on Patentability—PCT/EP2018/079523": pp. 1-16 (Jan. 23, 2020).
"International Search Report w/Written Opinion—PCT/EP2018/079523": pp. 1-16 (Dec. 17, 2018).
Jaehde, U., et al., "Dosis-Individualisierung in der Krebs-Chemotherapie: Zytostatika maßgeschneidert dosieren [Individualized dosage of cytostatics. Dose individualization in cancer chemotherapy]" Pharm Unserer Zeit (German w/Eng. Transl.), 35(2):150-156 (Feb. 21, 2006).
Jordan, G., et al., "Evaluation of the potential use of hybrid LC-MS/MS for active drug quantification applying the 'free analyte QC concept'" Bioanalysis 9(21):1705-1717 (Sep. 27, 2017).
Julius-Maximilians Universitat, "Annex I—Basis for Calculation-Chart":1-2 (Dec. 3, 2018).
Julius-Maximilians Universitat, "Chart: The bispecific antibodies of Harris":1 (Dec. 3, 2018).
Julius-Maximilians Universitat, "Chart-Kalkulation Css aus Dosisangaben":1 (Dec. 3, 2018).
Julius-Maximilians Universitat, "Overview of Antibody Formats—Chart":1 (Dec. 3, 2018).
Julius-Maximilians Universitat, "Predicted Non-associated variable domain fractions at different concentrations":1 (Dec. 3, 2018).
Julius-Maximilians Universitat, "Supplemental Data Chart":1-4 (Dec. 3, 2018).
Julius-Maximilians Universitat, "Vossius & Partner Response to EP Rule 161&162 Communication" (Claim Amendments),:1-8 (Mar. 2, 2015).
Julius-Maximilians-Universitat, "European Patent Application No. 12151125.7 entitled: 'Dual Antigen-Induced bipartite functional Complementation' filed Jan. 13, 2012":1-76.
Lum, L., et al., "Targeting T Cells with Bispecific Antibodies for Cancer Therapy" Biodrugs 25(6):365-379 (Dec. 1, 2011).
Manakas, A., et al., "Demibodies for Highly Specific Cell Detection and Killing" Poster (#209) 42nd Lorne Conference on Protein Structure and Function, Lorne, NSW-Australia, p. 1 (Feb. 5-9, 2017).
Masuda, K, et al., "Loss or down-regulation of HLA class I expression at the allelic level in freshly isolated leukemic blasts" Cancer Sci 98(1):102-108 (Nov. 3, 2006).
Mayer, K., et al., "TriFabs—Trivalent IgG-Shaped Bispecific Antibody Derivatives: Design, Generation, Characterization and Application for Targeted Payload Delivery" Int J Mol Sci 16(12):27497-27507 (Nov. 15, 2015).
Polymenis, M., et al., "Domain interactions and antigen binding of recombinant anti-Z-DNA antibody variable domains. The role of heavy and light chains measured by surface plasmon resonance" J Immunol 154(5):2198-2208 (Mar. 1, 1995).
Rothlisberger, D., et al., "Domain interactions in the Fab fragment: a comparative evaluation of the single-chain Fv and Fab format engineered with variable domains of different stability" J Mol Biol 347(4):773-789 (Apr. 8, 2005).
Shu, L., et al., "Secretion of a single-gene-encoded immunoglobulin from myeloma cells" PNAS 90(17):7995-7999 (Sep. 1, 1993).
Ueda, H., et al., "Open sandwich ELISA: a novel immunoassay based on the interchain interaction of antibody variable region" Nat Biotechnol 14(13):1714-1718 (Dec. 1, 1996).
Wang, X.B. et al., "A new recombinant single chain trispecific antibody recruits T lymphocytes to kill CEA (carcinoma embryonic antigen) positive tumor cells in vitro efficiently" J Biochemistry 135(4):555-565 (Apr. 1, 2004).
Ward, E., et al., "Binding activities of a repertoire of single immunoglobulin variable domains secreted from *Escherichia coli*" Nature 341(6242):544-546 (Oct. 12, 1989).
Annex WIPO ST.26 Sequence Listings ver1, 3 pages.

* cited by examiner

Figure 13

|  | Biotin | Fluo | Dig | VEGF | PDGF |
|---|---|---|---|---|---|
| Biotin | ☐ | ■ | ■ | ■ | ■ |
| Fluo | ■ | ☐ | ■ | ■ | ■ |
| Dig | ■ | ■ | ☐ | ■ | ■ |
| VEGF | ■ | ■ | ■ | ☐ | ■ |
| PDGF | ■ | ■ | ■ | ■ | ☐ | knob / E357K (rows) × hole / K370E (columns)

SEQUENCE LISTING

```
<160> NUMBER OF SEQ ID NOS: 92

<210> SEQ ID NO 1
<211> LENGTH: 225
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 2
<211> LENGTH: 324
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 3
<211> LENGTH: 375
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

```
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
             85                   90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro
370                 375

<210> SEQ ID NO 4
<211> LENGTH: 227
<212> TYPE: PRT
<213> ORGANISM: Homo sapiens

<400> SEQUENCE: 4

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60
```

```
Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu
225

<210> SEQ ID NO 5
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 5

Asp Lys Thr His Thr Cys Pro Pro Cys Pro Ala Pro Glu Ala Ala Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

```
                180             185              190
Asp Lys Ser Arg Trp Gln Gln Gly Asn Val Phe Ser Cys Ser Val Met
        195                 200             205

His Glu Ala Leu His Asn His Tyr Thr Gln Lys Ser Leu Ser Leu Ser
    210             215                 220

Pro
225

<210> SEQ ID NO 6
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200             205

His Glu Ala Leu His Asn His Tyr Thr Gln Lys Ser Leu Ser Leu Ser
    210             215                 220

Pro
225

<210> SEQ ID NO 7
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with S354C, T366W mutations

<400> SEQUENCE: 7

Asp Lys Thr His Thr Cys Pro Pro Cys Pro Ala Pro Glu Leu Leu Gly
```

```
       1               5                  10                 15
Gly Pro Ser Val Phe Leu Phe Pro Pro Lys Pro Lys Asp Thr Leu Met
            20                 25                 30

Ile Ser Arg Thr Pro Glu Val Thr Cys Val Val Val Asp Val Ser His
            35                 40                 45

Glu Asp Pro Glu Val Lys Phe Asn Trp Tyr Val Asp Gly Val Glu Val
     50                  55                 60

His Asn Ala Lys Thr Lys Pro Arg Glu Glu Gln Tyr Asn Ser Thr Tyr
 65                  70                 75                  80

Arg Val Val Ser Val Leu Thr Val Leu His Gln Asp Trp Leu Asn Gly
                85                 90                 95

Lys Glu Tyr Lys Cys Lys Val Ser Asn Lys Ala Leu Pro Ala Pro Ile
            100                105                110

Glu Lys Thr Ile Ser Lys Ala Lys Gly Gln Pro Arg Glu Pro Gln Val
            115                120                125

Tyr Thr Leu Pro Pro Cys Arg Asp Glu Leu Thr Lys Asn Gln Val Ser
     130                135                140

Leu Trp Cys Leu Val Lys Gly Phe Tyr Pro Ser Asp Ile Ala Val Glu
145                 150                155                160

Trp Glu Ser Asn Gly Gln Pro Glu Asn Asn Tyr Lys Thr Thr Pro Pro
                165                170                175

Val Leu Asp Ser Asp Gly Ser Phe Phe Leu Tyr Ser Lys Leu Thr Val
            180                185                190

Asp Lys Ser Arg Trp Gln Gln Gly Asn Val Phe Ser Cys Ser Val Met
            195                200                205

His Glu Ala Leu His Asn His Tyr Thr Gln Lys Ser Leu Ser Leu Ser
     210                215                220

Pro
225

<210> SEQ ID NO 8
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 8

Asp Lys Thr His Thr Cys Pro Pro Cys Pro Ala Pro Glu Ala Ala Gly
 1               5                  10                 15

Gly Pro Ser Val Phe Leu Phe Pro Pro Lys Pro Lys Asp Thr Leu Met
            20                 25                 30

Ile Ser Arg Thr Pro Glu Val Thr Cys Val Val Val Asp Val Ser His
            35                 40                 45

Glu Asp Pro Glu Val Lys Phe Asn Trp Tyr Val Asp Gly Val Glu Val
     50                  55                 60

His Asn Ala Lys Thr Lys Pro Arg Glu Glu Gln Tyr Asn Ser Thr Tyr
 65                  70                 75                  80

Arg Val Val Ser Val Leu Thr Val Leu His Gln Asp Trp Leu Asn Gly
                85                 90                 95

Lys Glu Tyr Lys Cys Lys Val Ser Asn Lys Ala Leu Pro Ala Pro Ile
            100                105                110

Glu Lys Thr Ile Ser Lys Ala Lys Gly Gln Pro Arg Glu Pro Gln Val
            115                120                125
```

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro
225

<210> SEQ ID NO 9
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a L234A, L235A and S354C, T366W mutations

<400> SEQUENCE: 9

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro
225

<210> SEQ ID NO 10
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 10

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 11
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 11

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr

```
                65                  70                  75                  80
Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
        210                 215                 220

Pro
225

<210> SEQ ID NO 12
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190
```

-continued

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro
225

<210> SEQ ID NO 13
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro
225

<210> SEQ ID NO 14
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 14

Asp Lys Thr His Thr Cys Pro Pro Cys Pro Ala Pro Glu Ala Ala Gly
```

```
1               5                   10                  15
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro
225

<210> SEQ ID NO 15
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125
```

```
Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro
225

<210> SEQ ID NO 16
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 16

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225
```

```
<210> SEQ ID NO 17
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 17

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 18
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 18

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
```

```
                65                  70                  75                  80
Thr Tyr Arg Val Val Ser Val Leu Thr Val Leu His Gln Asp Trp Leu
                    85                  90                  95

Asn Gly Lys Glu Tyr Lys Cys Lys Val Ser Asn Lys Gly Leu Pro Ser
                    100                 105                 110

Ser Ile Glu Lys Thr Ile Ser Lys Ala Lys Gly Gln Pro Arg Glu Pro
                    115                 120                 125

Gln Val Tyr Thr Leu Pro Pro Cys Gln Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220

Leu Ser Leu
225

<210> SEQ ID NO 19
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 19

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                    85                  90                  95

Asn Gly Lys Glu Tyr Lys Cys Lys Val Ser Asn Lys Gly Leu Pro Ser
                    100                 105                 110

Ser Ile Glu Lys Thr Ile Ser Lys Ala Lys Gly Gln Pro Arg Glu Pro
                    115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
                180                 185                 190
```

```
Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu
225

<210> SEQ ID NO 20
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 20

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 21
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 21

Glu Ser Lys Tyr Gly Pro Pro Cys Pro Pro Cys Pro Ala Pro Glu Phe
1               5                   10                  15
```

Glu Gly Gly Pro Ser Val Phe Leu Phe Pro Pro Lys Pro Lys Asp Thr
                    20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Cys Thr Leu Pro Pro Ser Gln Glu Glu Met Thr Lys Asn Gln
130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu
225

<210> SEQ ID NO 22
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 22

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln

```
                130                 135                 140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu
225

<210> SEQ ID NO 23
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 23

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Cys Thr Leu Pro Pro Ser Gln Glu Glu Met Thr Lys Asn Gln
                130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu
225

<210> SEQ ID NO 24
<211> LENGTH: 227
```

<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 25
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and Y349C, T366S, L368A,
      Y407V mutations

<400> SEQUENCE: 25

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Cys Thr Leu Pro Pro Ser Gln Glu Glu Met Thr Lys Asn Gln
130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu
225

<210> SEQ ID NO 26
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and S354C, T366W mutations

<400> SEQUENCE: 26

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Cys Gln Glu Glu Met Thr Lys Asn Gln
130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser

```
                195                 200                 205
Val Met His Glu Ala Leu His Asn His Tyr Thr Gln Lys Ser Leu Ser
        210                 215                 220

Leu Ser Leu
225

<210> SEQ ID NO 27
<211> LENGTH: 103
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 28
<211> LENGTH: 107
<212> TYPE: PRT
<213> ORGANISM: Homo sapiens

<400> SEQUENCE: 28

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 29
<211> LENGTH: 105
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30
```

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro
                100                 105

<210> SEQ ID NO 30
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X=S or P

<400> SEQUENCE: 30

Asp Lys Thr His Thr Cys Pro Xaa Cys Pro
 1               5                  10

<210> SEQ ID NO 31
<211> LENGTH: 7
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X=S or P

<400> SEQUENCE: 31

His Thr Cys Pro Xaa Cys Pro
 1               5

<210> SEQ ID NO 32
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X=S or P

<400> SEQUENCE: 32

Cys Pro Xaa Cys Pro
 1               5

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
                    50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 34
<211> LENGTH: 105
<212> TYPE: PRT
<213> ORGANISM: Homo sapiens

<400> SEQUENCE: 34

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                 20                  25                  30

Tyr Pro Gly Ala Val Thr Val Ala Trp Lys Ala Asp Ser Ser Pro Val
             35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 35
<211> LENGTH: 240
<212> TYPE: PRT
<213> ORGANISM: Artificial Sequence
<220> FEATURE:
<223> OTHER INFORMATION: MHCFcRP-hole-D356K-His8

<400> SEQUENCE: 35

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Lys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser His His His His His His His His
225                 230                 235                 240

<210> SEQ ID NO 36
<211> LENGTH: 240
<212> TYPE: PRT
<213> ORGANISM: Artificial Sequence
<220> FEATURE:
<223> OTHER INFORMATION: MHCFcRP-hole-E357K-His8

<400> SEQUENCE: 36

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Lys Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser His His His His His His His His
225                 230                 235                 240

<210> SEQ ID NO 37
<211> LENGTH: 240
<212> TYPE: PRT
<213> ORGANISM: Artificial Sequence
<220> FEATURE:
<223> OTHER INFORMATION: MHCFcRP-knob-K370E-His8
```

<400> SEQUENCE: 37

Asp Lys Thr His Thr Cys Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Trp Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Gly Ser His His His His His His His His
225                 230                 235                 240

<210> SEQ ID NO 38
<211> LENGTH: 240
<212> TYPE: PRT
<213> ORGANISM: Artificial Sequence
<220> FEATURE:
<223> OTHER INFORMATION: MHCFcRP-knob-K439E-His8

<400> SEQUENCE: 38

Asp Lys Thr His Thr Cys Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val

```
                115                 120                 125
Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Glu Ser Leu Ser Leu Ser
    210                 215                 220

Pro Gly Lys Gly Gly Gly Ser His His His His His His
225                 230                 235                 240

<210> SEQ ID NO 39
<211> LENGTH: 214
<212> TYPE: PRT
<213> ORGANISM: Artificial Sequence
<220> FEATURE:
<223> OTHER INFORMATION: anti-bio antibody full length light chain

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 450
<212> TYPE: PRT
```

<213> ORGANISM: Artificial Sequence
<220> FEATURE:
<223> OTHER INFORMATION: anti-bio antibody full length heavy chain-knob-cys

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 41
<211> LENGTH: 450
<212> TYPE: PRT
<213> ORGANISM: Artificial Sequence
<220> FEATURE:
<223> OTHER INFORMATION: anti-bio antibody full length heavy chain-hole-
      cys

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Lys Asp Thr
            20                  25                  30

Phe Phe Gln Trp Val Arg Gln Ala Pro Gly Gln Gly Leu Glu Trp Met
            35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 42
<211> LENGTH: 219
<212> TYPE: PRT
<213> ORGANISM: Artificial Sequence
<220> FEATURE:
<223> OTHER INFORMATION: anti-fluos antibody full length light chain

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

-continued

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 43
<211> LENGTH: 448
<212> TYPE: PRT
<213> ORGANISM: Artificial Sequence
<220> FEATURE:
<223> OTHER INFORMATION: anti-fluos antibody full length heavy chain-
      knob-cys

<400> SEQUENCE: 43

Gly Val Lys Leu Asp Glu Thr Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr

```
                        325                 330                 335
Ile Ser Lys Ala Lys Gly Gln Pro Arg Glu Pro Gln Val Tyr Thr Leu
                340                 345                 350
Pro Pro Cys Arg Asp Glu Leu Thr Lys Asn Gln Val Ser Leu Trp Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 44
<211> LENGTH: 448
<212> TYPE: PRT
<213> ORGANISM: Artificial Sequence
<220> FEATURE:
<223> OTHER INFORMATION: anti-fluos antibody full length heavy chain-
      hole-cys

<400> SEQUENCE: 44

Gly Val Lys Leu Asp Glu Thr Gly Gly Gly Leu Val Gln Pro Gly Gly
1               5                   10                  15
Ala Met Lys Leu Ser Cys Val Thr Ser Gly Phe Thr Phe Gly His Tyr
                20                  25                  30
Trp Met Asn Trp Val Arg Gln Ser Pro Glu Lys Gly Leu Glu Trp Val
                35                  40                  45
Ala Gln Phe Arg Asn Lys Pro Tyr Asn Tyr Glu Thr Tyr Tyr Ser Asp
                50                  55                  60
Ser Val Lys Gly Arg Phe Thr Ile Ser Arg Asp Asp Ser Lys Ser Ser
65              70                  75                  80
Val Tyr Leu Gln Met Asn Asn Leu Arg Val Glu Asp Thr Gly Ile Tyr
                85                  90                  95
Tyr Cys Thr Gly Ala Ser Tyr Gly Met Glu Tyr Leu Gly Gln Gly Thr
                100                 105                 110
Ser Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
        340                 345                 350

Pro Pro Ser Arg Asp Glu Leu Thr Lys Asn Gln Val Ser Leu Ser Cys
    355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 45
<211> LENGTH: 214
<212> TYPE: PRT
<213> ORGANISM: Artificial Sequence
<220> FEATURE:
<223> OTHER INFORMATION: anti-dig antibody full length light chain

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 46
<211> LENGTH: 219
<212> TYPE: PRT
<213> ORGANISM: Artificial Sequence
<220> FEATURE:
<223> OTHER INFORMATION: anti-LeY antibody full length light chain

<400> SEQUENCE: 46

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 47
<211> LENGTH: 214
<212> TYPE: PRT
<213> ORGANISM: Artificial Sequence
<220> FEATURE:
<223> OTHER INFORMATION: anti-PDGF antibody full length light chain

<400> SEQUENCE: 47

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 48
<211> LENGTH: 214
<212> TYPE: PRT
<213> ORGANISM: Artificial Sequence
<220> FEATURE:
<223> OTHER INFORMATION: anti-VEGF antibody full length light chain

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 49
<211> LENGTH: 228
<212> TYPE: PRT
<213> ORGANISM: Artificial Sequence
<220> FEATURE:
<223> OTHER INFORMATION: anti-dig antibody VH-CH1 fragment

<400> SEQUENCE: 49

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
            35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys
225

<210> SEQ ID NO 50
<211> LENGTH: 222
<212> TYPE: PRT
<213> ORGANISM: Artificial Sequence
<220> FEATURE:
<223> OTHER INFORMATION: anti-LeY antibody VH-CH1 fragment

<400> SEQUENCE: 50

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
```

```
                20              25              30
Tyr Met Tyr Trp Val Arg Gln Thr Pro Glu Lys Arg Leu Glu Trp Val
            35              40              45

Ala Tyr Ile Ser Asn Asp Asp Ser Ser Ala Ala Tyr Ser Asp Thr Val
        50              55              60

Lys Gly Arg Phe Thr Ile Ser Arg Asp Asn Ala Arg Asn Thr Leu Tyr
65              70              75              80

Leu Gln Met Ser Arg Leu Lys Ser Glu Asp Thr Ala Ile Tyr Tyr Cys
            85              90              95

Ala Arg Gly Leu Ala Trp Gly Ala Trp Phe Ala Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
            130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Lys Val Glu Pro Lys Ser Cys
            210             215             220
```

<210> SEQ ID NO 51
<211> LENGTH: 223
<212> TYPE: PRT
<213> ORGANISM: Artificial Sequence
<220> FEATURE:
<223> OTHER INFORMATION: anti-PDGF antibody VH-CH1 fragment

<400> SEQUENCE: 51

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Trp Met Ser Trp Val Arg Gln Ala Pro Glu Lys Gly Leu Glu Trp Val
            35              40              45

Ser Thr Ile Ser Asp Gly Gly Leu Thr Tyr Tyr Ala Asp Ser Val
        50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
            85              90              95

Ala Glu Ser Gly Gly Tyr Thr Asp Trp Leu Phe Gly Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
            130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
```

```
                    165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
        210                 215                 220

<210> SEQ ID NO 52
<211> LENGTH: 226
<212> TYPE: PRT
<213> ORGANISM: Artificial Sequence
<220> FEATURE:
<223> OTHER INFORMATION: anti-VEGF antibody VH-CH1 fragment

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 53
<211> LENGTH: 460
<212> TYPE: PRT
<213> ORGANISM: Artificial Sequence
<220> FEATURE:
<223> OTHER INFORMATION: anti-bio antibody full length heavy chain-hole-
      cys with C-terminal fusion

<400> SEQUENCE: 53

Asp Lys Thr His Thr Cys Pro Pro Cys Pro Ala Pro Glu Leu Leu Gly
1               5                   10                  15
```

Gly Pro Ser Val Phe Leu Phe Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Gly Ser Gly Gly Gly Ser Gln Val Gln
225                 230                 235                 240

Leu Val Gln Ser Gly Ala Glu Val Lys Lys Pro Gly Ser Ser Val Lys
            245                 250                 255

Val Ser Cys Lys Ser Ser Gly Phe Asn Asn Lys Asp Thr Phe Phe Gln
            260                 265                 270

Trp Val Arg Gln Ala Pro Gly Gln Gly Leu Glu Trp Met Gly Arg Ile
            275                 280                 285

Asp Pro Ala Asn Gly Phe Thr Lys Tyr Ala Gln Lys Phe Gln Gly Arg
290                 295                 300

Val Thr Ile Thr Ala Asp Thr Ser Thr Ser Thr Ala Tyr Met Glu Leu
305                 310                 315                 320

Ser Ser Leu Arg Ser Glu Asp Thr Ala Val Tyr Tyr Cys Ala Arg Trp
            325                 330                 335

Asp Thr Tyr Gly Ala Ala Trp Phe Ala Tyr Trp Gly Gln Gly Thr Leu
            340                 345                 350

Val Thr Val Ser Ser Ala Ser Thr Lys Gly Pro Ser Val Phe Pro Leu
            355                 360                 365

Ala Pro Ser Ser Lys Ser Thr Ser Gly Gly Thr Ala Ala Leu Gly Cys
            370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
            405                 410                 415

Ser Gly Leu Tyr Ser Leu Ser Ser Val Val Thr Val Pro Ser Ser Ser
            420                 425                 430

-continued

```
Leu Gly Thr Gln Thr Tyr Ile Cys Asn Val Asn His Lys Pro Ser Asn
            435                 440                 445

Thr Lys Val Asp Lys Lys Val Glu Pro Lys Ser Cys
    450                 455                 460

<210> SEQ ID NO 54
<211> LENGTH: 683
<212> TYPE: PRT
<213> ORGANISM: Artificial Sequence
<220> FEATURE:
<223> OTHER INFORMATION: anti-bio antibody full length heavy chain-hole-
      cys with N- and C-terminal fusion

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
                355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys Gly Gly Gly Gly Ser Gly Gly Gly Gly Ser Gln Val Gln Leu
                450                 455                 460

Val Gln Ser Gly Ala Glu Val Lys Lys Pro Gly Ser Ser Val Lys Val
465                 470                 475                 480

Ser Cys Lys Ser Ser Gly Phe Asn Asn Lys Asp Thr Phe Phe Gln Trp
                485                 490                 495

Val Arg Gln Ala Pro Gly Gln Gly Leu Glu Trp Met Gly Arg Ile Asp
                500                 505                 510

Pro Ala Asn Gly Phe Thr Lys Tyr Ala Gln Lys Phe Gln Gly Arg Val
                515                 520                 525

Thr Ile Thr Ala Asp Thr Ser Thr Ser Thr Ala Tyr Met Glu Leu Ser
530                 535                 540

Ser Leu Arg Ser Glu Asp Thr Ala Val Tyr Tyr Cys Ala Arg Trp Asp
545                 550                 555                 560

Thr Tyr Gly Ala Ala Trp Phe Ala Tyr Trp Gly Gln Gly Thr Leu Val
                565                 570                 575

Thr Val Ser Ser Ala Ser Thr Lys Gly Pro Ser Val Phe Pro Leu Ala
                580                 585                 590

Pro Ser Ser Lys Ser Thr Ser Gly Gly Thr Ala Ala Leu Gly Cys Leu
                595                 600                 605

Val Lys Asp Tyr Phe Pro Glu Pro Val Thr Val Ser Trp Asn Ser Gly
610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
                645                 650                 655

Gly Thr Gln Thr Tyr Ile Cys Asn Val Asn His Lys Pro Ser Asn Thr
                660                 665                 670

Lys Val Asp Lys Lys Val Glu Pro Lys Ser Cys
                675                 680

<210> SEQ ID NO 55
<211> LENGTH: 458
<212> TYPE: PRT
<213> ORGANISM: Artificial Sequence
<220> FEATURE:
<223> OTHER INFORMATION: anti-fluos antibody full length heavy chain-
      hole-cys with C-terminal fusion

<400> SEQUENCE: 55

Asp Lys Thr His Thr Cys Pro Pro Cys Pro Ala Pro Glu Leu Leu Gly

-continued

```
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
            50                  55                  60
His Asn Ala Lys Thr Lys Pro Arg Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Cys Thr Leu Pro Pro Ser Arg Asp Glu Leu Thr Lys Asn Gln Val Ser
                130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
                210                 215                 220
Pro Gly Lys Gly Gly Gly Ser Gly Gly Gly Ser Gly Val Lys
225                 230                 235                 240
Leu Asp Glu Thr Gly Gly Gly Leu Val Gln Pro Gly Gly Ala Met Lys
                245                 250                 255
Leu Ser Cys Val Thr Ser Gly Phe Thr Phe Gly His Tyr Trp Met Asn
                260                 265                 270
Trp Val Arg Gln Ser Pro Glu Lys Gly Leu Glu Trp Val Ala Gln Phe
                275                 280                 285
Arg Asn Lys Pro Tyr Asn Tyr Glu Thr Tyr Tyr Ser Asp Ser Val Lys
                290                 295                 300
Gly Arg Phe Thr Ile Ser Arg Asp Asp Ser Lys Ser Ser Val Tyr Leu
305                 310                 315                 320
Gln Met Asn Asn Leu Arg Val Glu Asp Thr Gly Ile Tyr Tyr Cys Thr
                325                 330                 335
Gly Ala Ser Tyr Gly Met Glu Tyr Leu Gly Gln Gly Thr Ser Val Thr
                340                 345                 350
Val Ser Ser Ala Ser Thr Lys Gly Pro Ser Val Phe Pro Leu Ala Pro
                355                 360                 365
Ser Ser Lys Ser Thr Ser Gly Gly Thr Ala Ala Leu Gly Cys Leu Val
                370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
                420                 425                 430
```

```
Thr Gln Thr Tyr Ile Cys Asn Val Asn His Lys Pro Ser Asn Thr Lys
        435                 440                 445

Val Asp Lys Lys Val Glu Pro Lys Ser Cys
    450                 455

<210> SEQ ID NO 56
<211> LENGTH: 679
<212> TYPE: PRT
<213> ORGANISM: Artificial Sequence
<220> FEATURE:
<223> OTHER INFORMATION: anti-fluos antibody full length heavy chain-
      hole-cys with N- and C-terminal fusion

<400> SEQUENCE: 56

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                    325                 330                 335
Ile Ser Lys Ala Lys Gly Gln Pro Arg Glu Pro Gln Val Cys Thr Leu
                340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Gly Gly Gly Ser Gly Gly Gly Ser Gly Val Lys Leu Asp Glu
450                 455                 460

Thr Gly Gly Gly Leu Val Gln Pro Gly Ala Met Lys Leu Ser Cys
465                 470                 475                 480

Val Thr Ser Gly Phe Thr Phe Gly His Tyr Trp Met Asn Trp Val Arg
                485                 490                 495

Gln Ser Pro Glu Lys Gly Leu Glu Trp Val Ala Gln Phe Arg Asn Lys
            500                 505                 510

Pro Tyr Asn Tyr Glu Thr Tyr Tyr Ser Asp Ser Val Lys Gly Arg Phe
        515                 520                 525

Thr Ile Ser Arg Asp Asp Ser Lys Ser Ser Val Tyr Leu Gln Met Asn
    530                 535                 540

Asn Leu Arg Val Glu Asp Thr Gly Ile Tyr Tyr Cys Thr Gly Ala Ser
545                 550                 555                 560

Tyr Gly Met Glu Tyr Leu Gly Gln Gly Thr Ser Val Thr Val Ser Ser
                565                 570                 575

Ala Ser Thr Lys Gly Pro Ser Val Phe Pro Leu Ala Pro Ser Ser Lys
            580                 585                 590

Ser Thr Ser Gly Gly Thr Ala Ala Leu Gly Cys Leu Val Lys Asp Tyr
        595                 600                 605

Phe Pro Glu Pro Val Thr Val Ser Trp Asn Ser Gly Ala Leu Thr Ser
    610                 615                 620

Gly Val His Thr Phe Pro Ala Val Leu Gln Ser Ser Gly Leu Tyr Ser
625                 630                 635                 640

Leu Ser Ser Val Val Thr Val Pro Ser Ser Ser Leu Gly Thr Gln Thr
                645                 650                 655

Tyr Ile Cys Asn Val Asn His Lys Pro Ser Asn Thr Lys Val Asp Lys
                660                 665                 670

Lys Val Glu Pro Lys Ser Cys
                675

<210> SEQ ID NO 57
<211> LENGTH: 450
<212> TYPE: PRT
<213> ORGANISM: Artificial Sequence
<220> FEATURE:
<223> OTHER INFORMATION: anti-bio antibody full length heavy chain-knob
      without hinge-region cysteine residues

<400> SEQUENCE: 57
```

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Asp Thr Tyr Gly Ala Ala Trp Phe Ala Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Ser Pro Pro Ser Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His

-continued

```
                420             425             430

Glu Ala Leu His Asn His Tyr Thr Gln Lys Ser Leu Ser Leu Ser Pro
            435                 440                 445

Gly Lys
    450

<210> SEQ ID NO 58
<211> LENGTH: 450
<212> TYPE: PRT
<213> ORGANISM: Artificial Sequence
<220> FEATURE:
<223> OTHER INFORMATION: anti-bio antibody full length heavy chain-hole
      without hinge-cysteine residues

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Ser Pro Pro Ser Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

-continued

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 59
<211> LENGTH: 448
<212> TYPE: PRT
<213> ORGANISM: Artificial Sequence
<220> FEATURE:
<223> OTHER INFORMATION: anti-fluos antibody full length heavy chain-
      knob without hinge-cysteine residues

<400> SEQUENCE: 59

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
                20                  25                  30

Trp Met Asn Trp Val Arg Gln Ser Pro Glu Lys Gly Leu Glu Trp Val
            35                  40                  45

Ala Gln Phe Arg Asn Lys Pro Tyr Asn Tyr Glu Thr Tyr Tyr Ser Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

-continued

His Thr Ser Pro Pro Ser Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 60
<211> LENGTH: 448
<212> TYPE: PRT
<213> ORGANISM: Artificial Sequence
<220> FEATURE:
<223> OTHER INFORMATION: anti-fluos antibody full length heavy chain-
      hole without hinge-cysteine residues

<400> SEQUENCE: 60

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
                130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Ser Pro Pro Ser Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Ser Cys
                355                 360                 365

Ala Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 61
<211> LENGTH: 240
<212> TYPE: PRT
<213> ORGANISM: Artificial Sequence
<220> FEATURE:
<223> OTHER INFORMATION: MHCFcRP-hole-D356K-His8 without hinge-cysteine
      residues

<400> SEQUENCE: 61

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45
```

Glu Asp Pro Glu Val Lys Phe Asn Trp Tyr Val Asp Gly Val Glu Val
50                  55                  60

His Asn Ala Lys Thr Lys Pro Arg Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Lys Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys Gly Gly Gly Ser His His His His His His
225                 230                 235                 240

<210> SEQ ID NO 62
<211> LENGTH: 240
<212> TYPE: PRT
<213> ORGANISM: Artificial Sequence
<220> FEATURE:
<223> OTHER INFORMATION: MHCFcRP-hole-E357K-His8 without hinge-cysteine
      residues

<400> SEQUENCE: 62

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Lys Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser His His His His His His His His
225                 230                 235                 240

<210> SEQ ID NO 63
<211> LENGTH: 240
<212> TYPE: PRT
<213> ORGANISM: Artificial Sequence
<220> FEATURE:
<223> OTHER INFORMATION: MHCFcRP-knob-K370E-His8 without hinge-cysteine
      residues

<400> SEQUENCE: 63

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser His His His His His His His His
225                 230                 235                 240

<210> SEQ ID NO 64
<211> LENGTH: 240
<212> TYPE: PRT
<213> ORGANISM: Artificial Sequence
<220> FEATURE:
<223> OTHER INFORMATION: MHCFcRP-knob-K439E-His8 without hinge-cysteine
      residues

<400> SEQUENCE: 64
```

```
Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Glu Ser Leu Ser Leu Ser
            210                 215                 220

Pro Gly Lys Gly Gly Gly Gly Ser His His His His His His
225                 230                 235                 240

<210> SEQ ID NO 65
<211> LENGTH: 9
<212> TYPE: PRT
<213> ORGANISM: Homo sapiens

<400> SEQUENCE: 65

Asp Lys Thr His Thr Cys Pro Pro Cys
1               5

<210> SEQ ID NO 66
<211> LENGTH: 9
<212> TYPE: PRT
<213> ORGANISM: Artificial Sequence
<220> FEATURE:
<223> OTHER INFORMATION: cys-free hinge region

<400> SEQUENCE: 66

Asp Lys Thr His Thr Ser Pro Pro Ser
1               5

<210> SEQ ID NO 67
<211> LENGTH: 6
<212> TYPE: PRT
<213> ORGANISM: Artificial Sequence
<220> FEATURE:
<223> OTHER INFORMATION: hexa-histidine tag

<400> SEQUENCE: 67
```

His His His His His His
1               5

<210> SEQ ID NO 68
<211> LENGTH: 8
<212> TYPE: PRT
<213> ORGANISM: Artificial Sequence
<220> FEATURE:
<223> OTHER INFORMATION: octa-histidine tag

<400> SEQUENCE: 68

His His His His His His His His
1               5

<210> SEQ ID NO 69
<211> LENGTH: 4
<212> TYPE: PRT
<213> ORGANISM: Artificial Sequence
<220> FEATURE:
<223> OTHER INFORMATION: peptidic linker

<400> SEQUENCE: 69

Gly Gly Gly Ser
1

<210> SEQ ID NO 70
<211> LENGTH: 5
<212> TYPE: PRT
<213> ORGANISM: Artificial Sequence
<220> FEATURE:
<223> OTHER INFORMATION: peptidic linker

<400> SEQUENCE: 70

Gly Gly Gly Gly Ser
1               5

<210> SEQ ID NO 71
<211> LENGTH: 4
<212> TYPE: PRT
<213> ORGANISM: Artificial Sequence
<220> FEATURE:
<223> OTHER INFORMATION: peptidic linker

<400> SEQUENCE: 71

Gln Gln Gln Ser
1

<210> SEQ ID NO 72
<211> LENGTH: 5
<212> TYPE: PRT
<213> ORGANISM: Artificial Sequence
<220> FEATURE:
<223> OTHER INFORMATION: peptidic linker

<400> SEQUENCE: 72

Gln Gln Gln Gln Ser
1               5

<210> SEQ ID NO 73
<211> LENGTH: 4
<212> TYPE: PRT
<213> ORGANISM: Artificial Sequence
<220> FEATURE:
<223> OTHER INFORMATION: peptidic linker

<400> SEQUENCE: 73

Ser Ser Ser Gly
1

<210> SEQ ID NO 74
<211> LENGTH: 5
<212> TYPE: PRT
<213> ORGANISM: Artificial Sequence
<220> FEATURE:
<223> OTHER INFORMATION: peptidic linker

<400> SEQUENCE: 74

Ser Ser Ser Ser Gly
1               5

<210> SEQ ID NO 75
<211> LENGTH: 8
<212> TYPE: PRT
<213> ORGANISM: Artificial Sequence
<220> FEATURE:
<223> OTHER INFORMATION: peptidic linker

<400> SEQUENCE: 75

Gly Gly Gly Ser Gly Gly Gly Ser
1               5

<210> SEQ ID NO 76
<211> LENGTH: 12
<212> TYPE: PRT
<213> ORGANISM: Artificial Sequence
<220> FEATURE:
<223> OTHER INFORMATION: peptidic linker

<400> SEQUENCE: 76

Gly Gly Gly Ser Gly Gly Gly Ser Gly Gly Gly Ser
1               5                   10

<210> SEQ ID NO 77
<211> LENGTH: 16
<212> TYPE: PRT
<213> ORGANISM: Artificial Sequence
<220> FEATURE:
<223> OTHER INFORMATION: peptidic linker

<400> SEQUENCE: 77

Gly Gly Gly Ser Gly Gly Gly Ser Gly Gly Gly Ser Gly Gly Gly Ser
1               5                   10                  15

<210> SEQ ID NO 78
<211> LENGTH: 20
<212> TYPE: PRT
<213> ORGANISM: Artificial Sequence
<220> FEATURE:
<223> OTHER INFORMATION: peptidic linker

<400> SEQUENCE: 78

Gly Gly Gly Ser Gly Gly Gly Ser Gly Gly Gly Ser Gly Gly Gly Ser
1               5                   10                  15

Gly Gly Gly Ser
            20

<210> SEQ ID NO 79
<211> LENGTH: 10
<212> TYPE: PRT
<213> ORGANISM: Artificial Sequence
<220> FEATURE:
<223> OTHER INFORMATION: peptidic linker

```
<400> SEQUENCE: 79

Gly Gly Gly Gly Ser Gly Gly Gly Gly Ser
1               5                   10

<210> SEQ ID NO 80
<211> LENGTH: 15
<212> TYPE: PRT
<213> ORGANISM: Artificial Sequence
<220> FEATURE:
<223> OTHER INFORMATION: peptidic linker

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 20
<212> TYPE: PRT
<213> ORGANISM: Artificial Sequence
<220> FEATURE:
<223> OTHER INFORMATION: peptidic linker

<400> SEQUENCE: 81

Gly Gly Gly Gly Ser Gly Gly Gly Gly Ser Gly Gly Gly Gly Ser Gly
1               5                   10                  15

Gly Gly Gly Ser
            20

<210> SEQ ID NO 82
<211> LENGTH: 17
<212> TYPE: PRT
<213> ORGANISM: Artificial Sequence
<220> FEATURE:
<223> OTHER INFORMATION: peptidic linker

<400> SEQUENCE: 82

Gly Ser Ser Ser Ser Ser Ser Ser Ser Ser Ser Ser Ser Ser Ser Ser
1               5                   10                  15

Gly

<210> SEQ ID NO 83
<211> LENGTH: 227
<212> TYPE: PRT
<213> ORGANISM: Artificial Sequence
<220> FEATURE:
<223> OTHER INFORMATION: affibody-MHCFcRP

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys Gly Gln Pro Arg Glu
            100                 105                 110
```

```
Pro Gln Val Tyr Thr Leu Pro Pro Ser Arg Asp Lys Leu Thr Lys Asn
            115                 120                 125

Gln Val Ser Leu Ser Cys Ala Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Val Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
        195                 200                 205

Ser Leu Ser Pro Gly Lys Gly Gly Gly Ser His His His His
    210                 215                 220

His His His
225

<210> SEQ ID NO 84
<211> LENGTH: 306
<212> TYPE: PRT
<213> ORGANISM: Artificial Sequence
<220> FEATURE:
<223> OTHER INFORMATION: affibody-VH

<400> SEQUENCE: 84

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys Gly Thr Gly Gly Gly Gly
    50                  55                  60

Ser Gly Gly Gly Gly Ser Gly Gly Gly Gly Ser Gly Gly Gly Gly Ser
65                  70                  75                  80

Glu Val Gln Leu Val Gln Ser Gly Ala Glu Val Lys Lys Pro Gly Ala
                85                  90                  95

Ser Val Lys Val Ser Cys Lys Ala Ser Gly Tyr Thr Phe Thr Asn Tyr
                100                 105                 110

Tyr Ile His Trp Val Arg Gln Ala Pro Gly Gln Gly Leu Glu Trp Ile
            115                 120                 125

Gly Trp Ile Tyr Pro Gly Asp Gly Asn Thr Lys Tyr Asn Glu Lys Phe
        130                 135                 140

Lys Gly Arg Ala Thr Leu Thr Ala Asp Thr Ser Thr Ser Thr Ala Tyr
145                 150                 155                 160

Leu Glu Leu Ser Ser Leu Arg Ser Glu Asp Thr Ala Val Tyr Tyr Cys
                165                 170                 175

Ala Arg Asp Ser Tyr Ser Asn Tyr Tyr Phe Asp Tyr Trp Gly Gln Gly
            180                 185                 190

Thr Leu Val Thr Val Ser Ser Gly Gln Pro Arg Glu Pro Gln Val Tyr
        195                 200                 205

Thr Leu Pro Pro Ser Arg Asp Glu Leu Thr Lys Asn Gln Val Ser Leu
    210                 215                 220

Trp Cys Leu Val Lys Gly Phe Tyr Pro Ser Asp Ile Ala Val Glu Trp
225                 230                 235                 240
```

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Lys Leu Thr Val Asp
            260                 265                 270

Lys Ser Arg Trp Gln Gln Gly Asn Val Phe Ser Cys Ser Val Met His
        275                 280                 285

Glu Ala Leu His Asn His Tyr Thr Gln Lys Ser Leu Ser Leu Ser Pro
    290                 295                 300

Gly Lys
305

<210> SEQ ID NO 85
<211> LENGTH: 7
<212> TYPE: PRT
<213> ORGANISM: Artificial Sequence
<220> FEATURE:
<223> OTHER INFORMATION: hinge region
<220> FEATURE:
<221> NAME/KEY: MISC_FEATURE
<222> LOCATION: (5)..(5)
<223> OTHER INFORMATION: X=S or P

<400> SEQUENCE: 85

His Thr Ser Pro Xaa Ser Pro
1               5

<210> SEQ ID NO 86
<211> LENGTH: 6
<212> TYPE: PRT
<213> ORGANISM: Artificial Sequence
<220> FEATURE:
<223> OTHER INFORMATION: hinge region#

<400> SEQUENCE: 86

His Thr Pro Ala Pro Glu
1               5

<210> SEQ ID NO 87
<211> LENGTH: 4
<212> TYPE: PRT
<213> ORGANISM: Artificial Sequence
<220> FEATURE:
<223> OTHER INFORMATION: C-tag

<400> SEQUENCE: 87

Glu Pro Glu Ala
1

<210> SEQ ID NO 88
<211> LENGTH: 9
<212> TYPE: PRT
<213> ORGANISM: Artificial Sequence
<220> FEATURE:
<223> OTHER INFORMATION: C-tag with linker

<400> SEQUENCE: 88

Gly Gly Gly Gly Ser Glu Pro Glu Ala
1               5

<210> SEQ ID NO 89
<211> LENGTH: 4
<212> TYPE: PRT
<213> ORGANISM: Homo sapiens
<220> FEATURE:
<221> NAME/KEY: MISC_FEATURE

```
<222> LOCATION: (3)..(3)
<223> OTHER INFORMATION: X = S or P

<400> SEQUENCE: 89

Cys Pro Xaa Cys
1

<210> SEQ ID NO 90
<211> LENGTH: 10
<212> TYPE: PRT
<213> ORGANISM: Homo sapiens

<400> SEQUENCE: 90

His Thr Cys Pro Pro Cys Pro Ala Pro Glu
1               5                   10

<210> SEQ ID NO 91
<211> LENGTH: 5
<212> TYPE: PRT
<213> ORGANISM: Homo sapiens

<400> SEQUENCE: 91

Asp Lys Thr His Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 92

His Thr Ser Pro Pro Ser Pro
1               5
```

METHOD FOR GENERATING MULTISPECIFIC ANTIBODIES FROM MONOSPECIFIC ANTIBODIES

CROSS REFERENCE TO RELATED APPLICATIONS

This application is a Continuation of International Application No. PCT/EP2018/078675, filed Oct. 19, 2018, claiming priority to EP application Ser. No. 17/197,616.0, filed Oct. 20, 2017, which are incorporated herein by reference in its entirety.

SEQUENCE LISTING

This application contains a Sequence Listing which has been submitted electronically in ASCII format and is hereby incorporated by reference in its entirety. Said ASCII copy, created on Feb. 26, 2025, is named P34497-US_ST25.txt and is 161,837 bytes in size.

Herein is reported an easy and scalable method for the generation of bi- and multispecific antibodies using a novel half-antibody exchange method.

BACKGROUND OF THE INVENTION

Current state of the art methods for biochemical conversion of monospecific antibody derivatives to assembled bispecific antibodies apply (i) half-antibody complementation reactions and (ii) IgG-IgG exchange reactions.

These technologies are disclosed e.g. in WO 2015/046467, Rispens et al., J. Biol. Chem. 289 (2014) 6098-6109, U.S. Pat. No. 9,409,989, WO 2013/060867, WO 2011/131746, WO 2011/133886, WO 2011/143545, WO 2010/151792, Gunasekaran et al., J. Biol. Chem. 285 (2010) 19637-19646, WO 2009/041613, WO 2009/089004, WO 2008/119353, WO 2007/114325, U.S. Pat. Nos. 8,765,412, 8,642,745, WO 2006/047340, WO 2006/106905, WO 2005/042582, WO 2005/062916, WO 2005/000898, U.S. Pat. Nos. 7,183,076, 7,951,917, Segal, D. M., et al., Curr. Opin. Immunol. 11 (1999) 558-562, WO 98/50431, WO 98/04592, Merchant, A. M., et al., Nat. Biotechnol. 16 (1998) 677-681, WO 96/27011, Carter, P., et al., Immunotechnol. 2 (1996) 73, WO 93/11162, and Kostelny, S. A., et al., J. Immunol. 148 (1992) 1547-1553.

State of the art methods for converting monospecific antibodies or antibody derivatives to bsAbs have drawbacks, such as, e.g., limitations concerning processes for and composition of post-assembly bsAb preparations.

For example, the half-antibody technology assembles monospecific and monovalent antibody sides to bivalent IgGs. Expression of the input molecules as well as the exchange reaction by itself generates not only half-antibodies but also IgG like bivalent (monospecific) antibody derivatives. Aggregates are also present in the input material as well as in the output of the assembly reactions. Both (bivalent monospecific antibodies and aggregates) need to be either quantitatively removed from assembled bsAb via elaborate purification approaches or (as quantitative removal is hard to achieve in high throughput manner) they 'contaminate' to some degree the bsAb preparations.

The Fab-arm exchange technology, for example, assembles bispecific bivalent IgGs from monospecific bivalent IgG-derivatives. Thus, the input into the exchange reaction is bivalent i.e. avidity enabled by default. To assure complete lack of remaining bivalent monospecific input material in exchange reactions that shall be subjected to avidity or agonistic antibody screens, it would have to be assured a complete removal of any remaining bivalent input as well as of any aggregates that may form during the exchange reaction. Due to high similarity of input and bsAb, elaborate procedures for quantitative removal are necessary (very hard to achieve in high throughput), or remaining bivalent input and aggregates will contaminate to some degree the final bsAb preparations.

Labrijn, A. F., et al., disclosed efficient generation of stable bispecific IgG1 by controlled Fab-arm exchange (Proc. Natl. Acad. Sci. USA 110 (2013) 5145-5150).

WO 2014/081955 disclosed heterodimeric antibodies and methods of use.

WO 2009/089004 discloses method for making antibody Fc-heterodimeric molecules using electrostatic steering effects. Therein it is disclosed that of four unique charge residue pairs involved in the domain-domain interaction (Asp356-Lys439', Glu357-Lys370', Lys392-Asp399', Asp399-Lys409') only Lys409-Asp399' is suitable for engineering as both the residues were structurally conserved as well as buried. In other three pairs case, at least one of the partner is solvent exposed (% ASA>10).

WO 2018/155611 disclosed a combination of a first antigen-binding molecule and a second antigen-binding molecule that do not bind by covalent bonding, which when mixed into a liquid form heterodimers more easily than homodimers. It is disclosed therein in one embodiment, more preferably, that substitution by other amino acids at the cysteine residue in either one or both of position 226 and position 229 in the EU numbering system is combined with a substitution of either one or both of first CH3 and second CH3 by other amino acid residues in at least one of position 357 or position 397 in the EU numbering system.

SUMMARY OF THE INVENTION

Herein is reported a method for the generation of multispecific antibodies by a half-antibody exchange reaction. It has been found that as starting material non-complete antibodies, such as 2/3-IgGs comprising an antibody light chain, an antibody heavy chain and an antibody heavy chain Fc-region fragment, wherein the heavy chain-heavy chain interaction is destabilized by an asymmetric perturbing mutation, preferably in the Fc-region fragment, are advantageous. This perturbing mutation has been found to foster the dissociation of the starting non-complete antibodies and the generation of correctly assembled (e.g. full length) bispecific antibodies.

The method according to the invention can be performed in the presence as well as in the absence of reducing agents. In the latter case in the starting antibodies, such as e.g. 2/3-IgGs or complete antibodies, no heavy chain-heavy chain disulfide bonds, such as e.g. hinge region disulfide bonds, are required and therefore present. Thus, the chain-exchange reaction and method according to the current invention allows also in-vitro assembly of bispecific antibodies without initial reduction. Therefore, intramolecular disulfide bonds between the heavy chains of the starting molecules (2/3-IgGs) can be removed, e.g. by mutagenesis PCR. Purification of the 2/3-IgGs can be operated on a protein L/SEC-method, which can be defined as a standard purification strategy for these molecules. Despite lack of all intermolecular disulfide bonds between the heavy chains, the correct formation of stable, i.e. isolatable, 2/3-IgGs takes place. Thus, with the starting molecules it was possible to realize an in-vitro generation of bispecific antibodies with a reduction-free chain-exchange reaction. After the chain-exchange reaction, purification of the formed bispecific antibody can be realized, e.g., by nickel absorption chromatography if a histidine-tag is used. Using this reduction-free chain-exchange reaction, a higher protein yield of purified bispecific antibody could be formed compared to the state of the art procedures relying on reductive chain-exchange reactions. Overall, the reduction-free chain exchange method according to the current invention enables a more efficient production of pure and functional bispecific antibodies.

In general, herein is reported a method for producing a (multispecific) binder/multimeric polypeptide comprising the following steps:
incubating
a first binder(, which is mono- or bispecific and heteromeric,)/multimeric polypeptide comprising a first (monomeric) polypeptide and a second (monomeric) polypeptide both comprising a human immunoglobulin (IgG1) CH3 domain,
wherein the CH3 domain of the first polypeptide comprises one or more mutations with respect to its wild-type sequence and the CH3 domain of the second polypeptide comprises one or more mutations with respect to its wild-type sequence, whereby the two or more mutations in the first and the second CH3 domain result in the formation of a heterodimer,
wherein the first polypeptide comprises at least one functional binding site or at least a part of a binding site,
wherein the second polypeptide comprises in the CH3 domain at least one/a first perturbing mutation different from the mutation required for heterodimerization (and selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
wherein the first polypeptide and the second polypeptide associate covalently or non-covalently with each other/form a covalent or non-covalent dimer/are covalently or non-covalently associated with each other/are a covalent or non-covalent dimer, (whereby the perturbing mutation in the second polypeptide results in a destabilizing interaction when the second polypeptide and the first polypeptide form a heterodimer,)
and
a second binder(, which is mono- or bispecific and heteromeric,)/multimeric polypeptide comprising a third (monomeric) polypeptide and a fourth (monomeric) polypeptide both comprising a human immunoglobulin (IgG1) CH3 domain,
wherein the CH3 domain of the third polypeptide comprises one or more mutations with respect to its wild-type sequence and the CH3 domain of the fourth polypeptide comprises one or more mutations with respect to its wild-type sequence, whereby the two or more mutations in the first and the second CH3 domain result in the formation of a heterodimer,
wherein the fourth polypeptide comprises at least one functional binding site or at least a part of a binding site,
wherein the third polypeptide comprises in the CH3 domain at least one/a second perturbing mutation different from the mutation required for heterodimerization (and selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T), whereby the fourth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the mutation in the third polypeptide is at a different position as the mutation in the second polypeptide,
wherein the third polypeptide and the fourth polypeptide associate covalently or non-covalently with each other/form a covalent or non-covalent dimer/are non-covalently or covalently associated with each other/are a non-covalent or covalent dimer, (whereby the perturbing mutation in the third polypeptide results in a destabilizing interaction when the third polypeptide and the fourth polypeptide form a heterodimer,)
wherein the (first) perturbing mutation in the second polypeptide and the (second) perturbing mutation in the third polypeptide result in an attractive interaction when the second polypeptide and the third polypeptide form a heterodimer,
and
recovering the binder comprising the first polypeptide and the fourth polypeptide and thereby producing the (multispecific) binder.

Herein is reported a method for producing a (multispecific) binder/multimeric polypeptide comprising the following steps:
incubating
a first binder(, which is mono- or bispecific and heteromeric,)/multimeric polypeptide comprising a first (monomeric) polypeptide and a second (monomeric) polypeptide both comprising a human immunoglobulin (IgG1) CH3 domain,
wherein i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
wherein the first polypeptide comprises at least one functional binding site or at least a part of a binding site,
wherein the second polypeptide comprises in the CH3 domain at least one/a first perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate covalently or non-covalently with each other/form a covalent or non-covalent dimer/are covalently or non-covalently associated with each other/are a covalent or non-covalent dimer, (whereby the perturbing mutation in the second polypeptide results in a destabilizing interaction when the second polypeptide and the first polypeptide form a heterodimer,)

and a second binder(, which is mono- or bispecific and heteromeric,)/multimeric polypeptide comprising a third (monomeric) polypeptide and a fourth (monomeric) polypeptide both comprising a human immunoglobulin (IgG1) CH3 domain, wherein i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole, wherein the fourth polypeptide comprises at least one functional binding site or at least a part of a binding site, wherein the third polypeptide comprises in the CH3 domain at least one/a second perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T), whereby the fourth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the mutation in the third polypeptide is at a different position as the mutation in the second polypeptide, wherein the third polypeptide and the fourth polypeptide associate covalently or non-covalently with each other/form a covalent or non-covalent dimer/are non-covalently or covalently associated with each other/are a non-covalent or covalent dimer, (whereby the perturbing mutation in the third polypeptide results in a destabilizing interaction when the third polypeptide and the fourth polypeptide form a heterodimer,)

wherein the (first) perturbing mutation in the second polypeptide and the (second) perturbing mutation in the third polypeptide result in an attractive interaction when the second polypeptide and the third polypeptide form a heterodimer, and recovering the binder comprising the first polypeptide and the fourth polypeptide and thereby producing the (multispecific) binder.

One method according to the invention is a method for producing a multimeric polypeptide comprising the following steps:

incubating a first multimeric starting polypeptide comprising a first polypeptide and a second polypeptide both comprising an immunoglobulin G CH3 domain, wherein a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob, b-1) the first polypeptide comprises at least one functional binding site or at least a part of a binding site, c-1) the second polypeptide comprises in the CH3 domain a first perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the first perturbing mutation, d-1) the first polypeptide and the second polypeptide are a dimer, and a second multimeric starting polypeptide comprising a third polypeptide and a fourth polypeptide both comprising an immunoglobulin G CH3 domain, wherein a-2) i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole, b-2) the fourth polypeptide comprises at least one functional binding site or at least a part of a binding site, c-2) the third polypeptide comprises in the CH3 domain a second perturbing mutation that is different from the mutations under a-2), whereby the fourth polypeptide comprises the respective immunoglobulin G wild-type amino acid residue (s) in its amino acid sequence at the amino acid position(s) interacting in the respective wild-type immunoglobulin G with the amino acid residue at the second perturbing mutation, d-2) the second perturbing mutation is at a different position then the first perturbing mutation, e-2) the third polypeptide and the fourth polypeptide are a dimer, f-2) the first perturbing mutation in the second polypeptide and the second perturbing mutation in the third polypeptide result in an attractive interaction when the second polypeptide and the third polypeptide form a heterodimer, and recovering the multimeric polypeptide comprising the first polypeptide and the fourth polypeptide and thereby producing the multimeric polypeptide.

In one embodiment the first to fourth polypeptide each comprise in N- to C-terminal direction a CH2 domain derived from a human IgG1 CH2 domain (a variant human IgG1 CH2 domain) and a CH3 domain derived from a human IgG1 CH3 domain (a variant human IgG1 CH3 domain).

In one embodiment the first to fourth polypeptide each comprise in N- to C-terminal direction i) independently of each other either the amino acid sequence DKTHTCPPC (SEQ ID NO: 65) or the amino acid sequence DKTHTSPPS (SEQ ID NO: 66), ii) a CH2 domain derived from a human IgG1 CH2 domain, and iii) a CH3 domain derived from a human IgG1 CH3 domain.

In one embodiment i) the first and the fourth polypeptide each further comprise a CH1 domain derived from a human IgG1 CH1 domain (a (variant) human IgG1 CH1 domain) and (independently of each other) a (heavy chain or a light chain) variable domain, or ii) the first or the fourth polypeptide comprise a CH1 domain derived from a human IgG1 CH1 domain (a (variant) human IgG1 CH1 domain) and the respective other polypeptide comprises a domain derived from a light chain constant domain (a (variant) human kappa or lambda CL domain) and each polypeptide further comprises a variable domain. In one embodiment the variable domain of the first polypeptide and the variable domain of the fourth polypeptide are a (different) heavy chain variable domain. In one embodiment the variable domain of the first polypeptide is a heavy chain variable domain and the variable domain of the fourth polypeptide is a light chain variable domain or vice versa.

In one embodiment the first and the fourth polypeptide can have the same or a different N- to C-terminal sequence and in case the first and the fourth polypeptide are different they are independently of each other selected from the group of polypeptides comprising in N- to C-terminal direction i) a heavy chain variable domain, (a CH1 domain derived from) a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and (a CH1 domain derived from) a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, (a CH1 domain derived from) a human IgG1 CH1 domain, and a heavy chain variable domain, iv) a scFv, optionally a peptidic linker, a hinge region of SEQ ID NO: 65 or 66, a CH2 domain derived from a human IgG1 CH2 domain, and a CH3 domain derived from a human IgG1 CH3 domain, v) a scFab, optionally a peptidic linker, a hinge region of SEQ ID NO: 65 or 66, a CH2 domain derived from a human IgG1 CH2 domain, and a CH3 domain derived from a human IgG1 CH3 domain, vi) a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a hinge region of SEQ ID NO: 65 or 66, a CH2 domain derived from a human IgG1 CH2 domain, a CH3 domain derived from a human IgG1 CH3 domain, optionally a peptidic linker, and a scFab.

viii) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second (CH1 domain derived from a) human IgG1 CH1 domain, ix) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a second heavy chain variable domain, x) a heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, xi) a heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, xii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, xiii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, xiv) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xv) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, xvi) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa.

In one embodiment one of the first and the fourth polypeptide comprises in N- to C-terminal direction a first heavy chain variable domain, a first (CH1 domain derived from a) human IgG1 CH1 domain, a second heavy chain variable domain, a first light chain constant domain, a hinge region of SEQ ID NO: 65 or 66, a CH2 domain derived from a human IgG1 CH2 domain, and a CH3 domain derived from a human IgG1 CH3 domain, and the other of the first and the fourth polypeptide comprises in N- to C-terminal direction the first heavy chain variable domain, a (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain. In one embodiment the binder comprising the polypeptide comprising two heavy chain variable domains further comprises a first light chain comprising a first light chain variable domain and a second light chain constant domain (pairing with the first heavy chain variable domain) and a (domain exchanged) second light chain comprising a second light chain variable domain and a (CH1 domain derived from a) human IgG1 CH1 domain (pairing with the second heavy chain variable domain) and the other binder further comprises the first light chain.

In one embodiment one of the first and the fourth polypeptide comprises in N- to C-terminal direction a first heavy chain variable domain, a first (CH1 domain derived from a) human IgG1 CH1 domain, a first light chain variable domain, a second (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain, and the other of the first and the fourth polypeptide comprises in N- to C-terminal direction the first heavy chain variable domain, a (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain. In one embodiment the binder comprising the polypeptide comprising two variable domains further comprises a first light chain comprising a second variable light chain domain and a first light chain constant domain (pairing with the first heavy chain variable domain) and a (domain exchanged) second light chain comprising a second heavy chain variable domain and second light chain constant domain (pairing with the first light chain variable domain) and the other binder further comprises the first light chain.

In one embodiment the first and the second binder/multimeric starting polypeptide each further comprise an antibody light chain.

In one embodiment the
the first binder/multimeric starting polypeptide comprises as first polypeptide a polypeptide selected from the group of polypeptides comprising in N- to C-terminal direction i) a heavy chain variable domain, a (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a (CH1 domain derived from a) human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a (CH1 domain derived from a) human IgG1 CH1 domain, and a heavy chain variable domain, iv) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second (CH1 domain derived from a) human IgG1 CH1 domain, v) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a human) IgG1 CH1 domain, and a second heavy chain variable domain, vi) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob or the mutations hole, and as second polypeptide a polypeptide selected from the group of polypeptides comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the first polypeptide comprises the mutations hole, or the mutations hole if the first polypeptide comprises the mutation knob, comprising a first perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate non-covalently or covalently with each other/form a non-covalent or covalent dimer, (whereby the perturbing mutation in the second polypeptide results in a destabilizing interaction when the second polypeptide and the first polypeptide form a heterodimer,)

and a third polypeptide comprising a light chain variable domain and a light chain constant domain, wherein the third polypeptide is covalently bound to the first polypeptide by a disulfide bond, and the second binder/multimeric starting polypeptide comprises as fourth polypeptide a polypeptide selected from the group of polypeptides comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the second polypeptide comprises the mutations hole, or the mutations hole if the second polypeptide comprises the mutation knob, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the fifth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction i) a heavy chain variable domain, a CH1 domain derived from a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a CH1 domain derived from a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a CH1 domain derived from a human IgG1 CH1 domain, and a heavy chain variable domain, iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain, v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain and a second heavy chain variable domain, vi) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob if the fourth polypeptide comprises the mutations hole, or the mutations hole if the fourth polypeptide comprises the mutation knob, wherein the fourth polypeptide and the fifth polypeptide associate non-covalently or covalently with each other/ form a non-covalent or covalent dimer, (whereby the perturbing mutation in the fourth polypeptide results in a destabilizing interaction when the fourth polypeptide and the fifth polypeptide form a heterodimer,) and a sixth polypeptide comprising a light chain variable domain and a light chain constant domain, wherein the sixth polypeptide is covalently bound to the fourth polypeptide by a disulfide bond.

In one embodiment the incubation step is in the presence of a reducing agent.

In one embodiment the incubation step is in the absence of a reducing agent.

In one embodiment i) the second polypeptide and the third polypeptide, or ii) the second polypeptide and the fifth polypeptide further comprise a (C-terminal) tag. In one embodiment the tag has the amino acid sequence HHHHHH (SEQ ID NO: 67) or HHHHHHHH (SEQ ID NO: 68) and the recovering is by chromatography on a metal (nickel) chelate affinity chromatography column. In one embodiment the tag has the amino acid sequence EPEA (SEQ ID NO: 87) and the recovering is by chromatography on a C-tag affinity chromatography column.

In one embodiment the the first binder/multimeric starting polypeptide comprises as first polypeptide a polypeptide selected from the group of polypeptides comprising in N- to C-terminal direction i) a heavy chain variable domain, a (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a (CH1 domain derived from a) human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a (CH1 domain derived from a) human IgG1 CH1 domain, and a heavy chain variable domain, iv) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second (CH1 domain derived from a) human IgG1 CH1 domain, v) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a human) IgG1 CH1 domain, and a second heavy chain variable domain, vi) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob or the mutations hole, and as second polypeptide a polypeptide selected from the group of polypeptides comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the first polypeptide comprises the mutations hole, or the mutations hole if the first polypeptide comprises the mutation knob, comprising a first perturbing mutation selected from the group of mutations consisting of D356S, D356A, D356K, E357S, E357A, E357L, E357F, E357K, K370E, and K439E, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate non-covalently or covalently with each other/form a non-covalent or covalent dimer, (whereby the perturbing mutation in the second polypeptide results in a destabilizing interaction when the second polypeptide and the first polypeptide form a heterodimer,)

and a third polypeptide comprising a light chain variable domain and a light chain constant domain, wherein the third polypeptide is covalently bound to the first polypeptide by a disulfide bond, and the second binder/multimeric starting polypeptide comprises as fourth polypeptide a polypeptide selected from the group of polypeptides comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the second polypeptide comprises the mutations hole, or the mutations hole if the second polypeptide comprises the mutation knob, comprising a second perturbing mutation selected from the group of mutations consisting of D356S, D356A, D356K, E357S, E357A, E357L, E357F, E357K, K370E, and K439E, whereby the fifth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction
- i) a heavy chain variable domain, a CH1 domain derived from a human IgG1 CH1 domain, a hinge region of SEQ ID NO: 65 or 66, a CH2 domain derived from a human IgG1 CH2 domain, and a CH3 domain derived from a human IgG1 CH3 domain,
- ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a CH1 domain derived from a human IgG1 CH1 domain,
- iii) a hinge region of SEQ ID NO: 65 or 66, a CH2 domain derived from a human IgG1 CH2 domain, a CH3 domain derived from a human IgG1 CH3 domain, optionally a peptidic linker, a CH1 domain derived from a human IgG1 CH1 domain, and a heavy chain variable domain,
- iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain,
- v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain and a second heavy chain variable domain,
- vi) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv,
- vii) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
- viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain,
- ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain,
- x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain,
- xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and
- xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob if the fourth polypeptide comprises the mutations hole, or the mutations hole if the fourth polypeptide comprises the mutation knob, wherein the fourth polypeptide and the fifth polypeptide associate non-covalently or covalently with each other/form a non-covalent or covalent dimer, (whereby the perturbing mutation in the fourth polypeptide results in a destabilizing interaction when the fourth polypeptide and the fifth polypeptide form a heterodimer,)

and a sixth polypeptide comprising a light chain variable domain and a light chain constant domain, wherein the sixth polypeptide is covalently bound to the fourth polypeptide by a disulfide bond.

One aspect as reported herein is a method for identifying a (bispecific) binder combination comprising the steps of
producing a multitude of (bispecific) binders by subjecting each combination of a first (monospecific) binder selected from a first multitude of (monospecific) binders and a second (monospecific) binder selected from a second (but different from the first multitude of monospecific binders) multitude of (monospecific) binders to the method according to the invention,
measuring individually the (amount of) simultaneous binding of each binder of the produced multitude of binders to at least two antigens in a binding assay, such as e.g. an ELISA or SPR assay, and
selecting a binder from the multitude of binders based on the result of the binding assay, such as e.g. the ELISA or SPR assay, and thereby identifying a (bispecific) binder combination.

One aspect as reported herein is a multimeric polypeptide comprising a first polypeptide and a second polypeptide
wherein both polypeptides comprise a human immunoglobulin (IgG1) CH3 domain,
wherein i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
wherein the first polypeptide comprises at least one functional binding site or at least a part of a binding site,
wherein the second polypeptide comprises in the CH3 domain at least one perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
wherein the first polypeptide and the second polypeptide associate non-covalently or covalently with each other/ form a non-covalent or covalent dimer, (whereby the perturbing mutation in the second polypeptide results in a destabilizing interaction when the second polypeptide and the first polypeptide form a heterodimer,).

In one embodiment
the first polypeptide is a polypeptide selected from the group of polypeptides comprising in N- to C-terminal direction
i) a heavy chain variable domain, a CH1 domain derived from a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a CH1 domain derived from a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, a CH1 domain derived from a human IgG1 CH1 domain, and a heavy chain variable domain,
iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain,
v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain, and a second heavy chain variable domain,
vi) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, and
vii) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain,
ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain,
x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain,
xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, and comprises the mutation knob or the mutations hole, and the second polypeptide is a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain comprising the mutation knob or the mutations hole, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation.

In one embodiment the multimeric polypeptide further comprises a third polypeptide comprising a light chain variable domain and a light chain constant domain that is covalently bound to the first polypeptide by at least one disulfide bond.

One aspect as reported herein is a composition comprising a first heterotrimeric polypeptide comprising as first polypeptide a polypeptide selected from the group of polypeptides comprising in N- to C-terminal direction i) a heavy chain variable domain, a CH1 domain derived from a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a CH1 domain derived from a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a CH1 domain derived from a human IgG1 CH1 domain, and a heavy chain variable domain, iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain, v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain, and a second heavy chain variable domain, vi) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, and vii) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a)

human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob or the mutations hole, and as second polypeptide a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain, comprising the mutation knob if the first polypeptide comprises the mutations hole, or the mutations hole if the first polypeptide comprises the mutation knob, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, and as third polypeptide a polypeptide comprising a light chain variable domain and a light chain constant domain covalently bound to the first polypeptide by a disulfide bond, and a second heterotrimeric polypeptide comprising as first (fourth) polypeptide a polypeptide selected from the group of polypeptide comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the second polypeptide of the first heterotrimer comprises the mutations hole, or the mutations hole if the second polypeptide of the first heterotrimer comprises the mutation knob, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the second (fifth) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the first (fourth) polypeptide is at a different position as the perturbing mutation in the second polypeptide of the first heterotrimer, and as second (fifth) polypeptide a polypeptide selected from the group of polypeptides comprising in N- to C-terminal direction i) a heavy chain variable domain, a CH1 domain derived from a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a CH1 domain derived from a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a CH1 domain derived from a human IgG1 CH1 domain, and a heavy chain variable domain, iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain, v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain, and a second heavy chain variable domain, vi) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the mutation knob if the first (fourth) polypeptide comprises the mutations hole, or the mutations hole if the first (fourth) polypeptide comprises the mutation knob, and as third (sixth) polypeptide a polypeptide comprising a light chain variable domain and a light chain constant domain covalently bound to the first (fourth) polypeptide by a disulfide bond, wherein i) the CH3 domain of the first polypeptide of the first heterotrimer comprises the mutation knob and the CH3 domain of the second polypeptide of the first heterotrimer comprises the mutations hole, or ii) the CH3 domain of the first polypeptide of the first heterotrimer comprises the mutations hole and the CH3 domain of the second polypeptide of the first heterotrimer comprises the mutation knob, whereby i) in case the first polypeptide of the first heterotrimer comprises the mutations hole the first polypeptide of the second heterotrimer (fourth) polypeptide comprises the mutation knob, or ii) in case the first polypeptide of the first heterotrimer comprises the mutation knob the first polypeptide of the second heterotrimer (fourth) polypeptide comprises the mutations hole, wherein the second polypeptide of the first heterotrimer and the first polypeptide of the second heterotrimer (fourth) polypeptide do not comprise the perturbing mutations at the same position/comprise perturbing mutations at different positions.

DETAILED DESCRIPTION OF EMBODIMENTS OF THE INVENTION

The invention is based, at least in part, on the finding that multispecific antibodies can be obtained by a half-antibody exchange reaction using as starting material non-complete, i.e. not bispecifically binding, antibodies. Exemplary non-complete antibodies are so called 2/3-IgGs. The exemplary 2/3-IgGs comprise an antibody light chain, an antibody heavy chain (the heavy chain and the light chain covalently associate with each other and form a binding site by the pair of their VH and VL domains) and an antibody heavy chain Fc-region fragment. Said heavy chain Fc-region fragment can itself be part of, e.g., a complete or extended or variant antibody heavy chain. The heavy chain::heavy chain Fc-region fragment pair and the (functional) binding site as present in the 2/3-IgG define the minimal structural elements required for the exchange reaction according to the current invention. In the non-complete antibodies, such as e.g. in said 2/3-IgGs, the interaction between the Fc-regions is destabilized by an asymmetric perturbing mutation, preferably present in the Fc-region fragment. Said perturbing mutation fosters the dissociation of the starting non-complete antibodies and the generation of correctly assembled complete bispecific antibodies in case a better matching complementary non-complete antibody is present.

The invention is based, at least in part, on the further finding that by using starting compounds as outlined above the method of the invention can be performed even in the absence of reducing agents. That is, disulfide bonds between the Fc-region fragment and the heavy chain are not required. Thus, the hinge region disulfide bonds as well as other heavy chain-heavy chain disulfide bonds can be removed from the starting non-complete antibodies. It has been found that the generation of the starting non-complete antibodies without said heavy chain-heavy chain disulfide bonds as well as the exchange reaction and the production of multispecific antibodies still work efficiently.

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, hinge, CH2 and CH3, which is herein further clarified by referring to "numbering according to Kabat EU index" in this case).

The CH3 domains in the Fc-region of the heavy chains of a bivalent bispecific antibody can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

The mutation T366W in the CH3 domain of an antibody heavy chain is denoted as "knob mutation" and the mutations T366S, L368A, Y407V in the CH3 domain of an antibody heavy chain are denoted as "mutations hole" (numbering according to Kabat EU index). An additional interchain disulfide bridge between the CH3 domains can also be used (Merchant, A. M., et al., Nature Biotech. 16 (1998) 677-681) e.g. by introducing a S354C mutation into the CH3 domain of the heavy chain with the "knob mutation" (denotes as "knob-cys mutations" or "mutations knob-cys") and by introducing a Y349C mutation into the CH3 domain of the heavy chain with the "hole mutations" (denotes as "hole-cys mutations" or "mutations hole-cys") (numbering according to Kabat EU index) or vice versa.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N. Y. (1987).

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "amino acid substitution" or "(amino acid" mutation" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used.

Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "antibody-dependent cellular cytotoxicity (ADCC)" is a function mediated by Fc receptor binding and refers to lysis of target cells mediated by an antibody Fc-region in the presence of effector cells. ADCC is measured in one embodiment by the treatment of a preparation of target expressing erythroid cells (e.g. K562 cells expressing recombinant target) with an Fc-region comprising 2/3-IgG as reported herein in the presence of effector cells such as freshly isolated PBMC (peripheral blood mononuclear cells) or purified effector cells from buffy coats, like monocytes or NK (natural killer) cells. Target cells are labeled with Cr-51 and subsequently incubated with the 2/3-IgG. The labeled cells are incubated with effector cells and the supernatant is analyzed for released Cr-51. Controls include the incubation of the target endothelial cells with effector cells but without the 2/3-IgG. The capacity of the 2/3-IgG to induce the initial steps mediating ADCC is investigated by measuring the binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

The term "CH1 domain" denotes the part of an antibody heavy chain polypeptide that extends approximately from EU position 118 to EU position 215 (EU numbering system). In one embodiment a CH1 domain comprises the amino acid sequence of

```
                              (SEQ ID NO: 27)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSC.
```

The term "CH2 domain" denotes the part of an antibody heavy chain polypeptide that extends approximately from EU position 231 to EU position 340 (EU numbering system according to Kabat). In one embodiment a CH2 domain comprises the amino acid sequence of

```
                              (SEQ ID NO: 28)
APELLGGPSV FLFPPKPKDT LMISRTPEVT CVWDVSHEDP

EVKFNWYVDG VEVHNAKTKP REEQESTYRW SVLTVLHQDW

LNGKEYKCKV SNKALPAPIE KTISKAK.
```

The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain comprises the amino acid sequence of

```
                              (SEQ ID NO: 29)
GQPREPQVYT LPPSRDELTK NQVSLTCLVK GFYPSDIAVE

WESNGQPENN YKTTPPVLDS DGSFFLYSKL TVDKSRWQQG

NVFSCSVMHE ALHNHYTQKS LSLSP.
```

The term "comprising" also includes the term "consisting of".

The term "complement-dependent cytotoxicity (CDC)" refers to lysis of cells induced by the Fc-region of an antibody as reported herein in the presence of complement. CDC is measured in one embodiment by the treatment of target expressing human endothelial cells with a 2/3-IgG as reported herein in the presence of complement. The cells are in one embodiment labeled with calcein. CDC is found if the 2/3-IgG induces lysis of 20% or more of the target cells at a concentration of 30 µg/ml. Binding to the complement factor C1q can be measured in an ELISA. In such an assay in principle an ELISA plate is coated with concentration ranges of the 2/3-IgG, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate]).

"Effector functions" refer to those biological activities attributable to the Fc-region of an antibody, which vary with the antibody class from which it is derived. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) presenting the Fc-region, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG type Fc-regions are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; Gessner, J. E., et al., Ann. Hematol. 76 (1998) 231-248.

Cross-linking of receptors for the Fc-region of IgG type antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by 103-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "hinge region" denotes the part of an antibody heavy chain polypeptide that joins in a wild-type antibody heavy chain the CH1 domain and the CH2 domain, e. g. from about position 221 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. In one embodiment the hinge region has the amino acid sequence DKTHTCPXCP (SEQ ID NO: 30), wherein X is either S or P. In one embodiment the hinge region has the amino acid sequence HTCPXCP (SEQ ID NO: 31), wherein X is either S or P. In one embodiment the hinge region has the amino acid sequence CPXCP (SEQ ID NO: 32), wherein X is either S or P. In one embodiment the hinge region has no internal disulfide bonds. This is achieved by substituting the cysteine residues in the sequence of SEQ ID NO: 32 (and likewise in SEQ ID NO: 30 and 31) by serine residues or by deleting the CPXC stretch (SEQ ID NO: 89) from the hinge region of SEQ ID NO: 30, 31 or 32.

The term "peptidic linker" denotes a linker of natural and/or synthetic origin. A peptidic linker consists of a linear chain of amino acids wherein the 20 naturally occurring amino acids are the monomeric building blocks which are connected by peptide bonds. The chain has a length of from 1 to 50 amino acid residues, preferred between 1 and 28 amino acid residues, especially preferred between 3 and 25 amino acid residues. The peptidic linker may contain repetitive amino acid sequences or sequences of naturally occurring polypeptides. The peptidic linker has the function to ensure that the domains of a 2/3-IgG can perform their biological activity by allowing the domains to fold correctly and to be presented properly. Preferably the peptidic linker is a "synthetic peptidic linker" that is designated to be rich in glycine, glutamine, and/or serine residues. These residues are arranged e.g. in small repetitive units of up to five amino acids, such as GGGS (SEQ ID NO: 69), GGGGS (SEQ ID NO: 70), QQQG (SEQ ID NO: 71), QQQQG (SEQ ID NO: 72), SSSG (SEQ ID NO: 73) or SSSSG (SEQ ID NO: 74). This small repetitive unit may be repeated for two to five times to form a multimeric unit, such as e.g. (GGGS) 2 (SEQ ID NO: 75), (GGGS) 3 (SEQ ID NO: 76), (GGGS) 4 (SEQ ID NO: 77), (GGGS) 5 (SEQ ID NO: 78), (GGGGS) 2 (SEQ ID NO: 79), (GGGGS) 3 (SEQ ID NO: 80), or (GGGGS) 4 (SEQ ID NO: 81). In one embodiment the peptidic linker is selected from the group of linkers of SEQ ID NO: 69 to 82. In one embodiment each of the peptidic linkers is selected independently of each other from the group of linkers consisting of SEQ ID NO: 69 to 82. In one preferred embodiment the peptidic linker/each peptidic linker is selected (independently of each other) from the group of linkers consisting of SEQ ID NO: 75 to 81. At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 82). All peptidic linkers can be encoded by a nucleic acid molecule and therefore can be recombinantly expressed. As the linkers are themselves peptides, the antifusogenic peptide is connected to the linker via a peptide bond that is formed between two amino acids.

An "antibody fragment" refers to a molecule other than an intact antibody that comprises a portion of an intact antibody that binds the antigen to which the intact antibody binds. Examples of antibody fragments include but are not limited to 2/3-IgGs, Fv, scFv, Fab, scFab, Fab', Fab'-SH, F(ab') 2; diabodies; linear antibodies; single-chain antibody molecules (e.g. scFv); and multispecific antibodies formed from antibody fragments. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g. *E. coli* or phage).

The term "antibody fragment" also includes a "Dual Acting Fab" or "DAF" comprising an antigen binding site that binds to two different antigens (see, US 2008/0069820, for example).

A "monospecific antibody" denotes an antibody that has a single binding specificity for one antigen. Monospecific antibodies can be prepared as full-length antibodies or antibody fragments (e.g. 2/3-IgG, F(ab') 2) or combinations thereof (e.g. full length antibody plus additional scFv or Fab fragments).

A "multispecific antibody" denotes an antibody that has binding specificities for at least two different epitopes on the same antigen or two different antigens. Multispecific antibodies can be prepared as full-length antibodies or antibody fragments (e.g. F(ab') 2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1). One multispecific antibody is a bispecific antibody. Multi-specific antibodies may also be made by engineering electrostatic steering effects for making antibody Fc-heterodimeric molecules (WO 2009/089004).

The term "binding to" denotes the binding of a binding site to its target, such as e.g. of an antibody binding site comprising an antibody heavy chain variable domain and an antibody light chain variable domain to the respective antigen. This binding can be determined using, for example, a BIAcore® assay (GE Healthcare, Uppsala, Sweden). That is, the term "binding (to an antigen)" denotes the binding of an antibody in an in vitro assay to its antigen(s). In one embodiment binding is determined in a binding assay in which the antibody is bound to a surface and binding of the antigen to the antibody is measured by Surface Plasmon Resonance (SPR). Binding means e.g. a binding affinity ($K_D$) of $10^{-8}$ M or less, in some embodiments of $10^{-13}$ to $10^{-8}$ M, in some embodiments of $10^{-13}$ to $10^{-9}$ M. The term "binding" also includes the term "specifically binding".

For example, in one possible embodiment of the BIAcore® assay the antigen is bound to a surface and binding of the antibody binding site is measured by surface plasmon resonance (SPR). The affinity of the binding is defined by the terms ka (association constant: rate constant for the association to form a complex), kd (dissociation constant; rate constant for the dissociation of the complex), and KD (kd/ka). Alternatively, the binding signal of a SPR sensorgram can be compared directly to the response signal of a reference, with respect to the resonance signal height and the dissociation behaviors.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

The term "binding site" denotes any proteinaceous entity that shows binding specificity to a target. This can be, e.g., a receptor, a receptor ligand, an anticalin, an affibody, an antibody, etc. Thus, the term "binding site" as used herein denotes a polypeptide that can specifically bind to or can be specifically bound by a second polypeptide. In one embodiment the binding site is selected from the group of polypeptides consisting of an antibody heavy chain variable domain, an antibody light chain variable domain, a pair of an antibody heavy chain and an antibody light chain variable domains, a receptor or functional fragment thereof, a receptor ligand or a functional fragment thereof, an enzyme or its substrate.

In case of an antibody the binding site comprises at least three HVRs (e.g. in case of a VHH) or six HVRs (e.g. in case of a naturally occurring, i.e. conventional, antibody). Generally, the amino acid residues of an antibody that are responsible for antigen binding are forming the binding site. These residues are normally contained in a pair of an antibody heavy chain variable domain and a cognate antibody light chain variable domain. The antigen-binding site of an antibody comprises amino acid residues from the "hypervariable regions" or "HVRs". "Framework" or "FR" regions are those variable domain regions other than the hypervariable region residues as herein defined. Therefore, the light and heavy chain variable domains of an antibody comprise from N- to C-terminus the regions FR1, HVR1/CDR1, FR2, HVR2/CDR2, FR3, HVR3/CDR3, and FR4 (immunoglobulin framework). Especially, the HVR3/CDR3 region of the heavy chain variable domain is the region, which contributes most to antigen binding and defines the binding specificity of an antibody. A "functional binding site" is capable of specifically binding to its target. The term "specifically binding to" denotes the binding of a binding site to its target in an in vitro assay, in one embodiment in a binding assay. Such binding assay can be any assay as long the binding event can be detected. For example, an assay in which the antibody is bound to a surface and binding of the antigen(s) to the antibody is measured by Surface Plasmon Resonance (SPR). Alternatively, a bridging ELISA can be used. Binding means a binding affinity from antibody (binder) to its target ($K_D$) of $10^{-8}$ M or less, in some embodiments of $10^{-13}$ to $10^{-8}$ M, in some embodiments of $10^{-13}$ to $10^{-9}$ M.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "Fc-region" denotes the C-terminal region of an immunoglobulin heavy chain that contains at least a part of the hinge region, the CH2 domain and the CH3 domain. In one embodiment, a human IgG heavy chain Fc-region extends from Asp221, or from Cys226, or from Pro230, to the carboxyl-terminus of the heavy chain. However, the C-terminal lysine (Lys447) of the Fc-region may or may not be present. The Fc-region is composed of two heavy chain Fc-region polypeptides, which can be covalently linked to each other via the hinge region cysteine residues forming inter-chain disulfide bonds.

The antibodies as produced in the method as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A and optionally P329G (numbering according to EU index of Kabat).

The term "full length antibody" denotes an antibody having a structure substantially similar to a native antibody structure. A full length antibody comprises two full length antibody light chains each comprising a light chain variable domain and a light chain constant domain, and two full length antibody heavy chains each comprising a heavy chain variable domain, a first constant domain, a hinge region, a second constant domain and a third constant domain. A full length antibody may comprise further domains, such as e.g. additional scFv or scFab conjugated to one or more of the chains of the full length antibody. These conjugates are also encompassed by the term full length antibody.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "derived from" denotes that a variant amino acid sequence is obtained from a parent amino acid sequence by introducing alterations/mutations at at least one position. Thus, a derived amino acid sequence differs from the corresponding parent amino acid sequence at at least one corresponding position. In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise, a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

In one embodiment one or both heavy chain Fc-region polypeptide(s) are derived from an Fc-region polypeptide of SEQ ID NO: 01 and have at least one amino acid mutation compared to the Fc-region polypeptide of SEQ ID NO: 01. In one embodiment the Fc-region polypeptide comprises/has from about one to about ten amino acid mutations, and in one embodiment from about one to about five amino acid mutations. In one embodiment the Fc-region polypeptide has at least about 80% homology with a human Fc-region polypeptide of SEQ ID NO: 01. In one embodiment the Fc-region polypeptide has least about 90% homology with a human Fc-region polypeptide of SEQ ID NO: 01. In one embodiment the Fc-region polypeptide has at least about 95% homology with a human Fc-region polypeptide of SEQ ID NO: 01.

The Fc-region polypeptide derived from a human Fc-region polypeptide of SEQ ID NO: 01, or 02 or 03, or 04 is further defined by the amino acid alterations that are contained. Thus, for example, the term P329G denotes an Fc-region polypeptide derived from a human Fc-region polypeptide with the mutation of proline to glycine at amino acid position 329 relative to the human Fc-region polypeptide of SEQ ID NO: 01, or 02, or 03, or 04.

A human IgG1 Fc-region polypeptide comprises the following amino acid sequence:

(SEQ ID NO: 01)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSP.

The following Fc-regions are variants derived from the wild-type human IgG1 Fc-region.

A human IgG1 Fc-region derived Fc-region polypeptide with the mutations L234A, L235A comprises the following amino acid sequence:

(SEQ ID NO: 05)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSP.

A human IgG1 Fc-region derived Fc-region polypeptide with Y349C, T366S, L368A and Y407V mutations comprises the following amino acid sequence:

(SEQ ID NO: 06)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSP.

A human IgG1 Fc-region derived Fc-region polypeptide with S354C, T366W mutations comprises the following amino acid sequence:

(SEQ ID NO: 07)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSP.

A human IgG1 Fc-region derived Fc-region polypeptide with L234A, L235A mutations and Y349C, T366S, L368A, Y407V mutations comprises the following amino acid sequence:

(SEQ ID NO: 08)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

```
CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSP.
```

A human IgG1 Fc-region derived Fc-region polypeptide with a L234A, L235A and S354C, T366W mutations comprises the following amino acid sequence:

```
                                       (SEQ ID NO: 09)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSP.
```

A human IgG1 Fc-region derived Fc-region polypeptide with a P329G mutation comprises the following amino acid sequence:

```
                                       (SEQ ID NO: 10)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSP.
```

A human IgG1 Fc-region derived Fc-region polypeptide with L234A, L235A mutations and P329G mutation comprises the following amino acid sequence:

```
                                       (SEQ ID NO: 11)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSP.
```

A human IgG1 Fc-region derived Fc-region polypeptide with a P329G mutation and Y349C, T366S, L368A, Y407V mutations comprises the following amino acid sequence:

```
                                       (SEQ ID NO: 12)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSP.
```

A human IgG1 Fc-region derived Fc-region polypeptide with a P329G mutation and S354C, T366W mutation comprises the following amino acid sequence:

```
                                       (SEQ ID NO: 13)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSP.
```

A human IgG1 Fc-region derived Fc-region polypeptide with L234A, L235A, P329G and Y349C, T366S, L368A, Y407V mutations comprises the following amino acid sequence:

```
                                       (SEQ ID NO: 14)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSP.
```

A human IgG1 Fc-region derived Fc-region polypeptide with L234A, L235A, P329G mutations and S354C, T366W mutations comprises the following amino acid sequence:

```
                                       (SEQ ID NO: 15)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSP.
```

A human IgG4 Fc-region polypeptide comprises the following amino acid sequence:

```
                                       (SEQ ID NO: 04)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSL.
```

The following Fc-regions are variants derived from the wild-type human IgG4 Fc-region.

A human IgG4 Fc-region derived Fc-region polypeptide with S228P and L235E mutations comprises the following amino acid sequence:

```
                                       (SEQ ID NO: 16)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSL.
```

A human IgG4 Fc-region derived Fc-region polypeptide with S228P, L235E mutations and P329G mutation comprises the following amino acid sequence:

(SEQ ID NO: 17)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSL.

A human IgG4 Fc-region derived Fc-region polypeptide with S354C, T366W mutations comprises the following amino acid sequence:

(SEQ ID NO: 18)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSL.

A human IgG4 Fc-region derived Fc-region polypeptide with Y349C, T366S, L368A, Y407V mutations comprises the following amino acid sequence:

(SEQ ID NO: 19)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSL.

A human IgG4 Fc-region derived Fc-region polypeptide with a S228P, L235E and S354C, T366W mutations comprises the following amino acid sequence:

(SEQ ID NO: 20)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSL.

A human IgG4 Fc-region derived Fc-region polypeptide with a S228P, L235E and Y349C, T366S, L368A, Y407V mutations comprises the following amino acid sequence:

(SEQ ID NO: 21)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSL.

A human IgG4 Fc-region derived Fc-region polypeptide with a P329G mutation comprises the following amino acid sequence:

(SEQ ID NO: 22)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSL.

A human IgG4 Fc-region derived Fc-region polypeptide with a P329G and Y349C, T366S, L368A, Y407V mutations comprises the following amino acid sequence:

(SEQ ID NO: 23)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSL.

A human IgG4 Fc-region derived Fc-region polypeptide with a P329G and S354C, T366W mutations comprises the following amino acid sequence:

(SEQ ID NO: 24)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSL.

A human IgG4 Fc-region derived Fc-region polypeptide with a S228P, L235E, P329G and Y349C, T366S, L368A, Y407V mutations comprises the following amino acid sequence:

(SEQ ID NO: 25)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSL.

A human IgG4 Fc-region derived Fc-region polypeptide with a S228P, L235E, P329G and S354C, T366W mutations comprises the following amino acid sequence:

(SEQ ID NO: 26)
ESKYGPPCPPCPAPEFEGGPSVFLFPPKPKDTLMISRTPEVTCVVVDVSQ

-continued

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSL.

A "humanized" antibody refers to an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the heavy chain variable domain VH (H1, H2, H3), and three in the light chain variable domain VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "light chain" denotes the shorter polypeptide chains of native IgG antibodies. The light chain of an antibody may be assigned to one of two types, called kappa (κ) and lambda (λ), based on the amino acid sequence of its constant domain. See SEQ ID NO: 33 for a human kappa light chain constant domain and SEQ ID NO: 34 for a human lambda light chain constant domain.

The term "paratope" refers to that part of a given antibody molecule that is required for specific binding between a target and a binding site. A paratope may be continuous, i.e. formed by adjacent amino acid residues present in the binding site, or discontinuous, i.e. formed by amino acid residues that are at sequentially different positions in the primary sequence, such as in the amino acid sequence of the HVRs/CDRs, but in close proximity in the three-dimensional structure, which the binding site adopts.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis, CE-SDS) or chromatographic (e.g., size exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "recombinant antibody", as used herein, denotes all antibodies (chimeric, humanized and human) that are prepared, expressed, created or isolated by recombinant means. This includes antibodies isolated from a host cell such as a NSO, HEK, BHK or CHO cell or from an animal (e.g. a mouse) that is transgenic for human immunoglobulin genes or antibodies expressed using a recombinant expression plasmid transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein as reported herein are in one preferred embodiment "bivalent" or "trivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "variant" denotes molecules which have an amino acid sequence that differs from the amino acid sequence of a parent molecule. Typically, such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent domain or Fc-region. In one embodiment the variant has an amino acid sequence that has from about 75% to less than 100% amino acid sequence identity with the amino acid sequence of the parent domain or Fc-region, especially from about 80% to less than 100%, especially from about 85% to less than 100%, especially from about 90% to less than 100%, and especially from about 95% to less than 100%. In one embodiment the parent domain or Fc-region and the variant domain or Fc-region differ by one (a single), two or three amino acid residue(s).

The term "domain crossover" as used herein denotes that in a pair of an antibody heavy chain VH-CH1 fragment and its corresponding cognate antibody light chain, i.e. in an antibody binding arm (i.e. in the Fab fragment), the domain sequence deviates from the natural sequence in that at least one heavy chain domain is substituted by its corresponding light chain domain and vice versa. There are three general types of domain crossovers, (i) the crossover of the CH1 and the CL domains, which leads to domain crossover light chain with a VL-CH1 domain sequence and a domain crossover heavy chain fragment with a VH-CL domain sequence (or a full length antibody heavy chain with a VH-CL-hinge-CH2-CH3 domain sequence), (ii) the domain crossover of the VH and the VL domains, which leads to domain crossover light chain with a VH-CL domain sequence and a domain crossover heavy chain fragment with a VL-CH1 domain sequence, and (iii) the domain crossover of the complete light chain (VL-CL) and the complete VH-CH1 heavy chain fragment ("Fab crossover"), which leads to a domain crossover light chain with a VH-CH1 domain sequence and a domain crossover heavy chain fragment with a VL-CL domain sequence (all aforementioned domain sequences are indicated in N-terminal to C-terminal direction).

As used herein the term "replaced by each other" with respect to corresponding heavy and light chain domains refers to the aforementioned domain crossovers. As such, when CH1 and CL domains are "replaced by each other" it is referred to the domain crossover mentioned under item (i) and the resulting heavy and light chain domain sequence. Accordingly, when VH and VL are "replaced by each other" it is referred to the domain crossover mentioned under item (ii); and when the CH1 and CL domains are "replaced by each other" and the VH1 and VL domains are "replaced by each other" it is referred to the domain crossover mentioned under item (iii). Bispecific antibodies including domain crossovers are reported, e.g. in WO 2009/080251, WO 2009/080252, WO 2009/080253, WO 2009/080254 and Schaefer, W. et al, Proc. Natl. Acad. Sci USA 108 (2011) 11187-11192.

Multispecific antibody produced with a method as reported herein can also comprises Fab fragments including a domain crossover of the CH1 and the CL domains as mentioned under item (i) above, or a domain crossover of the VH and the VL domains as mentioned under item (ii) above. The Fab fragments specifically binding to the same antigen(s) are constructed to be of the same domain sequence. Hence, in case more than one Fab fragment with a domain crossover is contained in the multispecific antibody, said Fab fragment(s) specifically bind to the same antigen.

II. Specific Methods and Compounds According to the Invention

For the identification of the best combination of binders for use in multispecific antibodies, e.g. bi- or trispecific antibodies, it is desired to test as many combinations as possible. Therefore, methods are required that allow to combine a multitude of different binding sites each with different binding specificities, i.e. binders, with each other and to screen for the best combination(s) in a binding or functional assay.

For example, each binder of a first multitude of binding sites with first binding specificity(ies) (e.g. different light chain variable domain and heavy chain variable domain pairs, Fv fragments) is combined with each binder of a second multitude of sites with second binding specificity (ies) (e.g. binding to a different epitope on the same antigen or to a different antigen). This results in the preparation of a combination matrix encompassing each combination of binding sites of said first multitude with each of said second multitude. Additionally, and preferably, also different formats with respect to valencies and functionalities are included in this combination matrix. The generated multispecific antibodies are then subjected to assays to identify those combinations and formats that possess the desired functionalities (e.g. by ranking according to functional performance and/or parameters desired and important for drug development). The size of combination matrices of two specificities growths exponentially with linear increasing number of input molecules, e.g. 100 'A-binders' and 100 'B-binders' generate 10.000 different 'A+B-bsAbs' (bsAb=bispecific antibody). Generation of such large numbers of different A+B bsAbs via individual design and generation of expression cassettes followed by expression and purification is cumbersome and poses a limit to the size of the matrices that can be assessed.

At least two tasks benefit from generation and screening combinations of many different input entities (different specificities, epitopes, geometries, affinities, and/or valencies): avidity-mediated binding improvement and generation of agonistic bsAbs.

The avidity-mediated binding improvement bases on antibody derivatives that have poor to no binding functionality in monovalent form with binding functionality achieved only by the physical connection of two (different) monovalent binding sites to a bi- (or even multi-) valent bsAb. Bi- or multivalency generates avidity with specificity dependent on binding of the two different binding sites.

The principle of bi- or multispecific agonistic antibodies is similar: functionality is elicited via simultaneous binding (this may include crosslinking) of different antigens while binding of just one monovalent binding entity has no activity.

The common denominator of the above principles is (no or at most poor functionality of individual monovalent binding entities and) desired functionality of bi- or multivalent combinations. The identification of desired binding site combinations is based on the assessment of binding and/or function of avidity-mediated binding or agonistic bsAbs (mediated by bi- or multivalency). It is, thus, for this screening required that the test antibodies, i.e. the bsAb generated, e.g., via the exchange reaction according to the current invention, do not contain any remaining (bivalent) monospecific molecules as those may generate false positive results. Equally or even more disturbing for the same reason are multivalent reaction side-products, such as, e.g., aggregates.

A) Method to Convert Monospecific Monovalent IgG Derivatives to Bispecific Bivalent IgG's The method according to the current invention achieves the conversion of monospecific (monovalent) antibodies or antibody fragments to bivalent bsAbs. The methods allow for the easy removal of unconverted starting material as well as bivalent but monospecific side products as well as aggregates formed during the reaction. That is, the method according to the invention solves amongst other things at least the two issues of avoiding bivalent monospecific antibodies as well as undesired aggregates to be present in the final preparation.

To achieve this, two non-functional half antibodies (only monospecific) are used as starting material. Exemplarily, so called 2/3-IgGs can be used as starting material. 2/3-IgGs are composed of a heavy chain with the first set of knob-into-hole (KiH) mutations, a light chain complementary thereto, as well as an Fc-region, which is made complementary to the Fc-region of the heavy chain by the respective complementary second set of knob-into-hole mutations. The complementary Fc-region can be, e.g., an Fc-region heavy chain fragment or a second heavy chain. To further foster correct assembly of the desired bi- (multi-) specific antibody the complementary Fc-region comprises besides the second complementary set of KiH mutations an additional perturbing (destabilizing) repulsive charge introducing mutation. Additionally, the complementary Fc-region may comprise an affinity tag (e.g. a His6 or C-Tag) for efficient removal of non-desired educts and products after the reaction. The second 2/3-IgG comprises complementary perturbing mutations that turn into attractive mutations once the antibody-halves exchange with each other, e.g. upon mixing.

The exchange reaction/method according to the current invention comprises the following step incubating a first (starting) heterodimeric polypeptide, which comprises a first polypeptide and a second polypeptide, with a second (starting) heterodimeric polypeptide, which comprises a third polypeptide and a fourth polypeptide, to crosswise exchange the second and the third polypeptide to form a third and a fourth heterodimeric polypeptide, and recovering the fourth (exchanged) heterodimeric polypeptide, which comprises the first polypeptide and the fourth polypeptide, wherein i) the second polypeptide comprises a (first perturbing) mutation resulting in a destabilization of the first heterodimeric polypeptide compared to a (heterodimeric) polypeptide identical to said first heterodimeric polypeptide except for said mutation in the second polypeptide, ii) the third polypeptide comprises a (second perturbing) mutation resulting in a destabilization of the second heterodimeric polypeptide compared to a heterodimeric polypeptide identical to said second (heterodimeric) polypeptide except for said mutation in the third polypeptide, iii) the (first perturbing) mutation in the second polypeptide and the (second perturbing) mutation in the third polypeptide result in a stabilization of the third (exchanged) heterodimeric polypeptide comprising said second polypeptide and said third polypeptide compared to the first (starting) heterodimeric polypeptide and/or to the second (starting) heterodimeric polypeptide, and iv) the fourth (exchanged) heterodimeric polypeptide is more stable compared to the first (starting) heterodimeric polypeptide and/or the second (starting) heterodimeric polypeptide.

Thus, the current invention is based, at least in part, on the finding that adding a single (one-sided, not paired) destabilizing (perturbing) mutation in a heterodimeric polypeptide is sufficient to foster polypeptide chain exchange with a second heterodimeric polypeptide comprising also one single (one-sided, not paired) destabilizing (perturbing) mutation as both resulting newly formed exchanged heterodimeric polypeptides have improved stability compared to the starting heterodimeric polypeptides (i.e. lower CH3-CH3 binding free energy). The only proviso that has to be followed is that the destabilizing (perturbing) mutations are introduced at positions that interact with each other once the respective polypeptides associate with each other.

This methodology can be applied to any heterodimeric polypeptide fulfilling the criteria as outlined above.

Nevertheless, the method according to the current invention is especially useful in the pharmaceutical area.

With the method according to the invention it is easily possible to generate large libraries of bispecific binders if the respective polypeptides of each of the heterodimeric starting polypeptides that associate with each other during the exchange reaction comprise one or more binding sites. Thus, one of the exchanged heterodimeric polypeptides obtained in the method according to the current invention will comprise these binding sites.

From the art different methods for the generation of heterodimeric polypeptides are known. Any of these methods can be used as long as the mutations required for the formation of the starting heterodimeric polypeptides do not interfere or overlap with the (perturbing) destabilizing mutations needed for the exchange reaction according to the current invention.

Turning back to the pharmaceutical area antibodies are the most widely used class of binders. Antibodies dimerize via interactions in their constant region, especially between the CH3 domains of the heavy chains.

Thus, the current invention is based, at least in part, on the finding that for performing the method according to the current invention the introduction of a single destabilizing mutations in one CH3 domain of a pair of CH3 domains is sufficient. In more detail, it has been found that the introduction of a first destabilizing mutation at position 357 in only one CH3 domain of the first starting heterodimeric polypeptide and a second destabilizing mutation at position 370 in only one CH3 domain of the second starting polypeptide fosters upon incubating the two starting heterodimeric polypeptides the spontaneous exchange of polypeptide chains between these starting polypeptides. One of the resulting exchanged polypeptides comprises the CH3 domain pair with the mutations at positions 357 and 370, respectively, which result in a stabilization of the exchanged heterodimer. The like can be achieved with the mutations at positions 356 and 439. The numbering of all positions is according to the EU index of Kabat. One preferred pair of mutations is E357K and K370E. Another preferred pair of mutations is D356K and K439E. The method according to the current invention can be applied to any IgG subclass, i.e. IgG1, IgG2, IgG3 and IgG4, as the residues in question are highly conserved. In one preferred embodiment the CH3 domain is of the IgG1 subclass.

The invention is based, at least in part, on the finding that the polypeptide chains of the starting heterodimeric polypeptides do not need to be covalently linked to each other, e.g. via disulfide bonds, to allow the formation and isolation of the starting heterodimeric polypeptides. In more detail, as the starting polypeptides are already heterodimers these will comprise further mutations for heterodimerization. It has been found that these mutations are sufficient to stabilize the starting heterodimers even in the presence of the destabilizing (perturbing) single one-sided mutation. Thereby the need for a covalent linkage of the chains in the starting heterodimeric polypeptides is no longer given. Thus, in one embodiment, in case of hinge region containing starting heterodimeric polypeptides these hinge regions either comprises the mutations C226S and C229S or a deletion of the entire CPXC (SEQ ID NO: 89) sequence (numbering according to Kabat EU index).

By the omission of disulfide bonds between the Fc-region comprising chains of the heterodimeric starting polypeptides no reducing agent has to be added to initiate the exchange reaction. This allows for milder reaction conditions. Additionally, disulfide bonds may be present in the starting heterodimeric polypeptides, such as e.g. in a Fab fragment.

The invention is based, at least in part, on the finding that exchanged heterodimeric polypeptides, e.g. those comprising the binding sites, can further be stabilized by the formation of disulfide bonds only after the exchange reaction. For example, mutations well established for the formation of heterodimeric antibodies are the knobs-into-holes mutations. These exist in two variants: without and with additional disulfide bond. Thus, one alternative starting heterodimeric polypeptide comprises the knobs-into-holes mutations for the formation of the starting heterodimeric polypeptides, and provides the knobs-into-holes cysteine residue only in the polypeptide chain that harbor the binding site(s). Thereby only in the exchanged heterodimeric polypeptide, which comprises the binding sites, both cysteine residues required for the formation of a disulfide bond at the corresponding matching positions are present. Thus, only in said exchanged product a disulfide bond is formed. This results in a further stabilization of the target exchanged heterodimeric polypeptide.

The invention is based, at least in part, on the finding that the presence of a tag in each of the polypeptide chains that also comprise the (perturbing) destabilizing mutation provides for an improved purification of the exchanged heterodimeric polypeptide that comprises the binding sites. Such as separation is possible from non-reacted starting material as well as not-target exchanged heterodimeric polypeptide as only the exchanged heterodimeric polypeptide comprising the binding sites does not comprise said tag.

The term "heterodimeric" as used herein denotes a polypeptide comprising at least two polypeptide chains that are not identical in amino acid sequences either in part or completely and that fulfill the requirements of the invention. The term also encompasses polypeptides comprising three or more polypeptide chains as long as at least two of them are heterodimeric according to the invention. Thus, the term "multimeric" denotes a polypeptide comprising at least three polypeptide chains whereof at least two are heterodimeric and fulfill the requirements of the invention.

The term "perturbing mutation" denotes a mutation that results in the destabilization of a (hetero)dimeric polypeptide. This destabilization is generally achieved by changing the charge of an amino acid residue, such e.g. by exchanging a positively charged amino acid residue with a negatively charged amino acid residue, or vice versa. Such an exchange results in like charges at interacting positions and, thus, in charge repulsion. One preferred pair of mutations is E357K and K370E. Another preferred pair of mutations is D356K and K439E. Additionally, the method according to the current invention can be applied to any IgG subclass, i.e. IgG1, IgG2, IgG3 and IgG4, as the residues in question are highly conserved. In one preferred embodiment the CH3 domain is of the IgG1 subclass.

A method to assess the effect of the CH3 domain mutation on dimer stability is disclosed in WO 2009/089004 (incorporated herein by reference). Therein it is outlined how EGAD software can be used to estimate the CH3-CH3 domain binding free energy (see also Pokala, N. and Handel, T. M., J. Mol. Biol. 347 (2005) 203-227, incorporated herein by reference in its entirety):

EGAD can be used to roughly compare the binding free energy of various mutations made at the CH3 domain interface. The binding free energy of a mutant is defined as $\Delta\Delta G_{mut} = \mu (\Delta G_{mut} - \Delta G_{wt})$ (mut=mutant, wt=wild-type). Where, $\mu$ (=0.1, in general) is the scaling factor used to normalize the predicted changes in binding affinity to have a slope of 1 when comparing with the experimental energies. The free energy of dissociation ($\Delta G$) is defined as the energy difference between the complex ($\Delta G_{bound}$) and free states ($\Delta G_{free}$).

The invention is in the following exemplified with specific, exemplary starting materials, i.e. 2/3-IgGs. This is presented as an exemplification of the general underlying concept and shall not be construed as a limitation of the invention. The true scope of the invention is set forth in the claims.

FIG. 1 shows the design and modular composition of 2/3-IgGs used as exemplary starting compounds in the methods according to the current invention. 2/3-IgGs are composed of three individual chains: one light chain (normally a full length light chain comprising a light chain variable domain and a light chain constant domain), one heavy chain (normally a full length heavy chain comprising a heavy chain variable domain and all heavy chain constant domains including a hinge region), and one complementary heavy chain Fc-region polypeptide (normally a heavy chain Fc-region fragment comprising at least a fragment of a hinge and CH2-CH3). The variable domains of the light chain and the heavy chain form a functional binding site, i.e. a VH-VL pair. The heavy chain (normally of the human IgG1 subclass) contains either i) the knob mutation or the hole mutations (the mutation T366W in the CH3 domain of an antibody heavy chain is denoted as "knob mutation" and the combination of the mutations T366S/L368A/Y407V in the CH3 domain of an antibody heavy chain are denoted as "hole mutations" (numbering according to Kabat EU index)), or ii) the knob-cys mutations or the hole-cys mutations (the combination of the mutations T366W/S354C in the CH3 domain of an antibody heavy chain is denoted as "knob-cys mutations" and the combination of the mutations T366S/L368A/Y407V/Y349C in the CH3 domain of an antibody heavy chain are denoted as "hole-cys mutations"; the inverted setting is likewise possible: T366W/Y349C and T366S/L368A/Y407V/S354C (numbering according to Kabat EU index)) in the CH3 domains to enable the formation of knob-into-hole Fc-region heterodimers. The complementary heavy chain Fc-region polypeptide can also be denoted as a 'dummy-Fc', i.e. an IgG1 derivative that lacks VH and CH1, starts at the N-terminus with the hinge region sequence (or a fragment thereof) and harbors a purification tag, e.g. His6 or His8 or C-Tag, at its C-terminus. In addition, the complementary heavy chain Fc-region polypeptide of the 2/3-IgG contains in its CH3 domains either the knob mutation or the hole mutations depending on the mutations in the heavy chain. In addition to the knob-mutation or the hole-mutations the heavy chain Fc-region polypeptide comprises at least one perturbing (i.e. destabilizing) mutation introducing one (i.e. a single additional) repulsive charge with respect to the wild-type sequence: e.g. D356K or E357K, respectively, in combination with K370E or K439E, respectively (SEQ ID NO: 35, 36, 37 and 38, which are also aspects of the current invention) (see FIG. 2). Such a mutated heavy chain Fc-region polypeptide is denoted as MHCFcRP in the following.

The heavy chain and the MHCFcRP can form two types of heterodimers depending on the distribution of the knob-into-hole mutations therein:
i) heavy chain-knob(-cys)::MHCFcRP-hole, and
ii) heavy chain-hole(-cys)::MHCFcRP-knob.

Thus, the 2/3-IgGs are heterodimers with associated light chain, i.e. heterotrimers. These are, however, somewhat 'flawed' as the charge mutation in the MHCFcRP is without matching counterpart in the heavy chain and, if present in the heavy chain, the MHCFcRP lacks the additional CH3 cysteine necessary to form an interchain disulfide bond to the heavy chain.

2/3-IgGs are monovalent, non-dimerising/aggregating, one-armed antibody derivatives that can be expressed and purified to similar yields as normal IgGs (see FIG. 3). This assures monovalency of the starting material. If a bivalent 2/3-IgG would be used this could be monospecific as well as bispecific.

The polypeptides that make up those flawed 2/3-IgGs, however, are capable to rearrange to bispecific antibodies as shown in FIG. 4.

The exchange reaction between the two starting molecules is driven by better complementarity of the KiH (knobs-into-holes) heavy chains (H-chains) to each other (no charge repulsion and optionally formation of a disulfide bond if free cysteine residues are present) as well as by better complementarity of the two MHCFcRPs to each other. In the reaction the Fc-region complexes of the two starting molecules dissociate and exchange polypeptides to form two more favorable complexes. This drives the reaction as follows:

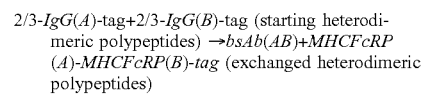

2/3-*IgG(A)*-tag+2/3-*IgG(B)*-tag (starting heterodimeric polypeptides) →*bsAb(AB)*+*MHCFcRP(A)*-*MHCFcRP(B)*-tag (exchanged heterodimeric polypeptides)

In the example as depicted in FIG. 4 the heavy chain (knob-cys) of starting 2/3-IgG (A) and the heavy chain (hole-cys) of starting 2/3-IgG (B) form a matching bispecific antibody heterotetramer (2×HC+2×LC).

The exchange reaction is initiated (in case hinge-region/inter-heavy-chain disulfide bonds are present) by a reduction step to break the disulfide bonds. If hinge-region-disulfide-bond-free 2/3-IgGs are used, then the reduction step can be omitted (see below). The chain rearrangement occurs spontaneously thereafter.

All 2/3-IgG starting molecules, all dimeric MHCFcRP by-products, as well as all aggregates that may be formed during the exchange reaction comprise at least one affinity tag (e.g. His6 or His8 or C-Tag). Thus, a single and simple, as well as high-throughput compatible absorption (affinity chromatography) step can be used to remove all undesired molecules including aggregates. For example, in case of the His6 tag this step is a metal chelate affinity chromatography (see FIGS. 6 and 7). The resulting purified bsAbs can be directly applied to screening procedures to identify bsAbs with desired functionalities (see FIG. 8).

See the examples below, especially examples 1 to 5.

B) Method to Convert Mono- and/or Bivalent Mono- or Bispecific IgG Derivatives to Bi-, Tri- or Tetravalent Bi-, Tri- or Tetraspecific Antibodies With the method according to the current invention it is not only possible to combine different binding specificities but also at the same time to produce these combinations within different formats and with differing valencies. This is achieved by expanding the starting materials used in the method as outlined in the previous section.

For example, starting from 2/3-IgGs as outlined in the previous section, the MHCFcRP is maintained unchanged but the heavy chain is used in different formats. Such formats can be, e.g., chains that have either one binding site at the C-terminus or at the N-terminus or two binding sites one at each terminus (one at the N-terminus and one at the C-terminus) (see FIGS. 9 and 10).

In this example, three different starting formats (N-terminal binding site, C-terminal binding site, N- and C-terminal binding sites) are combined with each other in the method according to the invention to result in 9 different bsAb formats that have different binding sites, different valencies, different geometries and different three-dimensional arrangement/positions of the individual binding sites (see FIG. 11).

As an example, 50 'binder-A' and 50 'binder-B' starting molecules can be expressed in the three formats each (N-terminal binding site, C-terminal binding site, N- and C-terminal binding sites), resulting in 150 (3*50) preparations of 2/3-IgG's for each binder as starting molecules. These can subsequently be shuffled and combined with the method according to the current invention. This generates 22.500 (50*3×50*3) different bsAbs.

For generation of the bsAbs the exchange driving principle (conversion of flawed input molecules to matching output-molecules) is not changed. The MHCFcRPs are also retained. Thus, only the heavy chain is changed/diversified.

FIGS. 1 and 9-10 show that three different starting molecules (2/3-IgG with N-terminal, C-terminal, N- and C-terminal binding site(s)) can be combined with each other in the exchange reaction according to the current invention to result in nine different bispecific formats. These differ in valencies, geometries and different positions of the individual binding sites.

Without being bound by this theory, it is assumed that exchange reactions based on temporary separation of flawed heteromultimers of two different 2/3-IgGs should result in products that contain preferentially matching Fc-region heterodimers. Exchanges therefore convert the monospecific 2/3-IgGs to bispecific IgGs (in different formats), as well as corresponding Fc-region heterodimer.

For the exemplary description of the exchange reactions, the input molecules are termed as follows:
'nA or nB' for molecules having the Fab arm at the normal N-terminus of the heavy chain (H-chain),
'cA or cB' for molecules having the Fab arm at the C-terminus of the H-chain,
'ncA or ncB' for molecules having a Fab arm at N-terminus as well as C-terminus of the H-chain.

The different format-exchange reactions are as follows:

2/3-IgG(nA)-tag+2/3-IgG(nB)-tag→bsAb(nAnB)+ (MHCFcRP)₂-tag

2/3-IgG(nA)-tag+2/3-IgG(cB)-tag→bsAb(nAcB)+ (MHCFcRP)₂-tag

2/3-IgG(nA)-tag+2/3-IgG(ncB)-tag→bsAb(nAncB)+ (MHCFcRP)₂-tag

2/3-IgG(cA)-tag+2/3-IgG(cB)-tag→bsAb(cAcB)+ (MHCFcRP)₂-tag

2/3-IgG(cA)-tag+2/3-IgG(nB)-tag→bsAb(cAnB)+ (MHCFcRP)₂-tag

2/3-IgG(cA)-tag+2/3-IgG(ncB)-tag→bsAb(cAncB)+ (MHCFcRP)₂-tag

2/3-IgG(ncA)-tag+2/3-IgG(nB)-tag→bsAb(ncAnB)+ (MHCFcRP)₂-tag

2/3-IgG(ncA)-tag+2/3-IgG(cB)-tag→bsAb(ncAcB)+ (MHCFcRP)₂-tag

2/3-IgG(ncA)-tag+2/3-IgG(ncB)-tag→bsAb(ncAncB)+ (MHCFcRP)₂-tag

If hinge-region disulfide bonds are present, the exchange reactions are initiated by a reduction step to break the interchain hinge region disulfide bonds. Chain exchange and rearrangement occurred spontaneously. All input molecules, all by-products, as well as all aggregates that may potentially form during the exchange reaction harbor an affinity tag (e.g. His6). The desired bsAb produced in the exchange reaction, however, do not carry an affinity-tag and were therefore removed via NiNTA affinity chromatography (absorption). The remaining bsAbs (in different formats) can directly be applied to screening procedures and analyses to identify and to rank bsAbs in formats with optimal functionality.

See Examples 6 and 7.

To show the general applicability of the method according to the invention further 2/3-IgG-based format variants have been prepared and subjected to the exchange reaction according to the current invention.

i) Non-Antibody Binder:

In a further format the Fab-region of one 2/3-IgG has been replaced by an affibody (see FIG. 19). The exchange reaction worked also (see FIG. 23, ELISA results).

See Example 13.

ii) Addition of a Third Binding Site (VH/VL-Pair) in the Fab-Region:

In a further format one of the 2/3-IgGs comprised a second Fab-region (Fab-extended-2/3-IgG; see FIG. 26). The exchange reaction worked also (see FIG. 27).

For the description of the exchange reactions, the input molecules are termed as follows:
'dA' for molecules having two Fab arms at the normal n-terminus of the heavy chain (Fab-extended-2/3-IgG)
'nB' for molecules having the Fab arm at the normal N-terminus of the heavy chain (H-chain),
'cB' for molecules having the Fab arm at the C-terminus of the H-chain,
'ncB' for molecules with Fab arms at N- as well as C-terminus of the H-chain.

The different format-exchange reactions are as follows:

2/3-IgG(dA)-tag+2/3-IgG(nB)-tag→bsAb(dAnB)+ (MHCFcRP)₂-tag

2/3-IgG(dA)-tag+2/3-IgG(cB)-tag→bsAb(dAcB)+ (MHCFcRP)₂-tag

2/3-IgG(dA)-tag+2/3-IgG(ncB)-tag→bsAb(dAncB)+ (MHCFcRP)₂-tag

See Examples 9, 15 and 16.

iii) Constrained Binders:

In a further format one of the 2/3-IgGs comprised instead of a Fab-region a constrained binder as described in WO 2017/191101 (incorporated herein by reference) (constrained-2/3-IgG, conA, conB; see FIG. 31). The exchange reaction worked also (see FIGS. 32, 33 and 34).

For the description of the exchange reactions, the input molecules are termed as follows:
'conA or conB' for molecules having a constrained binding site comprising the first part of the binding site N-terminal to the Fc-region and the second part of the binding site C-terminal to the Fc-region, wherein the first and the second part are associated with each other and form the binding site, these molecules are circular,
'nA or nB' for molecules having the Fab arm at the normal N-terminus of the heavy chain (H-chain),
'cA or cB' for molecules having the Fab arm at the C-terminus of the H-chain,
'ncA or ncB' for molecules with Fab arms at N- as well as C-terminus of the H-chain.

The different format-exchange reactions are as follows:

2/3-IgG(conA)-tag+2/3-IgG(nB)-tag→bsAb(nAnB)+ (MHCFcRP)₂-tag

2/3-*IgG(conA)*-tag+2/3-*IgG(cB)*-tag→*bsAb(nAcB)*+
(*MHCFcRP*)$_2$-tag

2/3-*IgG(conA)*-tag+2/3-*IgG(ncB)*-tag→*bsAb(nAncB)*+
(*MHCFcRP*)$_2$-tag

2/3-*IgG(conA)*-tag+2/3-*IgG(conB)*-tag→*bsAb(conA-conB)*+(*MHCFcRP*)$_2$-tag

2/3-*IgG(nA)*-tag+2/3-*IgG(nB)*-tag→*bsAb(nAnB)*+
(*MHCFcRP*)$_2$-tag

2/3-*IgG(nA)*-tag+2/3-*IgG(cB)*-tag→*bsAb(nAcB)*+
(*MHCFcRP*)$_2$-tag

2/3-*IgG(nA)*-tag+2/3-*IgG(ncB)*-tag→*bsAb(nAncB)*+
(*MHCFcRP*)$_2$-tag

2/3-*IgG(nA)*-tag+2/3-*IgG(conB)*-tag→*bsAb(nAconB)*+
(*MHCFcRP*)$_2$-tag

2/3-*IgG(cA)*-tag+2/3-*IgG(cB)*-tag→*bsAb(cAcB)*+
(*MHCFcRP*)$_2$-tag

2/3-*IgG(cA)*-tag+2/3-*IgG(nB)*-tag→*bsAb(cAnB)*+
(*MHCFcRP*)$_2$-tag

2/3-*IgG(cA)*-tag+2/3-*IgG(ncB)*-tag→*bsAb(cAncB)*+
(*MHCFcRP*)$_2$-tag

2/3-*IgG(cA)*-tag+2/3-*IgG(conB)*-tag→*bsAb(cAconB)*+
(*MHCFcRP*)$_2$-tag

2/3-*IgG(ncA)*-tag+2/3-*IgG(nB)*-tag→*bsAb(ncAnB)*+
(*MHCFcRP*)$_2$-tag

2/3-*IgG(ncA)*-tag+2/3-*IgG(cB)*-tag→*bsAb(ncAcB)*+
(*MHCFcRP*)$_2$-tag

2/3-*IgG(ncA)*-tag+2/3-*IgG(ncB)*-tag→*bsAb(ncAncB)*+
(*MHCFcRP*)$_2$-tag

2/3-*IgG(ncA)*-tag+2/3-*IgG(conB)*-tag→*bsAb(ncA-conB)*+(*MHCFcRP*)$_2$-tag

See Example 21.

C) Elimination of Fc-Region Interchain Disulfide Bonds and of the Reduction Step Heavy chain interchain disulfide bonds stabilize antibodies and define the flexibility of the Fab arms that are connected to the hinge. Exchange approaches of hinge-region comprising starting antibodies require the reduction of these disulfides before or during the exchange reaction as well as removal of the reducing agents upon completion of the exchange reaction (see Examples 3 and 7). It can be desired for some approaches and facilitate downstream processing of exchange products to avoid such a reduction step.

Thus, herein is reported as another aspect of the current invention an exchange reaction of starting molecules that have a hinge region but do not have interchain hinge region disulfide bonds.

To exemplify this 2/3-IgGs in which all disulfide bonds in the Fc-region have been eliminated have been produced. It has been found that such disulfide-depleted 2/3-IgGs can be produced and purified in an effective manner even without these interchain disulfide bonds (see FIG. 15). When using such disulfide-depleted 2/3-IgGs as starting molecules in the method according to the current invention reduction of the starting molecules and removal of reducing agents after the exchange reaction can be omitted. Thereby an improved procedure for generating bsAbs is provided (less processing steps and less side-products). The bsAbs produced from these disulfide-depleted 2/3-IgGs are functional and stable, held together by non-covalent Fc-Fc interactions without interchain disulfide bonds (see FIGS. 16 and 17).

Thus, removal of Fc-Fc/hinge-region interchain disulfide bonds eliminates the necessity of the reduction step to initiate the exchange reaction. The resulting bsAbs are functional bispecific molecules, held together by non-covalent Fc-Fc interactions without Fc-region interchain disulfide bonds. Elimination of Fc-Fc interchain disulfides, thus, allows for corresponding Fc-region mismatch driven exchange reactions without the need for reduction and re-oxidation, i.e. under physiological conditions. This facilitates preparation and (high-throughput) screening procedures.

In one embodiment the hinge region is disulfide-bond-free. The disulfide-bond-free hinge region comprises serine residues in place of the cysteine residues in the sequence of SEQ ID NO: 32. The reaction is efficient with or without hinge region disulfide bonds (see FIG. 24, ELISA according to example 3 or 12).

Beside the removal of the disulfide bonds in addition the hinge region can be shortened. By using such modified hinge regions bispecific antibodies can be obtained that provide for different distances between the individual binding sites (see FIG. 25). Thus, in one embodiment the hinge region has the amino acid sequence of SEQ ID NO: 31 (HTCPXCP, X=S or P), or SEQ ID NO: 85 (HTSPXSP, X=S or P), or SEQ ID NO: 86 (HTPAPE; CPXC of SEQ ID NO. 31 has been deleted).

See Examples 10, 11, 18 and 19.

It has been found that the assembly-concentration of the 2/3-IgGs has an influence on the efficiency of the chain exchange reaction and thereby the amount of bispecific antibody, which is formed. In one embodiment to ensure efficient chain-exchange reaction the concentration of the 2/3-IgGs is at least 0.1 µM, i.e. 0.1 µM or higher (up to 1 M), in one preferred embodiment 1 M or higher.

See Example 20 and FIG. 30.

In one preferred embodiment the starting multimers are mixed at an equimolar concentration.

D) Fc-Region Variants

In certain embodiments, one or more further amino acid modifications may be introduced into the Fc-region of a 2/3-IgG provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates a 2/3-IgG variant that possesses some but not all effector functions, which make it a desirable candidate for applications in which the half-life in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the 2/3-IgG lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g., Hellstrom, I. et al., Proc. Natl. Acad. Sci. USA 83

(1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006:1759-1769).

2/3-IgGs comprising Fc-regions with reduced effector function include those with substitution of one or more of Fc-region residues 238, 265, 269, 270, 297, 327 and 329 (U.S. Pat. No. 6,737,056). Such Fc-region mutants include Fc-region mutants with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain 2/3-IgGs comprise Fc-region variants with improved or diminished binding to FcRs (see, e.g., U.S. Pat. No. 6,737,056; WO 2004/056312, and Shields, R. L. et al., J. Biol. Chem. 276 (2001) 6591-6604).

In certain embodiments, a 2/3-IgG comprises an Fc-region variant with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

In one embodiment of all aspects the 2/3-IgG comprises (all positions according to EU index of Kabat)

i) an Fc-region of the human IgG1 subclass with the mutations P329G, L234A and L235A in both Fc-region polypeptides, or ii) an Fc-region of the human IgG4 subclass with the mutations P329G, S228P and L235E in both Fc-region polypeptides, or iii) an Fc-region of the human IgG1 subclass with the mutations P329G, L234A, L235A, I253A, H310A, and H435A in both Fc-region polypeptides, or with the mutations P329G, L234A, L235A, H310A, H433A, and Y436A in both Fc-region polypeptides, or iv) a heterodimeric Fc-region of the human IgG1 subclass whereof both Fc-region polypeptides comprise the mutations P329G, L234A and L235A and
 a) one Fc-region polypeptide comprises the mutation T366W, and the other Fc-region polypeptide comprises the mutations T366S, L368A and Y407V, or
 b) one Fc-region polypeptide comprises the mutations T366W and Y349C, and the other Fc-region polypeptide comprises the mutations T366S, L368A, Y407V, and S354C, or
 c) one Fc-region polypeptide comprises the mutations T366W and S354C, and the other Fc-region polypeptide comprises the mutations T366S, L368A, Y407V and Y349C,
 or v) a heterodimeric Fc-region of the human IgG4 subclass whereof both Fc-region polypeptides comprise the mutations P329G, S228P and L235E and
 a) one Fc-region polypeptide comprises the mutation T366W, and the other Fc-region polypeptide comprises the mutations T366S, L368A and Y407V, or
 b) one Fc-region polypeptide comprises the mutations T366W and Y349C, and the other Fc-region polypeptide comprises the mutations T366S, L368A, Y407V, and S354C, or
 c) one Fc-region polypeptide comprises the mutations T366W and S354C, and the other Fc-region polypeptide comprises the mutations T366S, L368A, Y407V and Y349C,
 or vi) a combination of one of i), ii), and iii) with one of iv), and v).

In one embodiment of all aspects as reported herein, a 2/3-IgG comprising a CH3 domain, comprises an additional C-terminal glycine-lysine dipeptide (G446 and K447, numbering according to Kabat EU index). In one embodiment of all aspects as reported herein, a 2/3-IgG comprising a CH3 domain comprises an additional C-terminal glycine residue (G446, numbering according to Kabat EU index).

The 2/3-IgG as reported herein comprises in one embodiment an Fc-region characterized by being of human subclass IgG1 with mutations PVA236, L234A/L235A, and/or GLPSS331 (numbering according to EU index of Kabat), or of subclass IgG4. In a further embodiment, the 2/3-IgG is characterized by comprising an Fc-region being of any IgG class, in one embodiment being of the IgG1 or IgG4 subclass, containing at least one mutation in E233, L234, L235, G236, D270, N297, E318, K320, K322, A327, A330, P331 and/or P329 (numbering according to EU index of Kabat). It is further in one embodiment that the 2/3-IgG comprises an Fc-region of the human IgG4 subclass which contains the mutation S228P, or the mutations S228P and L235E (Angal, S., et al., Mol. Immunol. 30 (1993) 105-108) (numbering according to EU index of Kabat).

The C-terminus of the Fc-region polypeptides comprised in the 2/3-IgG as reported herein can be a complete C-terminus ending with the amino acid residues PGK. The C-terminus can be a shortened C-terminus in which one or two of the C-terminal amino acid residues have been removed. In one preferred embodiment the C-terminus is a shortened C-terminus ending with the amino acid residues PG.

E) Heterodimerization

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference.

Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain).

Thereby the heavy chain comprising one engineered CH3 domain heterodimerizes with another heavy chain comprising the CH3 domain, which is engineered in a complementary manner. For this embodiment, the CH3 domain of the first heavy chain Fc-region polypeptide and the CH3 domain of the second heavy chain Fc-region polypeptide are engineered in a complementary manner by amino acid substitutions, such that the first heavy chain Fc-region polypeptide and the second heavy chain Fc-region polypeptide heterodimerize, whereas the first heavy chain Fc-region polypeptide and the second heavy chain Fc-region polypeptide do no longer homodimerize (e.g. for steric reasons).

The different approaches for supporting heavy chain heterodimerization known in the art, that were cited and included above, are contemplated as different alternatives used in providing the heterodimeric/multimeric polypeptides (e.g. 2/3-IgGs) as reported herein.

The CH3 domains of the 2/3-IgG as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chain Fc-region polypeptides containing these two CH3 domains. Each of the two CH3 domains (of the two heavy chain Fc-region polypeptides) can be the "knob", while the other is the "hole". A disulfide bridge can be additionally introduced to further stabilize the heterodimers (Merchant, A. M., et al., Nature Biotech. 16 (1998) 677-681; Atwell, S., et al., J. Mol. Biol. 270 (1997) 26-35) and increase the yield in the exchange reaction according to the current invention.

In one preferred embodiment the 2/3-IgG as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into one of the CH3 domains of the knobs chains and a E356C mutation or a S354C mutation into one of the CH3 domain of the hole chains (in the exchange reaction according to the current invention two multimers are used as starting materials on only one of the CH3 domains of said multimers comprises the additional cysteine residue so that only in the exchanged product the additional disulfide bond is formed). Thus in a another preferred embodiment, the 2/3-IgG as reported herein comprises the Y349C and T366W mutations in one of the CH3 domains of the first multimer and the E356C, T366S, L368A and Y407V mutations the respective complementary CH3 domain of the second multimer; or the 2/3-IgG as reported herein comprises the Y349C and T366W mutations in one of the CH3 domains of the first multimer and the S354C, T366S, L368A and Y407V mutations in the respective complementary CH3 domain of the second multimer (the additional Y349C mutation in one CH3 domain and the additional E356C or S354C mutation in the corresponding CH3 domain forming a interchain disulfide bridge) (numbering according to Kabat EU index).

But also other knobs-in-holes technologies as described in EP 1 870 459 A1, can be used alternatively or additionally. In one embodiment the 2/3-IgG as reported herein comprises the R409D and K370E mutations in the CH3 domain of the "knobs chain" and the D399K and E357K mutations in the CH3 domain of the "hole-chain" (numbering according to Kabat EU index).

In one embodiment the 2/3-IgG as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the 2/3-IgG as reported herein comprises the Y349C and T366W mutations in one of the CH3 domains and the S354C, T366S, L368A and Y407V mutations in the complementary CH3 domain, or the 2/3-IgG as reported herein comprises the Y349C and T366W mutations in one of the CH3 domains and the S354C, T366S, L368A and Y407V mutations in the complementary CH3 domain and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a 2/3-IgG to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a 2/3-IgG as reported herein.

In one embodiment of a 2/3-IgG as reported herein the approach described in EP 1 870 459 A1 is used to support heterodimerization of the first heavy chain and the second heavy chain of the 2/3-IgG. This approach is based on the introduction of charged amino acids with opposite charges at specific amino acid positions in the CH3/CH3-domain-interface between both, the first and the second heavy chain.

Accordingly, this embodiment relates to a 2/3-IgG as reported herein, wherein in the tertiary structure of the multimer the CH3 domain of the first heavy chain Fc-region polypeptide and the CH3 domain of the second heavy chain Fc-region polypeptide form an interface that is located between the respective CH3 domains, wherein the respective amino acid sequences of the CH3 domain of the first heavy chain Fc-region polypeptide and the CH3 domain of the second heavy chain Fc-region polypeptide each comprise a set of amino acids that is located within said interface in the tertiary structure of the 2/3-IgG, wherein from the set of amino acids that is located in the interface in the CH3 domain of one heavy chain Fc-region polypeptide a first amino acid is substituted by a positively charged amino acid and from the set of amino acids that is located in the interface in the CH3 domain of the other heavy chain Fc-region polypeptide a second amino acid is substituted by a negatively charged amino acid. The 2/3-IgG according to this embodiment is herein also referred to as "CH3 (+/−)-engineered 2/3-IgG" (wherein the abbreviation "+/−" stands for the oppositely charged amino acids that were introduced in the respective CH3 domains).

In one embodiment of said CH3 (+/−)-engineered 2/3-IgG as reported herein the positively charged amino acid is selected from K, R and H, and the negatively charged amino acid is selected from E or D.

In one embodiment of said CH3 (+/−)-engineered 2/3-IgG as reported herein the positively charged amino acid is selected from K and R, and the negatively charged amino acid is selected from E or D.

In one embodiment of said CH3 (+/−)-engineered 2/3-IgG as reported herein the positively charged amino acid is K, and the negatively charged amino acid is E.

In one embodiment of said CH3 (+/−)-engineered 2/3-IgG as reported herein in the CH3 domain of one heavy chain the amino acid R at position 409 is substituted by D and the amino acid K at position 370 is substituted by E, and in the CH3 domain of the other heavy chain the amino acid D at position 399 is substituted by K and the amino acid E at position 357 is substituted by K (numbering according to Kabat EU index).

In one embodiment of a 2/3-IgG as reported herein the approach described in WO 2013/157953 is used to support heterodimerization of the first heavy chain Fc-region polypeptide and the second heavy chain Fc-region polypeptide of the 2/3-IgG. In one embodiment of said 2/3-IgG as reported herein, in the CH3 domain of one heavy chain Fc-region polypeptide the amino acid T at position 366 is substituted by K, and in the CH3 domain of the other heavy chain Fc-region polypeptide the amino acid L at position 351 is substituted by D (numbering according to Kabat EU index). In another embodiment of said 2/3-IgG as reported herein, in the CH3 domain of one heavy chain Fc-region polypeptide the amino acid T at position 366 is substituted by K and the amino acid L at position 351 is substituted by K, and in the CH3 domain of the other heavy chain Fc-region polypeptide the amino acid L at position 351 is substituted by D (numbering according to Kabat EU index).

In another embodiment of said 2/3-IgG as reported herein, in the CH3 domain of one heavy chain Fc-region polypeptide the amino acid T at position 366 is substituted by K and the amino acid L at position 351 is substituted by K, and in the CH3 domain of the other heavy chain Fc-region polypeptide the amino acid L at position 351 is substituted by D (numbering according to Kabat EU index). Additionally, at least one of the following substitutions is comprised in the CH3 domain of the other heavy chain Fc-region polypeptide: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a 2/3-IgG as reported herein the approach described in WO 2012/058768 is used to support heterodimerization of the first Fc-region polypeptide and the second Fc-region polypeptide of the 2/3-IgG. In one embodiment of said 2/3-IgG as reported herein, in the CH3 domain of one heavy chain Fc-region polypeptide the amino acid L at position 351 is substituted by Y and the amino acid Y at position 407 is substituted by A, and in the CH3 domain of the other heavy chain Fc-region polypeptide the amino acid T at position 366 is substituted by A and the amino acid K at position 409 is substituted by F (numbering according to Kabat EU index). In another embodiment, in addition to the aforementioned substitutions, in the CH3 domain of the other heavy chain Fc-region polypeptide at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another embodiment of said 2/3-IgG as reported herein (engineered according to WO 2012/058768), in the CH3 domain of one heavy chain Fc-region polypeptide the amino acid L at position 351 is substituted by Y and the amino acid Y at position 407 is substituted by A, and in the CH3 domain of the other heavy chain Fc-region polypeptide the amino acid T at position 366 is substituted by V and the amino acid K at position 409 is substituted by F (numbering according to Kabat EU index). In another embodiment of said 2/3-IgG as reported herein, in the CH3 domain of one heavy chain Fc-region polypeptide the amino acid Y at position 407 is substituted by A, and in the CH3 domain of the other heavy chain Fc-region polypeptide the amino acid T at position 366 is substituted by A and the amino acid K at position 409 is substituted by F (numbering according to Kabat EU index). In said last aforementioned embodiment, in the CH3 domain of said other heavy chain Fc-region polypeptide the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a 2/3-IgG as reported herein the approach described in WO 2011/143545 is used to support heterodimerization of the first Fc-region polypeptide and the second Fc-region polypeptide of the 2/3-IgG. In one embodiment of said 2/3-IgG as reported herein, amino acid modifications in the CH3 domains of both heavy chain Fc-region polypeptides are introduced at positions 368 and/or 409 (numbering according to Kabat EU index).

In one embodiment of a 2/3-IgG as reported herein the approach described in WO 2011/090762 is used to support heterodimerization of the first Fc-region polypeptide and the second Fc-region polypeptide of the 2/3-IgG. WO 2011/090762 relates to amino acid modifications according to the "knob-into-hole" technology. In one embodiment of said CH3 (KiH)-engineered 2/3-IgG as reported herein, in the CH3 domain of one heavy chain Fc-region polypeptide the amino acid T at position 366 is substituted by W, and in the CH3 domain of the other heavy chain Fc-region polypeptide the amino acid Y at position 407 is substituted by A (numbering according to Kabat EU index). In another embodiment of said CH3 (KiH)-engineered 2/3-IgG as reported herein, in the CH3 domain of one heavy chain Fc-region polypeptide the amino acid T at position 366 is substituted by Y, and in the CH3 domain of the other heavy chain Fc-region polypeptide the amino acid Y at position 407 is substituted by T (numbering according to Kabat EU index).

In one embodiment of a 2/3-IgG as reported herein, which is of IgG2 isotype, the approach described in WO 2011/090762 is used to support heterodimerization of the first heavy chain Fc-region polypeptide and the second heavy chain Fc-region polypeptide of the 2/3-IgG.

In one embodiment of a 2/3-IgG as reported herein, the approach described in WO 2007/147901 is used to support heterodimerization of the first Fc-region polypeptide and the second Fc-region polypeptide of the 2/3-IgG. In one embodiment of said 2/3-IgG as reported herein, in the CH3 domain of one heavy chain Fc-region polypeptide the amino acid K at position 253 is substituted by E, the amino acid D at position 282 is substituted by K and the amino acid K at position 322 is substituted by D, and in the CH3 domain of the other heavy chain Fc-region polypeptide the amino acid D at position 239 is substituted by K, the amino acid E at position 240 is substituted by K and the amino acid K at position 292 is substituted by D (numbering according to Kabat EU index).

In one embodiment of a 2/3-IgG as reported herein, the approach described in WO 2007/110205 is used to support heterodimerization of the first polypeptide and the second polypeptide of the 2/3-IgG.

In one embodiment of all aspects as reported herein, the 2/3-IgG has a constant domain structure of an IgG type antibody. In one further embodiment of all aspects as reported herein, the 2/3-IgG is characterized in that said 2/3-IgG comprises an Fc-region of human subclass IgG1, or of human subclass IgG1 with the mutations L234A and L235A and optionally P329G. In one further embodiment of all aspects as reported herein, the 2/3-IgG is characterized in that said 2/3-IgG comprises an Fc-region of human subclass IgG2. In one further embodiment of all aspects as reported herein, the 2/3-IgG is characterized in that said 2/3-IgG comprises an Fc-region of human subclass IgG3. In one further embodiment of all aspects as reported herein, the 2/3-IgG is characterized in that said 2/3-IgG comprises an Fc-region of human subclass IgG4 or, of human subclass IgG4 with the additional mutation S228P and L235E and optionally P329G.

In one embodiment of all aspects the 2/3-IgG comprises a first Fc-region polypeptide and a second Fc-region polypeptide wherein
i) the first and the second Fc-region polypeptide comprise the mutation Y436A, or
ii) the first and the second Fc-region polypeptide comprise the mutations I253A, H310A and H435A, or
iii) the first and the second Fc-region polypeptide comprise the mutations H310A, H433A and Y436A, or
iv) the first and the second Fc-region polypeptide comprise the mutations L251D, L314D and L432D, or
v) the first Fc-region polypeptide comprises the mutation Y436A and the second Fc-region polypeptide comprises
  a) the mutations I253A, H310A and H435A, or
  b) the mutations H310A, H433A and Y436A, or
  c) the mutations L251D, L314D and L432D,
or
vi) the first Fc-region polypeptide comprises the mutations I253A, H310A and H435A and the second Fc-region polypeptide comprises
  a) the mutations H310A, H433A and Y436A, or
  b) the mutations L251D, L314D and L432D, or
vii) the first Fc-region polypeptide comprises the mutations H310A, H433A and Y436A and the second Fc-region polypeptide comprises
  a) the mutations L251D, L314D and L432D.

III. Exemplary Sets of Embodiments of the Invention

1st Exemplary Set of Embodiments of the Invention:
1. A method for producing a multimeric polypeptide comprising the following steps:
  incubating
    a first multimeric polypeptide comprising a first polypeptide and a second polypeptide both comprising an immunoglobulin G CH3 domain,
      wherein i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
      wherein the first polypeptide comprises at least one functional binding site or at least a part of a binding site,
      wherein the second polypeptide comprises in the CH3 domain a first perturbing mutation, whereby the first polypeptide comprises the respective immunoglobulin G wild-type amino acid residue(s) in its amino acid sequence at the amino acid position(s) interacting in the respective wild-type immunoglobulin G with the amino acid residue at the first perturbing mutation,
      wherein the first polypeptide and the second polypeptide are a dimer,
    and
    a second multimeric polypeptide comprising a third polypeptide and a fourth polypeptide both comprising an immunoglobulin G CH3 domain,
      wherein i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole,
wherein the fourth polypeptide comprises at least one functional binding site or at least a part of a binding site,
wherein the third polypeptide comprises in the CH3 domain a second perturbing mutation, whereby the fourth polypeptide comprises the respective immunoglobulin G wild-type amino acid residue(s) in its amino acid sequence at the amino acid position(s) interacting in the respective wild-type immunoglobulin G with the amino acid residue at the second perturbing mutation,
wherein the second perturbing mutation is at a different position then the first perturbing mutation,
wherein the third polypeptide and the fourth polypeptide are a dimer,
wherein the first perturbing mutation in the second polypeptide and the second perturbing mutation in the third polypeptide result in an attractive interaction when the second polypeptide and the third polypeptide form a heterodimer,
and
recovering the binder comprising the first polypeptide and the fourth polypeptide and thereby producing the (multispecific) binder.

2. The method according to embodiment 1, wherein the first to fourth polypeptide each comprise in N- to C-terminal direction a CH2 domain derived from an IgG1 CH2 domain and a CH3 domain derived from an IgG1 CH3 domain.

3. The method according to any one of embodiments 1 to 2, wherein the first to fourth polypeptide each comprise in N- to C-terminal direction i) independently of each other either the amino acid sequence DKTHTCPPC (SEQ ID NO: 65) or the amino acid sequence DKTH-TSPPS (SEQ ID NO: 66), ii) a CH2 domain derived from an IgG1 CH2 domain, and iii) a CH3 domain derived from an IgG1 CH3 domain.

4. The method according to any one of embodiments 1 to 3, wherein i) the first and the fourth polypeptide each further comprise a CH1 domain derived from an IgG1 CH1 domain and a variable domain, or ii) wherein the first or the fourth polypeptide comprise a CH1 domain derived from an IgG1 CH1 domain and the other polypeptide comprises a domain derived from a light chain constant domain and each polypeptide further comprises a variable domain.

5. The method according to embodiment 4, wherein the variable domain of the first polypeptide is a heavy chain variable domain and the variable domain of the fourth polypeptide is a light chain variable domain or vice versa and these domains form a binding site when the first and the fourth polypeptide form a 6. The method according to any one of embodiments 1 to 4, wherein the first and fourth polypeptide are independently of each other selected from the group of polypeptide comprising in N- to C-terminal direction
i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a scFv, optionally a peptidic linker, a hinge region of SEQ ID NO: 65 or 66, a CH2 domain derived from a human IgG1 CH2 domain, and a CH3 domain derived from a human IgG1 CH3 domain,
v) a scFab, optionally a peptidic linker, a hinge region of SEQ ID NO: 65 or 66, a CH2 domain derived from a human IgG1 CH2 domain, and a CH3 domain derived from a human IgG1 CH3 domain,
vi) a hinge region of SEQ ID NO: 65 or 66, a CH2 domain derived from a human IgG1 CH2 domain, a CH3 domain derived from a human IgG1 CH3 domain, optionally a peptidic linker, and a scFv,
vii) a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain,
ix) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain,
x) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv,
xi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
xii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain,
xiii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain,
xiv) a first heavy chain variable domain, a human IgG1 CH1 domain, a hinge region of SEQ ID NO: 65 or 66, a CH2 domain derived from a human IgG1 CH2 domain, a CH3 domain derived from a human IgG1

CH3 domain, optionally a peptidic linker, a second heavy chain variable domain, and a human kappa or lambda light chain constant domain, xv) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xvi) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target.

7. The method according to any one of embodiments 1 to 6, wherein the first and the second binder further comprise an antibody light chain.

8. The method according to any one of embodiments 1 to 7, wherein the the first binder comprises as first polypeptide a polypeptide selected from the group of polypeptides comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second a human IgG1 CH1 domain, v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 human IgG1 CH1 domain, and a second heavy chain variable domain, vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the mutation knob or the mutations hole, and as second polypeptide a polypeptide selected from the group of polypeptides comprising in N- to C-terminal direction a hinge region of SEQ ID NO: 65 or 66, a CH2 domain derived from a human IgG1 CH2 domain, and a CH3 domain derived from a human IgG1 CH3 domain, comprising the mutation knob if the first polypeptide comprises the mutations hole, or the mutations hole if the first polypeptide comprises the mutation knob, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the human immunoglobulin IgG1 wild-type amino acid residue(s) in its amino acid sequence at the amino acid position(s) interacting in the wild-type immunoglobulin IgG1 with the amino acid residue at the perturbing mutation, wherein the first polypeptide and the second polypeptide are a dimer, and a third polypeptide comprising a light chain variable domain and a light chain constant domain, wherein the third polypeptide is covalently bound to the first polypeptide by a disulfide bond, and the second binder comprises as fourth polypeptide a polypeptide selected from the group of polypeptide comprising in N- to C-terminal direction a hinge region of SEQ ID NO: 65 or 66, a CH2 domain derived from an human IgG1 CH2 domain, and a CH3 domain derived from a human IgG1 CH3 domain, comprising the mutation knob if the second polypeptide comprises the mutations hole, or the mutations hole if the second polypeptide comprises the mutation knob, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357E, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the fifth polypeptide comprises the human IgG1 wild-type amino acid residue(s) in its amino acid sequence at the amino acid position(s) interacting in a wild-type IgG1 with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain and a second heavy chain variable domain, vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the mutation knob if the fourth polypeptide comprises the mutations hole, or the mutations hole if the fourth polypeptide comprises the mutation knob, wherein the fourth polypeptide and the fifth polypeptide are a dimer, and
a sixth polypeptide comprising a light chain variable domain and a light chain constant domain,
wherein the sixth polypeptide is covalently bound to the fourth polypeptide by a disulfide bond.

9. The method according to any one of embodiments 1 to 8, wherein the incubation step is in the presence of a reducing agent.

10. The method according to any one of embodiments 1 to 9, wherein i) the second polypeptide and the third polypeptide, or ii) the second polypeptide and the fifth polypeptide further comprise a (C-terminal) tag.

11. The method according to embodiment 10, wherein the tag has the amino acid sequence HHHHHH (SEQ ID NO: 67) or HHHHHHHH (SEQ ID NO: 68) and the recovering is by chromatography on a metal (nickel) chelate affinity chromatography column.

12. A method for identifying a binder combination comprising the steps of
producing a multitude of binders by subjecting each combination of a first binder selected from a first multitude of binders and a second binder selected from a second multitude of binders to the method according to any one of embodiments 1 to 11,
measuring individually the simultaneous binding of each binder of the produced multitude of binders to at least two antigens in an ELISA assay, and
selecting a binder from the multitude of binders based on the result of the ELISA and thereby identifying a binder combination.

13. A multimeric polypeptide comprising a first polypeptide and a second polypeptide
wherein both polypeptides comprise a human immunoglobulin CH3 domain,
wherein i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
wherein the first polypeptide comprises at least one functional binding site or at least a part of a binding site,
wherein the second polypeptide comprises in the CH3 domain at least one perturbing mutation, whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation,
wherein the first polypeptide and the second polypeptide are a dimer.

14. The multimeric polypeptide according to embodiment 13, wherein
the first polypeptide is a polypeptide selected from the group of polypeptides comprising in N- to C-terminal direction
i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain,
v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain,
vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv,
vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain,
ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain,
x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain,
xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and
xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, and comprises the mutation knob or the mutations hole, and the second polypeptide is a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain comprising the mutation knob or the mutations hole, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the respective immunoglobulin IgG1 wild-type amino acid residue(s) in its amino acid sequence at the amino acid position(s) interacting in the respective wild-type immunoglobulin IgG1 with the amino acid residue at the perturbing mutation, and a third polypeptide comprising a light chain variable domain and a light chain constant domain covalently bound to the first polypeptide by a disulfide bond.

15. A composition comprising a first heterotrimeric polypeptide comprising as first polypeptide a polypeptide selected from the group of polypeptides comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the mutation knob or the mutations hole, and
as second polypeptide a polypeptide selected from the group of polypeptides comprising in N- to C-terminal direction
a hinge region of SEQ ID NO: 65 or 66, a CH2 domain derived from a human IgG1 CH2 domain, a CH3 domain derived from a human IgG1 CH3 domain,
comprising the mutation knob if the first polypeptide comprises the mutations hole, or the mutations hole if the first polypeptide comprises the mutation knob,
comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the first polypeptide comprises the respective immunoglobulin IgG1 wild-type amino acid residue(s) in its amino acid sequence at the amino acid position(s) interacting in the respective wild-type immunoglobulin IgG1 with the amino acid residue at the perturbing mutation,
and
as third polypeptide comprising a light chain variable domain and a light chain constant domain covalently bound to the first polypeptide by a disulfide bond,
and
a second heterotrimeric polypeptide comprising
as fourth polypeptide a polypeptide selected from the group of polypeptide comprising in N- to C-terminal direction
a hinge region of SEQ ID NO: 65 or 66, a CH2 domain derived from a human IgG1 CH2 domain, and a CH3 domain derived from a human IgG1 CH3 domain,
comprising the mutation knob if the second polypeptide of the first heterotrimer comprises the mutations hole, or the mutations hole if the second polypeptide of the first heterotrimer comprises the mutation knob,
comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, C349Y, S366T, A368L, V407Y, C354S, and W366T, whereby the fifth polypeptide comprises the respective immunoglobulin IgG1 wild-type amino acid residue(s) in its amino acid sequence at the amino acid position (s) interacting in the respective wild-type immunoglobulin IgG1 with the amino acid residue at the perturbing mutation, whereby the perturbing mutation in the fourth polypeptide is at a different position as the perturbing mutation in the second polypeptide,
and
as fifth polypeptide a polypeptide selected from the group of polypeptides comprising in N- to C-terminal direction
i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain,
v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain,
vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv,
vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain,
ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the mutation knob if the first (fourth) polypeptide comprises the mutations hole, or the mutations hole if the first (fourth) polypeptide comprises the mutation knob, and as sixth polypeptide a polypeptide comprising a light chain variable domain and a light chain constant domain covalently bound to the fourth polypeptide by a disulfide bond, wherein i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole, wherein the second and the fourth polypeptide do not comprise perturbing mutations at the same position.

2nd Exemplary Set of Embodiments of the Invention:

1. A method for producing a multimeric polypeptide comprising the following steps:
incubating
a first multimeric starting polypeptide comprising a first polypeptide and a second polypeptide both comprising an immunoglobulin G CH3 domain, wherein
a-1) i) the CH3 domain of the first polypeptide comprises the mutations knob-cys and the CH3 domain of the second polypeptide comprises the mutations hole, or ii) the CH3 domain of the first polypeptide comprises the mutations hole-cys and the CH3 domain of the second polypeptide comprises the mutation knob, b-1) the first polypeptide comprises at least one functional binding site or at least a part of a binding site, c-1) the second polypeptide comprises in the CH3 domain a first perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the first perturbing mutation, d-1) the first polypeptide and the second polypeptide form a dimer, and a second multimeric starting polypeptide comprising a third polypeptide and a fourth polypeptide both comprising an immunoglobulin G CH3 domain, wherein a-2) i) the CH3 domain of the third polypeptide comprises the mutation knob and the CH3 domain of the fourth polypeptide comprises the mutations hole-cys, or ii) the CH3 domain of the third polypeptide comprises the mutations hole and the CH3 domain of the fourth polypeptide comprises the mutations knob-cys, whereby i) in case the first polypeptide comprises the mutations hole-cys the fourth polypeptide comprises the mutations knob-cys, or ii) in case the first polypeptide comprises the mutations knob-cys the fourth polypeptide comprises the mutations hole-cys, b-2) the fourth polypeptide comprises at least one functional binding site or at least a part of a binding site, c-2) the third polypeptide comprises in the CH3 domain a second perturbing mutation that is different from the mutations under a-2), whereby the fourth polypeptide comprises the respective immunoglobulin G wild-type amino acid residue (s) in its amino acid sequence at the amino acid position(s) interacting in the respective wild-type immunoglobulin G with the amino acid residue at the second perturbing mutation, d-2) the second perturbing mutation is at a different position than the first perturbing mutation, e-2) the third polypeptide and the fourth polypeptide form a dimer, f-2) the first perturbing mutation in the second polypeptide and the second perturbing mutation in the third polypeptide (are designed to) result in an attractive interaction when the second polypeptide and the third polypeptide form a heterodimer, and recovering the multimeric polypeptide comprising the first polypeptide and the fourth polypeptide and thereby producing the multimeric polypeptide, with the numbering according to Kabat EU index.

2. The method according to embodiment 1, wherein the first perturbing mutation is E357K, the first polypeptide comprises at position 370 the amino acid residue K, the second perturbing mutation is K370E, and the fourth polypeptide comprises at position 357 the amino acid residue E.

3. The method according to embodiment 1, wherein the first perturbing mutation is D356K, the first polypeptide comprises at position 439 the amino acid residue K, the second perturbing mutation is K439E, and the fourth polypeptide comprises at position 356 the amino acid residue D.

4. A method for producing a multimeric polypeptide comprising the following steps:
incubating
a first multimeric starting polypeptide comprising a first polypeptide and a second polypeptide both comprising an immunoglobulin G CH3 domain, wherein
a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
b-1) the first polypeptide comprises at least one functional binding site or at least a part of a binding site,
c-1) the second polypeptide comprises in the CH3 domain a first perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the first perturbing mutation,
d-1) the first polypeptide and the second polypeptide form a dimer,
e-1) the first polypeptide comprises in the hinge region the amino acid sequence HTSPPSP (SEQ ID NO: 92) in place of the IgG1 wild-type amino acid sequence HTCPPCP (SEQ ID NO: 31),
and
a second multimeric starting polypeptide comprising a third polypeptide and a fourth polypeptide both comprising an immunoglobulin G CH3 domain, wherein
a-2) i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole,
b-2) the fourth polypeptide comprises at least one functional binding site or at least a part of a binding site,
c-2) the third polypeptide comprises in the CH3 domain a second perturbing mutation that is different from the mutations under a-2), whereby the fourth polypeptide comprises the respective immunoglobulin G wild-type amino acid residue(s) in its amino acid sequence at the amino acid position(s) interacting in the respective wild-type immunoglobulin G with the amino acid residue at the second perturbing mutation,
d-2) the second perturbing mutation is at a different position than the first perturbing mutation,
e-2) the third polypeptide and the fourth polypeptide form a dimer,
f-2) the first perturbing mutation in the second polypeptide and the second perturbing mutation in the third polypeptide result in an attractive interaction when the second polypeptide and the third polypeptide form a heterodimer,
g-2) the second polypeptide comprises the amino acid sequence HTSPPSP (SEQ ID NO: 92) in place of the IgG1 wild-type hinge region amino acid sequence HTCPPCP (SEQ ID NO: 31) or the amino acid sequence HTPAPE (SEQ ID NO: 86) in place of the IgG1 wild-type hinge region sequence HTCPPCPAPE (SEQ ID NO: 90),
and
recovering the multimeric polypeptide comprising the first polypeptide and the fourth polypeptide and thereby producing the multimeric polypeptide, with the numbering according to Kabat EU index.

5. The method according to embodiment 4, wherein the first perturbing mutation is E357K, the first polypeptide comprises at position 370 the amino acid residue K, the second perturbing mutation is K370E, and the fourth polypeptide comprises at position 357 the amino acid residue E.

6. The method according to embodiment 4, wherein the first perturbing mutation is D356K, the first polypeptide comprises at position 439 the amino acid residue K, the second perturbing mutation is K439E, and the fourth polypeptide comprises at position 356 the amino acid residue D.

7. A method for producing a multimeric polypeptide comprising the following steps:
incubating
a first multimeric starting polypeptide comprising a first polypeptide and a second polypeptide both comprising an immunoglobulin G CH3 domain, wherein
a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
b-1) the first polypeptide comprises at least one functional binding site or at least a part of a binding site,
c-1) the second polypeptide comprises in the CH3 domain the mutation E357K as first perturbing mutation and the first polypeptide comprises at position 370 the amino acid residue K,
d-1) the first polypeptide and the second polypeptide form a dimer,
and
a second multimeric starting polypeptide comprising a third polypeptide and a fourth polypeptide both comprising an immunoglobulin G CH3 domain, wherein
a-2) i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole,
b-2) the fourth polypeptide comprises at least one functional binding site or at least a part of a binding site,
c-2) the third polypeptide comprises in the CH3 domain the mutation K370E as second perturbing mutation and the fourth polypeptide comprises at position 357 the amino acid residue E,
d-2) the third polypeptide and the fourth polypeptide form a dimer,
f-2) the first perturbing mutation in the second polypeptide and the second perturbing mutation in the third polypeptide result in an attractive interaction when the second polypeptide and the third polypeptide form a heterodimer, and
recovering the multimeric polypeptide comprising the first polypeptide and the fourth polypeptide and thereby producing the multimeric polypeptide,
with the numbering according to Kabat EU index.

8. A method for producing a multimeric polypeptide comprising the following steps:
incubating
a first multimeric starting polypeptide comprising a first polypeptide and a second polypeptide both comprising an immunoglobulin G CH3 domain, wherein
a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
b-1) the first polypeptide comprises at least one functional binding site or at least a part of a binding site,
c-1) the second polypeptide comprises in the CH3 domain the mutation D356K as first perturbing mutation and the first polypeptide comprises at position 439 the amino acid residue K,
d-1) the first polypeptide and the second polypeptide form a dimer, and
a second multimeric starting polypeptide comprising a third polypeptide and a fourth polypeptide both comprising an immunoglobulin G CH3 domain, wherein
a-2) i) the CH3 domain of the third polypeptide comprises the mutation knob and the CH3 domain of the fourth polypeptide comprises the mutations hole, or ii) the CH3 domain of the third polypeptide comprises the mutations hole and the CH3 domain of the fourth polypeptide comprises the mutation knob, whereby i) in case the first polypeptide comprises the mutations hole the fourth polypeptide comprises the mutation knob, or ii) in case the first polypeptide comprises the mutation knob the fourth polypeptide comprises the mutations hole,
b-2) the fourth polypeptide comprises at least one functional binding site or at least a part of a binding site,
c-2) the third polypeptide comprises in the CH3 domain the mutation K439E as second perturbing mutation and the fourth polypeptide comprises at position 356 the amino acid residue D,
d-2) the third polypeptide and the fourth polypeptide form a dimer,
e-2) the first perturbing mutation in the second polypeptide and the second perturbing mutation in the third polypeptide result in an attractive interaction when the second polypeptide and the third polypeptide form a heterodimer, and
recovering the multimeric polypeptide comprising the first polypeptide and the fourth polypeptide and thereby producing the multimeric polypeptide,
with the numbering according to Kabat EU index.

9. The method according to any one of embodiments 4 to 8, wherein the first polypeptide comprises the mutation knob, the second polypeptide comprises the mutations hole, the third polypeptide comprises the mutation knob, and the fourth polypeptide comprises the mutations hole.

10. The method according to any one of embodiments 4 to 8, wherein the first polypeptide comprises the mutations knob-cys, the second polypeptide comprises the mutations hole, the third polypeptide comprises the mutation knob, and the fourth polypeptide comprises the mutations hole-cys.

11. The method according to any one of embodiments 1 to 10, wherein the first to fourth polypeptide each comprise in N- to C-terminal direction an IgG1 CH2 domain and an IgG1 CH3 domain.

12. The method according to any one of embodiments 1 to 3 and 7 to 11, wherein the first to fourth polypeptide each comprise in N- to C-terminal direction i) independently of each other either the amino acid sequence DKTHTCPPC (SEQ ID NO: 65) or the amino acid sequence DKTHTSPPS (SEQ ID NO: 66) or the amino acid sequence DKTHT (SEQ ID NO: 91), ii) an IgG1 CH2 domain, and iii) an IgG1 CH3 domain.

13. The method according to any one of embodiments 1 to 12, wherein i) the first and the fourth polypeptide each further comprise an IgG1 CH1 domain and a variable domain, or ii) wherein the first or the fourth polypeptide comprise an IgG1 CH1 domain and the other polypeptide comprises a light chain constant domain and each polypeptide further comprises a variable domain.

14. The method according to embodiment 13, wherein the variable domain of the first polypeptide is a heavy chain variable domain and the variable domain of the fourth polypeptide is a light chain variable domain or vice versa, and these domains form a binding site when the first and the fourth polypeptide form a 15. The method according to any one of embodiments 1 to 14, wherein the first and fourth polypeptide are independently of each other selected from
A) the group of polypeptide comprising in N- to C-terminal direction
i) a heavy chain variable domain, a human IgG1 CH1 domain, a hinge region of SEQ ID NO: 65 or 66 or 91, a CH2 domain derived from a human IgG1 CH2 domain, and a CH3 domain derived from a human IgG1 CH3 domain,
ii) a hinge region of SEQ ID NO: 65 or 66 or 91, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66 or 91, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a scFv, optionally a peptidic linker, a hinge region of SEQ ID NO: 65 or 66 or 91, a CH2 domain derived from a human IgG1 CH2 domain, and a CH3 domain derived from a human IgG1 CH3 domain,
v) a scFab, optionally a peptidic linker, a hinge region of SEQ ID NO: 65 or 66 or 91, a CH2 domain derived from a human IgG1 CH2 domain, and a CH3 domain derived from a human IgG1 CH3 domain,
vi) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv,
vii) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab,
viii) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a second human IgG1 CH1 domain,
ix) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a second heavy chain variable domain,
x) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv,
xi) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab,
xii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a light chain variable domain,
xiii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a light chain variable domain, and a second human IgG1 CH1 domain,
xiv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a human kappa or lambda light chain constant domain,
xv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and
xvi) a first part of the binding domain, optionally a first peptidic linker, a hinge region of SEQ ID NO: 65 or 66 or 91, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, or

B)

the group of polypeptide comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a scFv, optionally a peptidic linker, a hinge region of SEQ ID NO: 65 or 66, a CH2 domain derived from a human IgG1 CH2 domain, and a CH3 domain derived from a human IgG1 CH3 domain,
v) a scFab, optionally a peptidic linker, a hinge region of SEQ ID NO: 65 or 66, a CH2 domain derived from a human IgG1 CH2 domain, and a CH3 domain derived from a human IgG1 CH3 domain,
vi) a hinge region of SEQ ID NO: 65 or 66, a CH2 domain derived from a human IgG1 CH2 domain, a CH3 domain derived from a human IgG1 CH3 domain, optionally a peptidic linker, and a scFv,
vii) a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain,
ix) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, x) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, xi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, xii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, xiii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, xiv) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, XV) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xvi) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target.

16. The method according to any one of embodiments 1 to 15, wherein the first and the second multimeric starting polypeptide further comprise an antibody light chain.

17. The method according to any one of embodiments 1 to 16, wherein the

A)

the first multimeric starting polypeptide comprises as first polypeptide a polypeptide selected from the group of polypeptides comprising in N- to C-terminal direction i) a heavy chain variable domain, a human IgG1 CH1 domain, a hinge region of SEQ ID NO: 65 or 66 or 91, a human IgG1 CH2 domain, and a human IgG1 CH3 domain, ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain, iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second a human IgG1 CH1 domain, v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab, viii) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, comprising the mutation knob or the mutations hole,
and
as second polypeptide a polypeptide selected from the group of polypeptides comprising in N- to C-terminal direction
a hinge region of SEQ ID NO: 65 or 66 or 91, a human IgG1 CH2 domain, and a human IgG1 CH3 domain,
comprising the mutation knob if the first polypeptide comprises the mutations hole, or the mutations hole if the first polypeptide comprises the mutation knob,
comprising the perturbing mutation D356K, E357K, K370E, or K439E, whereby the first polypeptide comprises the human immunoglobulin IgG1 wild-type amino acid residue(s) in its amino acid sequence at the amino acid position(s) interacting in the wild-type immunoglobulin IgG1 with the amino acid residue at the perturbing mutation,
wherein the first polypeptide and the second polypeptide form a dimer, and
a third polypeptide comprising a light chain variable domain and a light chain constant domain,
wherein the third polypeptide is covalently bound to the first polypeptide by a disulfide bond,
and
the second multimeric starting polypeptide comprises
as fourth polypeptide a polypeptide selected from the group of polypeptide comprising in N- to C-terminal direction
a hinge region of SEQ ID NO: 65 or 66 or 91, a human IgG1 CH2 domain, and a human IgG1 CH3 domain,
comprising the mutation knob if the second polypeptide comprises the mutations hole, or the mutations hole if the second polypeptide comprises the mutation knob,
comprising the second perturbing mutation D356K, E357K, K370E, or K439E, whereby the fifth polypeptide comprises the human IgG1 wild-type amino acid residue(s) in its amino acid sequence at the amino acid position(s) interacting in a wild-type IgG1 with the amino acid residue at the perturbing mutation, whereby the perturbing mutation in the fourth polypeptide is at a different position as the perturbing mutation in the second polypeptide,
and
as fifth polypeptide a polypeptide selected from the group of polypeptides comprising in N- to C-terminal direction
i) a heavy chain variable domain, a human IgG1 CH1 domain, a hinge region of SEQ ID NO: 65 or 66 or 91, a human IgG1 CH2 domain, and a human IgG1 CH3 domain,
ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain,
iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second human IgG1 CH1 domain,
v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain and a second heavy chain variable domain,
vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv,
vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab,
viii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain,
ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain,
x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain,
xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, and
xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target,
comprising the mutation knob if the fourth polypeptide comprises the mutations hole, or the mutations hole if the fourth polypeptide comprises the mutation knob,
wherein the fourth polypeptide and the fifth polypeptide form a dimer, and
a sixth polypeptide comprising a light chain variable domain and a light chain constant domain,
wherein the sixth polypeptide is covalently bound to the fourth polypeptide by a disulfide bond,
or
B)
the first multimeric starting polypeptide comprises
as first polypeptide a polypeptide selected from the group of polypeptides comprising in N- to C-terminal direction
i) a heavy chain variable domain, a human IgG1 CH1 domain, a hinge region of SEQ ID NO: 65 or 66, a human IgG1 CH2 domain, and a human IgG1 CH3 domain,
ii) a hinge region of SEQ ID NO: 65 or 66, a human IgG1 CH2 domain, a human IgG1 CH3 domain, optionally a peptidic linker, a heavy chain variable domain, and a human IgG1 CH1 domain,
iii) a hinge region of SEQ ID NO: 65 or 66, a human IgG1 CH2 domain, a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second heavy chain variable domain, and a second a human IgG1 CH1 domain,
v) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second human IgG1 CH1 domain, and a second heavy chain variable domain,
vi) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFv,
vii) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFab,
viii) a heavy chain variable domain, a first human IgG1 CH1 domain, a hinge region of SEQ ID NO: 65 or 66, a human IgG1 CH2 domain, a human IgG1 CH3 domain, optionally a peptidic linker, a second human IgG1 CH1 domain, and a light chain variable domain,
ix) a heavy chain variable domain, a first human IgG1 CH1 domain, a hinge region of SEQ ID NO: 65 or 66, a human IgG1 CH2 domain, a human IgG1 CH3 domain, optionally a peptidic linker, a light chain variable domain, and a second human IgG1 CH1 domain,
x) a first heavy chain variable domain, a human IgG1 CH1 domain, a hinge region of SEQ ID NO: 65 or 66, a human IgG1 CH2 domain, a human IgG1 CH3 domain, optionally a peptidic linker, a second heavy chain variable domain, and a human kappa or lambda light chain constant domain,
xi) a first heavy chain variable domain, a human IgG1 CH1 domain, a hinge region of SEQ ID NO: 65 or 66, a human IgG1 CH2 domain, a human IgG1 CH3 domain, optionally a peptidic linker, a human kappa or lambda light chain constant domain, and a second heavy chain variable domain,
xii) a first part of the binding domain, optionally a first peptidic linker, a hinge region of SEQ ID NO: 65 or 66, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target,
comprising the mutation knob or the mutations hole,
and
as second polypeptide a polypeptide selected from the group of polypeptides comprising in N- to C-terminal direction
a hinge region of SEQ ID NO: 65 or 66, a human IgG1 CH2 domain, and a human IgG1 CH3 domain,
comprising the mutation knob if the first polypeptide comprises the mutations hole, or the mutations hole if the first polypeptide comprises the mutation knob,
comprising the perturbing mutation D356K, E357K, K370E, or K439E, whereby the first polypeptide comprises the human immunoglobulin IgG1 wild-type amino acid residue(s) in its amino acid sequence at the amino acid position(s) interacting in the wild-type immunoglobulin IgG1 with the amino acid residue at the perturbing mutation,
wherein the first polypeptide and the second polypeptide form a dimer, and
a third polypeptide comprising a light chain variable domain and a light chain constant domain,
wherein the third polypeptide is covalently bound to the first polypeptide by a disulfide bond,
and
the second multimeric starting polypeptide comprises
as fourth polypeptide a polypeptide selected from the group of polypeptide comprising in N- to C-terminal direction
a hinge region of SEQ ID NO: 65 or 66, a human IgG1 CH2 domain, and a human IgG1 CH3 domain,
comprising the mutation knob if the second polypeptide comprises the mutations hole, or the mutations hole if the second polypeptide comprises the mutation knob,
comprising the second perturbing mutation D356K, E357K, K370E, or K439E, whereby the fifth polypeptide comprises the human IgG1 wild-type amino acid residue(s) in its amino acid sequence at the amino acid position(s) interacting in a wild-type IgG1 with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction i) a heavy chain variable domain, a human IgG1 CH1 domain, a hinge region of SEQ ID NO: 65 or 66, a human IgG1 CH2 domain, and a human IgG1 CH3 domain, ii) a hinge region of SEQ ID NO: 65 or 66, a human IgG1 CH2 domain, a human IgG1 CH3 domain, optionally a peptidic linker, a heavy chain variable domain, and a human IgG1 CH1 domain, iii) a hinge region of SEQ ID NO: 65 or 66, a human IgG1 CH2 domain, a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second human IgG1 CH1 domain and a second heavy chain variable domain, vi) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFab, viii) a heavy chain variable domain, a human IgG1 CH1 domain, a hinge region of SEQ ID NO: 65 or 66, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a human IgG1 CH2 domain, a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, comprising the mutation knob if the fourth polypeptide comprises the mutations hole, or the mutations hole if the fourth polypeptide comprises the mutation knob, wherein the fourth polypeptide and the fifth polypeptide form a dimer, and a sixth polypeptide comprising a light chain variable domain and a light chain constant domain, wherein the sixth polypeptide is covalently bound to the fourth polypeptide by a disulfide bond.

18. The method according to any one of embodiments 1 to 17, wherein the incubation step is in the presence of a reducing agent.

19. The method according to any one of embodiments 1 to 18, wherein i) the second polypeptide and the third polypeptide, or ii) the second polypeptide and the fifth polypeptide further comprise a (C-terminal) tag.

20. The method according to embodiment 19, wherein
i) the tag has the amino acid sequence HHHHHH (SEQ ID NO: 67) or HHHHHHHH (SEQ ID NO: 68) and the recovering is by chromatography on a metal (nickel) chelate affinity chromatography column, or
ii) the tag has the amino acid sequence EPEA (SEQ ID NO: 87) and the recovering is by chromatography on a C-tag affinity chromatography column.

21. A method for identifying a multimeric polypeptide combination comprising the steps of
a) producing a multitude of multimeric polypeptides by subjecting each combination of a first multimeric starting polypeptide selected from a first multitude of multimeric polypeptide and a second multimeric starting polypeptide selected from a second multitude of multimeric polypeptides according to the method according to any one of embodiments 1 to 20,
b) measuring individually the simultaneous binding of each multimeric polypeptide of the multitude of multimeric polypeptides produced in step a) to at least two antigens in a binding assay, and
c) selecting a multimeric polypeptide from the multitude of multimeric polypeptides based on the result of the binding and thereby identifying a multimeric polypeptide combination.

22. The method according to embodiment 21, wherein the binding assay is an ELISA or an SPR method.

23. A multimeric polypeptide comprising mutation knob
a) a first polypeptide and a second polypeptide both comprising an immunoglobulin G CH3 domain, wherein
a-1) i) the CH3 domain of the first polypeptide comprises the mutations knob-cys and the CH3 domain of the second polypeptide comprises the mutations hole, or ii) the CH3 domain of the first polypeptide comprises the mutations hole-cys and the CH3 domain of the second polypeptide comprises the mutation knob, a-2) the first polypeptide comprises at least one functional binding site or at least a part of a binding site, a-3) the second polypeptide comprises in the CH3 domain a perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation, a-4) the first polypeptide and the second polypeptide form a dimer, or b) a first polypeptide and a second polypeptide both comprising an immunoglobulin G CH3 domain, wherein b-1) i) the CH3 domain of the second polypeptide comprises the mutation knob and the CH3 domain of the first polypeptide comprises the mutations hole-cys, or ii) the CH3 domain of the second polypeptide comprises the mutations hole and the CH3 domain of the first polypeptide comprises the mutations knob-cys, b-2) the first polypeptide comprises at least one functional binding site or at least a part of a binding site, b-3) the second polypeptide comprises in the CH3 domain a perturbing mutation that is different from the mutations under b-1), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation, b-4) the first polypeptide and the second polypeptide form a dimer, with the numbering according to Kabat EU index.

24. The multimeric polypeptide according to embodiment 23, wherein the perturbing mutation is E357K and the first polypeptide comprises at position 370 the amino acid residue K; or the perturbing mutation is K370E, and the first polypeptide comprises at position 357 the amino acid residue E.

25. The multimeric polypeptide according to embodiment 23, wherein the first perturbing mutation is D356K and the first polypeptide comprises at position 439 the amino acid residue K; or the perturbing mutation is K439E and the first polypeptide comprises at position 356 the amino acid residue D.

26. A multimeric polypeptide comprising a) a first polypeptide and a second polypeptide both comprising an immunoglobulin G CH3 domain, wherein a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob, a-2) the first polypeptide comprises at least one functional binding site or at least a part of a binding site, a-3) the second polypeptide comprises in the CH3 domain a perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation, a-4) the first polypeptide and the second polypeptide form a dimer, a-5) the first and/or second polypeptide comprises t the amino acid sequence HTSPPSP (SEQ ID NO: 92) in place of the IgG1 wild-type hinge region amino acid sequence HTCPPCP (SEQ ID NO: 31) or the amino acid sequence HTPAPE (SEQ ID NO: 86) in place of the IgG1 wild-type hinge region sequence HTCPPCPAPE (SEQ ID NO: 90), or b) a first polypeptide and a second polypeptide both comprising an immunoglobulin G CH3 domain, wherein b-1) i) the CH3 domain of the second polypeptide comprises the mutation knob and the CH3 domain of the first polypeptide comprises the mutations hole, or ii) the CH3 domain of the second polypeptide comprises the mutations hole and the CH3 domain of the first polypeptide comprises the mutation knob, b-2) the first polypeptide comprises at least one functional binding site or at least a part of a binding site, b-3) the second polypeptide comprises in the CH3 domain a perturbing mutation that is different from the mutations under a-2), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation, b-4) the first polypeptide and the second polypeptide form a dimer, b-5) the first and/or second polypeptide comprises the amino acid sequence HTSPPSP (SEQ ID NO: 92) in place of the IgG1 wild-type hinge region amino acid sequence HTCPPCP (SEQ ID NO: 31) or the amino acid sequence HTPAPE (SEQ ID NO: 86) in place of the IgG1 wild-type hinge region sequence HTCPPCPAPE (SEQ ID NO: 90).

27. The multimeric polypeptide according to embodiment 26, wherein the perturbing mutation is E357K and the first polypeptide comprises at position 370 the amino acid residue K; or the perturbing mutation is K370E, and the first polypeptide comprises at position 357 the amino acid residue E.

28. The multimeric polypeptide according to embodiment 26, wherein the first perturbing mutation is D356K and the first polypeptide comprises at position 439 the amino acid residue K; or the perturbing mutation is K439E and the first polypeptide comprises at position 356 the amino acid residue D.

29. A multimeric polypeptide comprising
a) a first polypeptide and a second polypeptide both comprising an immunoglobulin G CH3 domain, wherein
a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
a-2) the first polypeptide comprises at least one functional binding site or at least a part of a binding site,
a-3) the second polypeptide comprises in the CH3 domain the mutation E357K and the first polypeptide comprises at position 370 the amino acid residue K,
a-4) the first polypeptide and the second polypeptide form a dimer,
or
b) a first polypeptide and a second polypeptide both comprising an immunoglobulin G CH3 domain, wherein
b-1) i) the CH3 domain of the second polypeptide comprises the mutation knob and the CH3 domain of the first polypeptide comprises the mutations hole, or ii) the CH3 domain of the second polypeptide comprises the mutations hole and the CH3 domain of the first polypeptide comprises the mutation knob,
b-2) the first polypeptide comprises at least one functional binding site or at least a part of a binding site,
b-3) the second polypeptide comprises in the CH3 domain the mutation K370E and the first polypeptide comprises at position 357 the amino acid residue E,
b-4) the first polypeptide and the second polypeptide form a dimer,
with the numbering according to Kabat EU index.

30. A multimeric polypeptide comprising
a) a first polypeptide and a second polypeptide both comprising an immunoglobulin G CH3 domain, wherein
a-1) i) the CH3 domain of the first polypeptide comprises the mutation knob and the CH3 domain of the second polypeptide comprises the mutations hole, or ii) the CH3 domain of the first polypeptide comprises the mutations hole and the CH3 domain of the second polypeptide comprises the mutation knob,
a-2) the first polypeptide comprises at least one functional binding site or at least a part of a binding site,
a-3) the second polypeptide comprises in the CH3 domain the mutation D356K and the first polypeptide comprises at position 439 the amino acid residue K,
a-4) the first polypeptide and the second polypeptide form a dimer,
or
b) a first polypeptide and a second polypeptide both comprising an immunoglobulin G CH3 domain, wherein
b-1) i) the CH3 domain of the second polypeptide comprises the mutation knob and the CH3 domain of the first polypeptide comprises the mutations hole, or ii) the CH3 domain of the second polypeptide comprises the mutations hole and the CH3 domain of the first polypeptide comprises the mutation knob,
b-2) the first polypeptide comprises at least one functional binding site or at least a part of a binding site,
b-3) the second polypeptide comprises in the CH3 domain the mutation K439E and the first polypeptide comprises at position 356 the amino acid residue D,
b-4) the third polypeptide and the fourth polypeptide form a dimer,
with the numbering according to Kabat EU index.

31. The multimeric polypeptide according to any one of embodiments 26 to 30, wherein the first polypeptide comprises the mutation knob and the second polypeptide comprises the mutations hole; or the second polypeptide comprises the mutation knob and the first polypeptide comprises the mutations hole.

32. The multimeric polypeptide according to any one of embodiments 26 to 30, wherein the first polypeptide comprises the mutations knob-cys and the second polypeptide comprises the mutations hole; or the second polypeptide comprises the mutation knob and the first polypeptide comprises the mutations hole-cys.

33. The multimeric polypeptide according to any one of embodiments 29 to 32, wherein the first polypeptide and/or the second polypeptide comprises the amino acid sequence HTSPPSP (SEQ ID NO: 92) in place of the IgG1 wild-type hinge region amino acid sequence HTCPPCP (SEQ ID NO: 31) or the amino acid sequence HTPAPE (SEQ ID NO: 86) in place of the IgG1 wild-type hinge region sequence HTCPPCPAPE (SEQ ID NO: 90)

34. The multimeric polypeptide according to any one of embodiments 22 to 33, wherein
A)
the first polypeptide is a polypeptide selected from the group of polypeptides comprising in N- to C-terminal direction
i) a heavy chain variable domain, a human IgG1 CH1 domain, a hinge region of SEQ ID NO: 65 or 66 or 91, a human IgG1 CH2 domain, and a human IgG1 CH3 domain,
ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain,
iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second human IgG1 CH1 domain,
v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab, viii) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, and the second polypeptide is a polypeptide selected from the group of polypeptides comprising in N- to C-terminal direction a hinge region of SEQ ID NO: 65 or 66 or 91, a human IgG1 CH2 domain, a human IgG1 CH3 domain, comprising the mutation knob if the first polypeptide comprises the mutations hole, or the mutations hole if the first polypeptide comprises the mutation knob, comprising a mutation selected from the mutations D356K, E357K, K370E, or K439E, whereby the first polypeptide comprises the respective immunoglobulin IgG1 wild-type amino acid residue(s) in its amino acid sequence at the amino acid position(s) interacting in the respective wild-type immunoglobulin IgG1 with the amino acid residue at the perturbing mutation, and a third polypeptide comprising a light chain variable domain and a light chain constant domain covalently bound to the first polypeptide by a disulfide bond;

or

B) the first polypeptide is a polypeptide selected from the group of polypeptides comprising in N- to C-terminal direction i) a heavy chain variable domain, a human IgG1 CH1 domain, a hinge region of SEQ ID NO: 65 or 66, a human IgG1 CH2 domain, and a human IgG1 CH3 domain, ii) a hinge region of SEQ ID NO: 65 or 66, a human IgG1 CH2 domain, a human IgG1 CH3 domain, optionally a peptidic linker, a heavy chain variable domain, and a human IgG1 CH1 domain, iii) a hinge region of SEQ ID NO: 65 or 66, a human IgG1 CH2 domain, a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a human IgG1 CH2 domain, a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66, a human IgG1 CH2 domain, a human IgG1 CH3 domain, optionally a peptidic linker, and a scFab, viii) a heavy chain variable domain, a first human IgG1 CH1 domain, a hinge region of SEQ ID NO: 65 or 66, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a human IgG1 CH2 domain, a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, and the second polypeptide is a polypeptide selected from the group of polypeptides comprising in N- to C-terminal direction a hinge region of SEQ ID NO: 65 or 66, a human IgG1 CH2 domain, a human IgG1 CH3 domain, comprising the mutation knob if the first polypeptide comprises the mutations hole, or the mutations hole if the first polypeptide comprises the mutation knob, comprising a mutation selected from the mutations D356K, E357K, K370E, or K439E, whereby the first polypeptide comprises the respective immunoglobulin IgG1 wild-type amino acid residue(s) in its amino acid sequence at the amino acid position(s) interacting in the respective wild-type immunoglobulin IgG1 with the amino acid residue at the perturbing mutation, and a third polypeptide comprising a light chain variable domain and a light chain constant domain covalently bound to the first polypeptide by a disulfide bond.

3rd Exemplary Set of Embodiments of the Invention:

1. A method for producing a polypeptide comprising the following steps:

incubating a first multimer comprising a first polypeptide comprising i) an immunoglobulin G CH3 domain, and ii) at least one functional binding site or a part thereof, and a second polypeptide comprising an immunoglobulin G CH3 domain, wherein a-1) the CH3 domain of the first polypeptide comprises the mutations knob-cys and the CH3 domain of the second polypeptide comprises the mutations hole, or the CH3 domain of the first polypeptide comprises the mutations hole-cys and the CH3 domain of the second polypeptide comprises the mutation knob, a-2) the second polypeptide comprises in the CH3 domain a first mutation that is different from the mutations under a-1), and the introduction of the first mutation increases the CH3-CH3 binding free energy of the first multimer, and a second multimer comprising a third polypeptide comprising i) an immunoglobulin G CH3 domain, and a fourth polypeptide comprising i) an immunoglobulin G CH3 domain, and ii) at least one functional binding site or a part thereof wherein b-1) in case the first polypeptide comprises the mutations hole-cys the fourth polypeptide comprises the mutations knob-cys and the third polypeptide comprises the mutations hole, or in case the first polypeptide comprises the mutations knob-cys the fourth polypeptide comprises the mutations hole-cys and the third polypeptide comprises the mutations knob, b-2) the third polypeptide comprises in the CH3 domain a second mutation that is different from the mutations under a-1), a-2) and b-1), and the introduction of the second mutation increases the CH3-CH3 binding free energy of the second multimer, to form a third multimer comprising the second and the third polypeptide and a fourth multimer comprising the first and the fourth polypeptide, and recovering the fourth multimer and thereby producing the polypeptide.

2. The method according to embodiment 1, wherein the mutation under a-2) is E357K, the first polypeptide comprises at position 370 the amino acid residue K, the mutation under b-2) is K370E, and the fourth polypeptide comprises at position 357 the amino acid residue E with the positions numbered according to Kabat EU index.

3. The method according to embodiment 1, wherein the mutation under a-2) is D356K, the first polypeptide comprises at position 439 the amino acid residue K, the mutation under b-2) is K439E, and the fourth polypeptide comprises at position 356 the amino acid residue D with the positions numbered according to Kabat EU index.

4. The method according to any one of embodiments 1 to 3, wherein the first and/or second polypeptide comprises the amino acid sequence HTSPPSP (SEQ ID NO: 92) or the amino acid sequence HTPAPE (SEQ ID NO: 86), and wherein the fourth and/or third polypeptide comprises the amino acid sequence HTSPPSP (SEQ ID NO: 92) or the amino acid sequence HTPAPE (SEQ ID NO: 86).

5. A method for producing a polypeptide comprising the following steps:

incubating a first multimer comprising a first polypeptide comprising i) an immunoglobulin G CH3 domain, and ii) at least one functional binding site or a part thereof, and a second polypeptide comprising an immunoglobulin G CH3 domain, wherein a-1) the CH3 domain of the first polypeptide comprises the mutation knob and the CH3 domain of the second polypeptide comprises the mutations hole, or the CH3 domain of the first polypeptide comprises the mutations hole and the CH3 domain of the second polypeptide comprises the mutation knob, a-2) the second polypeptide comprises in the CH3 domain a first mutation that is different from the mutations under a-1), and the introduction of the first mutation increases the CH3-CH3 binding free energy of the first multimer, a-3) the first and/or second polypeptide comprises the amino acid sequence HTSPPSP (SEQ ID NO: 92) or the amino acid sequence HTPAPE (SEQ ID NO: 86), and a second multimer comprising a third polypeptide comprising i) an immunoglobulin G CH3 domain, and a fourth polypeptide comprising i) an immunoglobulin G CH3 domain, and ii) at least one functional binding site or a part thereof wherein b-1) in case the first polypeptide comprises the mutations hole the fourth polypeptide comprises the mutations knob and the third polypeptide comprises the mutations hole, or in case the first polypeptide comprises the mutations knob the fourth polypeptide comprises the mutations hole and the third polypeptide comprises the mutations knob, b-2) the third polypeptide comprises in the CH3 domain a mutation that is different from the mutations under a-1), a-2) and b-1), and the introduction of the second mutation increases the CH3-CH3 binding free energy of the second multimer, b-3) the fourth and/or third polypeptide comprises the amino acid sequence HTSPPSP (SEQ ID NO: 92) or the amino acid sequence HTPAPE (SEQ ID NO: 86), to form a third multimer comprising the second and the third polypeptide and a fourth multimer comprising the first and the fourth polypeptide, and recovering the fourth multimer and thereby producing the polypeptide.

6. The method according to embodiment 5, wherein the mutation under a-2) is E357K, the first polypeptide comprises at position 370 the amino acid residue K, the mutation under b-2) is K370E, and the fourth polypeptide comprises at position 357 the amino acid residue E with the positions numbered according to Kabat EU index.

7. The method according to embodiment 5, wherein the mutation under a-2) is D356K, the first polypeptide comprises at position 439 the amino acid residue K, the mutation under b-2) is K439E, and the fourth polypeptide comprises at position 356 the amino acid residue D with the positions numbered according to Kabat EU index.

8. The method according to any one of embodiments 1 or 5, wherein the first polypeptide comprises the respective immunoglobulin G wild-type amino acid residue(s) in the CH3 domain at the position(s) interacting with the mutated amino acid residue in the second polypeptide, and wherein the fourth polypeptide comprises the respective immunoglobulin G wild-type amino acid residue(s) in the CH3 domain at the position(s) interacting with the mutated amino acid residue in the third polypeptide.

9. A method for producing a polypeptide comprising the following steps:

incubating a first multimer comprising a first polypeptide comprising i) an immunoglobulin G CH3 domain, and ii) at least one functional binding site or a part thereof, and a second polypeptide comprising an immunoglobulin G CH3 domain, wherein a-1) the CH3 domain of the first polypeptide comprises the mutation knob and the CH3 domain of the second polypeptide comprises the mutations hole, or the CH3 domain of the first polypeptide comprises the mutations hole and the CH3 domain of the second polypeptide comprises the mutation knob, a-2) the first polypeptide comprises at position 370 the amino acid residue K and the second polypeptide comprises the mutation E357K, and a second multimer comprising a third polypeptide comprising i) an immunoglobulin G CH3 domain, and a fourth polypeptide comprising i) an immunoglobulin G CH3 domain, and ii) at least one functional binding site or a part thereof wherein b-1) in case the first polypeptide comprises the mutations hole the fourth polypeptide comprises the mutations knob and the third polypeptide comprises the mutations hole, or in case the first polypeptide comprises the mutations knob the fourth polypeptide comprises the mutations hole and the third polypeptide comprises the mutations knob, b-2) the third polypeptide comprises the mutation K370E and the fourth polypeptide comprises at position 357 the amino acid residue E, to form a third multimer comprising the second and the third polypeptide and a fourth multimer comprising the first and the fourth polypeptide, and recovering the fourth multimer and thereby producing the polypeptide, with the positions numbered according to Kabat EU index.

10. A method for producing a polypeptide comprising the following steps:

incubating a first multimer comprising a first polypeptide comprising i) an immunoglobulin G CH3 domain, and ii) at least one functional binding site or a part thereof, and a second polypeptide comprising an immunoglobulin G CH3 domain, wherein
- a-1) the CH3 domain of the first polypeptide comprises the mutation knob and the CH3 domain of the second polypeptide comprises the mutations hole,
  or
  the CH3 domain of the first polypeptide comprises the mutations hole and the CH3 domain of the second polypeptide comprises the mutation knob,
- a-2) the first polypeptide comprises at position 439 the amino acid residue K and the second polypeptide comprises the mutation D356K, and
a second multimer comprising
- a third polypeptide comprising
  - i) an immunoglobulin G CH3 domain,
  and
- a fourth polypeptide comprising
  - i) an immunoglobulin G CH3 domain, and
  - ii) at least one functional binding site or a part thereof wherein
- b-1) in case the first polypeptide comprises the mutations hole the fourth polypeptide comprises the mutations knob and the third polypeptide comprises the mutations hole,
  or
  in case the first polypeptide comprises the mutations knob the fourth polypeptide comprises the mutations hole and the third polypeptide comprises the mutations knob,
- b-2) the third polypeptide comprises the mutation K439E and the fourth polypeptide comprises at position 356 the amino acid residue D, to form a third multimer comprising the second and the third polypeptide
and a fourth multimer comprising the first and the fourth polypeptide, and
recovering the fourth multimer and thereby producing the polypeptide, with the positions numbered according to Kabat EU index.

11. The method according to any one of embodiments 1 to 10, wherein the CH3-CH3 binding free energy of a third multimer comprising the second polypeptide and the third polypeptide is lower than the CH3-CH3 binding free energy of the first multimer and/or the second multimer.

12. The method according to any one of embodiments 1 to 11, wherein the first polypeptide and the second polypeptide form a (isolatable) dimer, and the third polypeptide and the fourth polypeptide form a (isolatable) dimer.

13. The method according to any one of embodiments 4 to 12, wherein the first and/or second polypeptide comprise the amino acid sequence HTSPPSP (SEQ ID NO: 92) in place of the IgG wild-type hinge region amino acid sequence HTCPPCP (SEQ ID NO: 31), and/or wherein the first and/or second polypeptide comprise the amino acid sequence HTPAPE (SEQ ID NO: 86) in place of the IgG wild-type hinge region amino acid sequence HTCPPCPAPE (SEQ ID NO: 90), and/or wherein the third and/or fourth polypeptide comprise the amino acid sequence HTSPPSP (SEQ ID NO: 92) in place of the IgG wild-type hinge region amino acid sequence HTCPPCP (SEQ ID NO: 31), and/or wherein the third and/or fourth polypeptide comprise the amino acid sequence HTPAPE (SEQ ID NO: 86) in place of the IgG wild-type hinge region amino acid sequence HTCPPCPAPE (SEQ ID NO: 90)

14. The method according to any one of embodiments 5 to 13, wherein the first polypeptide comprises the mutation knob, the second polypeptide comprises the mutations hole, the third polypeptide comprises the mutation knob, and the fourth polypeptide comprises the mutations hole.

15. The method according to any one of embodiments 5 to 13, wherein the first polypeptide comprises the mutations knob-cys, the second polypeptide comprises the mutations hole, the third polypeptide comprises the mutation knob, and the fourth polypeptide comprises the mutations hole-cys.

16. The method according to any one of embodiments 1 to 15, wherein the first to fourth polypeptide each comprise in N- to C-terminal direction an IgG1 CH2 domain and an IgG1 CH3 domain.

17. The method according to any one of embodiments 1 to 16, wherein the first to fourth polypeptide each comprise in N- to C-terminal direction i) independently of each other either the amino acid sequence DKTH-TCPPC (SEQ ID NO: 65) or the amino acid sequence DKTHTSPPS (SEQ ID NO: 66) or the amino acid sequence DKTHT (SEQ ID NO: 91), ii) an IgG1 CH2 domain, and iii) an IgG1 CH3 domain.

18. The method according to any one of embodiments 1 to 17, wherein i) the first and the fourth polypeptide each further comprise an IgG1 CH1 domain and a variable domain, or ii) wherein the first or the fourth polypeptide comprise an IgG1 CH1 domain and the other polypeptide comprises a light chain constant domain and each polypeptide further comprises a variable domain.

19. The method according to embodiment 18, wherein the variable domain of the first polypeptide is a heavy chain variable domain and the variable domain of the fourth polypeptide is a light chain variable domain or vice versa, and these domains form a binding site in the polypeptide.

20. The method according to any one of embodiments 1 to 19, wherein the first and fourth polypeptide are independently of each other selected from the group of polypeptide comprising in N- to C-terminal direction
- i) a heavy chain variable domain, a human IgG1 CH1 domain, a hinge region of SEQ ID NO: 65 or 66 or 91, a CH2 domain derived from a human IgG1 CH2 domain, and a CH3 domain derived from a human IgG1 CH3 domain,
- ii) a hinge region of SEQ ID NO: 65 or 66 or 91, a CH2 domain derived from a human IgG1 CH2 domain, a CH3 domain derived from a human IgG1 CH3 domain, optionally a peptidic linker, a heavy chain variable domain, and a human IgG1 CH1 domain,
- iii) a hinge region of SEQ ID NO: 65 or 66 or 91, a CH2 domain derived from a human IgG1 CH2 domain, a CH3 domain derived from a human IgG1 CH3 domain, optionally a peptidic linker, a human IgG1 CH1 domain, and a heavy chain variable domain,
- iv) a scFv, optionally a peptidic linker, a hinge region of SEQ ID NO: 65 or 66 or 91, a CH2 domain derived from a human IgG1 CH2 domain, and a CH3 domain derived from a human IgG1 CH3 domain,
- v) a scFab, optionally a peptidic linker, a hinge region of SEQ ID NO: 65 or 66 or 91, a CH2 domain derived from a human IgG1 CH2 domain, and a CH3 domain derived from a human IgG1 CH3 domain, vi) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, vii) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, viii) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a second human IgG1 CH1 domain, ix) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a second heavy chain variable domain, x) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, xi) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, xii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a light chain variable domain, xiii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a light chain variable domain, and a second human IgG1 CH1 domain, xiv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xvi) a first part of the binding domain, optionally a first peptidic linker, a hinge region of SEQ ID NO: 65 or 66 or 91, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target.

21. The method according to any one of embodiments 1 to 20, wherein the first and the second multimer further comprise an antibody light chain that is associated with the first polypeptide and the fourth polypeptide, respectively.

22. The method according to any one of embodiments 1 to 21, wherein the the first multimer comprises
    as first polypeptide a polypeptide selected from the group of polypeptides comprising in N- to C-terminal direction
    i) a heavy chain variable domain, a human IgG1 CH1 domain, a hinge region of SEQ ID NO: 65 or 66 or 91, a human IgG1 CH2 domain, and a human IgG1 CH3 domain,
    ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain,
    iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain,
    iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second a human IgG1 CH1 domain,
    v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a second heavy chain variable domain,
    vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv,
    vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab,
    viii) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain,
    ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain,
    x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, comprising the mutation knob or the mutations hole, and as second polypeptide a polypeptide selected from the group of polypeptides comprising in N- to C-terminal direction a hinge region of SEQ ID NO: 65 or 66 or 91, a human IgG1 CH2 domain, and a human IgG1 CH3 domain, comprising the mutation knob if the first polypeptide comprises the mutations hole, or the mutations hole if the first polypeptide comprises the mutation knob, comprising the perturbing mutation D356K, E357K, K370E, or K439E, whereby the first polypeptide comprises the human immunoglobulin IgG1 wild-type amino acid residue(s) in its amino acid sequence at the amino acid position(s) interacting in the wild-type immunoglobulin IgG1 with the amino acid residue at the perturbing mutation, wherein the first polypeptide and the second polypeptide form a dimer, and a fifth polypeptide comprising a light chain variable domain and a light chain constant domain, wherein the third polypeptide is covalently bound to the first polypeptide by a disulfide bond, and the second multimer comprises as third polypeptide a polypeptide selected from the group of polypeptide comprising in N- to C-terminal direction a hinge region of SEQ ID NO: 65 or 66 or 91, a human IgG1 CH2 domain, and a human IgG1 CH3 domain, comprising the mutation knob if the second polypeptide comprises the mutations hole, or the mutations hole if the second polypeptide comprises the mutation knob, comprising the second perturbing mutation D356K, E357K, K370E, or K439E, whereby the fifth polypeptide comprises the human IgG1 wild-type amino acid residue(s) in its amino acid sequence at the amino acid position(s) interacting in a wild-type IgG1 with the amino acid residue at the perturbing mutation, whereby the perturbing mutation in the fourth polypeptide is at a different position as the perturbing mutation in the second polypeptide, and as fourth polypeptide a polypeptide selected from the group of polypeptides comprising in N- to C-terminal direction i) a heavy chain variable domain, a human IgG1 CH1 domain, a hinge region of SEQ ID NO: 65 or 66 or 91, a human IgG1 CH2 domain, and a human IgG1 CH3 domain, ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain, iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain and a second heavy chain variable domain, vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab, viii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target,
comprising the mutation knob if the fourth polypeptide comprises the mutations hole, or the mutations hole if the fourth polypeptide comprises the mutation knob,
wherein the fourth polypeptide and the fifth polypeptide form a dimer,
and
a sixth polypeptide comprising a light chain variable domain and a light chain constant domain,
wherein the sixth polypeptide is covalently bound to the fourth polypeptide by a disulfide bond.

23. The method according to any one of embodiments 1 to 3 and 9 to 12, wherein the incubation step is in the presence or the absence of a reducing agent.

24. The method according to any one of embodiments 4 to 8 and 13 to 22, wherein the incubation step is in the absence of a reducing agent.

25. The method according to any one of embodiments 1 to 24, wherein i) the second polypeptide and the third polypeptide further comprise a (C-terminal) tag.

26. The method according to embodiment 25, wherein
i) the tag has the amino acid sequence HHHHHH (SEQ ID NO: 67) or HHHHHHHH (SEQ ID NO: 68) and the recovering is by chromatography on a metal (nickel) chelate affinity chromatography column,
or
ii) the tag has the amino acid sequence EPEA (SEQ ID NO: 87) and the recovering is by chromatography on a C-tag affinity chromatography column.

27. A method for identifying a multispecific polypeptide comprising the steps of
a) producing a multitude of multispecific polypeptides by subjecting each combination of a first multimer selected from a first multitude of multimers specifically binding to a first target and a second multimer selected from a second multitude of multimer specifically binding to a second target (which is different from the first target) to a method according to any one of embodiments 1 to 26,
b) measuring individually for each member of the multitude of multispecific polypeptides produced in step a) the simultaneous binding to the two targets in a binding assay, and
c) selecting a multimeric polypeptide from the multitude of multimeric polypeptides based on the result of the binding assay and thereby identifying a multispecific polypeptide.

28. The method according to embodiment 27, wherein the binding assay is an ELISA or an SPR method.

29. An isolated multimeric polypeptide comprising
a) a first polypeptide and a second polypeptide both comprising an immunoglobulin G CH3 domain, wherein
a-1) i) the CH3 domain of the first polypeptide comprises the mutations knob-cys and the CH3 domain of the second polypeptide comprises the mutations hole, or ii) the CH3 domain of the first polypeptide comprises the mutations hole-cys and the CH3 domain of the second polypeptide comprises the mutation knob,
a-2) the first polypeptide comprises at least one functional binding site or at least a part of a binding site,
a-3) the second polypeptide comprises in the CH3 domain a perturbing mutation different from the mutations under a-1), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation,
a-4) the first polypeptide and the second polypeptide form a dimer,
or
b) a first polypeptide and a second polypeptide both comprising an immunoglobulin G CH3 domain, wherein
b-1) i) the CH3 domain of the second polypeptide comprises the mutation knob and the CH3 domain of the first polypeptide comprises the mutations hole-cys, or ii) the CH3 domain of the second polypeptide comprises the mutations hole and the CH3 domain of the first polypeptide comprises the mutations knob-cys,
b-2) the first polypeptide comprises at least one functional binding site or at least a part of a binding site,
b-3) the second polypeptide comprises in the CH3 domain a perturbing mutation that is different from the mutations under b-1), whereby the first polypeptide comprises the respective immunoglobulin G wild-type amino acid residue(s) in its amino acid sequence at the amino acid position(s) interacting in the respective wild-type immunoglobulin G with the amino acid residue at the perturbing mutation,
b-4) the first polypeptide and the second polypeptide form a dimer,
with the numbering according to Kabat EU index.

30. The multimeric polypeptide according to embodiment 29, wherein the perturbing mutation is E357K and the first polypeptide comprises at position 370 the amino acid residue K; or the perturbing mutation is K370E, and the first polypeptide comprises at position 357 the amino acid residue E.

31. The multimeric polypeptide according to embodiment 29, wherein the first perturbing mutation is D356K and the first polypeptide comprises at position 439 the amino acid residue K; or the perturbing mutation is K439E and the first polypeptide comprises at position 356 the amino acid residue D.

32. An isolated multimeric polypeptide comprising
a first polypeptide comprising
i) an immunoglobulin G CH3 domain,
and
ii) at least one functional binding site or a part thereof,
and
a second polypeptide comprising
an immunoglobulin G CH3 domain,
wherein
a-1) the CH3 domain of the first polypeptide comprises the mutations knob-cys and the CH3 domain of the second polypeptide comprises the mutations hole, or
the CH3 domain of the first polypeptide comprises the mutations hole-cys and the CH3 domain of the second polypeptide comprises the mutation knob,
a-2) the second polypeptide comprises in the CH3 domain a further mutation that is different from the mutations under a-1), and the introduction of the further mutation increases the CH3-CH3 binding free energy of the first multimer.

33. The isolated multimeric polypeptide according to embodiment 32, wherein the mutation under a-2) is E357K, and the first polypeptide comprises at position 370 the amino acid residue K; or wherein the mutation under a-2) is K370E, and the first polypeptide comprises at position 357 the amino acid residue E with the positions numbered according to Kabat EU index.

34. The isolated multimeric polypeptide according to embodiment 32, wherein the mutation under a-2) is D356K, the first polypeptide comprises at position 439 the amino acid residue K; or wherein the mutation under a-2) is K439E, and the first polypeptide comprises at position 356 the amino acid residue D with the positions numbered according to Kabat EU index.

35. The isolated multimeric polypeptide according to any one of embodiments 32 to 34, wherein the first and/or second polypeptide comprises the amino acid sequence HTSPPSP (SEQ ID NO: 92) or the amino acid sequence HTPAPE (SEQ ID NO: 86).

36. An isolated multimeric polypeptide comprising
a first polypeptide comprising
i) an immunoglobulin G CH3 domain, and
ii) at least one functional binding site or a part thereof,
and
a second polypeptide comprising
an immunoglobulin G CH3 domain,
wherein
a-1) the CH3 domain of the first polypeptide comprises the mutation knob and the CH3 domain of the second polypeptide comprises the mutations hole,
or
the CH3 domain of the first polypeptide comprises the mutations hole and the CH3 domain of the second polypeptide comprises the mutation knob,
a-2) the second polypeptide comprises in the CH3 domain a further mutation that is different from the mutations under a-1), and the introduction of the further mutation increases the CH3-CH3 binding free energy of the first multimer,
a-3) the first and/or second polypeptide comprises the amino acid sequence HTSPPSP (SEQ ID NO: 92) or the amino acid sequence HTPAPE (SEQ ID NO: 86).

37. The isolated multimeric polypeptide according to embodiment 36, wherein the mutation under a-2) is E357K, and the first polypeptide comprises at position 370 the amino acid residue K; or wherein the mutation under a-2) is K370E, and the first polypeptide comprises at position 357 the amino acid residue E with the positions numbered according to Kabat EU index.

38. The isolated multimeric polypeptide according to embodiment 36, wherein the mutation under a-2) is D356K, and the first polypeptide comprises at position 439 the amino acid residue K; or wherein the mutation under a-2) is K439E, and the first polypeptide comprises at position 356 the amino acid residue D with the positions numbered according to Kabat EU index.

39. The isolated multimeric polypeptide according to any one of embodiments 32 to 36, wherein the first polypeptide comprises the respective immunoglobulin G wild-type amino acid residue(s) in the CH3 domain at the position(s) interacting with the mutated amino acid residue in the second polypeptide.

40. An isolated multimeric polypeptide comprising
a first polypeptide comprising
i) an immunoglobulin G CH3 domain, and
ii) at least one functional binding site or a part thereof,
and
a second polypeptide comprising
an immunoglobulin G CH3 domain,
wherein
a-1) the CH3 domain of the first polypeptide comprises the mutation knob and the CH3 domain of the second polypeptide comprises the mutations hole,
or
the CH3 domain of the first polypeptide comprises the mutations hole and the CH3 domain of the second polypeptide comprises the mutation knob,
a-2) the first polypeptide comprises at position 370 the amino acid residue K and the second polypeptide comprises the mutation E357K,
or
the second polypeptide comprises the mutation K370E and the first polypeptide comprises at position 357 the amino acid residue E.

41. An isolated multimeric polypeptide comprising
a first polypeptide comprising
i) an immunoglobulin G CH3 domain, and
ii) at least one functional binding site or a part thereof,
and
a second polypeptide comprising
an immunoglobulin G CH3 domain,
wherein
a-1) the CH3 domain of the first polypeptide comprises the mutation knob and the CH3 domain of the second polypeptide comprises the mutations hole,
or
the CH3 domain of the first polypeptide comprises the mutations hole and the CH3 domain of the second polypeptide comprises the mutation knob,
a-2) the first polypeptide comprises at position 439 the amino acid residue K and the second polypeptide comprises the mutation D356K,
or
the second polypeptide comprises the mutation K439E and the first polypeptide comprises at position 356 the amino acid residue D.

42. The isolated multimeric polypeptide according to any one of embodiments 29 to 41, wherein the first polypeptide is selected from the group of polypeptide comprising in N- to C-terminal direction i) a heavy chain variable domain, a human IgG1 CH1 domain, a hinge region of SEQ ID NO: 65 or 66 or 91, a CH2 domain derived from a human IgG1 CH2 domain, and a CH3 domain derived from a human IgG1 CH3 domain, ii) a hinge region of SEQ ID NO: 65 or 66 or 91, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66 or 91, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a scFv, optionally a peptidic linker, a hinge region of SEQ ID NO: 65 or 66 or 91, a CH2 domain derived from a human IgG1 CH2 domain, and a CH3 domain derived from a human IgG1 CH3 domain, v) a scFab, optionally a peptidic linker, a hinge region of SEQ ID NO: 65 or 66 or 91, a CH2 domain derived from a human IgG1 CH2 domain, and a CH3 domain derived from a human IgG1 CH3 domain, vi) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, vii) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, viii) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a second human IgG1 CH1 domain, ix) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a second heavy chain variable domain, x) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, xi) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, xii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a light chain variable domain, xiii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a light chain variable domain, and a second human IgG1 CH1 domain, xiv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xvi) a first part of the binding domain, optionally a first peptidic linker, a hinge region of SEQ ID NO: 65 or 66 or 91, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target.

43. The isolated multimeric polypeptide according to any one of embodiments 29 to 42, further comprising an antibody light chain that is associated with the first polypeptide.

44. The isolated multimeric polypeptide according to embodiment 43, comprising as first polypeptide a polypeptide selected from the group of polypeptides comprising in N- to C-terminal direction i) a heavy chain variable domain, a human IgG1 CH1 domain, a hinge region of SEQ ID NO: 65 or 66 or 91, a human IgG1 CH2 domain, and a human IgG1 CH3 domain, ii) a hinge region of SEQ ID NO: 65 or 66 or 91, a human IgG1 CH2 domain, a human IgG1 CH3 domain, optionally a peptidic linker, a heavy chain variable domain, and a human IgG1 CH1 domain, iii) a hinge region of SEQ ID NO: 65 or 66 or 91, a human IgG1 CH2 domain, a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a second a human IgG1 CH1 domain, v) a first heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFv, vii) a heavy chain variable domain, a human IgG1 CH1 domain, a hinge region of SEQ ID NO: 65 or 66 or 91, a human IgG1 CH2 domain, a human IgG1 CH3 domain, optionally a peptidic linker, and a scFab, viii) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66 or 91, a human IgG1 CH2 domain, a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66 or 91, a human IgG1 CH2 domain, a human IgG1 CH3 domain, optionally a peptidic linker, a human kappa or lambda light chain constant domain, and a second heavy chain variable domain, xii) a first part of the binding domain, optionally a first peptidic linker, a hinge region of SEQ ID NO: 65 or 66 or 91, a human IgG1 CH2 domain, a human IgG1 CH3 domain, optionally a second peptidic linker, and a second part of the binding domain, wherein the first part of the binding domain and the second part of the binding domain form a functional binding site that specifically binds to a target, and as second polypeptide a polypeptide selected from the group of polypeptides comprising in N- to C-terminal direction a hinge region of SEQ ID NO: 65 or 66 or 91, a human IgG1 CH2 domain, and a human IgG1 CH3 domain, comprising the mutation knob if the first polypeptide comprises the mutations hole, or the mutations hole if the first polypeptide comprises the mutation knob, comprising the perturbing mutation D356K, E357K, K370E, or K439E, whereby the first polypeptide comprises the human immunoglobulin IgG1 wild-type amino acid residue(s) in its amino acid sequence at the amino acid position(s) interacting in the wild-type immunoglobulin IgG1 with the amino acid residue at the perturbing mutation, and as third polypeptide a polypeptide comprising a light chain variable domain and a light chain constant domain, wherein the third polypeptide is covalently bound to the first polypeptide by a disulfide bond.

45. The isolated multimeric polypeptide according to any one of embodiments 29 to 44, wherein the second polypeptide further comprise a (C-terminal) tag.

46. The isolated multimeric polypeptide according to embodiment 45, wherein i) the tag has the amino acid sequence HHHHHH (SEQ ID NO: 67) or HHHHHHHH (SEQ ID NO: 68), or ii) the tag has the amino acid sequence EPEA (SEQ ID NO: 87).

The following examples, sequences and figures are provided to aid the understanding of the present invention, the true scope of which is set forth in the appended claims.

It is understood that modifications can be made in the procedures set forth without departing from the spirit of the invention.

DESCRIPTION OF THE FIGURES

FIG. 13: Matrix for the generation and characterization of bsAb diversity via exchange reaction according to the current invention using a miniaturized high-throughput- and automation-compatible approach.

EXAMPLES

Example 1

Design and Modular Composition of 2/3-IgGs
General Remarks

Figure 1:
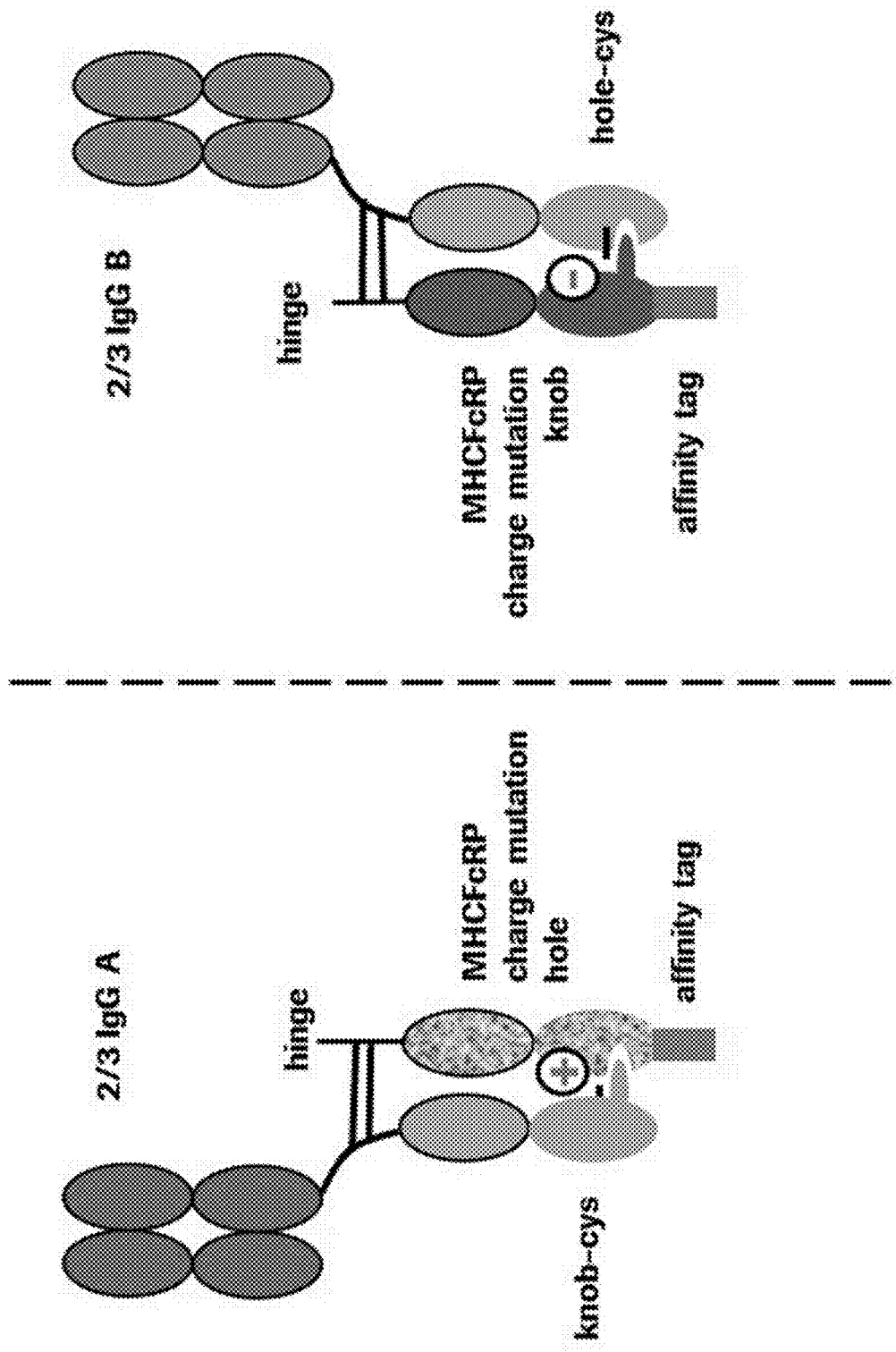
FIG. 1: Design and modular composition of 2/3-IgGs that can be used in the method according to the current invention.
Figure 2:
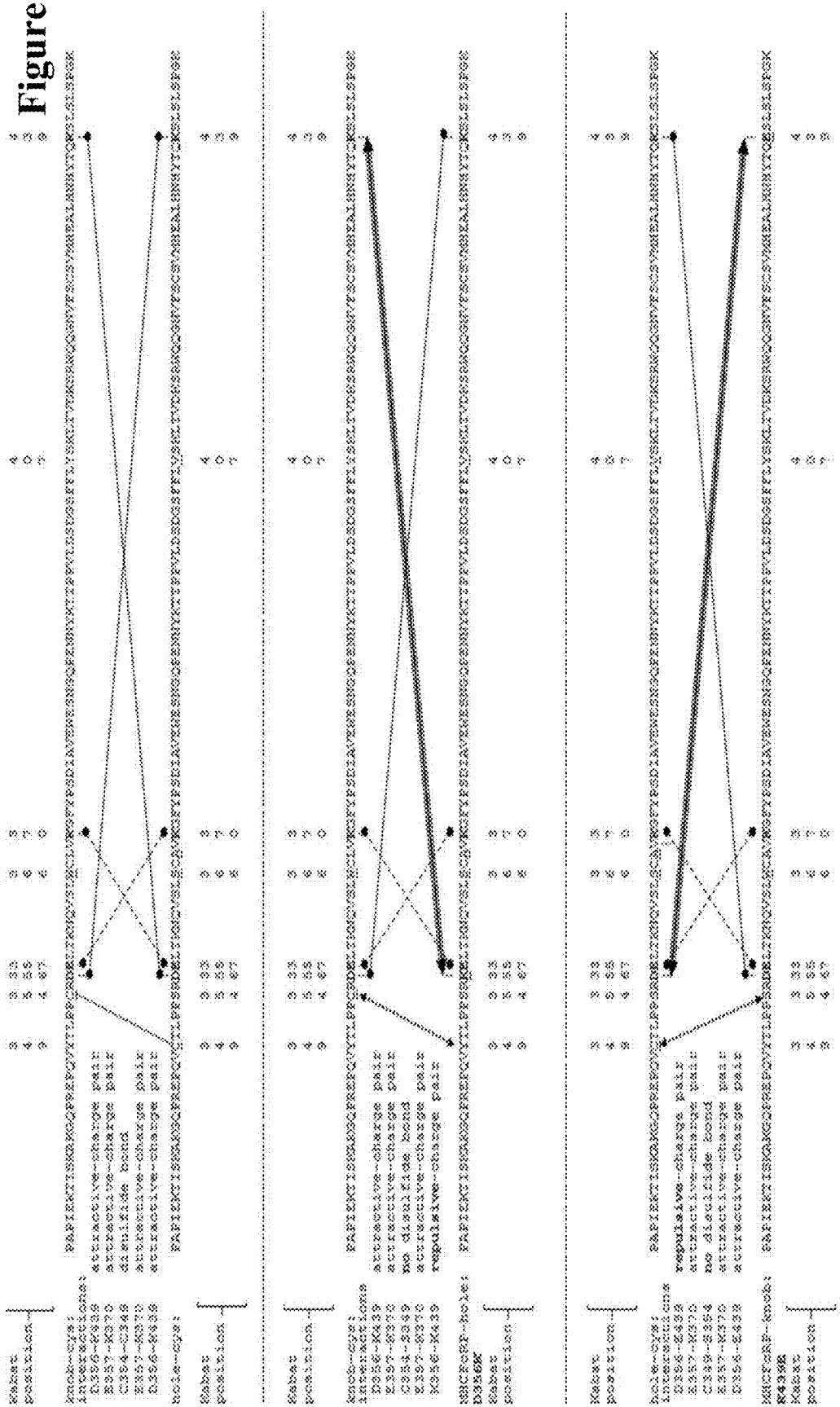
FIG. 2: Interactions between knob-cys and hole-cys heavy chains (upper part) and knob-cys heavy chain and MHCFcRP (middle and lower part). The covalent disulfide bond is indicated with a dashed line, attractive interaction pairs are depicted with line between full spheres, repulsive interactions or resulting steric hindrance are indicated with double arrows lines.

FIG. 1 shows the design and modular composition of the 2/3-IgGs used in the methods according to the current invention. These 2/3-IgGs are composed of three individual chains: one light chain (normally a full length light chain comprising a light chain variable domain and a light chain constant domain), one heavy chain (normally a full length heavy chain comprising a heavy chain variable domain and all heavy chain constant domains including a hinge region) and one heavy chain Fc-region polypeptide (normally a heavy chain Fc-region fragment comprising hinge-CH2-

CH3). The variable domains of the light chain and the heavy chain form a functional binding site. The heavy chain (normally derived from the human IgG1 subclass) contains either the knob-cys mutations or the hole-cys mutations (the mutations T366W and S354C in the CH3 domain of an antibody heavy chain is denoted as "knob-cys mutations" and the mutations T366S, L368A, Y407V, Y349C in the CH3 domain of an antibody heavy chain are denoted as "hole-cys mutations" (numbering according to Kabat EU index)) in CH3 to enable the formation of knob-into-hole Fc-region dimers. The heavy chain Fc-region polypeptide is a so called 'dummy-Fc'/HCFcRP (see below), i.e. an IgG1 derivative that lacks VH and CH1, starts at the N-terminus with the hinge region sequence and harbors a His6 tag at its C-terminus. In addition, the heavy chain Fc-region polypeptide of the 2/3-IgG contains in its CH3 domains either the knob mutation or the hole mutations (the mutation T366W in the CH3 domain of an antibody heavy chain is denoted as "knob mutation" and the mutations T366S, L368A, Y407V in the CH3 domain of an antibody heavy chain are denoted as "hole mutations" (numbering according to Kabat EU index)). In addition to the knob- or hole-mutation(s) the heavy chain Fc-region polypeptide comprises a destabilizing mutation introducing one (i.e. a single additional) repulsive charge with respect to the wild-type sequence: D356K or E357K or K370E or K439E; SEQ ID NO: 35 to 38; this mutated heavy chain Fc-region polypeptide is denoted as MHCFcRP in the following.

The heavy chain and the MHCFcRP can form two types of heterodimers depending on the distribution of the knob-into-hole mutations therein:

i) heavy chain-knob::MHCFcRP-hole, and
ii) heavy chain-hole::MHCFcRP-knob.

Those heterodimers are, however, somewhat 'flawed' as the complementary Fc-region lacks the additional CH3 cysteine necessary to form interchain disulfides to the heavy chain, and also these contain charge mutations without matching heavy chain counterparts.

Example 2

Expression and Purification of 2/3-IgGs According to the Invention

Expression of 2/3-IgGs was achieved by co-transfection of plasmids encoding light chain, heavy chain (with knob or hole mutations) and matching MHCFcRP (hole or knob) into mammalian cells (e.g. HEK293) via state of the art technologies.

In more detail, for example, for the production of the 2/3-IgGs by transient transfection (e.g. in HEK293 cells) expression plasmids based either on a cDNA organization with or without a CMV-Intron A promoter or on a genomic organization with a CMV promoter were applied.

Beside the antibody expression cassettes, the plasmids contained:

an origin of replication, which allows replication of this plasmid in *E. coli,*
a β-lactamase gene, which confers ampicillin resistance in *E. coli.,* and
the dihydrofolate reductase gene from *Mus musculus* as a selectable marker in eukaryotic cells.

The transcription unit of each antibody gene was composed of the following elements:

unique restriction site(s) at the 5'-end
the immediate early enhancer and promoter from the human cytomegalovirus,
followed by the Intron A sequence in the case of the cDNA organization,
a 5'-untranslated region of a human antibody gene,
an immunoglobulin heavy chain signal sequence,
the antibody chain either as cDNA or in genomic organization (the immunoglobulin exon-intron organization is maintained),
a 3'-non-translated region with a polyadenylation signal sequence, and
unique restriction site(s) at the 3'-end.

The fusion genes comprising the antibody chains were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The 2/3-IgGs were generated by transient transfection with the respective plasmid using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with the respective expression plasmid and 293Fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with ca. 42 mL mix of A) 20 mL Opti-MEM (Invitrogen) with 600 µg total plasmid DNA (1 µg/mL) and B) 20 ml Opti-MEM+1.2 mL 293 fectin or fectin (2 µL/mL). According to the glucose consumption glucose solution was added during the course of the fermentation. Correctly assembled 2/3-IgGs were secreted into culture supernatants like standard IgGs. The supernatant containing the secreted 2/3-IgG was harvested after 5-10 days and 2/3-IgGs were either directly purified from the supernatant or the supernatant was frozen and stored.

Because 2/3-IgGs contain an Fc-region they were purified by applying standard protein A affinity chromatography.

The antibodies were purified from cell culture supernatants by affinity chromatography using MabSelectSure-Sepharose™ (GE Healthcare, Sweden) and Superdex 200 size exclusion (GE Healthcare, Sweden) chromatography.

Briefly, sterile filtered cell culture supernatants were captured on a MabSelectSuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted antibody fractions were pooled and neutralized with 2 M Tris, pH 9.0. The antibody pools were further purified by size exclusion chromatography using a Superdex 200 26/60 GL (GE Healthcare, Sweden) column equilibrated with 20 mM histidine, 140 mM NaCl, pH 6.0. The 2/3-IgG containing fractions were pooled, concentrated to the required concentration using Vivaspin ultrafiltration devices (Sartorius Stedim Biotech S.A., France) and stored at −80° C.

Purity and integrity were analyzed after each purification step by CE-SDS using microfluidic Labchip technology (Caliper Life Science, USA). Protein solution (5 µl) was prepared for CE-SDS analysis using the HT Protein Express Reagent Kit according manufacturer's instructions and analyzed on LabChip GXII system using a HT Protein Express Chip. Data were analyzed using LabChip GX Software.

The following 2/3-IgGs have been produced by co-expression of corresponding L-chain, H-chain and MHCFcRP encoding plasmids:

|  | MHCFcRP | anti-fluorescein-2/3-IgG-knob-cys + | | anti-biocytinamid-2/3-IgG-hole-cys + | |
|---|---|---|---|---|---|
|  |  | D356K-hole | E357K-hole | K370E-knob | K439E-knob |
| HEK293 | protein A [mg/L] | 122 | 94 | 129 | 117 |
|  | SEC [% yield] | >70 | >50 | >70 | >70 |
| Expi™ | protein A [mg/L) | >200 | >200 | >200 | >200 |
|  | SEC [% yield] | >90 | >90 | >80 | >80 |

Figure 3:
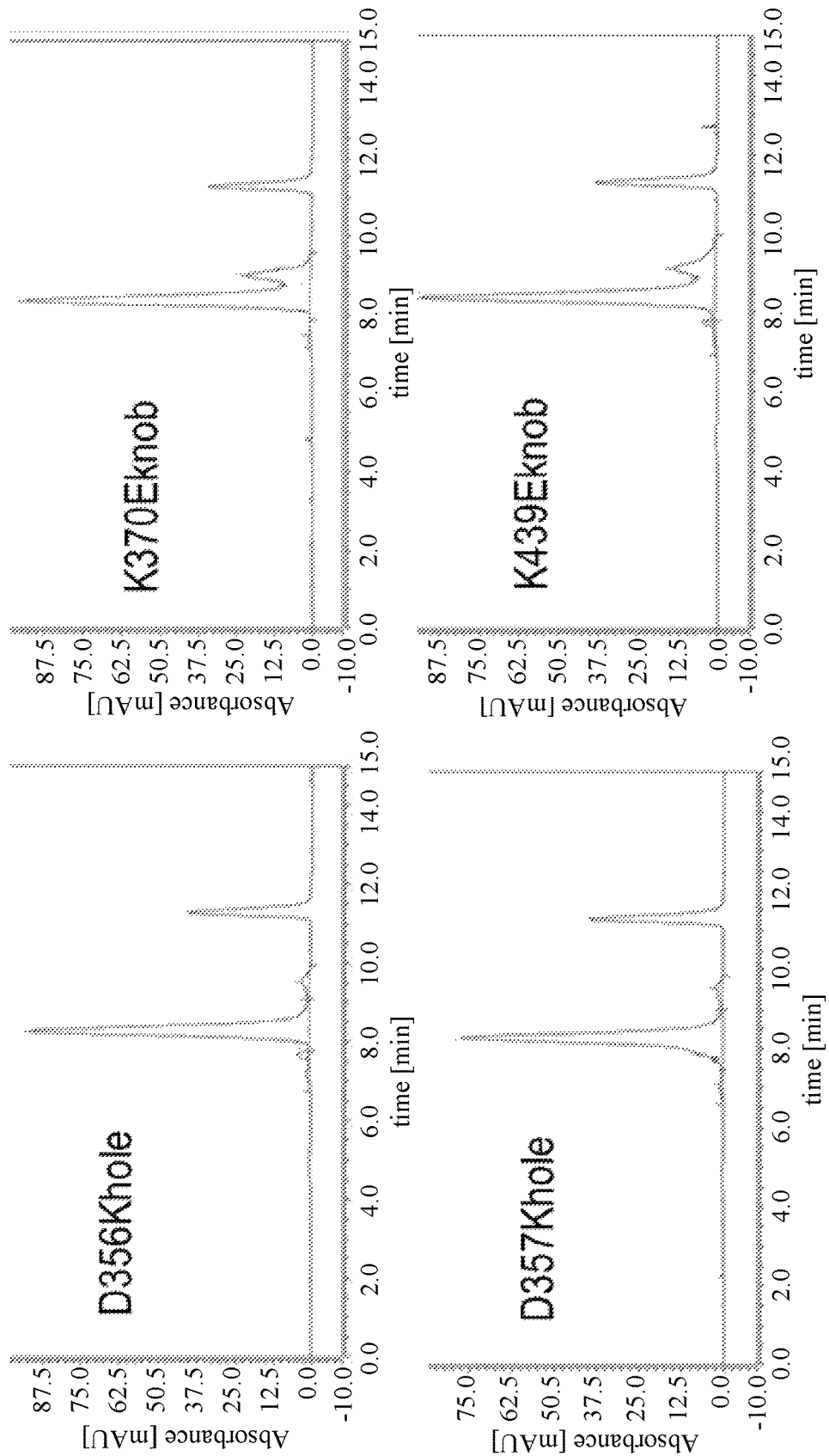
FIG. 3: SEC chromatograms of the purified 2/3-IgGs with different MHCFcRPs: shown are SEC profiles of 2/3-IgG preparations following Protein A extraction from cell culture supernatants; the main peak of each profile represent the 2/3-IgG; with fluos or bio specificities (see Example 2).

The corresponding SEC chromatograms are shown in FIG. 3.

In addition to the protein A method as outlined above likewise protein L can be used.

Briefly, sterile filtered cell culture supernatants were captured on a KappaSelect resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 50 mM sodium citrate at pH 2.5. The eluted antibody fractions were pooled and neutralized with 1 M Tris, pH 9.0. The antibody pools were further purified by size exclusion chromatography using a Superdex 200 26/60 GL (GE Healthcare, Sweden) column equilibrated with 20 mM histidine, 140 mM NaCl, pH 6.0. The 2/3-IgG containing fractions were pooled, concentrated to the required concentration using Vivaspin ultrafiltration devices (Sartorius Stedim Biotech S.A., France) and stored at −80° C.

Example 3

Generation of Bispecific Antibodies (bsAbs) by 2/3-IgG-Exchange Reaction

Figure 4:
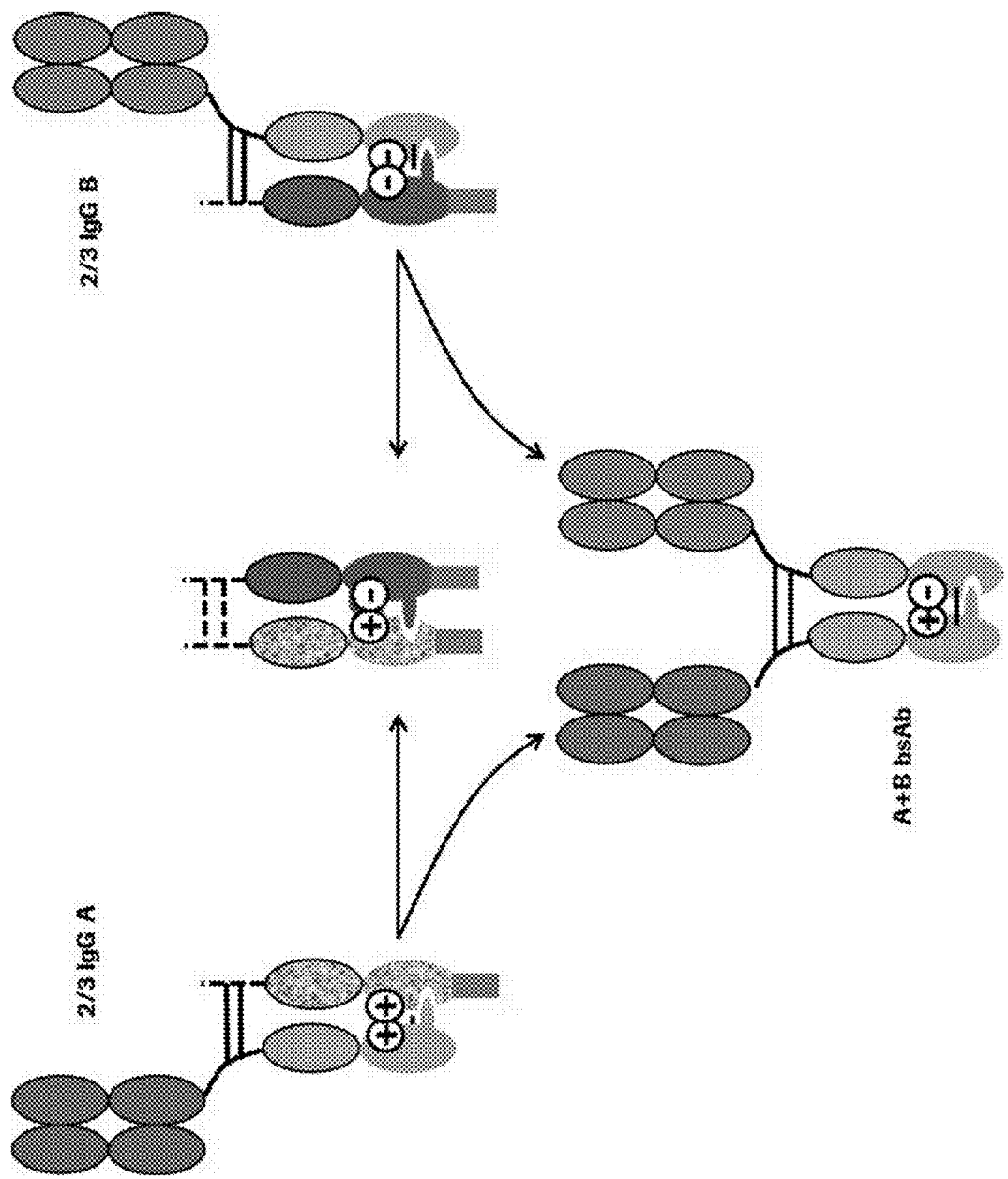
FIG. 4: Generation of bsAbs (bispecific antibodies) by exchange reaction according to the current invention exemplified with 2/3-IgGs.

The 2/3-IgGs that contain a light chain, a heavy chain and MHCFcRP have been generated in two types of KiH heterodimers: full length heavy chain-knob::MHCFcRP-hole and full length heavy chain-hole::MHCFcRP-knob. Both types of 2/3-IgGs are somewhat 'flawed' as the MHCFcRP lacks the additional CH3 cysteine necessary to form interchain disulfides to the heavy chain, and the MHCFcRP contains charge mutations without matching full length heavy chain counterpart(s). The modules that make up those flawed heterodimers, however, are capable to rearrange to bispecific heterodimers with matching charges as shown in FIG. 4. The full length heavy chain (knob-cys) of 2/3-IgG A and the full length heavy chain (hole-cys) from 2/3-IgG B form a matching heterodimer. Matching heterodimers are also formed when MHCFcRP (hole-charge) interacts with MHCFcRP (knob-charge). Thus, exchange reactions based on temporary separation of starting heterodimers of two different 2/3-IgGs resulted in products that contain preferentially (charge) matching heterodimers. Exchange reactions therefore converted two monospecific 2/3-IgGs to one bispecific IgG and one MHCFcRP heterodimer:

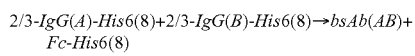
2/3-IgG(A)-His6(8)+2/3-IgG(B)-His6(8)→bsAb(AB)+ Fc-His6(8)

The exchange reaction was initiated by a reduction step (e.g. by applying 2-MEA or TCEP at various concentrations) to break especially the hinge-region interchain disulfide bonds. Chain rearrangement occurred spontaneously thereafter.

Different TCEP concentrations were applied to initiate the exchange.

Therefore, anti-fluorescein-2/3-IgG and anti-biocytinamid-2/3-IgG input molecules were mixed in equimolar amounts at a protein concentration of 100 μg/ml in a total volume of 40 μl 1×PBS+0.05% Tween 20 with the indicated TCEP concentrations on a 384 well REMP® plate (Brooks, #1800030). After centrifugation, plates were sealed and incubated for one hour at 27° C.

A biotin-fluorescein bridging ELISA was subsequently used to quantify bispecific antibody.

Therefore, white Nunc® MaxiSorp™ 384 well plates were coated with 1 μg/ml albumin-fluorescein isothiocyanate conjugate (Sigma, #A9771) and incubated overnight at 4° C. After washing 3 times with 90 μl PBST-buffer (PBST, bidest water, 10×PBS+0.05% Tween 20) blocking buffer (1×PBS, 2% gelatin, 0.1% Tween-20) was added 90 μl/well and incubated for one hour at room temperature. After washing 3 times with 90 μl PBST-buffer, 25 μl of a 1:10 dilution of each exchange reaction was added to each well. After incubation for one hour at room temperature, plates were again washed 3 times with 90 μl PBST-buffer. 25 μl/well biotin-Cy5 conjugate in 0.5% BSA, 0.025% Tween-20, 1×PBS was added to a final concentration of 0.1 μg/ml and plates were incubated for one hour at room temperature. After washing 6 times with 90 μl PBST-buffer, 25 μl 1×PBS were added to each well. Cy5 fluorescence was measured at an emission wavelength of 670 nm (excitation at 649 nm) on a Tecan Safire 2 Reader.

Figure 5:
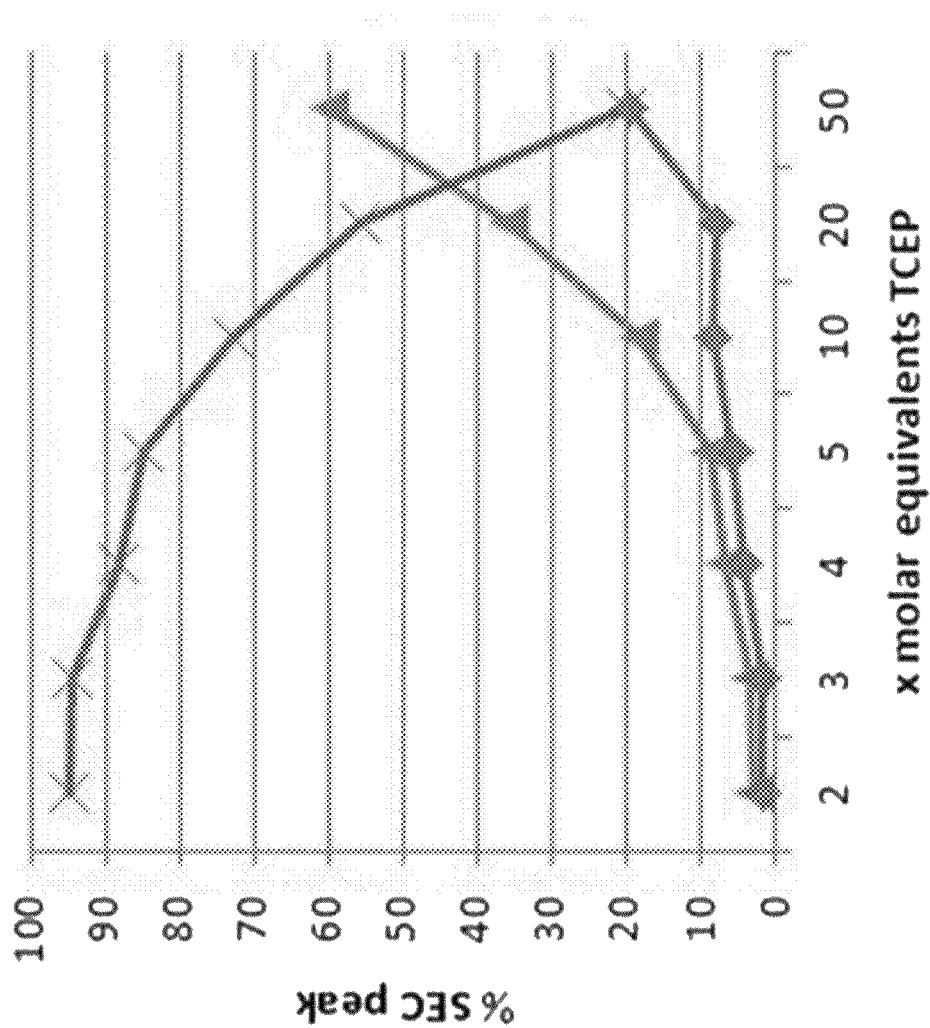
FIG. 5: TCEP (x molar equivalents in relation to 2/3 input IgGs) is applied to (partially) reduce the hinge-disulfide bonds. SEC differentiates 2/3-IgG starting molecule, generated bsAb and dimeric MHCFcRP. All reactions at different TCEP concentrations were stopped after the same incubation time (triangle: bsAb; cross: 2/3-IgG, diamond: dimeric MHCFcRP).

FIG. 5 shows the results of analyses of the redox conditions for generation of bsAbs by 2/3-IgG-exchange. TCEP is applied to (partially) reduce the hinge-disulfide bonds between the heavy chain Fc-region polypeptides, i.e. between the full length half-IgG and the MHCFcRP. Chain exchange can be identified by SEC which differentiates 2/3-IgG input, bsAb output and MHCFcRP by-product. The yields of the exchange reactions depending on the ratio between 2/3-IgG and TCEP are shown in FIG. 5 (for comparison all reaction were analyzed after the same reaction time).

Figure 6:
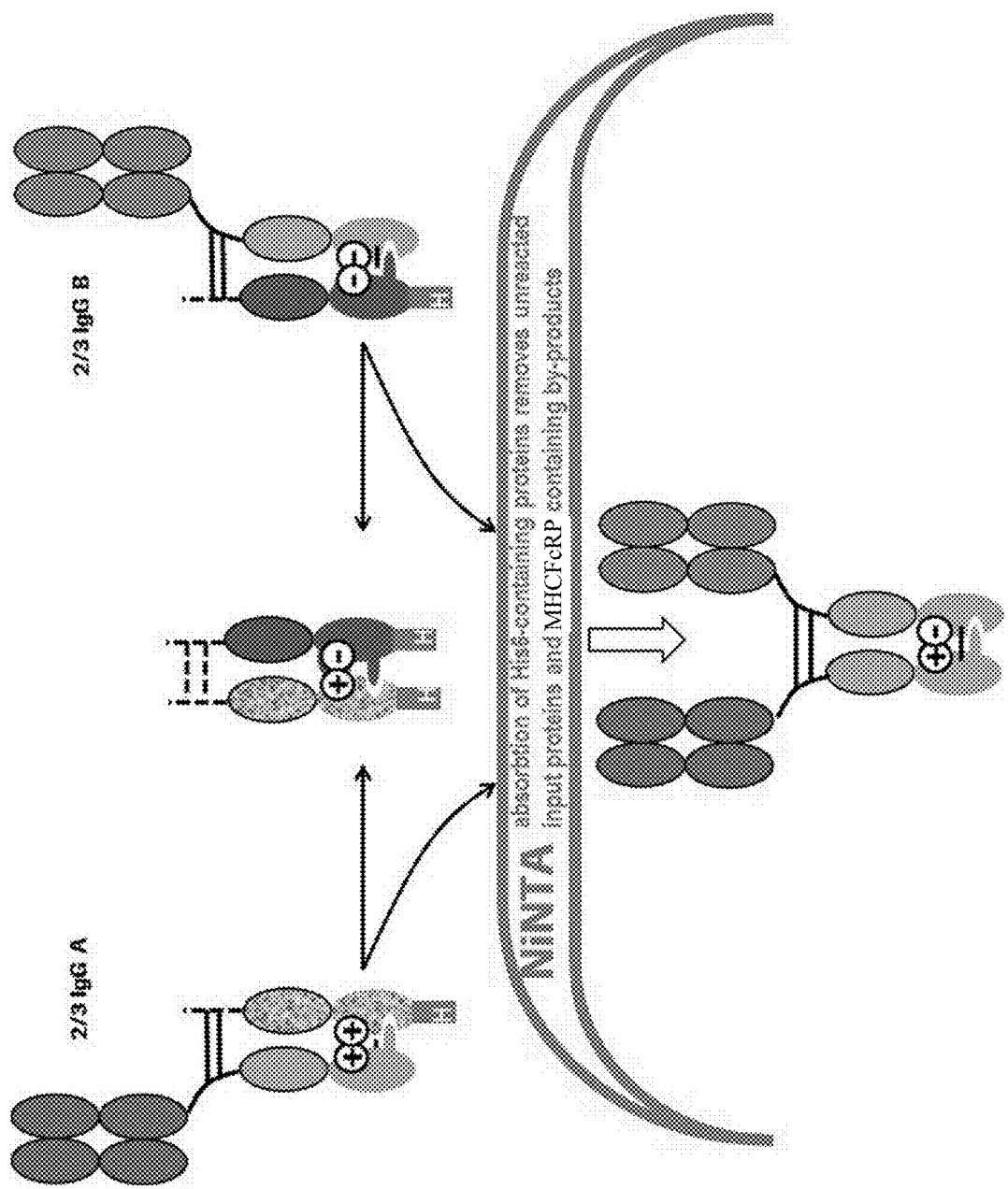
FIG. 6: Removal of undesired non-reacted input molecules and by-products from desired bsAb products.
Figure 7:
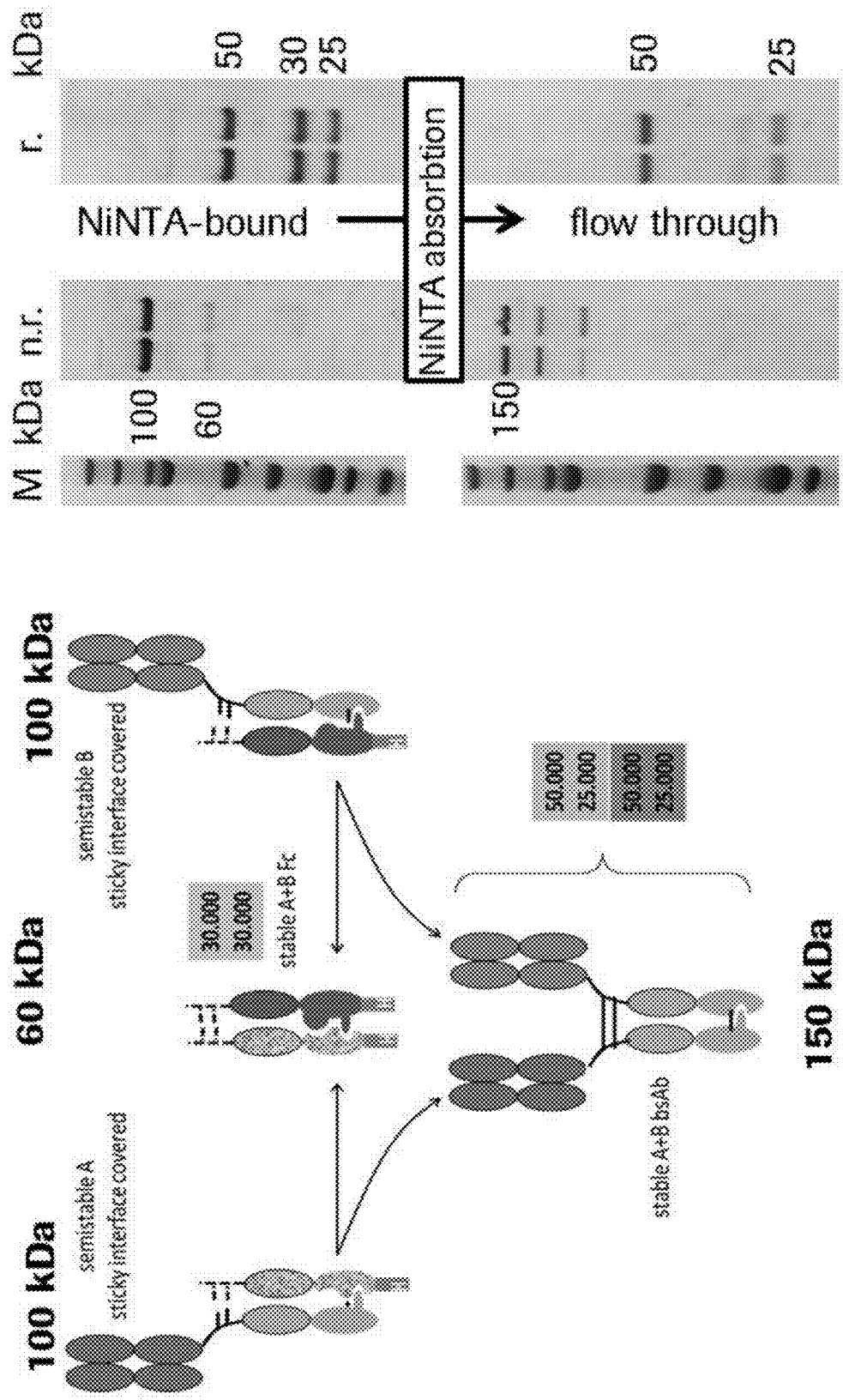
FIG. 7: SDS-page of the NiNTA-purification; n.r.=non-reduced; r=reduced; NiNTA-bound (upper panel) represents proteins eluted from NiNTA, NiNTA flow through (lower panel) are proteins that do not contain a His-6 or His-8 Tag; n.r.=non-reduced, r.=reduced; M=marker.

All 2/3-IgG starting molecules, all non-wanted by-products, as well as all aggregates that were potentially generated during the exchange reaction harbor affinity tags (His6 or His8). The desired bsAb produced in the exchange reaction is the only molecule that does not carry a His-tag. Therefore, a simple NiNTA absorption step was applied to remove all undesired molecules (see FIGS. 6 and 7). The remaining bsAbs (not depleted by NiNTA absorption) were directly applied to screening procedures and analyzed to identify bsAbs with desired functionalities.

Example 4

Figure 8:
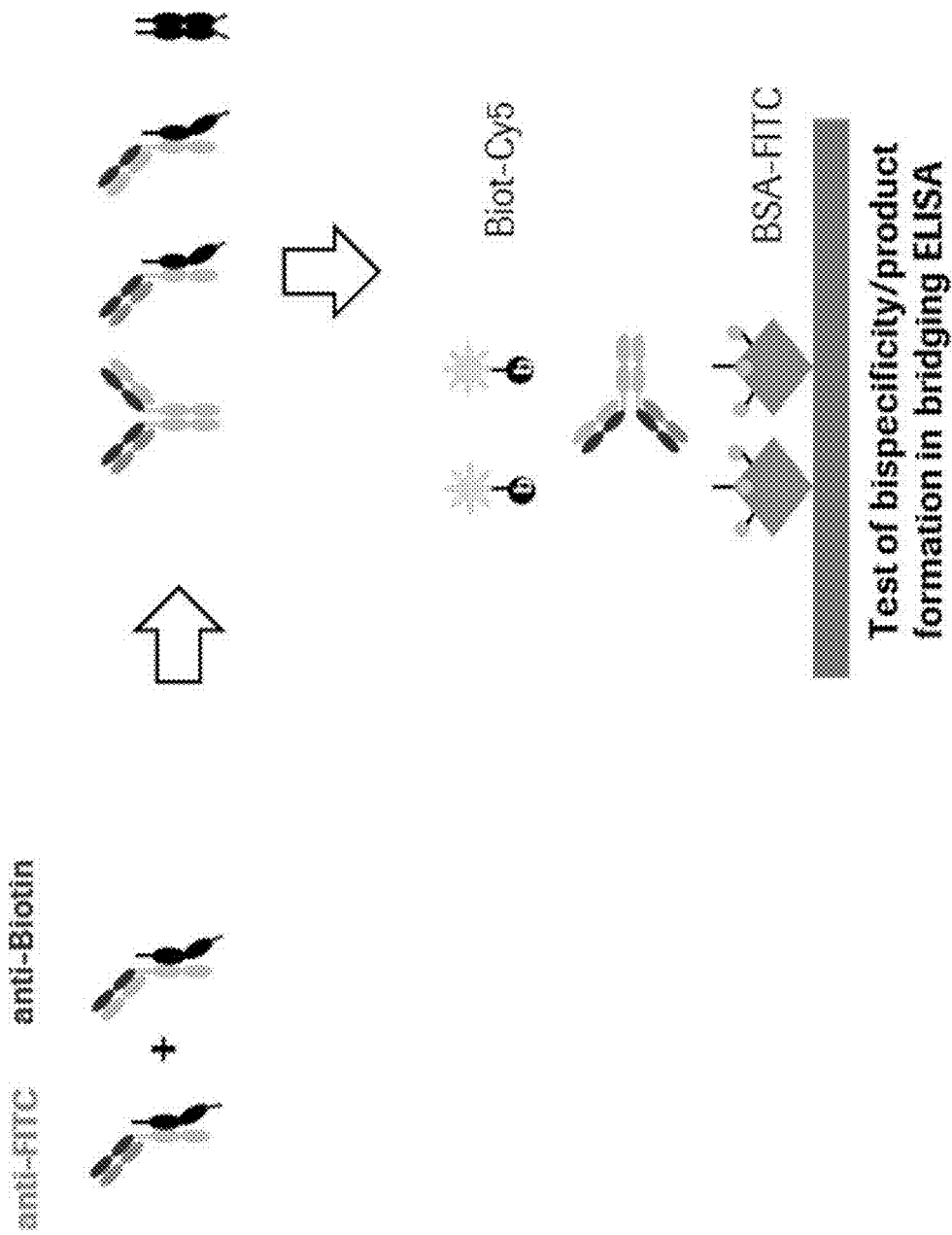
FIG. 8: Bispecific functionality of bsAbs generated by exchange reaction according to the invention. Functionality was assessed by a bridging ELISA that enables detection of simultaneous binding of binding sites of a bispecific antibody. Antigen A coated to the ELISA plate was fluorescein (fluos-BSA) and antigen B was bio-Cy5 which becomes detected by its fluorescence.

Functional Assessment of Bispecific Antibodies (bsAbs) Generated by 2/3-IgG-Exchange Reaction Bispecific functionality of bsAbs that were generated as products of 2/3-IgG-exchange reactions was evaluated by bridging-ELISA assays. FIG. 8 shows as an example the binding result for an anti-fluorescein/biocytinamid bispecific antibody generated by an exchange reactions according to the current invention. In the reaction biocytinamid (bio)-binding 2/3-IgG and a fluorescein (fluos)-binding 2/3-IgG as starting molecules were employed. The fluos-binding arm of anti-fluos/bio bispecific antibodies bind to fluos-BSA coated ELISA plates. Subsequent exposure to bio-Cy5 generates signals only upon bsAb-mediated capture of bio-Cy5 via the bio-binding arm of the bsAb. Because bridging-mediated signals occur only with bsAbs but not with either monospecific Fluos or Bio binders, no signals were observed when using only 2/3-IgGs in the assay. Because of that and because the exchange reaction does not force molecule aggregation, such bridging ELISA can be performed directly on exchange reaction mixes, without requiring prior NiNTA-mediated depletion of non-bsAb molecules. Signals observed when applying the reaction mix indicated successful generation and presence of functional bsAbs. Signal generation via bridging ELISA was dependent on the amount of input entities used in the exchange reaction.

Example 5

The Exchange Reaction as Reported Herein is Functional Independent of Binding Specificities or V-Region Composition of Starting 2/3-IgGs A variety of 2/3-IgGs was produced to evaluate if 2/3-IgG production as well as exchange reactions work for different antibodies independent of their binding specificities and V-region composition, as well as for different antibody combinations.

Therefore, 2/3-IgGs with binding specificities for biocytinamid (bio), digoxigenin (dig), fluorescein (fluos), LeY-carbohydrate (LeY), VEGF and PDGF were used. These were produced by co-transfection of expression plasmids encoding full length light chains, knob- or hole-full length heavy chains and mutated heavy chain Fc-region polypeptides as described above.

| Chain | SEQ ID NO: |
|---|---|
| MHCFcRPs | |
| hole-D356K-His8 | 35 |
| hole-E357K-His8 | 36 |
| knob-K370E-His8 | 37 |
| knob-K439E-His8 | 38 |
| anti-bio antibody full length light chain | 39 |
| anti-bio antibody full length heavy chain-knob-cys | 40 |
| anti-bio antibody full length heavy chain-hole-cys | 41 |
| anti-fluos antibody full length light chain | 42 |
| anti-fluos antibody full length heavy chain-knob-cys | 43 |
| anti-fluos antibody full length heavy chain-hole-cys | 44 |
| anti-dig antibody full length light chain | 45 |
| anti-LeY antibody full length light chain | 46 |
| anti-PDGF antibody full length light chain | 47 |
| anti-VEGF antibody full length light chain | 48 |
| anti-dig antibody VH-CH1 fragment | 49 |
| anti-LeY antibody VH-CH1 fragment | 50 |
| anti-PDGF antibody VH-CH1 fragment | 51 |
| anti-VEGF antibody VH-CH1 fragment | 52 |

SEQ ID NO: 49-52 describe the VH-CH1 region of 2/3-IgGs with specificities for dig, VEGF, PDGF and LeY. Those were fused to the hinge-CH2-CH3 regions (i.e. replace the bio VH-CH1 regions) of SEQ ID NO: 40 and 41 to generate complete H-chains with desired specificity. The MHCFcRPs applied for generating these molecules are listed as SEQ ID NO: 35-38.

All of these 2/3-IgGs could be produced and purified to similar yields as for standard IgGs under comparable conditions (see Example 2). Examples for expression of these 2/3-IgGs with different binding specificities are shown in the following Table.

| 2/3-IgG = 1/2-IgG-hole-cys + MHCFcRP-knob-E357K | | | | | |
|---|---|---|---|---|---|
| | anti-dig | anti-VEGF | anti-PDGF | anti-LeY | anti-fluos |
| Protein A [mg/L] | 76 | 76 | 96 | 81 | 94 |
| SEC [% yield] | 40-60 | >70 | >90 | >95 | >50 |

In the exchange-matrix, which was applied to generate bsAbs of different specificity, combinations of 2/3-IgGs with binding specificities for fluorescein, biocytinamid, VEGF, PDGF and digoxigenin in all combinations as shown in the following Table were employed.

| exchange reaction | | MHCFcRP-knob-E357K | | | |
|---|---|---|---|---|---|
| between | | bio | fluos | Dig | VEGF | PDGF |
| MHCFcRP-hole-K370E | bio | — | bio fluos | bio dig | bio VEGF | bio PDGF |
| | fluos | fluos bio | — | fluos dig | fluos VEGF | fluos PDGF |
| | dig | dig bio | dig fluos | — | dig VEGF | dig PDGF |
| | VEGF | VEGF bio | VEGF fluos | VEGF Dig | — | VEGF PDGF |
| | PDGF | PDGF bio | PDGF fluos | PDGF Dig | PDGF VEGF | — |

The chain exchange of starting 2/3-IgGs and generation of bsAbs with desired specificity combinations was monitored by bridging ELISA (see Example 4), wherein plate-coated antigens and signal-generating antigen-conjugates/complexes 5 were applied that match the different bsAb specificity combinations. The results of the bridging ELISA applied to assess the functionalities of different bsAb combinations are shown in the following Tables. Only bsAbs that recognize their cognate pair of antigens present as capturing or detection antigen generate signals in the bridging ELISA. Other bsAbs generated in the matrix are negative due to absence of at least one specificity.

TABLE

Bridging ELISA confirms the functionality of bsAbs generated. Shown are the relative signal intensities within one assay at the input molecule concentration 1.3 µM. The highest value is set to 100% as a reference.

| assay capture detection exchange reaction | | biocytinamid-fluorescein fluorescein-albumin biocytinamid-Cy5 MHCFcRP-hole-K370E | | | |
|---|---|---|---|---|---|
| between | | bio | fluos | dig | VEGF | PDGF |
| MHCFcRP-knob-E357K | bio | — | 100% | 2.5% | 2.5% | 1.9% |
| | fluos | 97.6% | — | 2.5% | 1.9% | n.a. |
| | dig | 2.2% | 2.5% | — | 2.2% | 2.2% |
| | VEGF | 1.9% | 2.2% | 2.3% | — | 2.3% |
| | PDGF | 1.8% | n.a. | 2.3% | 1.9% | — |

| assay capture detection exchange reaction | | digoxigenin-fluorescein fluorescein-albumin digoxygenin-Cy5 MHCFcRP-hole-K370E | | | |
|---|---|---|---|---|---|
| between | | bio | fluos | dig | VEGF | PDGF |
| MHCFcRP-knob-E357K | bio | — | 1.9% | 1.6% | 1.4% | 1.3% |
| | fluos | 2.4% | — | 100% | 2.8% | n.a. |
| | dig | 2.0% | 52.5% | — | 2.0% | 1.5% |

TABLE-continued

Bridging ELISA confirms the functionality of bsAbs generated. Shown are the relative signal intensities within one assay at the input molecule concentration 1.3 µM. The highest value is set to 100% as a reference.

|  |  |  |  |  |  |
|---|---|---|---|---|---|
| VEGF | 1.5% | 1.5% | 1.5% | — | 1.5% |
| PDGF | 1.5% | n.a. | 1.8% | 2.8% | — |

| assay capture | VEGF-biocytinamid |
|---|---|
| detection | VEGF |
| exchange reaction | biocytinamid-Cy5 |
|  | MHCFcRP-hole-K370E |

| between |  | bio | fluos | dig | VEGF | PDGF |
|---|---|---|---|---|---|---|
| MHCFcRP-knob-E357K | bio | — | 9.0% | 9.3% | 100% | 10.1% |
|  | fluos | 10.2% | — | 9.4% | 9.9% | n.a. |
|  | dig | 9.0% | 9.1% | — | 8.7% | 9.9% |
|  | VEGF | 78.3% | 9.2% | 9.3% | — | 9.5% |
|  | PDGF | 10.5% | n.a. | 9.2% | 10.9% | — |

| assay capture | PDGF-biocytinamid |
|---|---|
| detection | PDGF |
| exchange reaction | biocytinamid-Cy5 |
|  | MHCFcRP-hole-K370E |

| between |  | bio | fluos | dig | VEGF | PDGF |
|---|---|---|---|---|---|---|
| MHCFcRP-knob-E357K | bio | — | 3.0% | 4.1% | 4.4% | 81.8% |
|  | fluos | 3.2% | — | 3.1% | 3.3% | n.a. |
|  | dig | 3.3% | 3.2% | — | 3.3% | 3.4% |
|  | VEGF | 4.0% | 3.1% | 3.1% | — | 3.2% |
|  | PDGF | 100% | n.a. | 3.9% | 3.2% | — |

| assay capture | digoxigenin-VEGF |
|---|---|
| detection | VEGF |
| exchange reaction | digoxygenin-Cy5 |
|  | MHCFcRP-hole-K370E |

| between |  | bio | fluos | dig | VEGF | PDGF |
|---|---|---|---|---|---|---|
| MHCFcRP-knob-E357K | bio | — | 7.2% | 6.2% | 6.4% | 6.1% |
|  | fluos | 6.5% | — | 6.3% | 6.5% | n.a. |
|  | dig | 6.2% | 6.7% | — | 59.7% | 7.0% |
|  | VEGF | 6.1% | 6.6% | 100% | — | 7.0% |
|  | PDGF | 6.0% | n.a. | 5.9% | 6.5% | — |

| assay capture | digoxigenin-PDGF |
|---|---|
| detection | PDGF |
| exchange reaction | digoxygenin-Cy5 |
|  | MHCFcRP-hole-K370E |

| between |  | bio | fluos | dig | VEGF | PDGF |
|---|---|---|---|---|---|---|
| MHCFcRP-knob-E357K | bio | — | 3.0% | 2.9% | 2.9% | 3.0% |
|  | fluos | 3.7% | — | 3.2% | 2.8% | n.a. |
|  | dig | 2.9% | 3.1% | — | 3.5% | 62.3% |
|  | VEGF | 3.1% | 3.3% | 3.0% | — | 2.9% |
|  | PDGF | 3.7% | n.a. | 100% | 3.8% | — |

N.a. = not available.

For the VEGF containing bispecific antibodies the same assays have been performed. These also showed only signals above background levels for the respective combinations.

It can be seen that the exchange reaction according to the current invention is a generally applicable method: exchange reactions lead to functional bsAb independent of binding specificities or V-region composition of the starting molecules.

Example 6

Design, Composition and Generation of Format Variants

The 2/3-IgG-exchange reaction of Example 4 was expanded to starting molecules that have either one binding site at the C-terminus of the heavy chain, or heavy chains with binding sites at N- as well as C-terminus. For generation of the exchanged bsAbs the exchange driving principle (conversion of flawed input heterodimers to matching output-heterodimers) was kept unaltered. The composition of the MHCFcRPs was also retained as described above.

Figure 9:
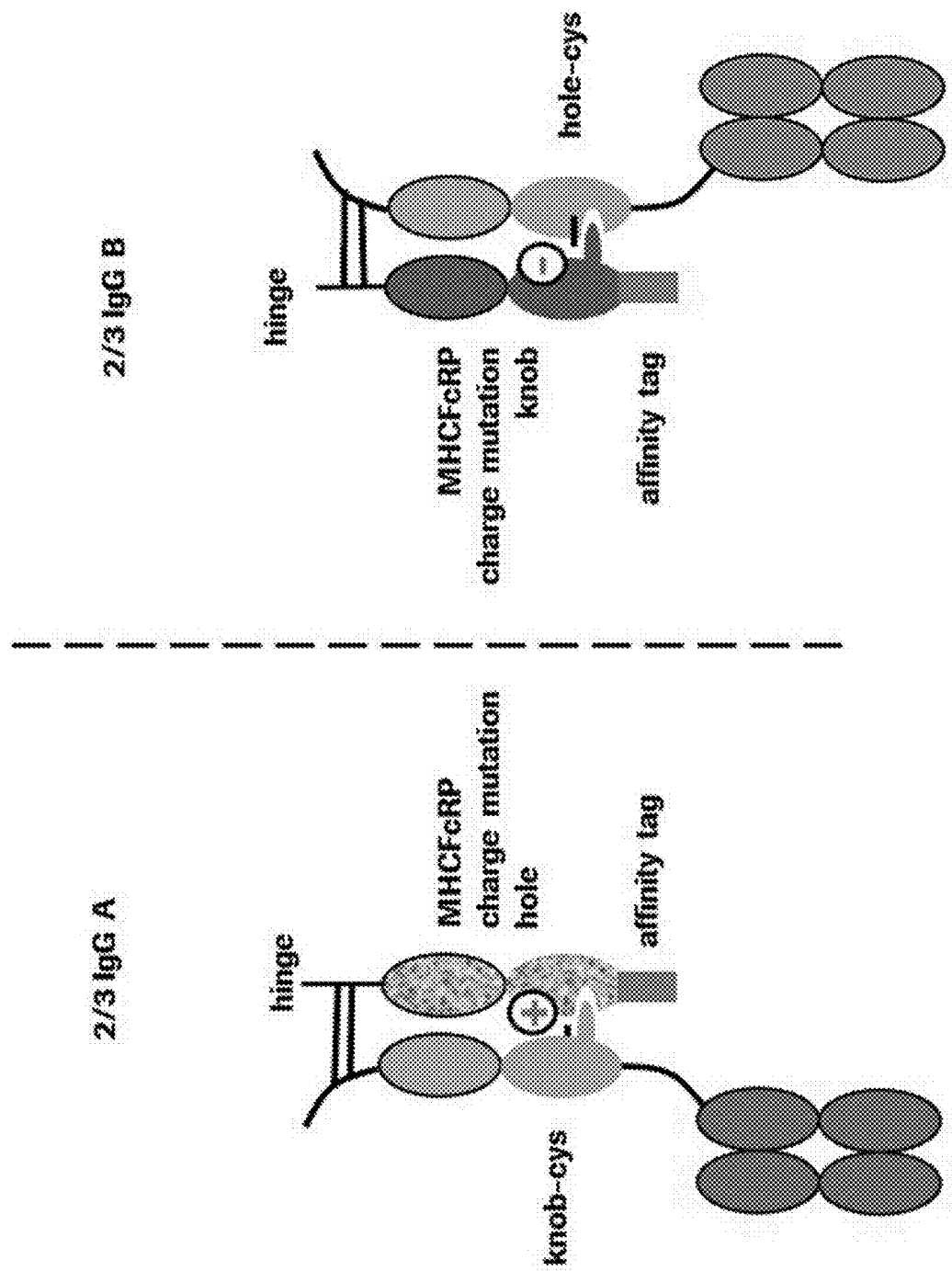
FIG. 9: Exemplary 2/3-IgGs for 2/3-IgG-exchange reaction with binding sites at the C-terminus of the heavy chain.
Figure 10:
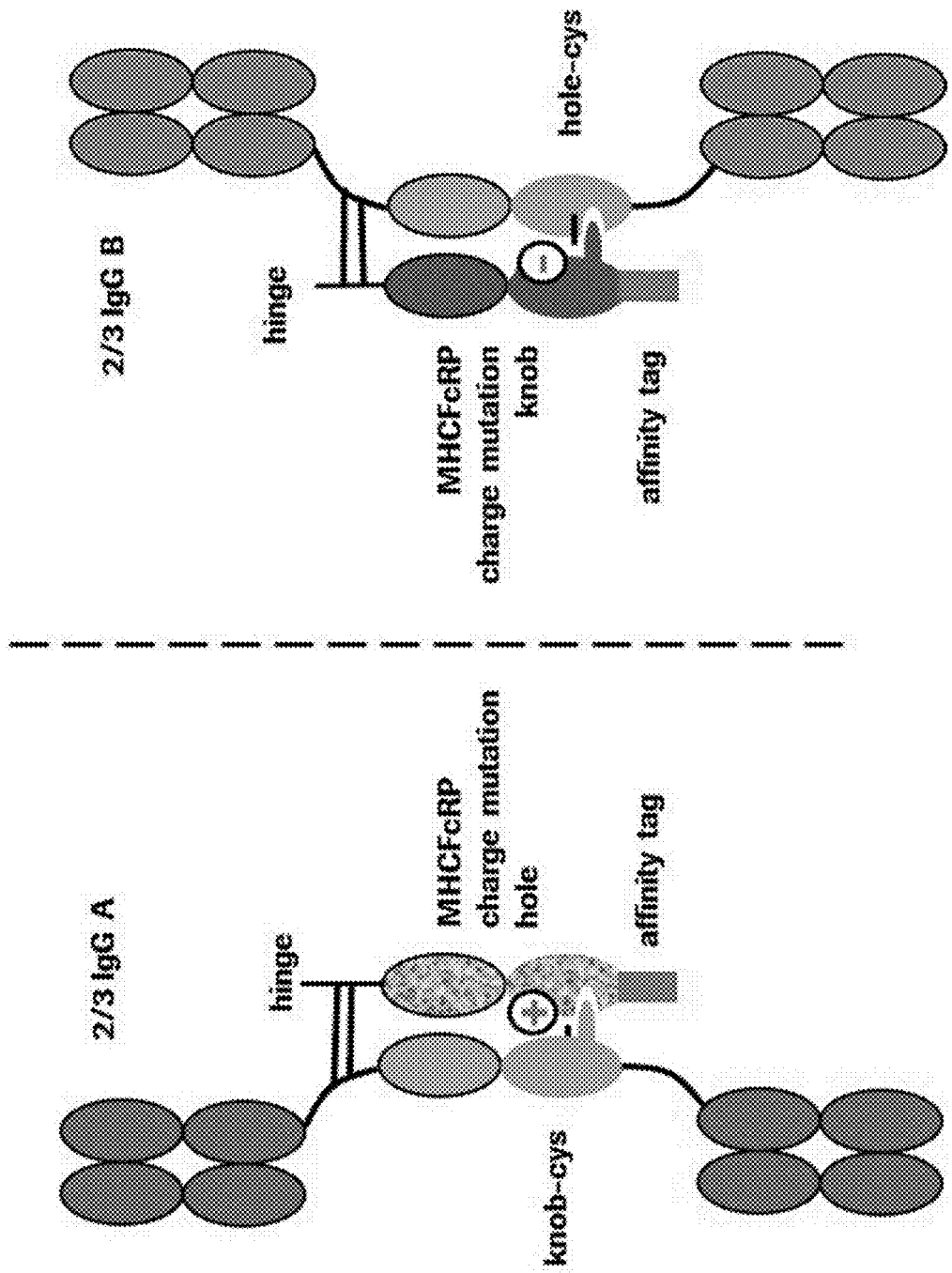
FIG. 10: Exemplary 2/3-IgGs for 2/3-IgG-exchange reaction with binding sites at the N-terminus and the C-terminus of the heavy chain.

FIGS. 1 and 9 to 10 show the modular composition of the three 2/3-IgG formats that were applied to generate different bsAb formats. One of the 2/3-IgGs has one Fab arm at the N-terminal position. Another of the 2/3-IgGs has the Fab arm attached via a flexible linker to the C-terminus of the heavy chain (i.e. it starts at the N-terminus with the hinge-region). The third 2/3-IgG has the C-terminal Fab arm as well as the N-terminal Fab arm.

Expression of these 2/3-IgG variants was achieved by co-transfection of plasmids encoding light chain, heavy chain (knob or hole) and corresponding MHCFcRP (hole or knob) into mammalian cells (e.g. HEK293) (see Example 2).

Sequences of the full length heavy chains modified used for the generation of the different bsAb formats are as follows:

| chain | SEQ ID NO: |
|---|---|
| MHCFcRPs |  |
| hole-D356K-His8 | 35 |
| hole-E357K-His8 | 36 |
| knob-K370E-His8 | 37 |
| knob-K439E-His8 | 38 |
| anti-bio antibody full length heavy chain-hole-cys with C-terminal fusion | 53 |
| anti-bio antibody full length heavy chain-hole-cys with N- and C-terminal fusion | 54 |
| anti-fluos antibody full length heavy chain-hole-cys with C-terminal fusion | 55 |
| anti-fluos antibody full length heavy chain-hole-cys with N- and C-terminal fusion | 56 |

The 2/3-IgGs are secreted into culture supernatants like standard IgGs and were purified by standard protein A affinity chromatography (see Example 2). Size-exclusion and mass-spec analytics revealed correct assembly of purified 2/3-IgG variants as well as absence of undesired dimers and aggregates. Expression yields of 2/3-IgGs were similar to those observed with standard IgGs in the same expression systems. The respective data is presented in the following Table.

|  | anti-fluorescein antibody-knob-cys + MHCFcRP-hole-E357K | | | anti-biocytinamid antibody - hole-cys + MHCFcRP-knob-K370E | | |
|---|---|---|---|---|---|---|
| SEQ ID NO: | 43 + 36 (N-Fc) | 55 + 36 (C-Fc) | 56 + 36 (NC-Fc) | 41 + 37 (N-Fc) | 53 + 37 (C-Fc) | 54 + 37 (NC-Fc) |
| Protein A [mg/L] | 94 | 94 | 75 | 129 | 87 | 75 |
| SEC [% yield] | 55 | 90 | 87 | 40-80 | 61 | 63 |

Example 7

Characterization of bsAbs with Combined Binding Functionalities in Different Valencies, Stoichiometries and Geometries Three different starting molecules (2/3-IgG with N-terminal, C-terminal, N- and C-terminal binding site(s)) can be combined with each other in the method according to the current invention to result in nine different bsAb formats. These differ in valencies, geometries and positions of the individual binding sites. The exchange reaction to generate these different bsAbs was performed under the same conditions as outlined in Example 3.

All types of input formats are 'flawed' as the MHCFcRP lacks the additional CH3 cysteine necessary to form interchain disulfides to the heavy chain and as it contains a repulsive charge mutation (i.e. a charge without matching full length heavy chain counterpart). The heavy chains that make up those "flawed" heterodimers rearrange to form (charge and disulfide) matching heterodimers in the method according to the current invention. The different types of full length heavy chains (knob-cys with hole-cys) form matching heterodimers. Matching heterodimers are also formed from the MHCFcRP (hole-charge with knob-charge).

Without being bound by this theory it is assumed that exchange reactions based on temporary separation of flawed heterodimers of two different 2/3-IgGs results in products that contain preferentially perfectly matching heterodimers with matching charges and, if present, cysteine residues for the formation of disulfide bonds. Exchanges therefore convert the monospecific 2/3-IgGs to bispecific IgGs (in different formats), as well as corresponding (variable region free, i.e. non-target binding competent) Fc-region heterodimer.

For the description of the exchange reactions, the input molecules are termed:

'nA or nB' for molecules having the Fab arm at the normal N-terminus of the full length heavy chain (H-chain)

'cA or cB' for molecules having the Fab arm at the C-terminus of the H-chain

'ncA or ncB' for molecules with Fab at N- as well as C-terminus of the H-chain

The different format-exchange reactions are as follows:

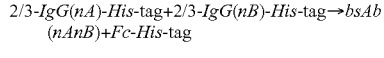

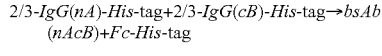

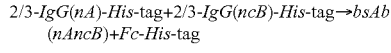

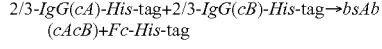

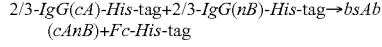

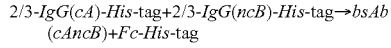

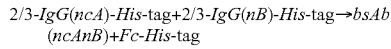

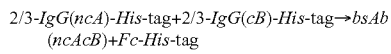

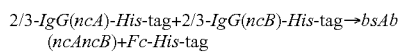

Exchange reactions are initiated by a reduction step to break the interchain (hinge-region) disulfide bonds, chain rearrangement occurs spontaneously thereafter. All input molecules, all by-products, as well as all aggregates that may potentially form during the exchange reaction harbor affinity tags (e.g. a His6- or His8-tag). The bsAb products of the exchange reaction, however, do not carry the affinity tag and can therefore be separated via affinity (e.g. NiNTA) absorption chromatography. The bsAbs (in different formats) can directly be applied to screening procedures and analyses to identify and to rank the different bsAbs formats with optimal functionality.

The bispecific formats were generated by exchanging the above described input 2/3-IgGs in a 384 well MTP format followed by bridging ELISA to assess functional assembly. Therefore, the exchange partners (2/3-IgG molecule 1 consisting of a full length heavy chain containing the hole-cys mutations and an MHCFcRP-knob-K370E; 2/3-IgG molecule 2 consisting of a full length heavy chain containing the knob-cys mutations and a MHCFcRP-hole-E357K) were mixed in equimolar amounts (4 μM) in a total volume of 100 μl 1×PBS+0.05% Tween 20. Protein solutions were diluted in 11 times 1:2 in a 384-deep well plate (Greiner 384 Masterblock®). 20 μl of each sample from the dilution series were mixed with 20 μl of a 0.5 mM TCEP solution to a final protein concentration of 200-0.2 μg/ml and 0.25 mM TCEP on a 384 well REMP® plate (Brooks, #1800030). After centrifugation, plates were sealed and incubated for one hour at 37° C.

As control examples, bsAbs containing bio-binding functionality on one side and fluorescein-binding functionality on the other side were used. Functionality of the resulting bsAbs was assessed by biotin-fluorescein bridging ELISA. Therefore, white Nunc® MaxiSorp™ 384 well plates were coated with 1 μg/ml albumin-fluorescein isothiocyanate conjugate (Sigma, #A9771) and incubated overnight at 4° C. After washing 3 times with 90 μl PBST-buffer (PBST, double distilled water, 10×PBS Roche #11666789001+ 0.05% Tween 20), 90 μl/well blocking buffer (1×PBS, 2% BSA, 0.1% Tween 20) was added and incubated for one hour at room temperature. After washing 3 times with 90 μl PBST-buffer 25 μl of a 1:4 dilution of each exchange reaction was added to each well. After incubation for one hour at room temperature, plates were again washed 3 times with 90 μl PBST-buffer. 25 μl/well biotin-Cy5 conjugate in 0.5% BSA, 0.025% Tween 20, 1×PBS was added to a final concentration of 0.1 μg/ml and plates were incubated for one hour at room temperature. After washing 6 times with 90 μl PBST-buffer, 25 μl 1×PBS were added to each well. Cy5 fluorescence was measured at an emission wavelength of 670 nm (excitation at 649 nm) on a Tecan Safire 2 Reader.

Figure 11:
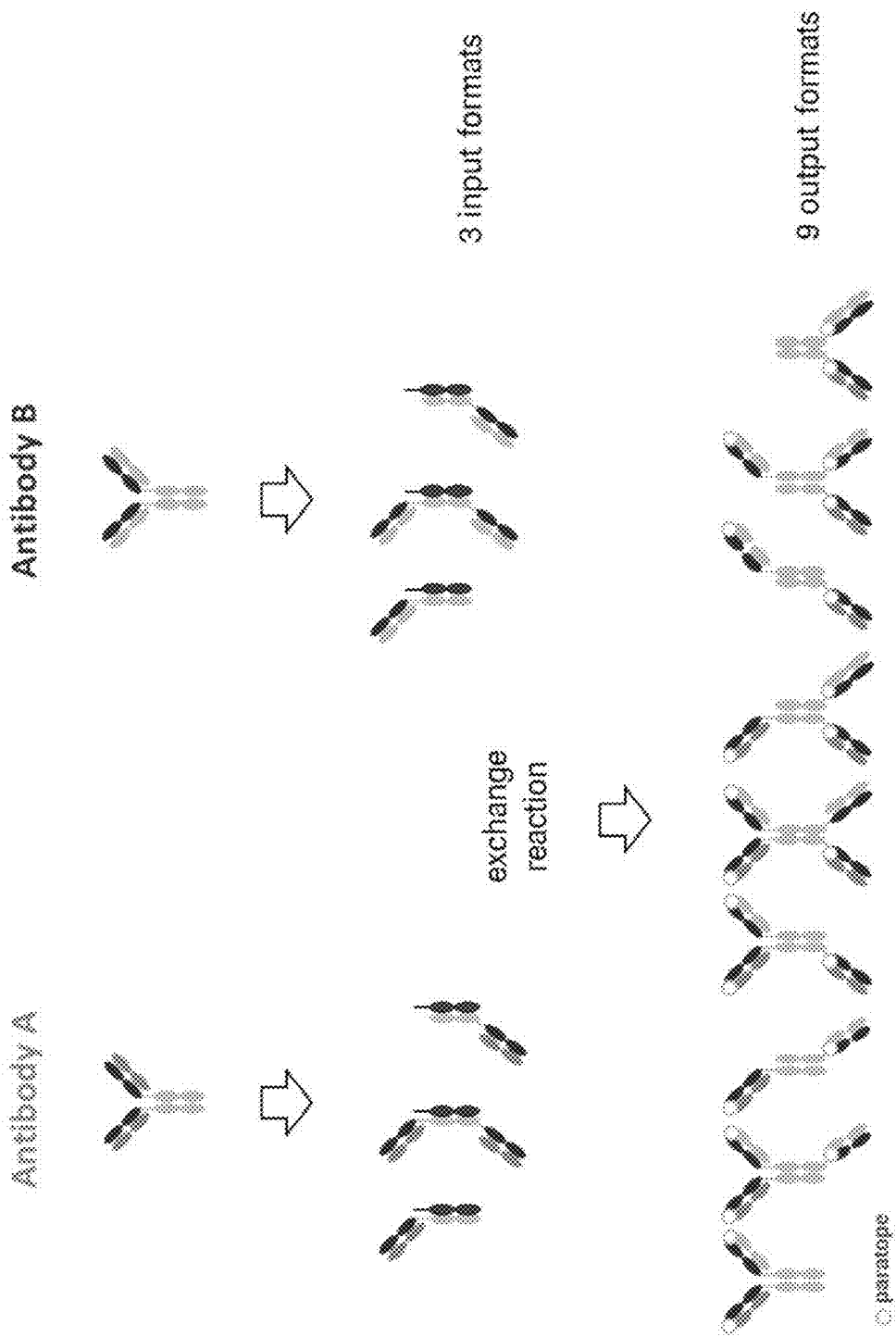
FIG. 11: IgG-exchange reaction using starting materials of different binding specificity and formats, exemplified with 2/3-IgGs.

Different bsAb formats via exchange of 2/3-IgGs of different formats were generated with one fluorescein binding entity and one biocytinamid binding entity. Input molecules and exchange-derived output molecules are shown in FIG. 11.

Figure 12:
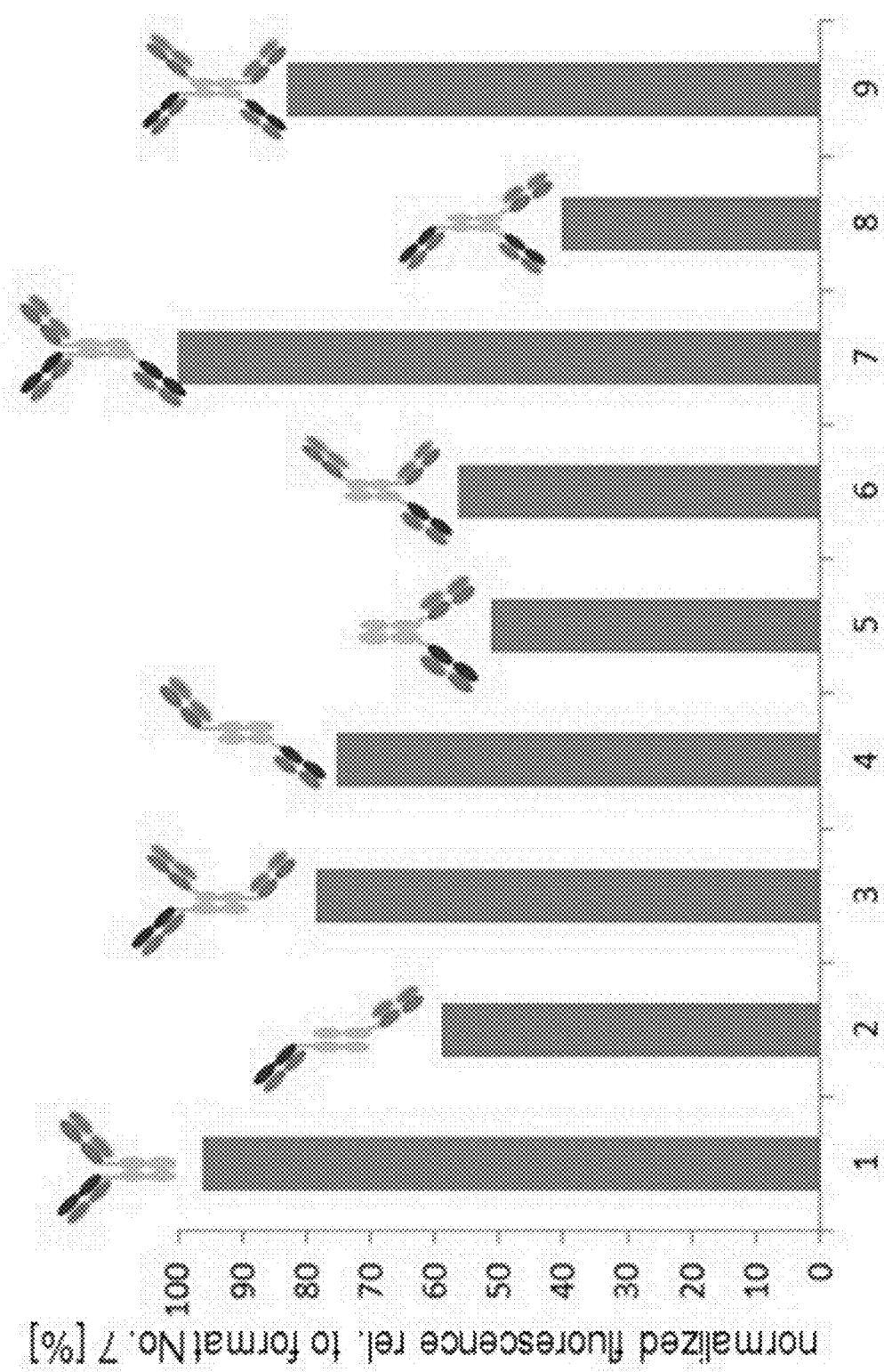
FIG. 12: Different bsAb format matrix generated via exchange reaction according to the current invention using exemplary 2/3-IgG. The matrix was generated with a fluorescein binding entity and a biocytinamid binding entity. Input molecules and exchange-derived output molecules are shown in FIG. 10. Functionality of generated bsAbs was assessed by bridging ELISA using fluos-BSA as capture antigen and bio-Cy5 to detect bispecific binding functionality. Signals derived from bridging ELISA shows all formats have bispecific binding efficacy.

Functionality of generated bsAbs was assessed by bridging ELISA as shown in FIG. 12, using fluos-BSA as capture antigen and bio-Cy5 to detect bispecific bridging binding functionality. All different formats result in a bridging ELISA signal.

These results show the feasibility to generate different formats using a method according to the current invention via chain exchange reactions in a robust and high-throughput compatible manner.

Example 8

Generation of Functional bsAbs by 2/3-IgG-Exchange and Screening/Identification of bsAbs with Desired Functionality is Compatible with Miniaturization and High-Throughput as Well as Automation Technologies Application of high-throughput and automation technologies is desired and in many instance necessary to handle large numbers of different bsAbs-differing in binding site sequence and/or format. It has therefore been analyzed if bsAb generation via the 2/3-IgG exchange method according to the current invention, as well as analysis/screening of the functionality, i.e. bispecific binding, of the thereby generated bispecific antibodies, can be miniaturized in order to be compatible with high throughput and automation technologies.

Therefore, 2/3-IgG exchange reactions were performed and the reaction products were analyzed in miniaturized scale in 348 well plates.

A matrix screen was set up in 384 well MTP format as follows: The exchange partners (2/3-IgG molecule 1 consisting of a full length heavy chain containing the hole-cys mutations and an MHCFcRP-knob-K370E; 2/3-IgG molecule 2 consisting of a full length heavy chain containing the knob-cys mutations and a MHCFcRP-hole-E357K) were mixed in equimolar amounts (4 µM) in a total volume of 30 µl 1×PBS+0.05% Tween 20. Protein solutions were diluted four times 1:3 in a 384-deep well plate (Greiner 384 Masterblock®). 20 µl of each sample from the dilution series were mixed with 20 µl of a 0.5 mM TCEP solution to a final protein concentration of 2 µM-0.025 µM and 0.25 mM TCEP on a 384 well REMP® plate (Brooks, #1800030). After centrifugation, plates were sealed and incubated for one hour at 37° C.

Figure 14:
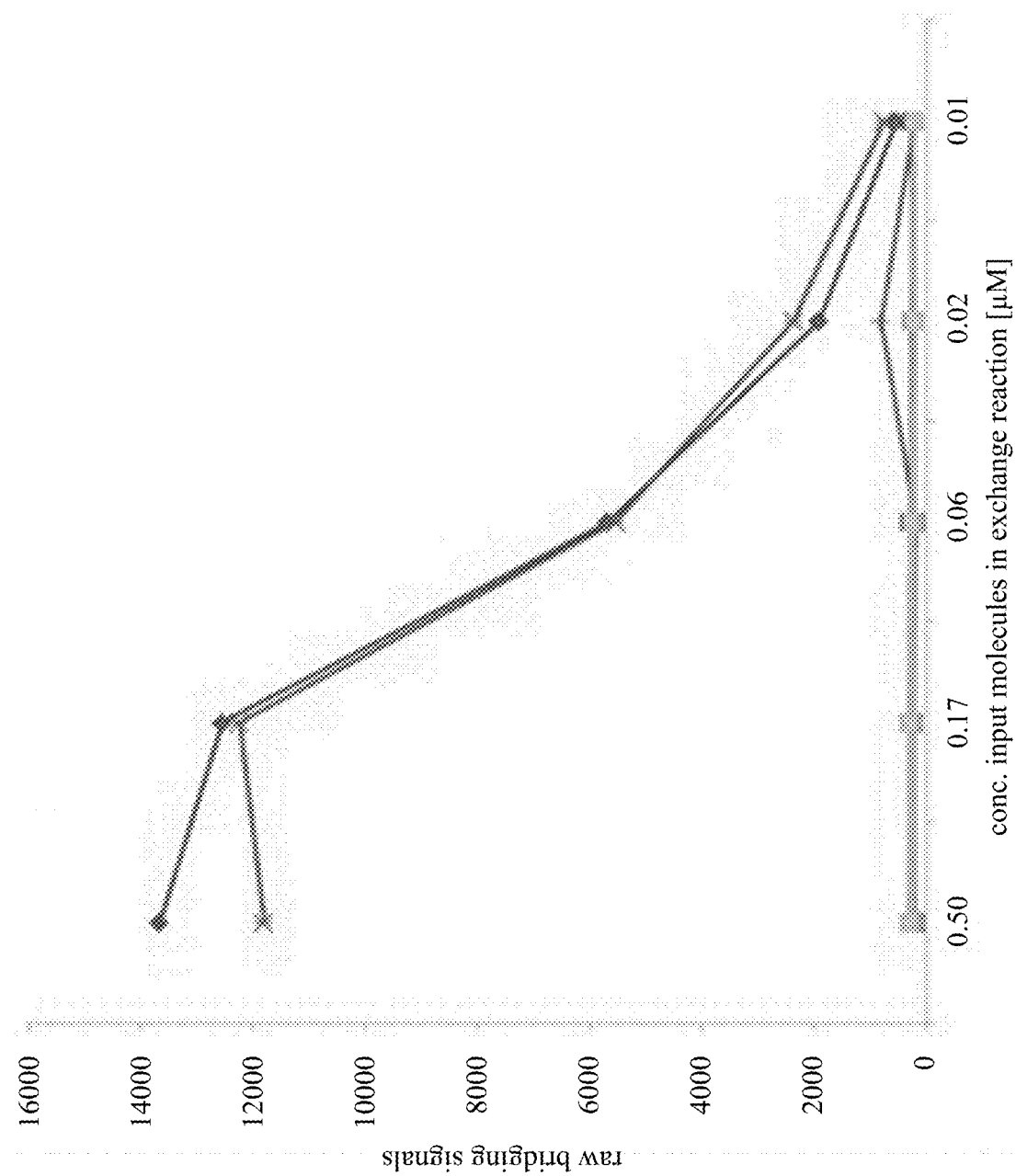
FIG. 14: Bispecific antibody formation via exchange according to the method of the current invention with HTS technology. Shown is the signal of an exemplary bridging ELISA showing concentration dependent fluorescence signals that are indicative for bispecific antibody formation. Fluos-bio bridging ELISA, cross: fluos [hole/K370E]+bio [knob/E357K], diamond: bio [hole/K370E]+fluos [knob/E357K]. All other curves: 2/3 IgG input molecules without cognate exchange partners do not show bridging signal.

The functionality of the thereby generated bsAbs was subsequently assessed via bridging ELISA (see above) in a miniaturized high-throughput format: White Nunc® MaxiSorp™ 384 well plates were coated with 1 µg/ml albumin-fluorescein isothiocyanate conjugate (Sigma, #A9771), 1 µg/ml PDGF (CST, #8912) or 1 µg/ml VEGF121 and incubated overnight at 4° C. After washing 3 times with 90 µl PBST-buffer (PBST, double distilled water, 10×PBS+ 0.05% Tween 20) blocking buffer (1×PBS, 2% BSA, 0.1% Tween 20) was added 90 µl/well and incubated for one hour at room temperature. After washing 3 times with 90 µl PBST-buffer 25 µl of a 1:4 dilution of each exchange reaction was added to each well. After incubation for 1 h at room temperature, plates were again washed 3 times with 90 µl PBST-buffer. 25 µl/well biotin-Cy5 conjugate or dig-Cy5 conjugate in 0.5% BSA, 0.025% Tween 20, 1×PBS was added to a final concentration of 0.1 µg/ml and plates were incubated for one hour at room temperature. After washing 6 times with 90 µl PBST-buffer, 25 µl 1×PBS were added to each well. Cy5 fluorescence was measured at an emission wavelength of 670 nm (excitation at 649 nm) on a Tecan Safire 2 Reader. The details of the exchange reactions and bridging ELISAs these analyses with 2/3-IgG modules that bind either VEGF or PDGF or dig or bio or fluos are shown in FIG. 13. The results of one exemplary these analysis is shown in FIG. 14 and demonstrates that 2/3-IgG-exchange reactions and subsequent functional analyses can be performed and are compatible with high-throughput and automation technologies.

Example 9

Generation of bsAbs with Three Binding Sites that Target a First Antigen with One Binding Site and a Further Antigen with the Two Other Binding Sites The method according to the current invention can be used for the generation of T-cell bispecific antibodies (TCBs). These can have a format as described before (see e.g. WO 2013/026831). For the TCB-exchange approach, one H-chain (either with knob-cys or with hole-cys as described above) contains a CD3-binding CrossFab-derived entity N-terminal of its hinge, further being extended at the N-terminus by another antibody-derived targeting entity. The exchange reaction is carried out under the same conditions described above and results in a TCB harboring a CD3 binding entity and two additional binding entities. These can bind to a target cell antigen. Those molecules can simultaneously bind to CD3 on T-cells and to an antigen on a target (e.g. tumor) cell and thereby induce killing of target cells.

Example 10

Design and Generation of 2/3-IgGs without Fc-Region Interchain Disulfide Bonds (in Hinge Region as Well as CH3 Domain)

Figure 15:
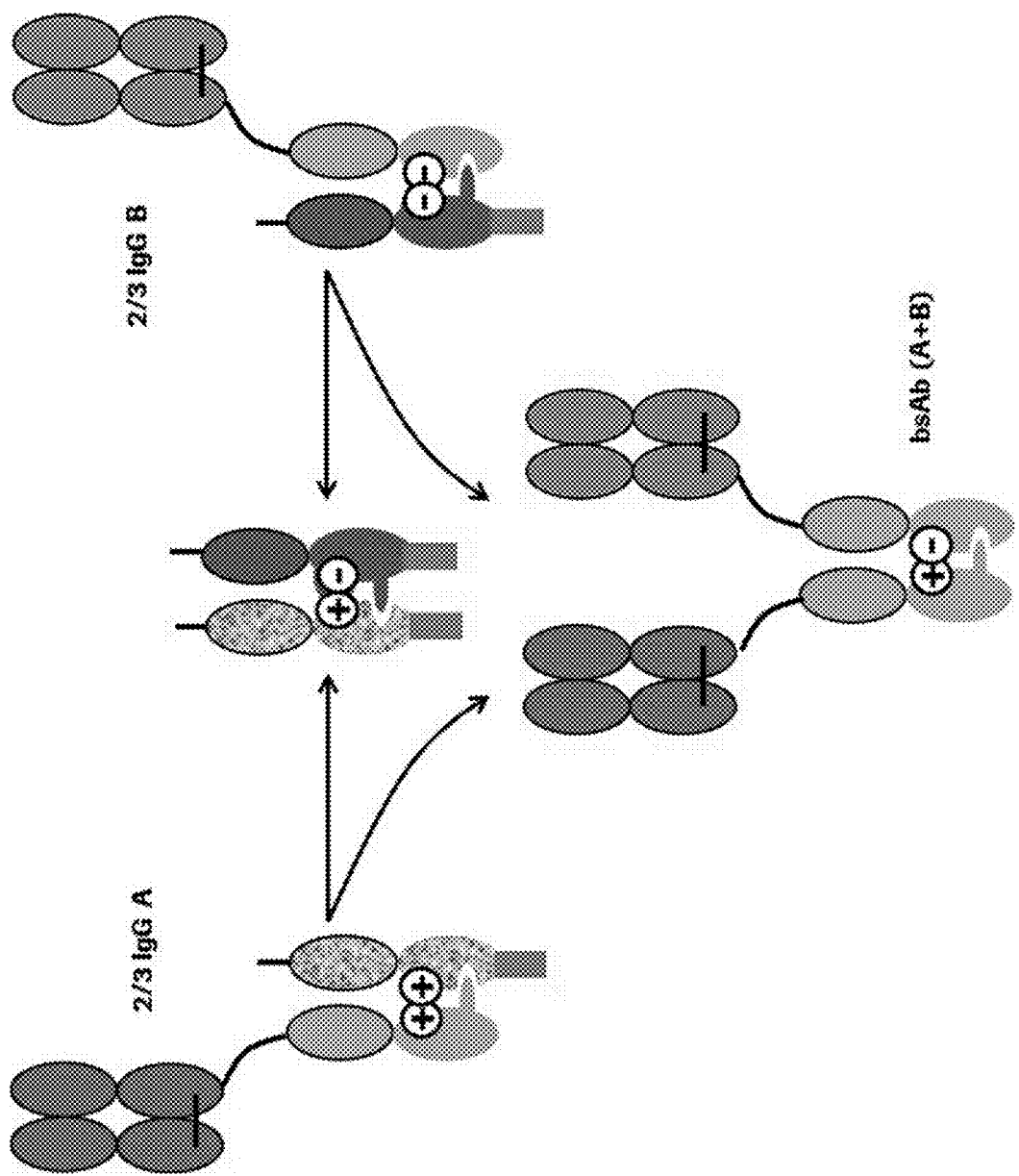
FIG. 15: Scheme of the exchange reaction according to the current invention exemplified with 2/3-IgGs without hinge-region and CH3 domain interchain disulfide bonds. This enables chain-exchange reaction in the method according to the current invention without the need to add a reducing agent.

Chain exchange with Fc-region (hinge region) disulfide containing 2/3-IgGs requires reduction as initial step to enable chain separation and subsequent assembly of desired bsAbs. To avoid the reduction step and the associated need to remove the reducing agent 2/3-IgGs without hinge region disulfide bonds were generated. The principle is shown in FIG. 15. The cysteine residues in the hinge region responsible for hinge-disulfide formation were removed by mutation to serine. Also the CH3-cysteine at position 354 or 349 that forms the KiH associated disulfide bond has been omitted. The respective amino acid sequences are:

| Chain | SEQ ID NO: |
|---|---|
| anti-bio antibody full length heavy chain-knob without hinge-region cysteine residues | 57 |
| anti-bio antibody full length heavy chain-hole without hinge-cysteine residues | 58 |
| anti-fluos antibody full length heavy chain-knob without hinge-cysteine residues | 59 |
| anti-fluos antibody full length heavy chain-hole without hinge-cysteine residues | 60 |
| MHCFcRP | |
| hole-D356K-His8 without hinge-cysteine residues | 61 |
| hole-E357K-His8 without hinge-cysteine residues | 62 |
| knob-K370E-His8 without hinge-cysteine residues | 63 |
| knob-K439E-His8 without hinge-cysteine residues | 64 |

Figure 16:
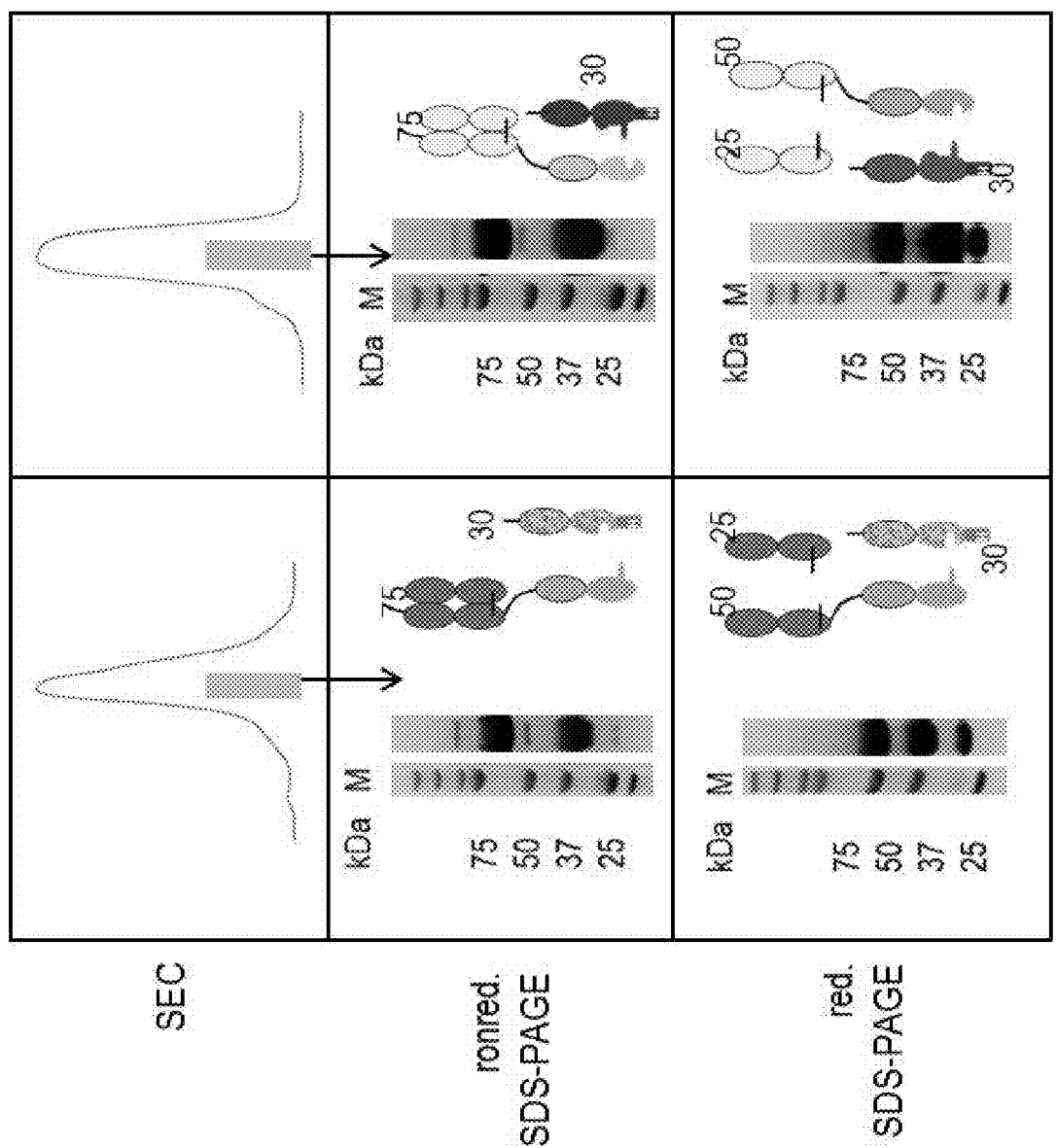
FIG. 16: The 2/3-IgGs without interchain disulfide bridges were secreted into culture supernatants like standard IgGs, purified by standard protein A affinity and size exclusion chromatography, and analyzed by SDS-PAGE confirming the desired 100 kDa 2/3-IgG as expression product. This proves correct assembly of the purified 2/3-IgG-derivatives without interchain disulfide bridges as well as absence of undesired dimers and aggregates. Purification of i) anti-bio antibody light chain (SEQ ID NO: 39)+anti-bio antibody heavy chain-knob without hinge region cysteine residues (SEQ ID NO: 57)+MHCFcRP-hole-E357K without hinge regions cysteine residues (SEQ ID NO: 62) (left) and ii) anti-fluos antibody light chain (SEQ ID NO: 42)+anti-fluos antibody full length heavy chain-hole without hinge region disulfide bonds (SEQ ID NO: 60)+MHCFcRP-knob-K370E without hinge region cysteine residues (SEQ ID NO: 63) (right).

Expression of the above 2/3-IgGs was achieved by co-transfection of plasmids encoding light chain, full length heavy chain (knob or hole) and corresponding MHCFcRP (hole or knob) into mammalian cells (e.g. HEK293) (see Example 2). The 2/3-IgGs were secreted into culture supernatants like standard IgGs and were thereafter purified by standard protein A affinity and size exclusion chromatography (see Example 2). Subsequent analytics via size exclusion chromatography and SDS-PAGE the desired 100 kDa 2/3-IgG expression product (FIG. 16). This proves correct assembly of the 2/3-IgG as well as absence of undesired dimers and aggregates. This is surprising as such molecules are not stabilized by disulfides between the Fc-regions (neither hinge region nor CH3 domain). The purification yield of anti-fluos- and anti-bio-2/3-IgGs without Fc-region interchain disulfide bonds are presented in the following Table

| | anti-bio antibody light chain (SEQ ID NO: 39) + anti-bio antibody heavy chain-knob without hinge region cysteine residues (SEQ ID NO: 57) + MHCFcRP-hole-E357K without hinge regions cysteine residues (SEQ ID NO: 62) | anti-fluos antibody light chain (SEQ ID NO: 42) + anti-fluos antibody full length heavy chain-hole without hinge region disulfide bonds (SEQ ID NO: 60) + MHCFcRP-knob-K370E without hinge region cysteine residues (SEQ ID NO: 63) |
|---|---|---|
| Protein A [mg/L] | >100 | >100 |
| SEC yield [mg/L 100 kDa] | >50 | >50 |

Example 11

Generation of Functional bsAbs by 2/3-IgG-Exchange Reaction without Reduction

Figure 17:
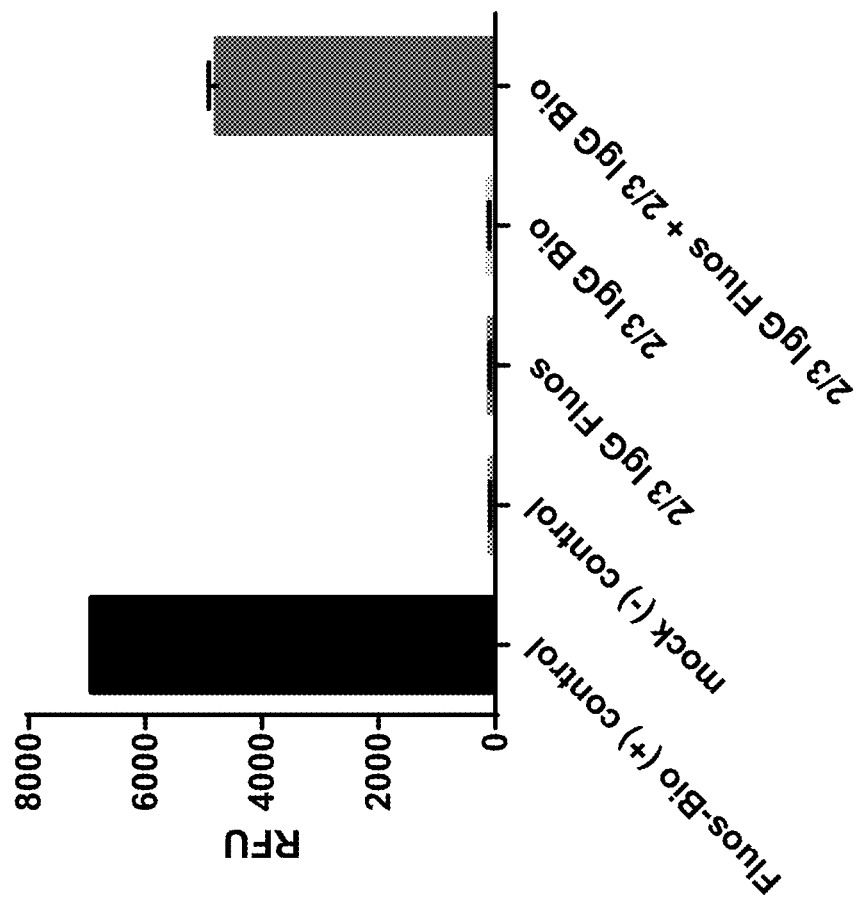
FIG. 17: Results of the exchange reaction according to the current invention with starting materials without hinge-region disulfide bonds: 2.5 µM concentration of input molecules with purified bsAb as positive control demonstrate successful bsAb generation via chain exchange with monospecific 2/3-IgG input molecules without Fc-region interchain disulfide bonds.

The 2/3-IgGs that do not contain Fc-region interchain disulfide bonds were subjected to chain exchange reactions as described above (see Example 3), except for omitting the initial reduction step. The 2/3-IgGs either contained fluos- or bio-binding sites and Fc-regions without interchain disulfide bonds between the full length heavy chain and MHCFcRP. Composition and production of these 2/3-IgGs was described in Example 10. Following exchange reactions without initiating reduction, a bridging ELISA was performed to demonstrate bispecific functionality of bsAbs. The bridging ELISA comprised the addition of exchange reaction products to immobilized fluos-BSA, followed by wash steps and subsequent addition of bio-Cy5 to probe for presence of the $2^{nd}$ binding arm of the bsAb (see previous examples for details of the bridging ELISA). Only correct assembled functional bsAbs can bind by their fluos-binding site to the assay plate, are retained and generate signals by capturing and retaining bio-Cy5. Molecules without bispecificity do not generate signals as they either do not bind to the plate (bio-only binder) or cannot capture the signal generating bio-Cy5 (fluos-only binder). The results of these analyses (performing the exchange reaction in this example at 2.5 µM concentration of input molecules with purified bsAb as positive control) are shown in FIG. 17. The results demonstrate successful bsAb generation via chain exchange with monospecific 2/3-IgG input molecules without Fc-region interchain disulfide bonds. Productive chain exchange took place without requirement of initial reduction. Thus, removal of inter Fc-region polypeptide disulfide bonds eliminated the necessity of an initial reduction step. The resulting bsAbs are held together by non-covalent Fc-Fc interactions. Elimination of Fc-Fc interchain disulfides thus allows for corresponding Fc-region mismatch driven exchange reactions without the need for reduction.

Example 12

Chain Exchange Reactions are Driven by Partially De-Stabilized Full Length Heavy Chain—MHCFcRP Interfaces The driver for conversion of 2/3-IgGs to bsAbs is a designed 'flawed' interface between the full length heavy chain and the MHCFcRP. This artificial repulsive interface is the result of mutations introduced into the knob- or hole-CH3 domains of the MHCFcRP. The MHCFcRP still associate with the corresponding ("normal") knob- or hole-partners during expression of 2/3 IgGs (see examples above). Those molecules have sufficient stability to present 2/3-IgGs as well behaved molecules without undesired aggregation tendencies.

Without being bound by this theory, the exchange reaction according to the current invention leading to bsAbs occurs when two complementary 2/3-IgGs come into close distance and the full length antibody heavy chain::MHCFcRP pairs are partially released next to each other. Re-assembly of the matching, i.e. not charged repulsed, knob-hole full length heavy chains should be favored under such conditions because the full length antibody heavy chain (CH3) interfaces are perfect. Thus, the full length heavy chains of the formed bsAb remain associated with preference over re-formation of the partially imperfect (charge mismatched) 2/3-IgG molecules. Thus, a designed partially de-stabilized (charge repulsed) CH3 interface is a key parameter for successful directed chain exchange reactions.

Partial de-stabilization of the Fc interface, especially the CH3-CH3 interface, can be achieved by mutating CH3 residues of the MHCFcRP while maintain the interacting residues on the full length antibody heavy chain.

Exemplary mutations that can be introduced into the CH3 domain of the MHCFcRP affecting the full length antibody heavy chain::MHCFcRP interface are provided in the following Table.

| position (EU numbering) | perturbing mutation(s) |
|---|---|
| 345E | R |
| 347Q | K |
| 349Y | W or E |
| 351L | F or Y |
| 354S | E or V |
| 356D | S or A or K |
| 357E | S or A or L or F or K |
| 360K | S or E |
| 362Q | E |
| 364S | V or L |
| 366T | I |
| 368L | F or V |
| 370K | E |
| 390N | E |
| 392K | E or D |
| 394T | I |
| 397V | Y |
| 399D | A or K |
| 400S | K |
| 401D | R |
| 405F | W |
| 407Y | W or L or I |
| 409K | D or E or I |
| 439K | E |
| 441L | Y |

Some of the mutations include exchanges that place altered charges into the interface. Charge mutations either weaken or break previously existing stabilizing charge pairs or result in repulsion effects, or in both.

Similarly, amino acids with differently sized side chains can be introduced to generate steric repulsion effects. Such mutations either weaken or interfere with existing hydrophobic interface interactions or generate steric hindrances, or combine both.

Mutations that partially de-stabilize via charge and/or steric effects can also be combined with each other.

Furthermore, a first 2/3-IgG that contains charge and/or steric alterations introduced into its MHCFcRP can be combined with a second 2/3-IgG that contains different charge and/or steric alterations introduced into its MHCFcRP which match those of the MHCFcRP from the first 2/3-IgG.

The 2/3-IgGs as well as the resulting bsAbs assemble in a manner in which paired CH3 domains harbor knob-mutations on one side and hole-mutations on the other. Therefore, 'back-mutation' to wild-type composition of corresponding knob- or hole-residues of the MHCFcRP generate also interface disturbances. Such combinations of knob- or hole-CH3-domains with wild-type domains are listed in the following Table.

| CH3 hole | |
| --- | --- |
| position (EU numbering) | perturbing backmutation |
| 349C* | Y |
| 366S | T |
| 368A | L |
| 407V | Y |
| CH3 knob | |
| Fc position (EU numbering) | perturbing backmutation |
| 354C* | S |
| 366W | T |

These backmutations can be applied to partially destabilize the CH3-CH3-interface.

These backmutations can also be applied in combination with other perturbing mutations incl. those described in the previous Table.

All partially perturbing individual mutations or combination of mutations as described above can also be chosen in a manner that they partially destabilize the 2/3-IgG, yet stabilize a knob-MHCFcRP::hole-MHCFcRP heterodimer as the 2nd product of the exchange reaction and thereby shifting the reaction equilibrium further to the product side (exchange reaction).

Example 13

Figure 18:
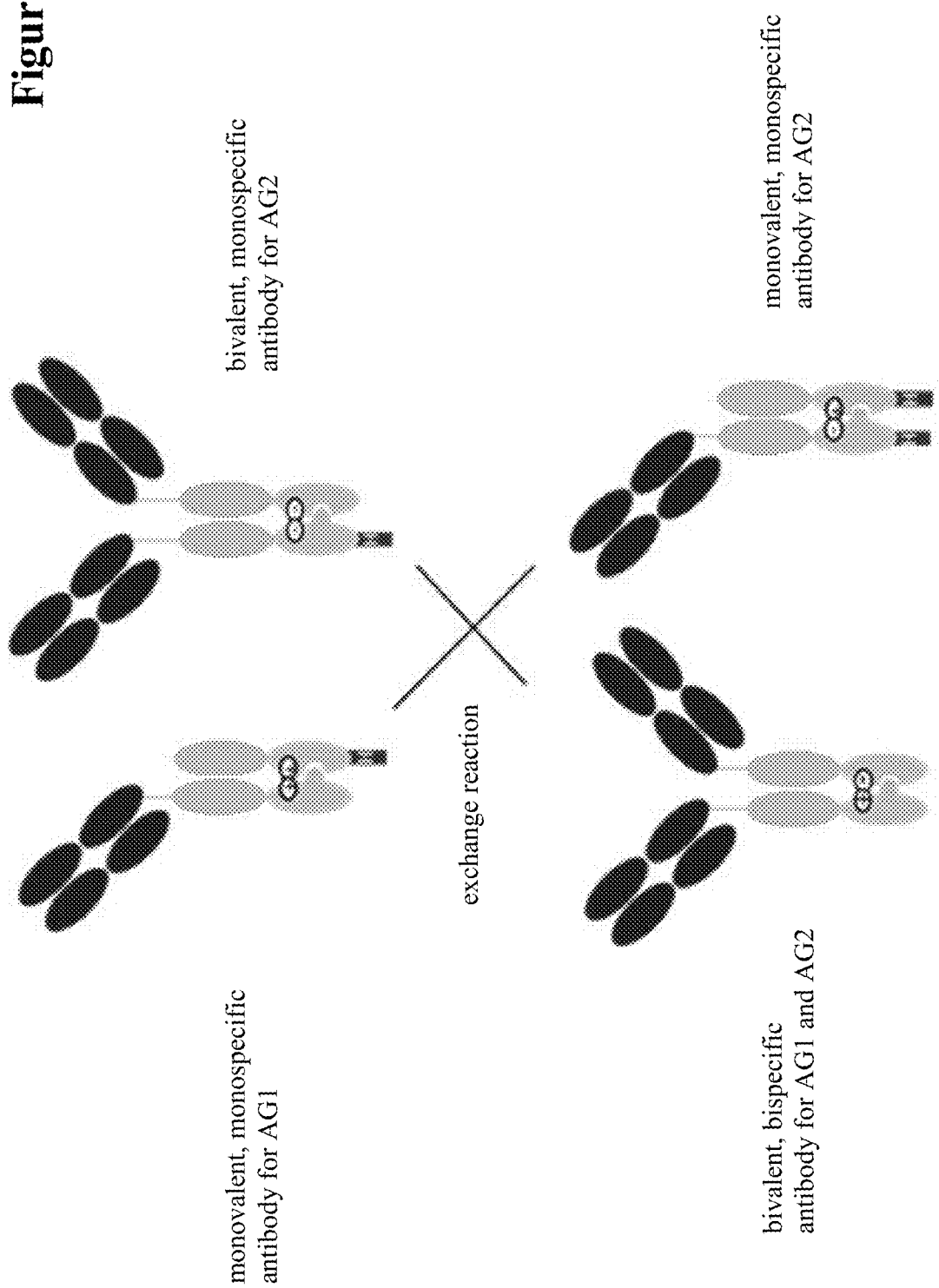
FIG. 18: Generation of bsAbs (bispecific antibodies) by exchange reaction according to the current invention exemplified with a 2/3 IgG (left) and an IgG (right).

Design of 2/3-IgGs that Enable Targeting with Non-Antibody Moiety and Chain-Exchange Reaction The exchange reaction according to the current invention utilizes interface mutations between CH3 knob-and-hole entities to drive the chain exchange reactions. FIG. 18 demonstrates the principle: interaction of two molecules each with H-chain heterodimers composed of 'imperfect' Fc-interfaces exchange their H-chains to form two new entities each with 'perfect' H-H chain interfaces. This principle can be applied to generate large varieties of bispecific antibodies and formats, e.g. for screening purposes.

Figure 19:
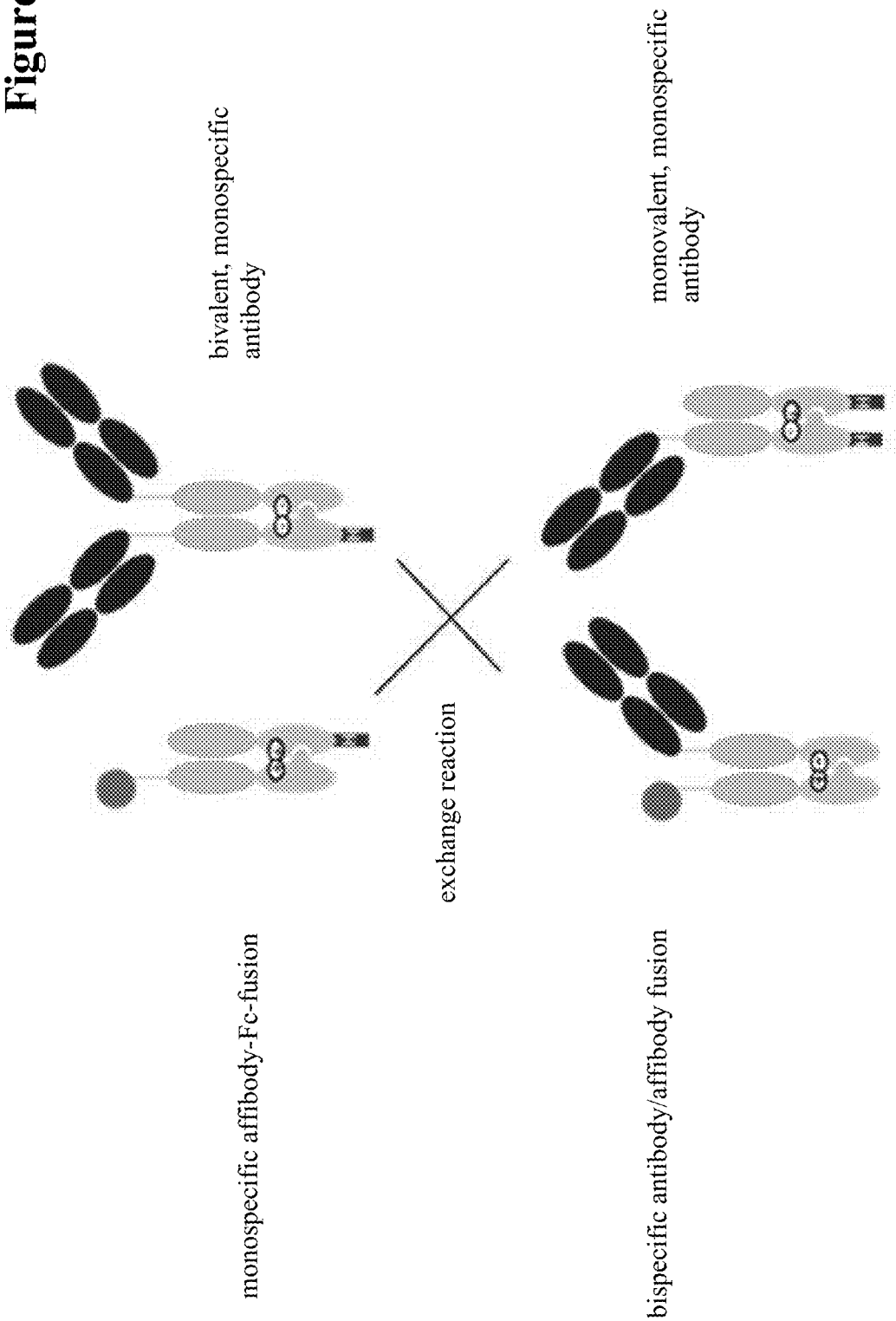
FIG. 19: Generation of bsAbs (bispecific antibodies) by exchange reaction according to the current invention exemplified with a 2/3 IgG where the Fab has been replaced by an affibody (left) and an IgG (right).

The stem-unit can be used with any binder, such as e.g. non-antibody moieties. A molecule was designed that contains a non-antibody binding unit, an affibody targeting HER2 (ZHER2:342; Orlova et al., Cancer Res. 66 (2006) 4339-4348), replacing the conventional Fab binding unit in the 2/3-IgG. The amino acid sequences of the two polypeptide chains are SEQ ID NO: 83 and 84. The principle according to the invention applies also in this case and is specifically for this exchange reaction shown in FIG. 19.

The molecules have been produced as outlined in Example 2 and the exchange reaction has been performed as outlined in Example 3.

In more detail, sequences for expression were generated by gene synthesis or mutagenesis and were cloned into CMV promoter based expression plasmids. The constructs harbored the Her2 affibody binder in their binding entity that is to become subject to the chain exchange reaction according to the invention.

Transient expression was performed in FreeStyle™ 293-F cells (Invitrogen) according to the manufacturer's instruction. Briefly, HEK293-F cells (Invitrogen) growing in suspension in a shake flask in serum-free FreeStyle™ 293 expression medium (Invitrogen) were transfected with the respective expression plasmid and 293-Fectin™ (Invitrogen). For 2 L shake flask (Corning) HEK293-F cells were seeded at a density of $1*10^6$ cells/mL in 600 mL and incubated at 120 rpm, 8% $CO_2$. The following day the cells were transfected at a cell density of approx. $1.5*10^6$ cells/mL with approx. 42 mL mix of 20 mL Opti-MEM (Invitrogen) with 600 μg total plasmid DNA (1 μg/mL) and 20 ml Opti-MEM+1.2 mL 293 fectin (2 μL/mL). Bolus glucose solution and a feed solution were added during the course of the expression according to the manufacturer's protocol. Correctly assembled proteins were secreted into culture supernatants. The supernatant was harvested 6 days after transfection.

Purification of the affibody-containing protein was performed by affinity chromatography using Complete™ His-Tag purification resin (Roche, Switzerland), followed by Superdex 200 size exclusion (GE Healthcare, Sweden) chromatography. Briefly, sterile filtered cell culture supernatant was captured on Complete™ His-Tag purification resin equilibrated with 50 mM $Na_2HPO_4$ and 300 mM NaCl, pH 7.4, washed with equilibration buffer and eluted with 50 mM $Na_2HPO_4$, 300 mM NaCl and 250 mM imidazole, pH 7.4. The eluted protein fractions were pooled, concentrated to 2 ml total volume using Vivaspin ultrafiltration devices (Sartorius Stedim Biotech S.A., France) and further purified by size exclusion chromatography using a Superdex 200 16/60 GL (GE Healthcare, Sweden) column equilibrated with 20 mM histidine, 140 mM NaCl, pH 6.0. The protein containing fractions were pooled, concentrated to the required concentration and stored at −80° C.

Figure 20:
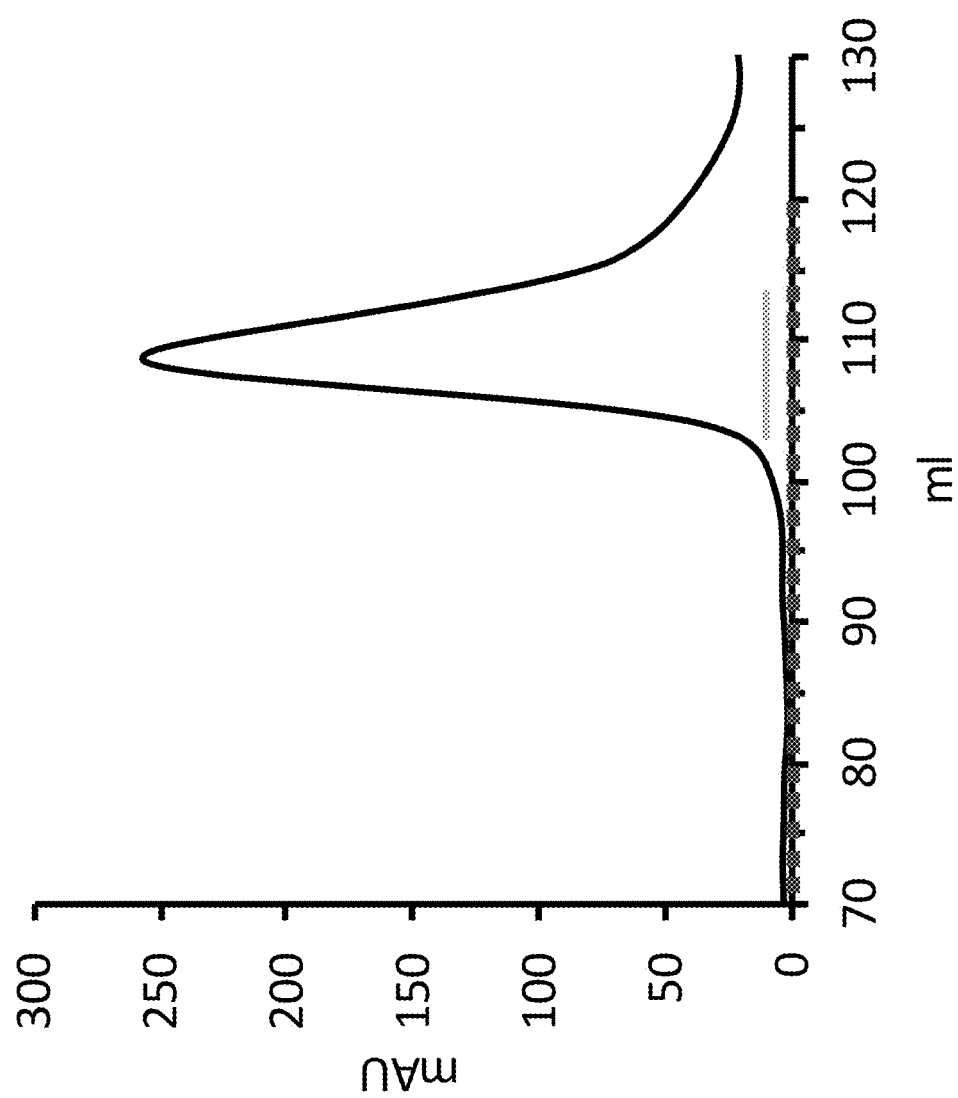
FIG. 20: SEC chromatogram of the purified affibody construct for use in the exchange reaction according to the current invention after Complete™ His-Tag purification from cell culture supernatant; the horizontal line indicates the fractions pooled for further studies.
Figure 21:
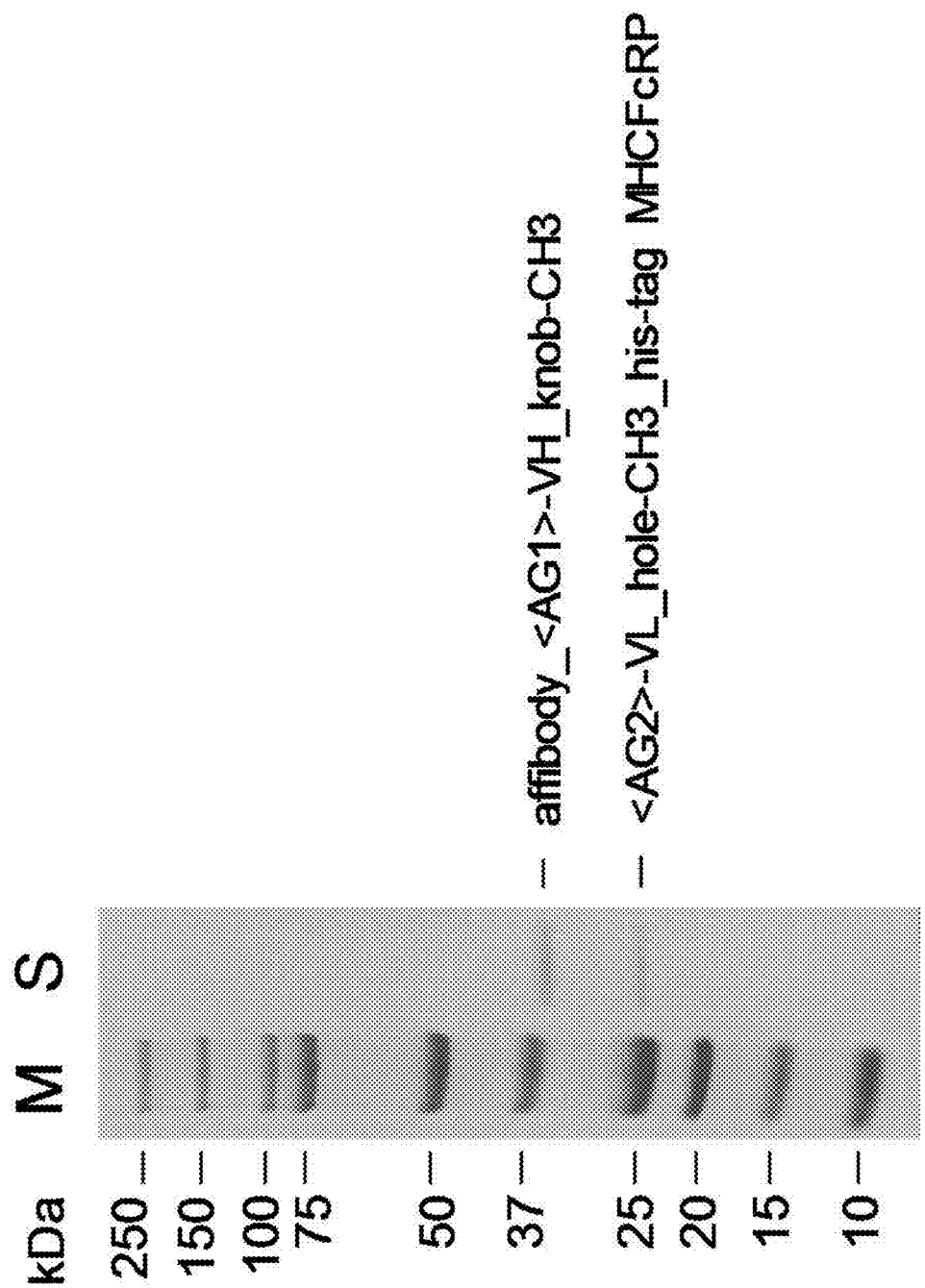
FIG. 21: SDS-PAGE of the SEC-purified affibody construct to be used in the exchange reaction according to the current invention; M=marker, S=sample.

Purity and correct composition is shown in FIG. 20 (SEC profile after affinity purification) and FIG. 21 (SDS-PAGE of purified material). The production yield was comparable to other Fab-containing 2/3-IgGs (5.8 mg/L culture).

The exchange reaction according to the current invention was performed with the protein carrying the non-antibody affibody moiety. Therefore, the protein was mixed with a LeY-targeting prodrug molecule (see FIG. 19 for exchange reaction scheme) at 2 μM each in a total volume of 300 μl in 20 mM histidine, 140 mM NaCl, pH 6.0, followed by 1h incubation at 37° C.

Figure 22:
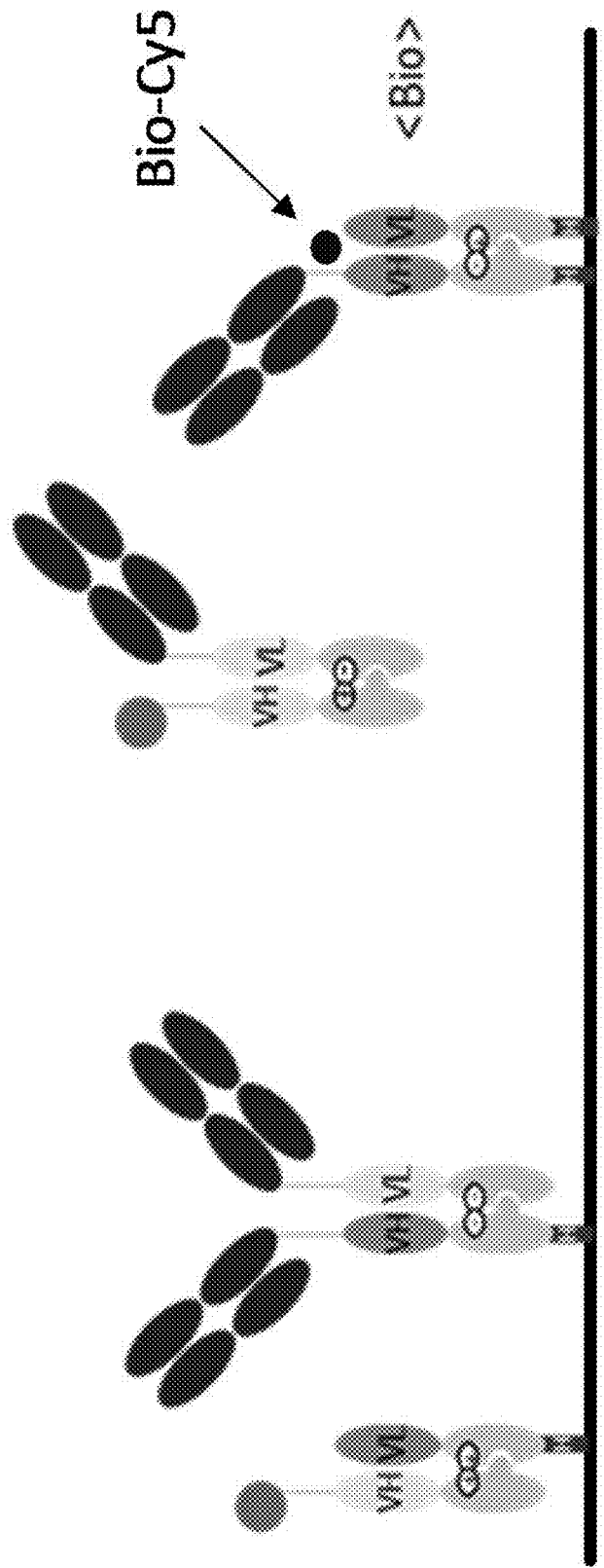
FIG. 22: ELISA assay scheme. Reactants carry His-tags and are able to bind to Ni-coated plates, but have no functional biotin (Bio)-binding entity and hence do not bind Bio-Cy5. Only upon chain exchange in the exchange reaction according to the current invention the functional anti-biotin binding site is generated, which enables Bio-Cy5 capture and fluorescent signal detection.
Figure 23:
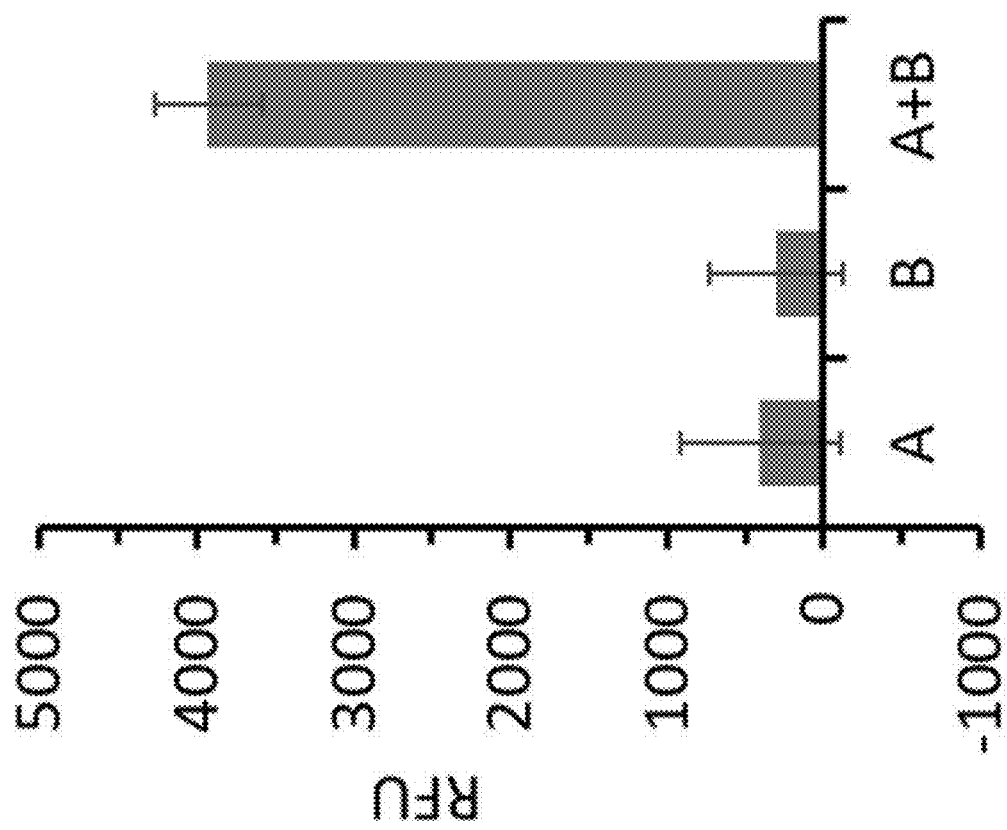
FIG. 23: ELISA assay results. The ELISA confirms chain exchange between entities carrying Fab arms and non-antibody binding scaffolds.

The successful exchange reaction according to the current invention of the pro-drug entities to functional binding molecules was demonstrated by ELISA. The ELISA assay principle is shown in FIG. 22. Reactants carry His-tags, but yet do not have a functional antigen-binding, i.e. biotin-binding, entity. Only upon chain exchange the biotin-binding site (VH/VL-pair, anti-biotin Fv) is formed, which is a functional binding site and allows for Bio-Cy5 capture and fluorescent signal detection. For the ELISA samples were diluted to 1 μM of reactant protein concentration in 1×PBS with 1% (w/v) bovine serum albumin, applied at 100 μl to Black Pierce© Nickel Coated 96-well plates (Thermo Fisher Scientific, USA) and incubated for one hour at room temperature. After washing three times with 250 μl PBST-buffer (1×PBS+0.05% Tween 20), 100 μl of 100 ng/ml biotin-Cy5 conjugate in PBST was added. Thereafter an incubation for one hour at room temperature was carried out. After washing four times with 250 μl PBST-buffer, 100 μl PBST was added to each well. Cy5 fluorescence was measured at an emission wavelength of 675 nm (excitation at 647 nm) on a Tecan Infinite M200 Pro Reader. FIG. 23 shows the results of the ELISA and reveals successful chain exchange and activation of the binding Fv from inactive prodrug entities. This demonstrates that non-antibody moieties can be used in the exchange reaction according to the invention and thereby for pro-drug activation.

Example 14

Nickel Affinity Chromatography.

The removal of the unreacted starting material as well as histidine-tag harboring exchange product can be performed using nickel affinity chromatography.

The nickel affinity chromatography was performed using 0.2 ml HisPur™ Ni-NTA Spin Columns (ThermoScientific) according to the manufacturer's instructions. The crude reactions mixture of the exchange reaction was applied to the equilibrated column. For increased contact between sample and the agarose-based affinity material the columns were incubated for one hour at room temperature. Optionally the columns can be spun during the incubation. Non-bound material was eluted by centrifugation in flow-thought mode with wash-buffer. After washing for three times bound material was eluted using the elution buffer according to the manufacturer's instructions.

Example 15

Expression and Purification of Fab-Extended-2/3-IgGs According to the Invention

Expression of Fab-extended-2/3-IgGs was achieved by co-transfection of plasmids encoding Fab-extended-light chain, Fab-extended-heavy chain (with knob or hole mutations) and matching MHCFcRP (hole or knob) into mammalian cells (e.g. HEK293) via state of the art technologies.

In more detail, for example, for the production of the Fab-extended-2/3-IgGs by transient transfection (e.g. in HEK293 cells) expression plasmids based either on a cDNA organization with or without a CMV-Intron A promoter or on a genomic organization with a CMV promoter were applied. The plasmid contained one expression cassette for the Fab-extended-heavy chain and each an expression cassette for the two light chains.

Beside the antibody expression cassettes, the plasmids contained:
an origin of replication, which allows replication of this plasmid in *E. coli,*
a β-lactamase gene, which confers ampicillin resistance in *E. coli.*, and
the dihydrofolate reductase gene from *Mus musculus* as a selectable marker in eukaryotic cells.

The transcription unit of each antibody gene was composed of the following elements:
unique restriction site(s) at the 5'-end
the immediate early enhancer and promoter from the human cytomegalovirus,
followed by the Intron A sequence in the case of the cDNA organization,
a 5'-untranslated region of a human antibody gene,
an immunoglobulin heavy chain signal sequence,
the respective antibody chain either as cDNA or in genomic organization (the immunoglobulin exon-intron organization is maintained),
a 3'-non-translated region with a polyadenylation signal sequence, and
unique restriction site(s) at the 3'-end.

The fusion genes were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The Fab-extended-2/3-IgGs were generated by transient transfection with the respective plasmid using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with the respective expression plasmid and 293Fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL mix of A) 20 mL Opti-MEM (Invitrogen) with 600 μg total plasmid DNA (1 μg/mL) and B) 20 ml Opti-MEM+1.2 mL 293 fectin or fectin (2 μL/mL). According to the glucose consumption glucose solution was added during the course of the fermentation. Correctly assembled Fab-extended-2/3-IgGs were secreted into culture supernatants like standard IgGs. The supernatant containing the secreted Fab-extended-2/3-IgG was harvested after 5-10 days and Fab-extended-2/3-IgGs were either directly purified from the supernatant or the supernatant was frozen and stored.

Because Fab-extended-2/3-IgGs contain an Fc-region they were purified by applying standard protein A affinity chromatography.

The antibodies were purified from cell culture supernatants by affinity chromatography using MabSelectSure-Sepharose™ (GE Healthcare, Sweden) and Superdex 200 size exclusion (GE Healthcare, Sweden) chromatography.

Briefly, sterile filtered cell culture supernatants were captured on a MabSelectSuRe resin equilibrated with PBS buffer (10 Mm $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted Fab-extended-2/3-IgG fractions were pooled and neutralized with 2 M Tris, pH 9.0. The pools were further purified by size exclusion chromatography using a Superdex 200 26/60 GL (GE Healthcare, Sweden) column equilibrated with 20 mM histidine, 140 mM NaCl, pH 6.0. The Fab-extended-2/3-IgG containing fractions were pooled, concentrated to the required concentration using Vivaspin ultrafiltration devices (Sartorius Stedim Biotech S.A., France) and stored at −80° C.

Purity and integrity were analyzed after each purification step by CE-SDS using microfluidic Labchip technology (Caliper Life Science, USA). Protein solution (5 μl) was prepared for CE-SDS analysis using the HT Protein Express Reagent Kit according manufacturer's instructions and analyzed on LabChip GXII system using a HT Protein Express Chip. Data were analyzed using LabChip GX Software.

Figure 27:
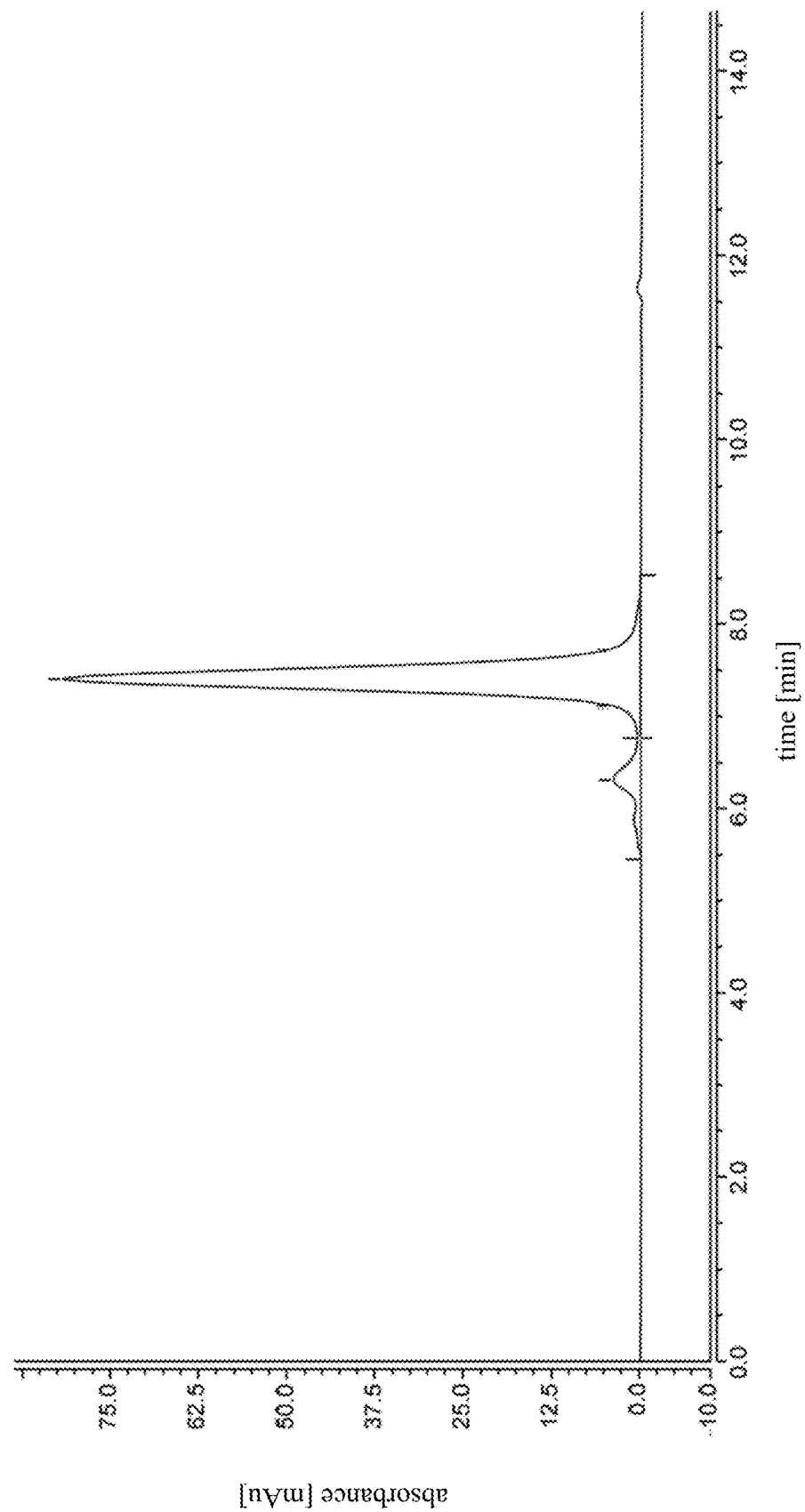
FIG. 27: SEC chromatogram of the purified Fab-extended 2/3-IgG.

The following exemplary Fab-extended-2/3-IgGs has been produced by co-expression of corresponding L-chain, H-chain and MHCFcRP encoding plasmids: anti-fluorescein-anti-CD3-2/3-IgG-knob-cys+anti-biotin-E357K-hole-MHCFcRP. The corresponding SEC chromatogram is shown in FIG. 27. The monomer content according to SEC was 93.4%. The monomer content according to CE-SDS was 100%. The mass was confirmed by MS.

Example 16

Generation of Bispecific Antibodies (bsAbs) by 2/3-IgG-Exchange Reaction with Fab-Extended-2/3-IgGs as Starting Material The Fab-extended-2/3-IgG that contain two light chains, a heavy chain and MHCFcRP has been generated as KiH heterodimer: full length heavy chain-knob::MHCFcRP-hole. The Fab-extended-2/3-IgG is somewhat 'flawed' as the MHCFcRP contains a charge mutation without matching charge in the full length heavy chain counterpart. The modules that make up those flawed heterodimers, however, are capable to rearrange to bispecific heterodimers with matching charges. The full length heavy chain (knob) of the Fab-extended-2/3-IgG A and the full length heavy chain (hole) from 2/3-IgG B form a matching heterodimer. Matching heterodimers are also formed when MHCFcRP (hole-charge) interacts with MHCFcRP (knob-charge). Thus, exchange reactions based on temporary separation of starting heterodimers of two different 2/3-IgGs resulted in products that contain preferentially (charge) matching heterodimers. Exchange reactions therefore converted two monospecific 2/3-IgGs to one bispecific IgG and one MHCFcRP heterodimer:

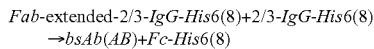

Fab-extended-2/3-IgG-His6(8)+2/3-IgG-His6(8)
→bsAb(AB)+Fc-His6(8)

The exchange reaction was initiated by a reduction step (e.g. by applying 2-MEA or TCEP at various concentrations) to break especially the hinge-region interchain disulfide bonds. Chain rearrangement occurred spontaneously thereafter.

Figure 26:
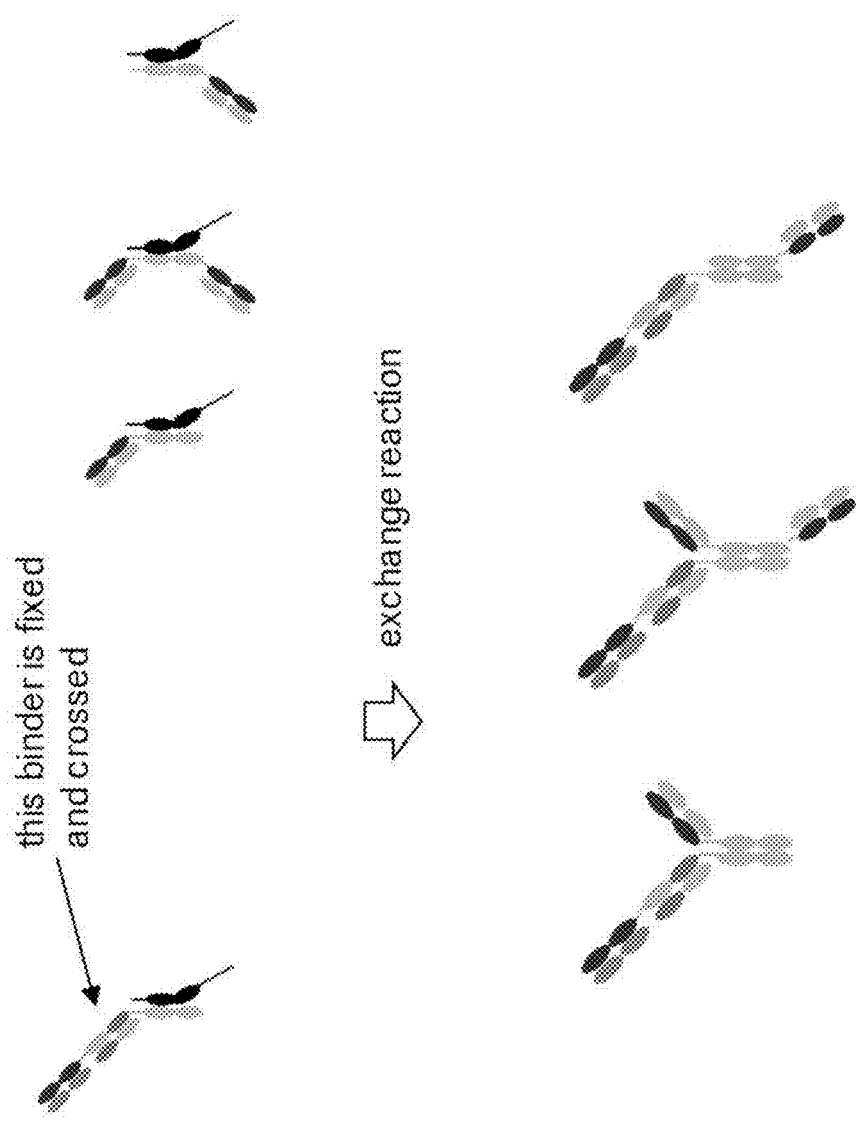
FIG. 26: Exchange reaction according to the current invention with a 2/3-IgG comprising a second Fab-region.

The procedure for the three exchange reactions with the Fab-extended 2/3-IgG as shown in FIG. 26 was as follows:

1 mg of Fab-extended-2/3-IgG(dA) was mixed with 1 mg of the respective 2/3-IgG format (nB or cB or ncB) in 1×PBS-buffer in a total volume of 2 ml. 16× molar equivalents of TCEP in 1×PBS-buffer were added to the mixture. Samples were incubated for one hour at 37° C. and 350 rpm agitation. After the incubation time, samples were purified via NiNTA chromatography columns (HisComplete™, Roche, Basel, Switzerland) and assembled bispecific antibodies were collected in the flow-through. The flow through was further incubated overnight at room temperature. Samples were then analyzed by analytical SEC, CE-SDS and mass spectroscopy methods.

The results of the exchange reaction are presented in the following table:

| bispecific antibody<br><FITC> = anti-FITC Fab<br><CD3> = anti-CD3 Fab<br><Biotin> = anti-biotin Fab<br>HC = heavy chain | yield [%] | SEC monomer [%] | CE-SDS (non-reducing) monomer [%] | MS |
|---|---|---|---|---|
| <FITC><CD3>-knob-HC (dA)<br><Biotin>-hole-n-HC (nB) | 6 | 96 | 44.7 | confirmed |
| <FITC><CD3>-knob-HC (dA)<br><Biotin>-hole-nc-HC (ncB) | 14 | 94 | 43.4 | confirmed |
| <FITC><CD3>-knob-HC (dA)<br><Biotin>-hole-c-HC (cB) | 17 | 93 | 48.5 | confirmed |

Figure 28:
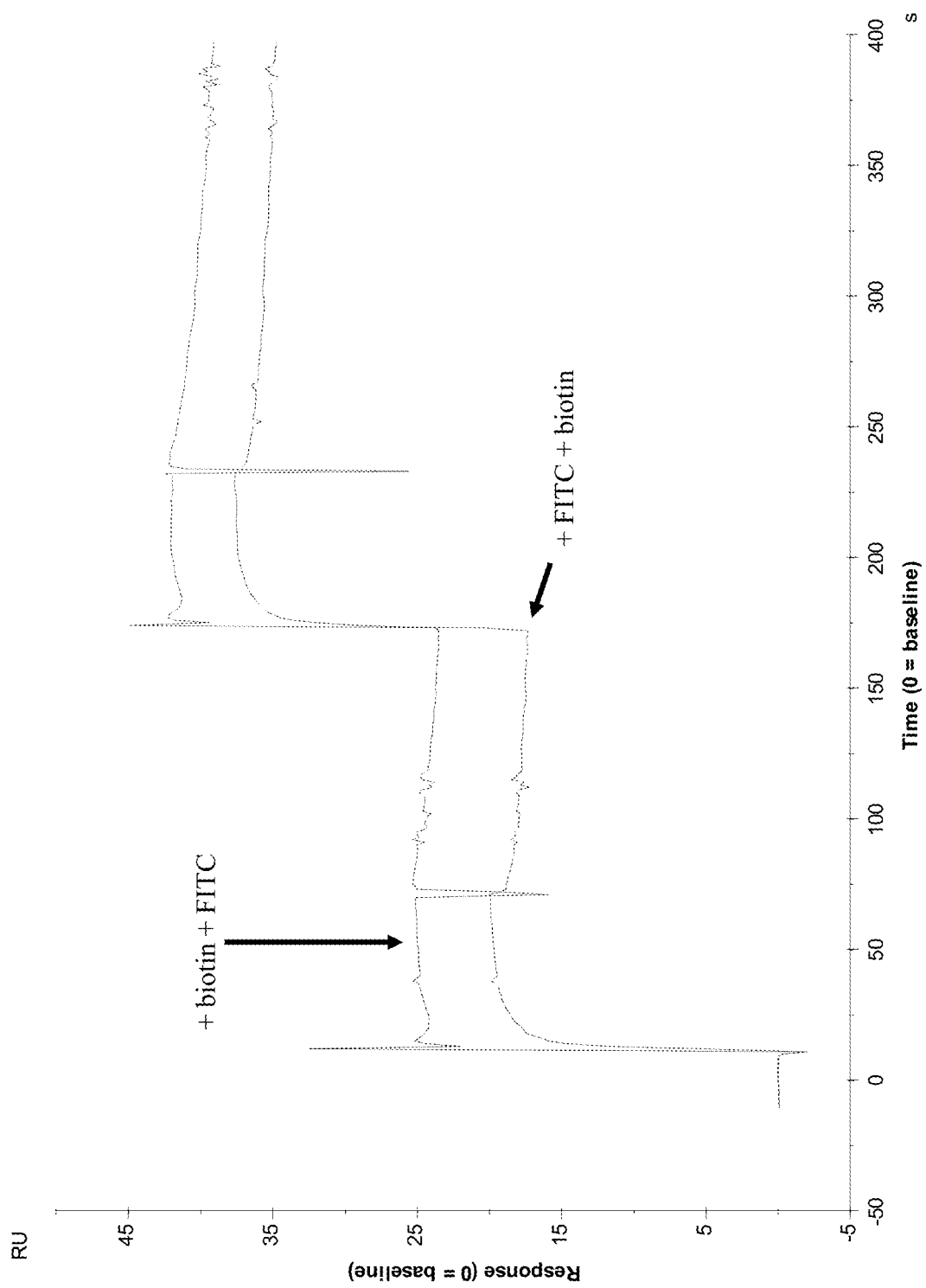
FIG. 28: SPR sensogram for the bispecific antibody <FITC><CD3>-knob-HC (dA)+<Biotin>-hole-nc-His (ncB) obtained by consecutive injections of a Biotin- or FITC-labelled protein (once the biotin-labelled first and the FITC-labelled second and once the FITC-labelled has been injected first and the biotin-labelled second).

Binding to biotin and FITC was investigated by surface plasmon resonance using a BIAcore T200 instrument (GE Healthcare). All experiments were performed at 25° C. using HBS-P (10 mM HEPES, 140 mM NaCl, 0.05% Tween 20 pH 7.4) as running and dilution buffer. Anti-human Fc antibodies (GE Healthcare #BR100839) were immobilized on a Series S CM5 Sensor Chip (GE Healthcare #29104988) using standard amine coupling chemistry. The bispecific antibodies were captured onto the surface followed by consecutive injections of a Biotin- or FITC-labelled protein (once the biotin-labelled first and the FITC-labelled second and once the FITC-labelled has been injected first and the biotin-labelled second). Association was monitored for 60 seconds, dissociation for 120 seconds at concentrations of 10 µg/ml each. The surface was regenerated by injecting 3 M MgCl$_2$ for 60 seconds. Bulk refractive index differences were corrected by subtracting the response obtained from a mock surface. Blank injections were subtracted (double referencing). Two exemplary SPR sensograms for the bispecific antibody <FITC><CD3>-Knob-HC (dA)+<Biotin>-Hole-nc-His (ncB) is shown in FIG. 28 (the two sensograms represent first addition of biotin, second addition of FITC and first addition of FITC, second addition of biotin). The results for all combinations are shown in the following table:

| bispecific antibody | Biotin | FITC |
|---|---|---|
| <FITC><CD3>-knob-HC (dA)<br><Biotin>-hole-n-HC (nB) | binding | binding |
| <FITC><CD3>-knob-HC (dA)<br><Biotin>-hole-nc-HC (ncB) | binding | binding |
| <FITC><CD3>-knob-HC (dA)<br><Biotin>-hole-c-HC (cB) | binding | binding |

All starting molecules, all non-wanted by-products, as well as all aggregates that were potentially generated during the exchange reaction harbor affinity tags (His6 or His8). The desired bispecific antibodies produced in the exchange reaction is the only molecule that does not carry a His-tag. Therefore, a simple NiNTA absorption step can be applied to remove all undesired molecules. The remaining bispecific antibody from the flow-through can be directly applied to screening procedures and analysis to identify bispecific antibodies with desired functionalities.

Example 17

Alternative Tags for Purification after the Exchange Reaction

The EPEA C-tag (SEQ ID NO: 87) has been used instead of the poly-histidine-tag in these experiments to show that the exchange reaction is not influenced by the employed tag.

2/3-IgGs like those in Example 6 have been expressed and purified using a C-tag with short linker (SEQ ID NO: 88) fused to the respective terminus. The results of the production and purification of these 2/3-IgGs is shown in the following table.

| 2/3-IgG | yield after purification [mg/L]* | SEC monomer peak [%] | CE-SDS monomer [%] | Mass spectrometry |
|---|---|---|---|---|
| Fluo-knob-n-HC + hole-MHCFcRP(E357K)-C-Tag | 64.3 | 96.9 | 95.1 | confirmed |
| Biotin-hole-n-HC + knob-MHCFcRP(K370E)-C-Tag | 110.0 | 95.7 | 93.6 | confirmed |
| Fluo-knob-c HC + hole-MHCFcRP(E357K)-C-Tag | 52.1 | 95.5 | 98.4 | confirmed |
| Fluo-knob-nc HC + hole-MHCFcRP(E357K)-C-Tag | 23.4 | 96.1 | 95.6 | confirmed |
| Biotin-hole-c HC + knob-MHCFcRP(K370E)-C-Tag | 83.5 | 88.5 | 89.0 | confirmed |
| Biotin-hole-nc HC + knob-MHCFcRP(K370E)-C-Tag | 33.5 | 98.5 | 98.0 | confirmed |

The exchange reaction was performed as follows:

Each 300 µl of the respective starting 2/3-IgGs (c=1 mg/ml; total 600 µl) were mixed. TCEP was added in a 15× molar excess. The sample was incubated at 37° C. and 400 rpm. 360 µl of sample was mixed with 200 µl C-tag resin (Thermo Scientific; 50% Slurry washed with 1×PBS pH 7.4) and incubated in a spin cup column for 60 min at RT and 800 rpm agitation. After incubation, the spin column was centrifuged for 5 min at RT, 800 rpm and the flow-through was collected. The Resin was washed several times with 1×PBS pH 7.4 (100 µl and subsequent centrifugation step). After washing, resin of sample a was mixed with 100 µl HCl-buffer pH 2.6 and incubated for 30 min at RT and 800 rpm agitation. Eluate was generated by centrifugation for 5 min at RT and 800 rpm).

Figure 29:
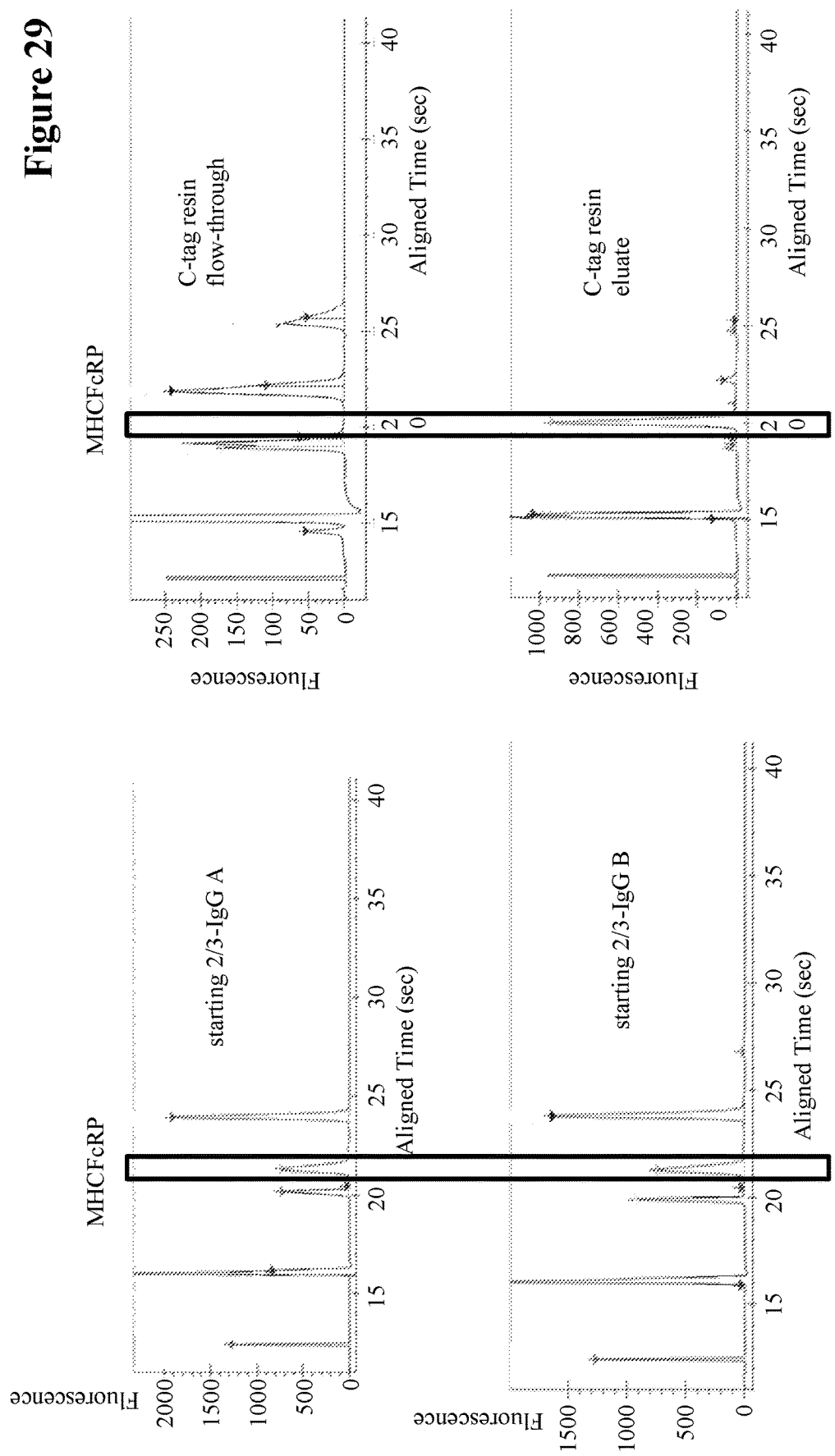
FIG. 29: Non-reduced CE-SDS chromatograms for the starting 2/3-IgGs comprising a C-tag and the reaction mixture after the exchange reaction according to the invention. Starting 2/3-IgG A is Fluo-knob-n-HC+hole-MHCFcRP (E357K)—C-Tag and starting 2/3-IgG B is Biotin-hole-n-HC+knob-MHCFcRP (K370E)-C-Tag. It can be seen that the bispecific antibody is formed and can be collected in the flow-through. The C-tagged MHCFcRP is bound after the exchange reaction to the C-tag resin and can be eluted therefrom. Thereby a separation and purification is achieved.

The non-reduced CE-SDS chromatograms for an exemplary exchange reaction of 2/3-IgG A (Fluo-knob-n-HC+hole-MHCFcRP (E357K)—C-Tag) with 2/3-IgG B (Biotin-hole-n-HC+knob-MHCFcRP (K370E)-C-Tag) are shown in FIG. 29. It can be seen that the bispecific antibody is formed and can be collected in the flow-through. The C-tagged MHCFcRP is bound after the exchange reaction to the C-tag resin and can be eluted therefrom. Thereby a separation and purification is achieved.

Example 18

Production of Bispecific Antibodies by 2/3-IgG-Exchange Reaction without Reduction Chain exchange with Fc-region disulfide containing 2/3-IgGs requires reduction as initial step to enable chain separation and subsequent re-assembly to form the desired bispecific antibodies. To avoid the reduction step and the therewith associated side-reactions as the 2/3-IgGs also contain non-hinge-disulfide bonds (disulfide shuffling), 2/3-IgGs without disulfides between H-chain Fc and MHCFcRP Fc were generated. This was achieved by mutating the cysteines responsible for hinge-disulfide formation in knob- and hole half-antibodies, as well as of the knob- or hole MHCFcRP chains. The CH3-cysteines that forms the KiH associated interchain disulfides between half-antibodies were also removed.

To eliminate the two cysteines that form H-H interchain disulfides, IgG1-derivatives without hinge-interchain disulfides was generated by exchanging the two cysteines in their H-chain hinge region to serine. Thereby, the hinge region sequence of wild-type IgG1 . . . HTCPXCP . . . (SEQ ID NO: 31) was altered to encode . . . HTSPXSP . . . (SEQ ID NO: 85).

Another entity without hinge-interchain disulfides was generated by deleting the entire sequence stretch of the hinge region that contributes to interchain disulfide formation. Therefore, the CPPC sequence of the hinge region of normal IgG1 was deleted to generate a shorter hinge with the sequence . . . HTPAPE . . . (SEQ ID NO: 86).

Figure 25:
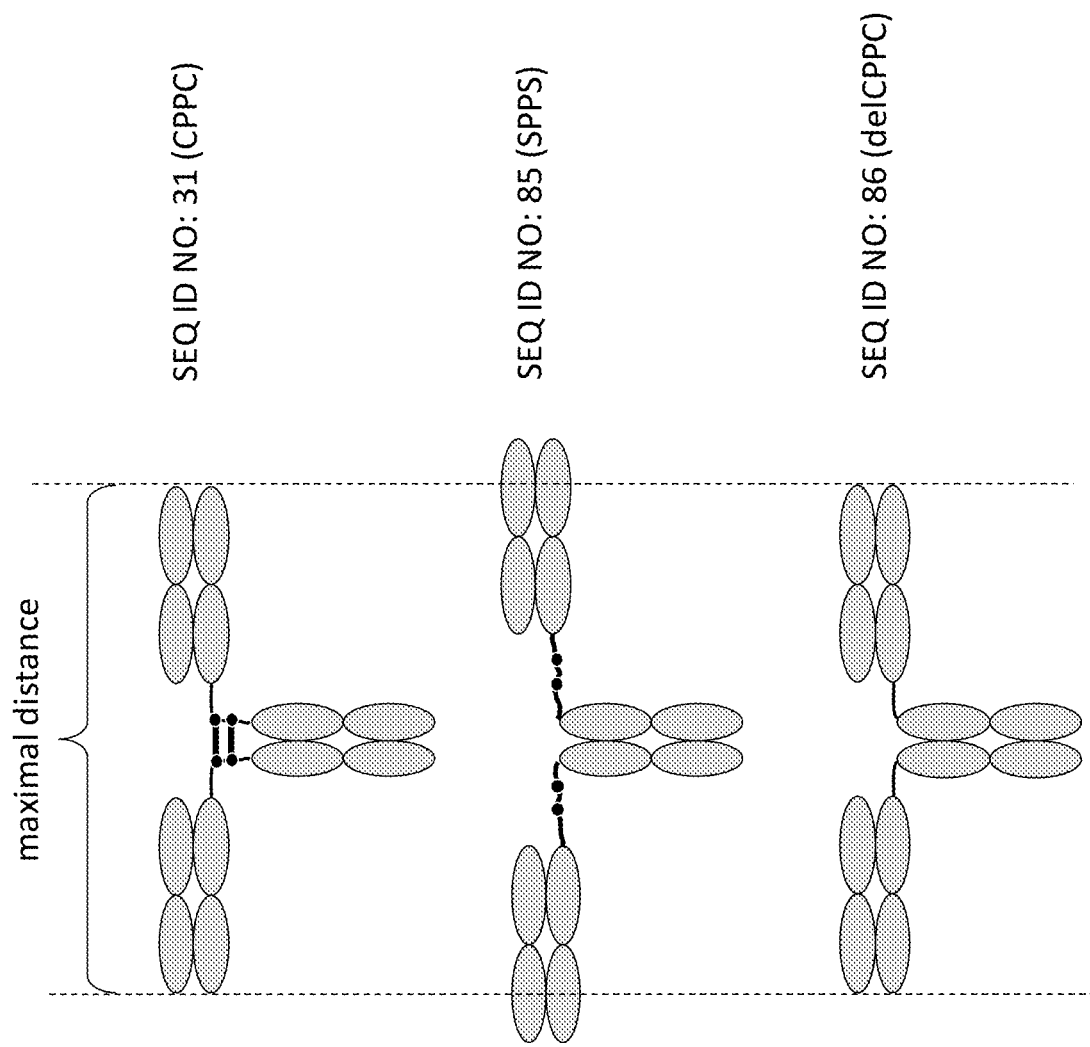
FIG. 25: By modification of the IgG1 hinge region, i.e. by removal of the disulfide bonds or by shortening the hinge region, different distances between the individual binding sites can be engineered.

FIG. 25 shows that replacement of cysteines with serins generates antibodies which—due to release of otherwise restricting hinge-disulfides—have an extended spanning distance.

Expression of 2/3 IgGs without HC-HC-interchain disulfide bonds was achieved by co-transfecting into mammalian cells CMV-promoter driven expression plasmids in the same manner as described above for disulfide-containing entities. Transient transfection into HEK293 cells of expression plasmids lead to CMV-promoter driven co-expression of the individual 2/3-IgGs, assembly in secretory compartments and subsequent secretion into culture supernatants.

2/3 IgGs without HC-HC interchain disulfides were secreted into cell culture supernatants and harbored Fc-regions as well as kappa L-chains. They were therefore purified by capturing in a first step by Protein A or by KappaSelect resins. A subsequent step separated according to size by size exclusion chromatography (SEC). This 2-step protocol enabled efficient recovery of the 2/3 IgG derivatives from cell culture supernatants in a robust and effective manner with yields similar to those observed with standard antibodies.

Example 19

Generation of Bispecific Antibodies by 2/3-IgG-Exchange Reaction without Reduction The 2/3-IgGs that contain a light chain, a heavy chain and complementary Fc-region have been generated in two types of KiH heterodimers: heavy chain-knob::corresponding Fc-region-hole and heavy chain-hole::corresponding Fc-region-knob. Both types of 2/3 IgGs are 'flawed' as the complementary Fc-region contains charge mutations without matching H-chain counterparts. The modules that make up those flawed heterodimers, however, are capable to rearrange to perfect heterodimers: heavy chain (knob) of 2/3-IgG A and the heavy chain (hole) from 2/3-IgG B form a perfect heterodimer. Perfect heterodimers are also formed when complementary Fc-region (hole-charge) interact with complementary Fc-region (knob-charge). Thus, exchange reactions based on temporary separation of starting heterodimers of two different 2/3-IgG types resulted in products that contain preferentially perfect heterodimers. Exchange reactions therefore converted two monospecific 2/3-IgGs to one bispecific IgG and one complementary Fc-region heterodimer.

The exchange reaction of original 2/3-IgGs that contain CH3 knob-hole and/or hinge-interchain disulfides must be initiated by a reduction step as shown in the previous examples. Reducing agents such as TCEP are added to break the disulfides, chain rearrangement occurs thereafter. In contrast, the 2/3-IgG derivatives without interchain HC-HC disulfide bonds do not require a reduction step to initiate chain exchange because their H-chains are not interconnected by disulfide bonds.

To analyze if and to what degree conversion of 2/3-IgGs to bsAbs depends on initial reduction, exchange reactions of the 2/3-IgGs (with and without interchain disulfides) were performed with and without reduction. Monovalent monospecific 2/3-IgGs that bind either Bio or Fluos (described above) were used as input molecules. In consequence, exchange reactions generate bivalent bispecific bsAbs that bind Bio as well as Fluos. The formation and bispecific functionality of the generated bsAbs was assessed by a bridging ELISA as described in above. The bridging ELISA consisted of addition of exchange reaction mixtures to immobilized Fluos-BSA, followed by wash steps and subsequent addition of Bio-Cy5 to probe for presence of the 2nd binding arm of the bispecific antibody. Only correct assembled functional bispecific antibodies are retained by their Fluos-binding arm on the assay plate and generate signals by capturing and retaining Bio-Cy5 and thereby generate assay signals. Monospecific input molecules or 'false' molecules without bispecificity generate no signals as they either do not bind to the plate (Bio-binder only) or cannot capture the signal generating Bio-Cy5 (Fluos-binder only).

Figure 24:
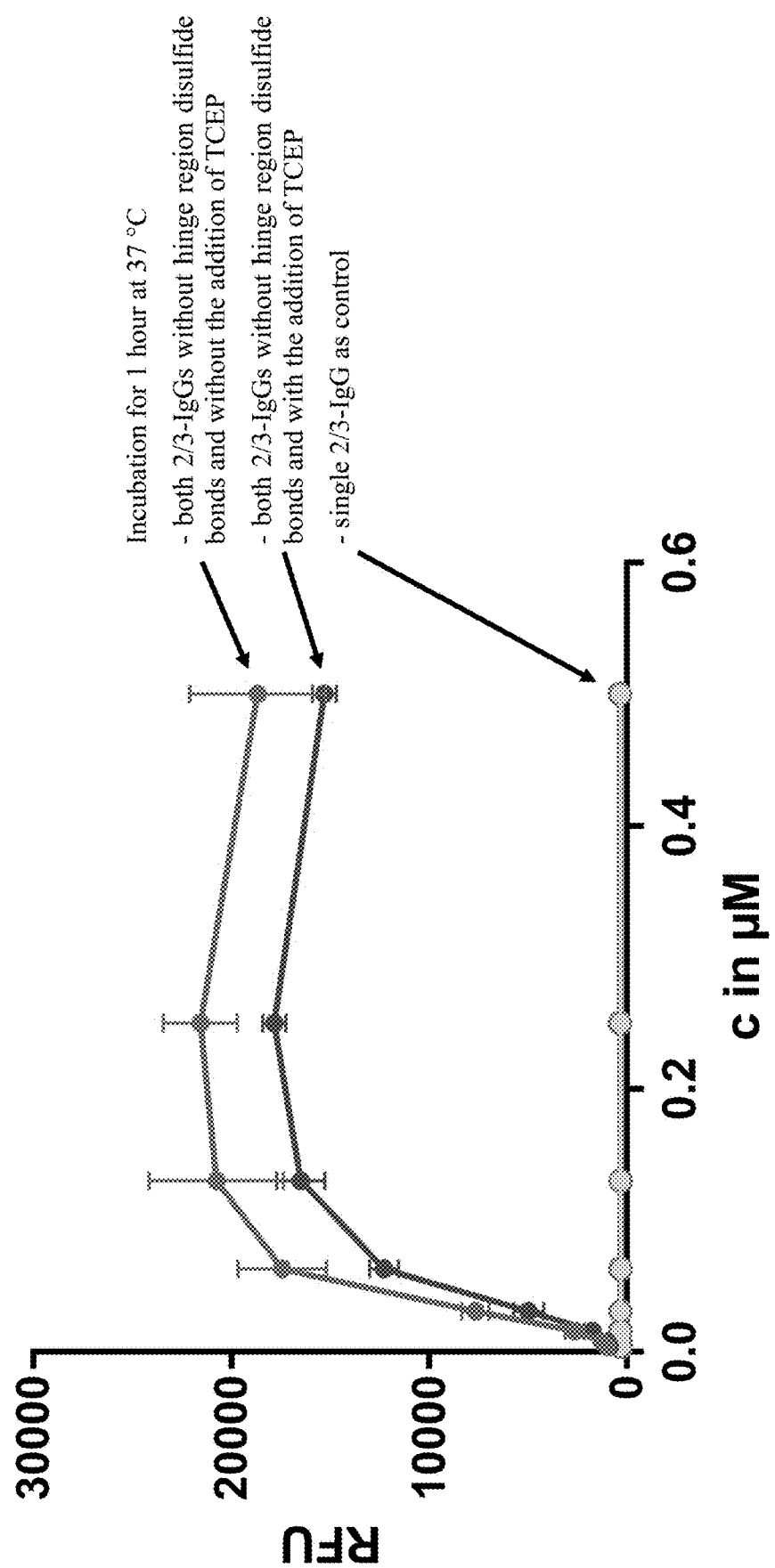
FIG. 24: Exchange reaction according to the current invention performed with 2/3-IgGs with and without hinge-region disulfide bonds, i.e. under reducing (red) and non-reducing (green) conditions. The exchange reaction was monitored used the bridging assay described in the examples. Negative control (grey) were both monospecific 2/3-IgG starting molecules.

FIG. 24 shows the results of these bridging ELISA analyses of parent (interchain disulfide containing) and H-H interchain disulfide-lacking 2/3-IgG exchange reactions with and without the initiating reduction step. Fluos-binding arm on the assay plate and generate signals by capturing and retaining Bio-Cy5 and thereby generate assay signals. Monospecific input molecules or 'false' molecules without bispecificity generate no signals as they either do not bind to the plate (Bio-binder only) or cannot capture the signal generating Bio-Cy5 (Fluos-binder only). FIG. 24 shows the results of these bridging ELISA analyses of parent (interchain disulfide containing) and H-H interchain disulfide-lacking 2/3-IgG exchange reactions with and without the initiating reduction step. We observed that the initial reduction was essential to enable chain exchange for 2/3-IgGs that contain hinge-disulfides. Those 2/3-IgGs with hinge-disulfides were converted to bispecific antibodies only when exchange is initiated by reduction. In contrast, effective bispecific antibody generation was achieved applying the 2/3-IgGs without hinge (and CH3) interchain disulfides. Chain exchange of those molecules generates bispecific antibodies under reducing conditions in the same manner as described above for hinge-connected entry molecules. However, initiating reduction was not essential for productive chain exchange of these molecules as productive chain exchange took also place without initial reduction, i.e. in the absence of a reducing agent. Thus, removal of Fc-Fc interchain disulfides eliminated the necessity of an initiating reduction step. The resulting bispecific antibodies are held together without hinge region interchain disulfide bonds. Thus, effective formation of bispecific antibodies takes place upon combining those hinge-disulfide free 2/3-IgGs in a spontaneous manner and the reduction step for initiation of the exchange reaction can be dispensed when using 2/3-IgGs without HC-HC-chain disulfide bonds.

Example 20

Chain Exchange Reactions are Concentration Dependent

The driver for conversion of 2/3-IgGs to bispecific antibodies is a designed 'partially flawed' interface between the Fc-regions. This special interface is the result of mutations introduced into the knob- or hole CH3 domains of the MHCFcRP Fc molecule. Mutated CH3 domains still associate with the corresponding normal knob- or hole-partners during expression of 2/3-IgGs. Those molecules are also of sufficient stability to present 2/3-IgGs as well behaved molecules without undesired aggregation tendencies. The productive chain exchange reaction leading to bispecific antibodies occurs when two complementary 2/3-IgGs come into close distance and H-chain::MHCFcRP pairs are partially released next to each other. Re-assembly of the knob-hole H-chains to form bispecific antibodies without destabilizing mutations is favored under such conditions because those H-chain (CH3) interfaces match better. Thus, the chains of bispecific antibodies products remain associated with preference over re-formation of the partially imperfect 2/3-IgG input molecules. Because of that, a designed partially de-stabilized CH3 interface is a key parameter for successful directed chain exchange reactions. Partial de-stabilization of the Fc interface can be achieved by mutating CH3 residues of the MHCFcRP chain as described herein before.

One other essential requirement (in addition to partially destabilized interfaces) for exchange reactions to occur is that two complementary 2/3-IgGs must come into proximity to enable chain exchange. The probability of entities to come into proximity, in turn, should depend on their concentrations in the exchange reaction.

Figure 30:
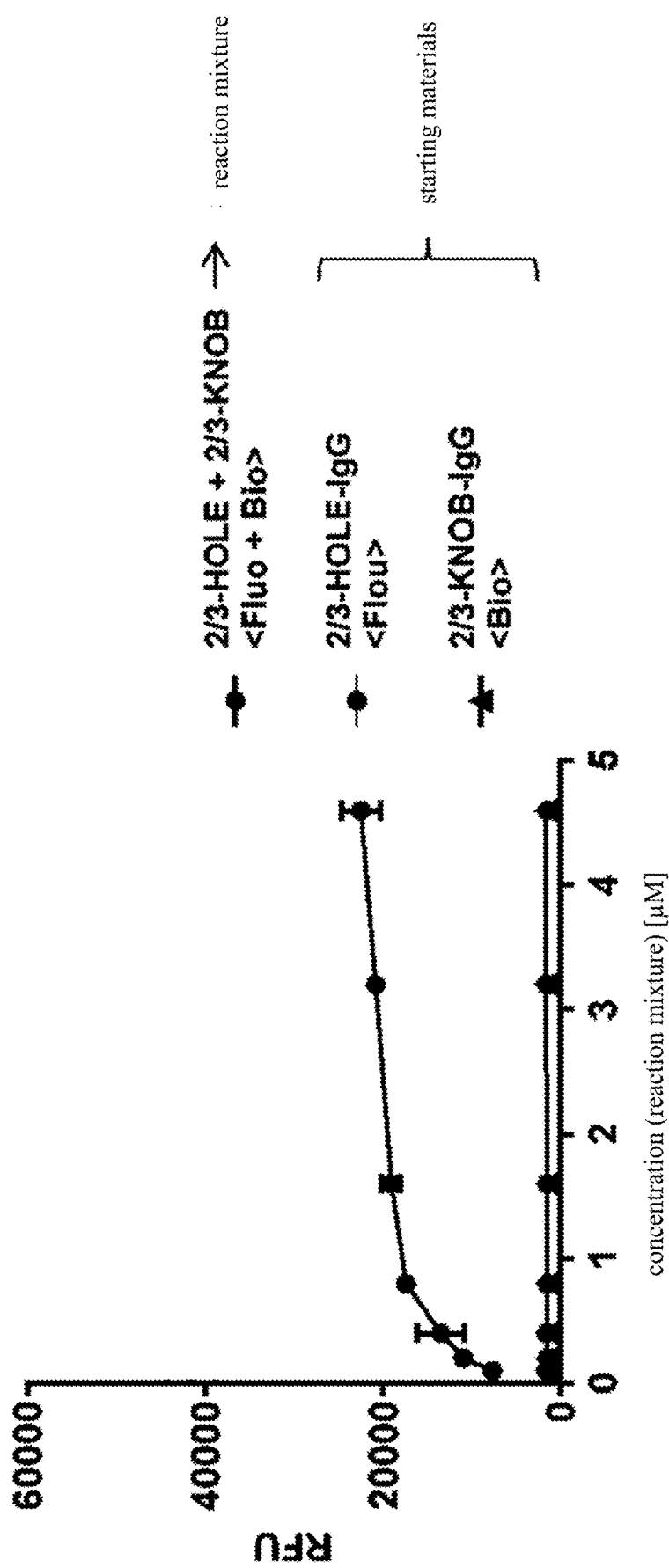
FIG. 30: Concentration dependence of the exchange reaction.

Exchange reactions were set up under non-reducing conditions applying Bio- and Fluos-binding 2/3-IgGs without HC-HC interchain disulfide bonds at different concentrations. After completion of the exchange reaction, all reaction mixes were brought to 'equal educt concentration' by diluting with exchange buffer samples with higher educt concentrations to that of the lowest experimental sample. Bridging ELISA was subsequently applied to determine the relative amount of functional bsAb in each experimental sample. Because identical amounts of educts are present in the dilution-aligned samples, concentration-independence would result in equal/similar ELISA values in all samples. Vice-versa, consecutively increased signals with higher educt concentrations in the reaction would indicate concentration dependent chain exchange. The results of these analyses revealed ELISA signals to reach a plateau in reactions that contained educt concentrations of >2 µM. Thus, at and above those concentrations, educt concentrations have only a limited effect on efficacy of the exchange reaction. Lower educt concentrations generated ELISA signals to become reduced in a dose dependent manner. Thus, below a certain threshold, generation of bsAb by exchange is significantly influenced by educt concentration due to reduced probabilities of educt interactions to occur. The results are shown in FIG. 30.

| concentration [µM] | | | |
|---|---|---|---|
| 2/3-IgG A | 2/3-IgG B | in exchange reaction | in ELISA |
| 9.2 | 9.2 | 4.6 | 0.05 |
| 6.4 | 6.4 | 3.2 | 0.05 |
| 3.2 | 3.2 | 1.6 | 0.05 |
| 1.6 | 1.6 | 0.8 | 0.05 |
| 0.8 | 0.8 | 0.4 | 0.05 |
| 0.4 | 0.4 | 0.2 | 0.05 |
| 0.2 | 0.2 | 0.1 | 0.05 |
| 0.1 | 0.1 | 0.05 | 0.05 |

Example 21

Generation of Bispecific Antibodies (bsAbs) by 2/3-IgG-Exchange Reaction with Constrained-2/3-IgGs as Starting Material The constrained-2/3-IgG that is circular and the binding site is formed by a first part N-terminal to the Fc-region and a second part C-terminal to the Fc-region, wherein the first and the second part are associated with each other and form the binding site, and MHCFcRP has been generated as KiH heterodimer: full length circular heavy chain-knob: MHCFcRP-hole. The constrained-2/3-IgG is somewhat 'flawed' as the MHCFcRP lacks the additional CH3 cysteine necessary to form interchain disulfides to the heavy chain, and the MHCFcRP contains charge mutations without matching charge in the full length heavy chain counterpart. The modules that make up those flawed heterodimers, however, are capable to rearrange to bispecific heterodimers with matching charges. The full length or the full length constrained heavy chain (knob-cys) of the 2/3-IgG A and the full length or constrained heavy chain (hole-cys) from 2/3-IgG B form a matching heterodimer. Matching heterodimers are also formed when MHCFcRP (hole-charge) interacts with MHCFcRP (knob-charge). Thus, exchange reactions based on temporary separation of starting heterodimers of two different 2/3-IgGs resulted in products that contain preferentially (charge) matching heterodimers. Exchange reactions therefore converted two monospecific 2/3-IgGs to one bispecific IgG and one MHCFcRP heterodimer:

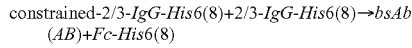

constrained-2/3-*IgG-His*6(8)+2/3-*IgG-His*6(8)→*bsAb* (*AB*)+*Fc-His*6(8)

The exchange reaction was initiated by a reduction step to break especially the hinge-region interchain disulfide bonds. Chain rearrangement occurred spontaneously thereafter.

Figure 31:
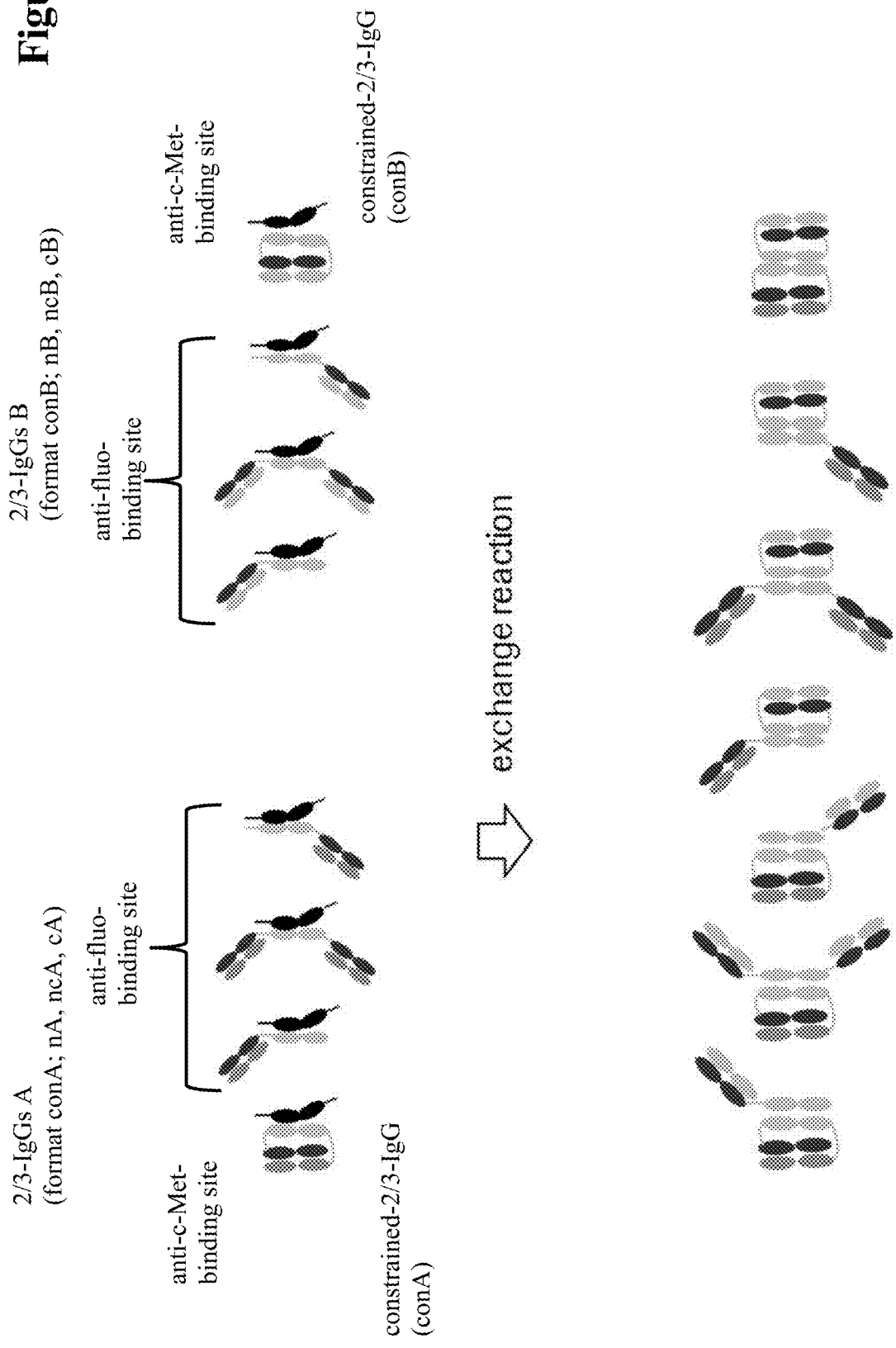
FIG. 31: Exchange reaction according to the current invention with a 2/3-IgG comprising a constrained binding site.
Figure 32:
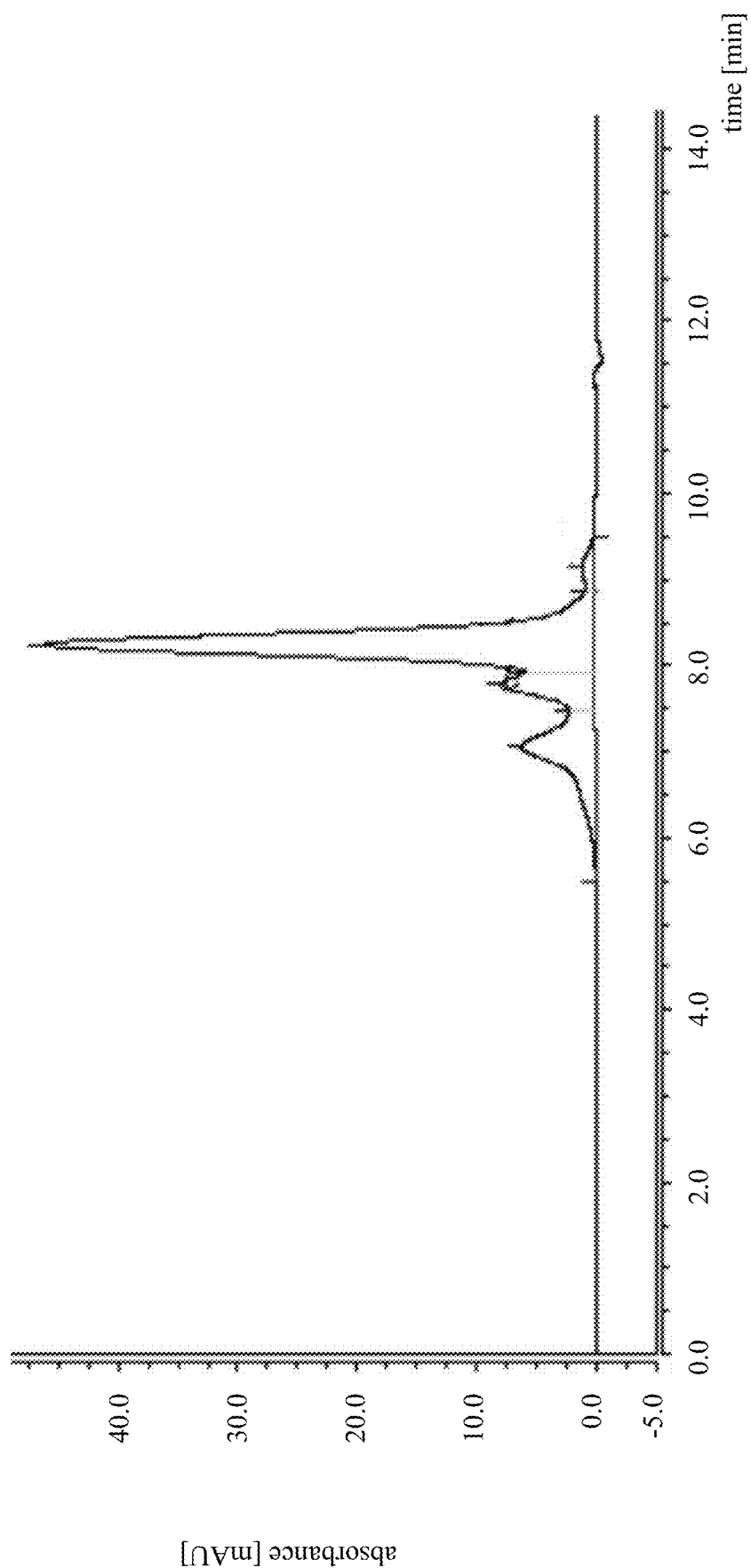
FIG. 32: Analytical SEC chromatogram for the obtained conAconB exchange reaction product.

The procedure for the exchange reactions as shown in FIG. 31 was as follows:

1 mg of "Input Format A" was mixed with 1 mg of "Input format B" in 1×PBS-buffer in a total volume of 2 ml. 16× molar equivalents of TCEP in 1×PBS-buffer were added to the mixture. Samples were incubated for one hour at 37° C. and 350 rpm agitation. After the incubation time, samples were purified via NiNTA Chromatography columns (His-Complete™, Roche, Switzerland) and assembled bispecific antibodies were collected in the flow through. The flow through was further incubated overnight at room temperature. Samples were then analyzed by analytical SEC, CE-SDS and mass spectroscopy methods.

The results of the exchange reaction are presented in the following table:

| bispecific antibody<br><cMET> = anti-cMET Fab<br><Biotin> = anti-biotin Fab<br><FITC> = anti-FITC Fab<br>HC = heavy chain | Yield [%] | SEC monomer [%] | CE-SDS Monomer non-reducing [%] | MS |
|---|---|---|---|---|
| <cMET>-knob-con-HC<br><Biotin>-hole-n-HC | 50.5 | 95.4 | 30.6 | confirmed |
| <cMET>-knob-con-HC<br><Biotin>-hole-nc-HC | 40 | 96.8 | 50 | confirmed |
| <cMET>-knob-con-HC<br><Biotin>-hole-c-HC | 36 | 92.9 | 25.4 | confirmed |
| <cMET>-hole-con-HC<br><FITC>-knob-n-HC | 11 | 76.7 | 46.3 | confirmed |
| <cMET>-hole-con-HC<br><FITC>-knob-nc-HC | 10.4 | 77.7 | 40 ? | confirmed |
| <cMET>-hole-con-HC<br><FITC>-knob-c-HC | 20 | 64 | 17 | confirmed |
| <cMET>-knob-con-HC<br><cMET>-hole-con-HC | 41 | 70 | 89 | confirmed |

Binding to c-MET, Biotin and FITC was investigated by surface plasmon resonance using a BIAcore T200 instrument (GE Healthcare). All experiments were performed at 25° C. using HBS-P (10 mM HEPES, 140 mM NaCl, 0.05% Tween 20 pH 7.4) as running and dilution buffer. Anti-human His-tag antibodies (GE Healthcare #28995056) were immobilized on a Series S CM5 Sensor Chip (GE Healthcare #29104988) using standard amine coupling chemistry. C-MET-Fc (R&D Systems #358-MT) was injected onto the surface followed by injection of either a Biotin-, or a FITC-labelled protein at a concentration of 10 µg/ml each. The association and dissociation phases were monitored for 2 min for each binding event. The surface was regenerated by injecting 10 mM Glycine pH 1.5 for 60 seconds. Bulk refractive index differences were corrected by subtracting the response obtained from a mock surface. Blank injections were subtracted (double referencing).

Figure 33:
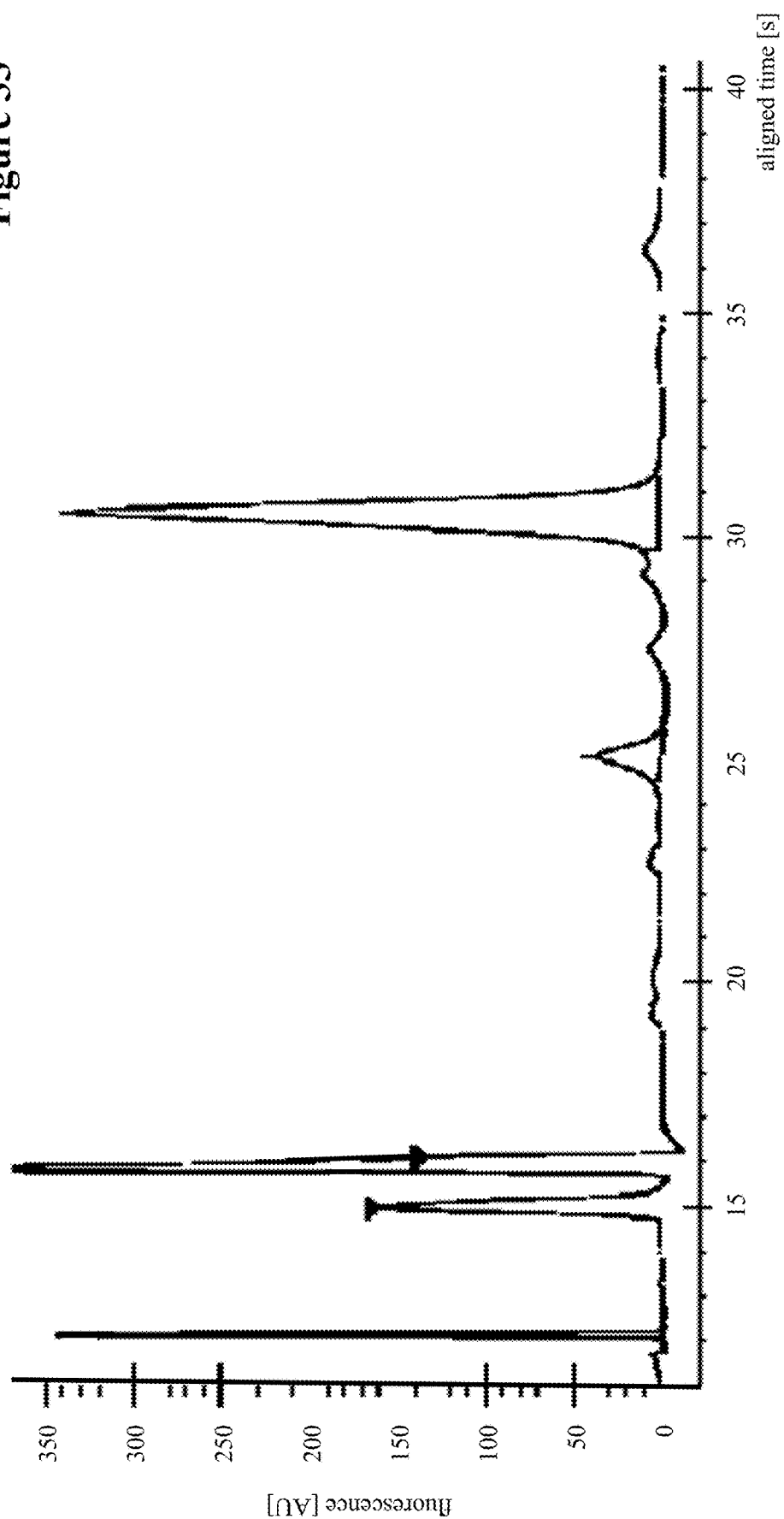
FIG. 33: Non-reduced CE-SDS chromatogram for the obtained conAconB exchange reaction product.
Figure 34:
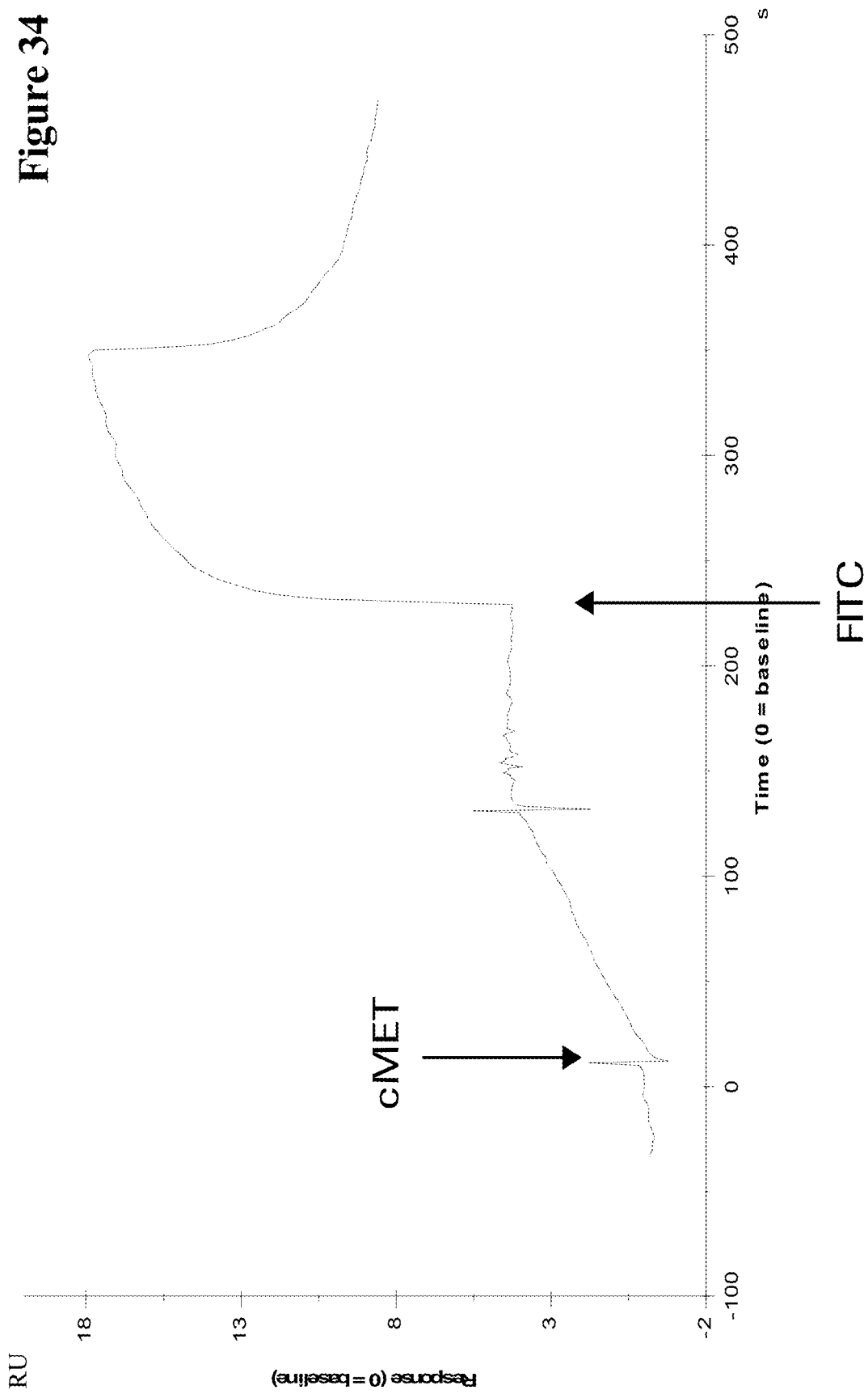
FIG. 34: SPR sensogram for the bispecific antibody <cMET>-hole-HC (conA)+<Fluo>-knob-c-His (ncB) obtained by consecutive injections of a cMET- and Fluo-labelled protein.

In a second setup, c-MET as well as anti-human Fc antibody (GE Healthcare #BR100839) were immobilized on a Series S CM5 Sensor Chip. Contorsbodies were injected onto both flow cells for 30 seconds at a concentration of 10 µg/ml. The surface was regenerated by injecting 3 M $MgCl_2$ for 60 seconds. Bulk refractive index differences were corrected by subtracting the response obtained from a mock surface. Blank injections were subtracted (double referencing). For evaluation, the resulting c-MET binding response was normalized to the response derived from anti-human Fc antibody binding an exemplary SPR sensorgram for the bispecific antibody <cMET>-hole-con-HC (*conA*)+<Fluo>-knob-c-His (cB) is shown in FIG. 33. The results for all combinations are shown in the following table:

| bispecific antibody | cMET | Biotin | FITC |
|---|---|---|---|
| <cMET>-knob-con-HC<br><Biotin>-hole-n-HC | binding | binding | n/a |
| <cMET>-knob-con-HC<br><Biotin>-hole-nc-HC | binding | binding | n/a |
| <cMET>-knob-con-HC<br><Biotin>-hole-c-HC | binding | binding | n/a |
| <cMET>-hole-con-HC<br><Fluo>-knob-n-HC | binding | n/a | binding |
| <cMET>-hole-con-HC<br><Fluo>-knob-nc-HC | binding | n/a | binding |
| <cMET>-hole-con-HC<br><Fluo>-knob-c-HC | binding | n/a | binding |
| <cMET>-knob-con-HC<br><cMET>-hole-con-HC | binding | n/a | n/a |

| bispecific antibody | cMET | Biotin | FITC |
|---|---|---|---|
| <cMET>-knob-con-HC | binding | n/a | n/a |
| <cMET>-hole-con-HC | binding | n/a | n/a | n/a indicates that the respective binding site is not present in the bispecific antibody and thereby no binding can be expected.

All starting molecules, all non-wanted by-products, as well as all aggregates that were potentially generated during the exchange reaction harbor affinity tags (His6 or His8). The desired bispecific antibodies produced in the exchange reaction is the only molecule that does not carry a His-tag. Therefore, a simple NiNTA absorption step can be applied to remove all undesired molecules. The remaining bispecific antibody from the flow-through can be directly applied to screening procedures and analysis to identify bispecific antibodies with desired functionalities.

The invention claimed is:

1. A method for producing a heterodimeric exchanged polypeptide comprising the following steps:
   incubating:
   a first heterodimeric starting polypeptide comprising
      a first polypeptide comprising
         an immunoglobulin G CH3 domain,
         and
         at least one functional binding site or a part thereof,
      and
      a second polypeptide comprising
         an immunoglobulin G CH3 domain
      wherein the first and second polypeptide form said heterodimeric starting polypeptide, and wherein
      the CH3 domain of the first polypeptide comprises the mutations knob-cys and the CH3 domain of the second polypeptide comprises the mutations hole,
      or
      the CH3 domain of the first polypeptide comprises the mutations hole-cys and the CH3 domain of the second polypeptide comprises the mutation knob,
      the second polypeptide comprises in the CH3 domain a further mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, LA41Y, C349Y, S366T, A368L, V407Y, C354S, and W366T,
   and
   a second heterodimeric starting polypeptide comprising
      a third polypeptide comprising
         an immunoglobulin G CH3 domain,
         and
      a fourth polypeptide comprising
         an immunoglobulin G CH3 domain,
         and
         at least one functional binding site or a part thereof
      wherein the third and fourth polypeptide form a heterodimer; and wherein
      in case the first polypeptide comprises the mutations hole-cys the fourth polypeptide comprises the mutations knob-cys and the third polypeptide comprises the mutations hole,
      or
      in case the first polypeptide comprises the mutations knob-cys the fourth polypeptide comprises the mutations hole-cys and the third polypeptide comprises the mutations knob; and
      the third polypeptide comprises in the CH3 domain a further mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, LA41Y, C349Y, S366T, A368L, V407Y, C354S, and W366T wherein said further mutation is different from the mutations present in the CH3 domain of the first polypeptide and the second polypeptide, to exchange the second and the third polypeptide to form a third heterodimeric exchanged polypeptide comprising the second and the third polypeptide and a fourth heterodimeric exchanged polypeptide comprising the first and the fourth polypeptide;

and recovering the fourth heterodimeric exchanged polypeptide.

2. The method according to claim 1, wherein the CH3 domain of the second polypeptide comprises a mutation E357K, the first polypeptide comprises at position 370 the amino acid residue K, the CH3 domain of the third polypeptide comprises a mutation K370E, and the fourth polypeptide comprises at position 357 the amino acid residue E with the positions numbered according to Kabat EU index.

3. The method according to claim 1, wherein the CH3 domain of the second polypeptide comprises a mutation D356K, the first polypeptide comprises at position 439 the amino acid residue K, the CH3 domain of the third polypeptide comprises a mutation K439E, and the fourth polypeptide comprises at position 356 the amino acid residue D with the positions numbered according to Kabat EU index.

4. The method according to any one of claims 1 to 3, wherein the first and/or second polypeptide comprises the amino acid sequence HTSPPSP (SEQ ID NO: 92) or the amino acid sequence HTPAPE (SEQ ID NO: 86), and wherein the fourth and/or third polypeptide comprises the amino acid sequence HTSPPSP (SEQ ID NO: 92) or the amino acid sequence HTPAPE (SEQ ID NO: 86).

5. The method according to any one of claims 1 to 3, wherein the first polypeptide comprises the mutations knob-cys, the second polypeptide comprises the mutations hole, the third polypeptide comprises the mutation knob, and the fourth polypeptide comprises the mutations hole-cys.

6. The method according to any one of claims 1-3 or 5, wherein the first to fourth polypeptide each comprise in N- to C-terminal direction an IgG1 CH2 domain and an IgG1 CH3 domain.

7. The method according to claim 1, wherein the first to fourth polypeptide each comprise in N- to C-terminal direction i) independently of each other either the amino acid sequence DKTHTCPPC (SEQ ID NO: 65) or the amino acid sequence DKTHTSPPS (SEQ ID NO: 66) or the amino acid sequence DKTHT (SEQ ID NO: 91), ii) an IgG1 CH2 domain, and iii) an IgG1 CH3 domain.

8. The method according to claim 1, wherein the first and the fourth polypeptide each further comprise an IgG1 CH1 domain and a variable domain.

9. The method according to claim 8, wherein the variable domain of the first polypeptide is a heavy chain variable domain and the variable domain of the fourth polypeptide is a light chain variable domain or vice versa, and these domains form a binding site in the fourth heterodimeric exchanged polypeptide.

10. The method according to claim 1, wherein the first and fourth polypeptide are independently of each other selected from the group of polypeptide comprising in N- to C-terminal direction i) a heavy chain variable domain, a human IgG1 CH1 domain, a hinge region of SEQ ID NO: 65 or 66 or 91, a CH2 domain derived from a human IgG1 CH2 domain, and a CH3 domain derived from a human IgG1 CH3 domain, ii) a hinge region of SEQ ID NO: 65 or 66 or 91, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66 or 91, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a scFv, optionally a peptidic linker, a hinge region of SEQ ID NO: 65 or 66 or 91, a CH2 domain derived from a human IgG1 CH2 domain, and a CH3 domain derived from a human IgG1 CH3 domain, v) a scFab, optionally a peptidic linker, a hinge region of SEQ ID NO: 65 or 66 or 91, a CH2 domain derived from a human IgG1 CH2 domain, and a CH3 domain derived from a human IgG1 CH3 domain, vi) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, vii) a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, viii) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a second human IgG1 CH1 domain, ix) a first heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a second heavy chain variable domain, x) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFv, xi) a heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, and a scFab, xii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second human IgG1 CH1 domain, and a light chain variable domain, xiii) a heavy chain variable domain, a first human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a light chain variable domain, and a second human IgG1 CH1 domain, xiv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xv) a first heavy chain variable domain, a human IgG1 CH1 domain, a hinge region of SEQ ID NO: 65 or 66 or 91, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xvi) a first part of the binding domain, optionally a first peptidic linker, a hinge region of SEQ ID NO: 65 or 66 or 91, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target.

11. The method according to claim 1, wherein the first and the second heterodimeric polypeptide further comprise an antibody light chain that is associated with the first polypeptide and the fourth polypeptide, respectively.

12. The method according to claim 1, wherein the incubation step is in the absence of a reducing agent.

13. The method according to claim 1, wherein the second polypeptide and the third polypeptide further comprise a C-terminal tag.

14. The method according to claim 13, wherein
i) the tag has the amino acid sequence HHHHHH (SEQ ID NO: 67) or HHHHHHHH (SEQ ID NO: 68) and the recovering is by chromatography on a metal (nickel) chelate affinity chromatography column, or
ii) the tag has the amino acid sequence EPEA (SEQ ID NO: 87) and the recovering is by chromatography on a C-tag affinity chromatography column.

15. The method according to claim 1, wherein the hinge region of the first heterodimeric starting polypeptide and the hinge region of the second heterodimeric starting polypeptide comprises the mutations C226S and C229S or a deletion of the entire CPXC (SEQ ID NO: 89) sequence, wherein the numbering is according to Kabat EU index.

* * * * *